(12) United States Patent
Horlick et al.

(10) Patent No.: US 12,365,737 B2
(45) Date of Patent: Jul. 22, 2025

(54) ANTI-IL-18BP ANTIBODIES

(71) Applicant: Lassen Therapeutics, Inc., San Diego, CA (US)

(72) Inventors: Robert A. Horlick, San Diego, CA (US); Helen Toni Jun, San Diego, CA (US); Magdalena S. Willen, San Diego, CA (US); Christine M. Chidester, San Diego, CA (US); Mark G. Barrett, Wellesley, MA (US); David J. King, Encinitas, CA (US); Deborah A. Witherden, San Diego, CA (US)

(73) Assignee: Lassen Therapeutics, Inc., San Diego, CA (US)

( * ) Notice: Subject to any disclaimer, the term of this patent is extended or adjusted under 35 U.S.C. 154(b) by 0 days.

(21) Appl. No.: 18/817,109

(22) Filed: Aug. 27, 2024

(65) Prior Publication Data
US 2024/0417479 A1    Dec. 19, 2024

Related U.S. Application Data

(63) Continuation of application No. PCT/US2024/010447, filed on Jan. 5, 2024.

(60) Provisional application No. 63/596,580, filed on Nov. 6, 2023, provisional application No. 63/590,348, filed on Oct. 13, 2023, provisional application No. 63/437,526, filed on Jan. 6, 2023.

(51) Int. Cl.
C07K 16/28    (2006.01)
A61K 39/395   (2006.01)
A61K 38/20    (2006.01)
C07K 14/715   (2006.01)

(52) U.S. Cl.
CPC ...... *C07K 16/2866* (2013.01); *A61K 39/3955* (2013.01); *A61K 38/20* (2013.01); *C07K 14/715* (2013.01); *C07K 2317/24* (2013.01); *C07K 2317/33* (2013.01); *C07K 2317/76* (2013.01); *C07K 2317/92* (2013.01)

(58) Field of Classification Search
CPC ............ C07K 16/2866; C07K 14/715; A61K 39/3955
See application file for complete search history.

(56) References Cited

U.S. PATENT DOCUMENTS

| | | | |
|---|---|---|---|
| 4,946,778 A | 8/1990 | Ladner et al. |
| 5,091,513 A | 2/1992 | Huston et al. |
| 5,132,405 A | 7/1992 | Huston et al. |
| 5,464,758 A | 11/1995 | Gossen et al. |
| 5,624,821 A | 4/1997 | Winter et al. |
| 5,814,618 A | 9/1998 | Bujard et al. |
| 6,210,922 B1 | 4/2001 | Côté et al. |
| 6,376,190 B1 | 4/2002 | Gold et al. |
| 6,387,620 B1 | 5/2002 | Smith et al. |
| 6,596,541 B2 | 7/2003 | Murphy et al. |
| 6,765,087 B1 | 7/2004 | Casterman et al. |
| 6,838,254 B1 | 1/2005 | Hamers et al. |
| 7,029,872 B2 | 4/2006 | Gerngross |
| 7,030,226 B2 | 4/2006 | Sun et al. |
| 7,112,715 B2 | 9/2006 | Chambon et al. |
| 7,166,697 B1 | 1/2007 | Galanis et al. |
| 7,217,797 B2 | 5/2007 | Hinton et al. |
| 7,244,592 B2 | 7/2007 | Hoogenboom et al. |
| 7,326,681 B2 | 2/2008 | Gerngross |
| 7,425,619 B2 | 9/2008 | Koenig et al. |
| 7,462,697 B2 | 12/2008 | Couto et al. |
| 7,629,163 B2 | 12/2009 | Gerngross |
| 7,662,925 B2 | 2/2010 | Lazar et al. |
| 7,700,321 B2 | 4/2010 | McPherson et al. |
| 7,732,570 B2 | 6/2010 | Hinton et al. |
| 8,008,449 B2 | 8/2011 | Korman et al. |
| 8,436,148 B2 | 5/2013 | Dinarello et al. |
| 8,993,731 B2 | 3/2015 | Tyson |
| 9,073,994 B2 | 7/2015 | Honjo et al. |
| 9,084,776 B2 | 7/2015 | Korman et al. |
| 9,102,725 B2 | 8/2015 | Korman et al. |
| 9,102,727 B2 | 8/2015 | Freeman et al. |
| 9,102,728 B2 | 8/2015 | Tyson |
| 9,181,342 B2 | 11/2015 | Davis |
| 9,217,034 B2 | 12/2015 | Li et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 2003/0108532 A1 | 6/2003 | Benson et al. |
| 2003/0118592 A1 | 6/2003 | Ledbetter et al. |

(Continued)

FOREIGN PATENT DOCUMENTS

| | | |
|---|---|---|
| WO | WO-9311161 A1 | 6/1993 |
| WO | WO-9413804 A1 | 6/1994 |

(Continued)

OTHER PUBLICATIONS

Aalberse, R.C. et al. (2002). "IgG4 breaking the rules," Immunology 105:9-19.

Allen, D., et al.; "Validation of peptide mapping for protein identity and genetic stability. Biologics and biotechnology section, pharmaceutical research and manufacturers of America," Biologicals.; 24(3):255-574 (1996).

(Continued)

*Primary Examiner* — Zachary C Howard
(74) *Attorney, Agent, or Firm* — COOLEY LLP

(57) ABSTRACT

Provided are antibodies that bind to interleukin-18 binding protein (IL-18BP) and related compositions, which may be used in any of a variety of therapeutic or diagnostic methods, including the treatment or diagnosis of cancers and other diseases.

25 Claims, 20 Drawing Sheets

Specification includes a Sequence Listing.

(56) References Cited

U.S. PATENT DOCUMENTS

| | | |
|---|---|---|
| 2003/0190311 A1 | 10/2003 | Dall'Acqua et al. |
| 2004/0175756 A1 | 9/2004 | Kolkman et al. |
| 2005/0037421 A1 | 2/2005 | Honda et al. |
| 2005/0048512 A1 | 3/2005 | Kolkman et al. |
| 2005/0053973 A1 | 3/2005 | Kolkman et al. |
| 2005/0089932 A1 | 4/2005 | Kolkman et al. |
| 2005/0221384 A1 | 10/2005 | Kolkman et al. |
| 2006/0058510 A1 | 3/2006 | Skerra et al. |
| 2006/0173170 A1 | 8/2006 | Chamberlain et al. |
| 2007/0082365 A1 | 4/2007 | Lipovsek et al. |
| 2007/0092521 A1 | 4/2007 | McPherson et al. |
| 2007/0111281 A1 | 5/2007 | Sondermann et al. |
| 2007/0148170 A1 | 6/2007 | Desjarlais et al. |
| 2008/0139791 A1 | 6/2008 | Lipovsek et al. |
| 2008/0206246 A1 | 8/2008 | Ravetch et al. |
| 2008/0220049 A1 | 9/2008 | Chen et al. |
| 2009/0010921 A1 | 1/2009 | Umana et al. |
| 2009/0017023 A1 | 1/2009 | Koenig et al. |
| 2009/0082274 A1 | 3/2009 | Stumpp et al. |
| 2009/0163699 A1 | 6/2009 | Chamberlain et al. |
| 2009/0226421 A1 | 9/2009 | Parren et al. |
| 2010/0080794 A1 | 4/2010 | Tsuji et al. |
| 2010/0092997 A1 | 4/2010 | Nakamura et al. |
| 2010/0143254 A1 | 6/2010 | Dall'Acqua et al. |
| 2010/0203046 A1 | 8/2010 | Van Vlijmen et al. |
| 2010/0209424 A1 | 8/2010 | Roopenian et al. |
| 2010/0249382 A1 | 9/2010 | Desjarlais et al. |
| 2010/0255013 A1 | 10/2010 | Presta |
| 2012/0039906 A1 | 2/2012 | Olive |
| 2013/0245104 A1 | 9/2013 | De Fougerolles et al. |
| 2014/0112915 A1 | 4/2014 | Bardroff et al. |
| 2014/0147454 A1 | 5/2014 | Chakraborty et al. |
| 2014/0243399 A1 | 8/2014 | Schrum et al. |
| 2014/0364341 A1 | 12/2014 | Mansfield et al. |
| 2015/0111248 A1 | 4/2015 | Bancel et al. |
| 2015/0203579 A1 | 7/2015 | Papadopoulos et al. |
| 2019/0070262 A1 | 3/2019 | Ring et al. |
| 2023/0027029 A1 | 1/2023 | Zhang et al. |

FOREIGN PATENT DOCUMENTS

| | | |
|---|---|---|
| WO | WO-9909063 A1 | 2/1999 |
| WO | WO-0042072 A2 | 7/2000 |
| WO | WO-0107480 A2 | 2/2001 |
| WO | WO-0220565 A2 | 3/2002 |
| WO | WO-2004016750 A2 | 2/2004 |
| WO | WO-2005047337 A1 | 5/2005 |
| WO | WO-2006079372 A1 | 8/2006 |
| WO | WO-2012177595 A1 | 12/2012 |
| WO | WO-2012177595 A9 | 3/2013 |
| WO | WO-2014126277 A1 | 8/2014 |
| WO | WO-2015032932 A1 | 3/2015 |
| WO | WO-2016139297 A1 | 9/2016 |
| WO | WO-2018060447 A1 | 4/2018 |
| WO | WO-2019051015 A1 | 3/2019 |
| WO | WO-2019213686 A1 | 11/2019 |
| WO | WO-2021146590 A2 | 7/2021 |
| WO | WO-2023143535 A1 | 8/2023 |
| WO | WO-2023178192 A1 | 9/2023 |
| WO | WO-2023215834 A1 | 11/2023 |
| WO | WO-2024148232 A2 | 7/2024 |
| WO | WO-2024148241 A1 | 7/2024 |
| WO | WO-2024148243 A1 | 7/2024 |
| WO | WO-2025003753 A1 | 1/2025 |

OTHER PUBLICATIONS

Altschul, S. F., et al., "Gapped BLAST and PSI-BLAST: a new generation of protein database search programs", Nucleic Acids Research (1997); 25(17): 3389-3402.

Anicetti, et al., Purity analysis of protein pharmaceuticals produced by recombinant DNA technology, Trends in Biotechnology, Dec. 1989, 7(12); pp. 342-349.

Bird et al., Single-chain antigen-binding proteins. Science; 242(4877):423-426 (1988).

Bitter et al. Expression and secretion vectors for yeast. Methods Enzymol 153:516-544 (1987).

Bottino, C., et al.; "Identification of PVR (CD155) and Nectin-2 (CD112) as cell surface ligands for the human DNAM-1 (CD226) activating molecule," J. Exp. Med.; 198(4):557-567 (2003).

Bowers et al., Humanization of antibodies using heavy chain complementarity-determining region 3 grafting coupled with in vitro somatic hypermutation. J Biol Chem., 288(11):7688-7696 (2013).

Brinkman et al., The making of bispecific antibodies, Mabs; 9(2):182-212 (2017).

Broglie, et al., Light-regulated expression of a pea ribulose-1,5-bisphosphate carboxylase small subunit gene in transformed plant cells, Science, May 1984, 224(4651); pp. 838-843.

Bruner et al.: Size exclusion HPLC method for the determination of acidic fibroblast growth factor in viscous formulations. Journal of Pharmaceutical and Biomedical Analysis; 15(12):1929-1935 (1997).

Carter et al., "Humanization of an anti-p185HER2 antibody for human cancer therapy," Proceedings of the National Academy of Sciences, May 1992, 89(10), pp. 4285-4289.

Chao et al., "Isolating and engineering human antibodies using yeast surface display," Nature Protocols, Aug. 2006, 1(2), pp. 755-768.

Clynes R., et al., "Fc Receptors are Required in Passive and Active Immunity to Melanoma," Proceedings of the National Academy of Sciences of the United States of America, Jan. 20, 1998, vol. 95, No. 2, pp. 652-656.

Co, M. S., et al., "Humanized antibodies for antiviral therapy," Proceedings of the National Academy of Sciences (1991) 88(7):2869-2873.

Co, M.S., et al.; "Chimeric and humanized antibodies with specificity for the CD33 antigen," J Immunol.; 148(4):1149-1154 (1992).

Colbere-Garapin, F., et al.; "A new dominant hybrid selective marker for higher eukaryotic cells," Journal of Molecular biology, Jul. 1981, 150(1):1-14.

Coruzzi, G., et al.; "Tissue-specific and light-regulated expression of a pea nuclear gene encoding the small subunit of ribulose-1,5-bisphosphate carboxylase," EMBO J. (1984); 3(8):1671-1679.

Croft, M., et al.; "The significance of OX40 and OX40L to T-cell biology and immune disease," Immunological Reviews; 229(1):173-191 (2009).

Davies, D.R., et al.; "Antibody-antigen complexes," Annu Rev Biochem.; 59:439-473 (1990).

Davies J., et al., "Expression of GnTIII in a Recombinant Anti-CD20 CHO Production Cell Line: Expression of Antibodies with Altered Glycoforms Leads to an Increase in ADCC Through Higher Affinity for FCgammaRIII," Biotechnology Bioengineering, Aug. 20, 2001, vol. 74, No. 04, pp. 288-294.

Denardo et al., Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts. Clin Cancer Res.; 4(10):2483-2490 (1998).

Derre, L., et al. (2010). "BTLA mediates inhibition of human tumor-specific CD8+ T cells that can be partially reversed by vaccination." The Journal of clinical investigation. 120(1):157-167.

Detry, S., et al.; "Structural basis of human IL-18 sequestration by the decoy receptor IL-18 binding protein in inflammation and tumor immunity," J Biol Chem.; 298(5):101908, 16 pages (2022).

Ehrlich, P. et al., "Isolation of an active heavy-chain variable domain from a homogeneous rabbit antibody by cathepsin B digestion of the aminoethylated heavy chain," Biochemistry, Aug. 1, 1980, vol. 19, No. 17, pp. 4091-4096.

Ellington et al., "In vitro selection of RNA molecules that bind specific ligands," Nature; 346(6287):818-822 (1990).

Engelhard, et al., The insect tracheal system: a conduit for the systemic spread of Autographa californica M nuclear polyhedrosis virus, Proceedings of the National Academy of Sciences, Apr. 1994, 91(8); pp. 3224-3227.

(56) References Cited

OTHER PUBLICATIONS

Fuhrmann-Benzakein, et al., "Inducible and irreversible control of gene expression using a single transgene," 28(23):E99, 5 pages (2000).
Gerngross, Advances in the production of human therapeutic proteins in yeasts and filamentous fungi, Nat Biotechnol., Nov. 2004, 22(11); pp. 1409-1414.
Gorman et al. "Reshaping a therapeutic CD4 antibody." Proceedings of the National Academy of Sciences (1991); 88.10: 4181-4185.
Graham, T.L. et al. (1977). "Characteristics of a Human Cell Line Transformed by DNA From Human Adenovirus Type 5," J. Gen. Virol., vol. 36, pp. 59-72.
Hamilton, et al., Humanization of yeast to produce complex terminally sialylated glycoproteins, Science, Sep. 2006, 313(5792); pp. 1441-1443.
Hamilton et al., Production of complex human glycoproteins in yeast. Science; 301(5637):1244-1246 (2003).
Hartman, et al., Two Dominant-Acting Selectable Markers for Gene Transfer Studies in Mammalian Cells, Proceedings of the National Academy of Sciences of the United States of America, Nov. 1988, 85(21); pp. 8047-8051.
He, L-Z., et al.; "Agonist anti-human CD27 monoclonal antibody induces T cell activation and tumor immunity in human CD27-transgenic mice," J Immunol.; 191(8):4174-4183 (2013).
Hochman, J. et al., "Folding and interaction of subunits at the antibody combining site," Biochemistry, Jun. 1, 1976, vol. 15, No. 12, pp. 2706-2710.
Holliger, P., et al., ""Diabodies": small bivalent and bispecific antibody fragments", Proceedings of the National Academy of Sciences (1993); 90(14): 6444-6448.
Holliger, P., et al., "Engineering bispecific antibodies", Current Opinion in Biotechnology (1993); 4(4):446-449.
Hu, S., et al., "Minibody: a novel engineered anti-carcinoembryonic antigen antibody fragment (single-chain Fv-CH3) which exhibits rapid, high-level targeting of xenografts", Cancer Research (1996); 56(13):3055-3061.
Huang et al., "Role of LAG-3 in regulatory T cells" Immunity, (2004); 21(4):503-513.
Huston, J. S., et al., "Protein engineering of antibody binding sites: recovery of specific activity in an anti-digoxin single-chain Fv analogue produced in *Escherichia coli*", Proceedings of the National Academy of Sciences (1988); 85(16):5879-5883.
Ill, C. et al., "Design and construction of a hybrid immunoglobulin domain with properties of both heavy and light chain variable regions," Protein Engineering, Design and Selection, Aug. 1997, vol. 10, Issue 8, pp. 949-957.
Im S-H., et al.; "Rat interleukin-18 binding protein: cloning, expression, and characterization," J Interferon Cytokine Res. (2002); 22(3):321-328.
Inbar et al., "Localization of antibody-combining sites within the variable portions of heavy and light chains". Proceedings of the National Academy of Sciences. Sep. 1972; 69(9):2659-62.
Indra, A.K., et al.; "Temporally-controlled site-specific mutagenesis in the basal layer of the epidermis: comparison of the recombinase activity of the tamoxifen-inducible Cre-ER(T) and Cre-ER(T2) recombinases," Nucleic Acids Research, Nov. 1999, 27(22); pp. 4324-4327.
International Search Report and Written Opinion for PCT Application No. PCT/US2024/010445 dated May 7, 2024, 17 pages.
International Search Report and Written Opinion for PCT Application No. PCT/US2024/010447 dated Apr. 23, 2024, 17 pages.
Johnson, P., et al.; "Clinical and biological effects of an agonist anti-CD40 antibody: a Cancer Research UK phase I study," Clin Cancer Res.; 21(6):1321-1328 (2015).
Johnston, R.J., et al.; "The immunoreceptor TIGIT regulates antitumor and antiviral CD8(+) T cell effector function," Cancer Cell, 26(6):923-937 (2014).
Jun, H.T., et al.; "Abstract 1824: Discovery and evaluation of an anti-IL18BP antibody to enhance anti-tumor immunity," Cancer Res. (2023) 83(7_Supplement): pp. 1824-1824.
Kelly et al., "How to study proteins by circular dichroism," Biochim Biophys Acta; 1751(2):119-139 (2005).
Kettleborough et al., "Humanization of a mouse monoclonal antibody by CDR-grafting: the importance of framework residues on loop conformation." Protein Engineering (1991); 4.7:773-783.
Kim, S.H., et al.; "Structural requirements of six naturally occurring isoforms of the IL-18 binding protein to inhibit IL-18," PNAS USA; 97(3):1190-1195 (2000).
Kimura, T., et al.; "Expression, purification and structural analysis of human IL-18 binding protein: a potent therapeutic molecule for allergy," Allergol Int.; 57(4):367-376 (2008).
Kinoshita, M., et al.; "Paradoxical effect of IL-18 therapy on the severe and mild *Escherichia coli* infections in burn-injured mice," Ann Surg.; 240(2):313-320 (2004).
Kohler et al., Derivation of specific antibody-producing tissue culture and tumor lines by cell fusion. Eur. J. Immunol.; 6(7):511-519 (1976).
Kormann, et al., Expression of therapeutic proteins after delivery of chemically modified mRNA in mice. Nat Biotechnol.; 29(2):154-157 (2011).
Kramer et al., "Transgene control engineering in mammalian cells," Methods Mol. Biol., 308:123-143 (2005).
Kurtulus, S., et al.; "TIGIT predominantly regulates the immune response via regulatory T cells," J Clin Invest.; Nov. 2015, 125(11):4053-4062, [with retraction], 13 pages.
Kwon, K., et al.; "High quality protein microarray using in situ protein purification," BMC Biotechnol., Aug. 2009, 9:72; 10 pages.
Li, et al., Optimization of humanized IgGs in glycoengineered Pichia pastoris, Nature Biotechnology, Feb. 2006, 24(2); pp. 210-215.
Li, X., et al.; "Emerging immune checkpoints for cancer therapy," Acta Oncol., Nov. 2015; 54(10):1706-1713.
Lin, et al., Automated 96-well purification of hexahistidine-tagged recombinant proteins on MagneHis Ni(2)+-particles, Methods Mol Biol., 2009, 498; pp. 129-141.
Lines, J.L., et al.; "VISTA is an immune checkpoint molecule for human T cells," Cancer Res.; 74(7):1924-1932 (Apr. 2014).
Lobuglio et al., "Mouse/human chimeric monoclonal antibody in man: kinetics and immune response." Proceedings of the National Academy of Sciences (1989); 86.11:4220-4224.
Logan, et al., Adenovirus tripartite leader sequence enhances translation of mRNAs late after infection, Proc. Natl. Acad. Sci. U.S.A., 1984, 81(12); pp. 3655-3659.
Lonberg and Huszar, "Human Antibodies from Transgenic Mice," International Reviews of Immunology, Jan. 1995, 13(1), pp. 65-93.
Lonberg, N., "Transgenic approaches to human monoclonal antibodies," The Pharmacology of Monoclonal Antibodies, Handbook of Experimental Pharmacology, 1994, vol. 113, pp. 49-101.
Lowy I., et al., "Isolation of Transforming DNA: Cloning the Hamster Aprt Gene," Cell, Dec. 1980, vol. 22 (3), pp. 817-823.
Maddox, et al., Elevated serum levels in human pregnancy of a molecule immunochemically similar to eosinophil granule major basic protein, J Exp Med., Oct. 1983, 158(4); pp. 1211-1226.
Maeda et al. "Construction of reshaped human antibodies with HIV-neutralizing activity." Human Antibodies (1991); 2(3):124-134.
Martin, F. et al., "The affinity-selection of a minibody polypeptide inhibitor of human interleukin-6," EMBO Journal, Nov. 15, 1994, 13(22):5303-5309.
Mather, et al., Culture of testicular cells in hormone-supplemented serum-free medium, Annals of the New York Academy of Sciences, Jun. 1982, 383; pp. 44-68.
Mather, J.P. (1980). "Establishment and Characterization of Two Distinct Mouse Testicular Epithelial Cell Lines," Biol. Reprod., vol. 23, pp. 243-251.
Maxwell, et al., A simple in vivo assay for increased protein solubility, Protein Sci., Sep. 1999, 8(9); pp. 1908-1911.

(56) References Cited

OTHER PUBLICATIONS

Meagher, et al., Deconvolution of the fluorescence emission spectrum of human antithrombin and identification of the tryptophan residues that are responsive to heparin binding, J Biol Chem., 273(36):23283-23289 (1998).
Mullen, T.E., et al.; "Accelerated antibody discovery targeting the SARS-CoV-2 spike protein for COVID-19 therapeutic potential," Antibody Therapeutics.; 4(3):185-196 (2021).
Muyldermans, S. et al., "Sequence and structure of VH domain from naturally occurring camel heavy chain immunoglobulins lacking light chains," Protein Eng. 7(9):1129-1135 (1994).
Nagamine, et al., Electrochemical screening of recombinant protein solubility in *Escherichia coli* using scanning electrochemical microscopy (SECM), Biotechnol Bioeng., Apr. 2007, 96(5); pp. 1008-1013.
Neuberger, M., "Generating high-avidity human Mabs in mice, " Nature Biotechnology, Jul. 1996, 14(7), pp. 826 (1page).
No, et al., Ecdysone-inducible gene expression in mammalian cells and transgenic mice, Proceedings of the National Academy of Sciences, Apr. 1996, 93(8); pp. 3346-3351.
Pardoll, D.M.; "The blockade of immune checkpoints in cancer immunotherapy," Nature Reviews Cancer; 12(4):252-264 (2012).
Park, S.Y., et al.; "Interleukin-18 Binding Protein in Immune Regulation and Autoimmune Diseases," Biomedicines; 10(7):1750:1-17 (2022).
Peterson, et al., Enzymatic cleavage of peptide-linked radiolabels from immunoconjugates, Bioconjug Chem.; 10(4):553-537 (1999).
Philips, G.K., et al.; "Therapeutic uses of anti-PD-1 and anti-PD-L1 antibodies," International Immunology; 27(1):39-46 (2015).
Pilotte, L., et al.; "Reversal of tumoral immune resistance by inhibition of tryptophan 2,3-dioxygenase," PNAS USA; 109(7):2497-2502 (2012).
Pimenova, T., et al.; "Epitope mapping on bovine prion protein using chemical cross-linking and mass spectrometry," J. Mass Spectrometry; 43(2):185-195 (2008).
Platten, M. et al.; "Cancer Immunotherapy by Targeting IDO1/TDO and Their Downstream Effectors," Front Immunol.; 5:673; pp. 1-7 (2015).
Presta, L. G. et al., "Engineering therapeutic antibodies for improved function," Biochemical Society Transactions (2002) 30(4):487-490.
Qing, et al., Cold-shock induced high-yield protein production in *Escherichia coli*, Nat Biotechnol., Jul. 2004, 22(7):877-882.
Queen C. et al. (Dec. 1989), "A Humanized Antibody That Binds to the Interleukin 2 Receptor," Proceedings of the National Academy of Sciences, vol. 86, No. 24, pp. 10029-10033.
RCSB Protein Data Bank: "RCSB PDB-3F62: Crystal Structure of Human IL-18 in complex with Ectromelia virus IL-18 Binding Protein," Jan. 1, 2009 (Jan. 1, 2009), [retrieved on Jun. 12, 2024] from URL: https://www.rcsb.org/structure/3f62, 4 pages.
Reiter, Y., et al., "Engineering antibody Fv fragments for cancer detection and therapy: Disulfide-stabilized Fv fragments," Nature Biotechnology (Oct. 1996); 14(10):1239-1245.
Rhodes, et al., Transformation of maize by electroporation of embryos, Methods Mol Biol, 1995, 55; pp. 121-131.
Ridgway, J. B. B., et al., "'Knobs-into-holes' engineering of antibody CH3 domains for heavy chain heterodimerization", Protein Engineering, Design and Selection (1996); 9(7):617-621.
Riechmann, L., et al., "Reshaping human antibodies for therapy", Nature (1988); 332(6162):323-327.
Robertson, M.J., et al.; "Clinical and biological effects of recombinant human interleukin-18 administered by intravenous infusion to patients with advanced cancer," Clinical Cancer Res.; 12(14 Pt 1):4265-4273 (2006).
Rosser, et al., Transient transfection of CHO-K1-S using serum-free medium in suspension: a rapid mammalian protein expression system, Protein Expr Purif., Apr. 2005, 40(2); pp. 237-243.
Sato et al. "Reshaping a human antibody to inhibit the interleukin 6-dependent tumor cell growth." Cancer Research (1993); 53.4:851-856.
Schaer, D.A., et al.; "GITR pathway activation abrogates tumor immune suppression through loss of regulatory T cell lineage stability," Cancer Immunol Res.; 1(5):320-331 (2013).
Scharf et al., "Heat stress promoters and transcription factors," Results Probl Cell Differ., 1994, 20:125-162.
Shao, Z., et al.; "CD137 ligand, a member of the tumor necrosis factor family, regulates immune responses via reverse signal transduction," J Leukoc Biol.; 89(1):21-29 (2011).
Sharma, P., et al.; "The future of immune checkpoint therapy," Science; 348(6230):56-61 (2015).
Sheridan, C.; "IDO inhibitors move center stage in immuno-oncology," Nature Biotechnology; 33(4):321-322 (2015).
Shields et al. "High resolution mapping of the binding site on human IgG1 for FcγRI, FcγRII, FcγRIII, and FcRn and design of IgG1 variants with improved binding to the FcγR" Journal of Biological Chemistry (2001); 276(9):6591-6604.
Shields, et al., "Lack of Fucose on Human IgG1 N-Linked Oligosaccharide Improves Binding to Human FcγRIII and Antibody-dependent Cellular Toxicity." The Journal of Biological Chemistry (2002); 277(30):26733-26740.
Shimp, et al., Production and characterization of clinical grade *Escherichia coli* derived Plasmodium falciparum 42 kDa merozoite surface protein 1 (MSP1(42)) in the absence of an affinity tag, Protein Expr Purif., Nov. 2006, 50(1); pp. 58-67.
Shinkawa T., et al., "The Absence of Fucose but Not the Presence of Galactose or Bisecting N-Acetylglucosamine of Human IgG1 Complex-type Oligosaccharades Shows the Critical Role of Enhancing Antibody-dependent Cellular Cytotoxicity," The Journal of Biological Chemistry, Jan. 31, 2003, vol. 278, No. 5, pp. 3466-3473.
Silverman J., et al., "Multivalent Avimer Proteins Evolved by Exon Shuffling of a Family of Human Receptor Domains," Nature Biotechnology, Nature Publishing Group, Dec. 2005, vol. 23, No. 12, pp. 1556-1561.
Sitaraman, et al., High-throughput protein expression using cell-free system, Methods Mol Biol. 2009, 498; pp. 229-244.
Skerra, A. "Alternative binding proteins: anticalins—harnessing the structural plasticity of the lipocalin ligand pocket to engineer novel binding activities", FEBS J. (2008); 275(11):2677-2683.
Stenvall, et al., High-throughput solubility assay for purified recombinant protein immunogens, Biochim Biophys Acta., 1752(1):6-10 (2005).
Structural Genomics Consortium et al., "Protein Production and Purification," Nature Methods, 2008, vol. 5 No. 2, pp. 135-146.
Stumpp et al., "DARPins: a true alternative to antibodies," Curr Opin Drug Discov Devel., 10(2):153-159 (2007).
Tahara-Hanaoka, S., et al.; "Functional characterization of DNAM-1 (CD226) interaction with its ligands PVR (CD155) and nectin-2 (PRR-2/CD112)," Int Immunol.; 16(4):533-538 (2004).
Takamatsu et al., "Expression of bacterial chloramphenicol acetyltransferase gene in tobacco plants mediated by TMV-RNA," EMBO J., (1987); 6(2):307-311.
Tempst P.R., et al., "Reshaping a Human Monoclonal Antibody to Inhibit Human Respiratory Syncytial Virus Infection In Vivo." Nature Biotechnology, Mar. 1991, vol. 9 (3), pp. 266-271.
Thomas, L.J., et al.; "Targeting human CD27 with an agonist antibody stimulates T-cell activation and antitumor immunity," Oncoimmunology; 3(1):e27255, pp. 1-4; doi:10.4161/onci.27255 (2014).
Topalian, S.L., et al.; "Immune checkpoint blockade: A common denominator approach to cancer therapy," Cancer Cell.; 27(4):450-461 (2015).
Traunecker, A. et al., "Janusin: New molecular design for bispecific reagents," Int J Cancer Suppl., Jan. 1992, vol. 7, pp. 51-52.
Traunecker et al., "Bispecific single chain molecules (Janusins) target cytotoxic lymphocytes on HIV infected cells," The EMBO Journal, Dec. 1991, 10(12), pp. 3655-3659.
Tuerk et al., "Systematic evolution of ligands by exponential enrichment: RNA ligands to bacteriophage T4 DNA polymerase," Science, 1990, 249(4968):505-510.
Umana P., et al., "Engineered Glycoforms of an Antineuroblastoma IgG1 With Optimized Antibody-dependent Cellular Cytotoxic Activity," Nature Biotechnology, Feb. 1999, vol. 17, No. 2, pp. 176-180.

(56) References Cited

OTHER PUBLICATIONS

UniProtKB O95998 (Gene ID: 10068) IL18BP "Interleukin-18-binding protein," Jul. 7, 2009 version 2; [retrieved online Sep. 12, 2024] URL: https://www.uniprot.org/uniprotkb/095998/entry, 10 pages.
Urlaub et al., "Isolation of Chinese hamster cell mutants deficient in dihydrofolate reductase activity," Proc. Natl. Acad. Sci. USA, 1980, 77(7), pp. 4216-4220.
Van Heeke et al, "Expression of Human Asparagine Synthetase in *Escherichia coli*," The Journal of Biological Chemistry, 264(10):5503-5509 (1989).
Vecchie, A., et al.; "IL-18 and infections: Is there a role for targeted therapies?" J Cell Physiol.; 236(3):1638-1657; Epub Aug. 13, 2020, 20 pages (2021).
Verhoeyen, M. et al., "Reshaping Human Antibodies: Grafting an Antilysozyme Activity," Science 239(4847):1534-1536 (1988).
Vonderheide, R.H., et al.; "Agonistic CD40 antibodies and cancer therapy," Clin Cancer Res.; 19(5):1035-1043 (2013).
Wang, T., et al.; "IL-18 and IL-18 Binding Protein Are Related to Disease Severity of Myelodysplastic Syndromes," Blood; 140(Suppl. 1):12297, 1 page (2022).
Ward et al., Binding activities of a repertoire of single immunoglobulin variable domains secreted from *Escherichia coli*, Nature (1989) 341(6242):544-546.
Wigler et al., "Transformation of mammalian cells with an amplifiable dominant-acting gene," Proceedings of the National Academy and Sciences, vol. 77, No. 6, Jun. 1980, pp. 3567-3570.
Wigler M., et al.; "Transfer of Purified Herpes Virus Thymidine Kinase Gene to Cultured Mouse Cells," Cell, 11(1):223-232 (1977).
Wigley, et al., "Protein solubility and folding monitored in vivo by structural complementation of a genetic marker protein," Nature Biotechnology, 19(2):131-136 (2001).
Wildt, et al., The humanization of N-glycosylation pathways in yeast, Nat Rev Microbiol, Feb. 2005, 53(2):119-128.
Winter, et al., The expression of heat shock protein and cognate genes during plant development, Results Probl Cell Differ. 1991, 17; pp. 85-105.
Witherden, D.A., et al.; "1076: Discovery and evaluation of an anti-IL18BP antibody to enhance anti-tumor immunity," Journal for Immuno Therapy of Cancer (2023); 11(Supp 1):A1-A1731, p. A1185, Abstract only; doi: 10.1136/jitc-2023-SITC2023.1076, 1 page.
Workman, C.J., et al.; "Lymphocyte activation gene-3 (CD223) regulates the size of the expanding T cell population following antigen activation in vivo," J Immunol.; 172(9):5450-5455 (2004).
Workman, C.J., et al.; "The CD4-related molecule, LAG-3 (CD223), regulates the expansion of activated T cells," Eur J Immunol.; 33(4):970-979 (2003).
Worn, A. et al. "Stability Engineering of Antibody Single-chain Fv Fragments," J. Mol.Biol., 2001, 305(5):989-1010.
Yazaki, et al., "Expression of recombinant antibodies in mammalian cell lines," Methods Mol Biol., 248:255-268 (2004).
Zhou, T., et al.; "IL-18BP is a secreted immune checkpoint and barrier to IL-18 immunotherapy," Nature. 583(7817):609-614, 29 pages (2020).
Zimmermann, K., "A triglycine linker improves tumor uptake and biodistributions of 67-Cu-labeled anti-neuroblastoma MAb chCE7 F(ab')2 fragments," Nucl Med Biol., 1999; 26(8):943-950.
Zuckerman et al., "The characterization and functional significance of plasma membrane Fc Receptors," CRC Crit Rev Microbiol., 7(1):1-26 (1978).

| Original mAb (murine) | SA04a | SA44a |
|---|---|---|
| | ↓ | ↓ |
| Humanized mAb | SA50a | SA301a |
| Cross-reactivity: | human, cyno, not mouse | human, cyno, not mouse |

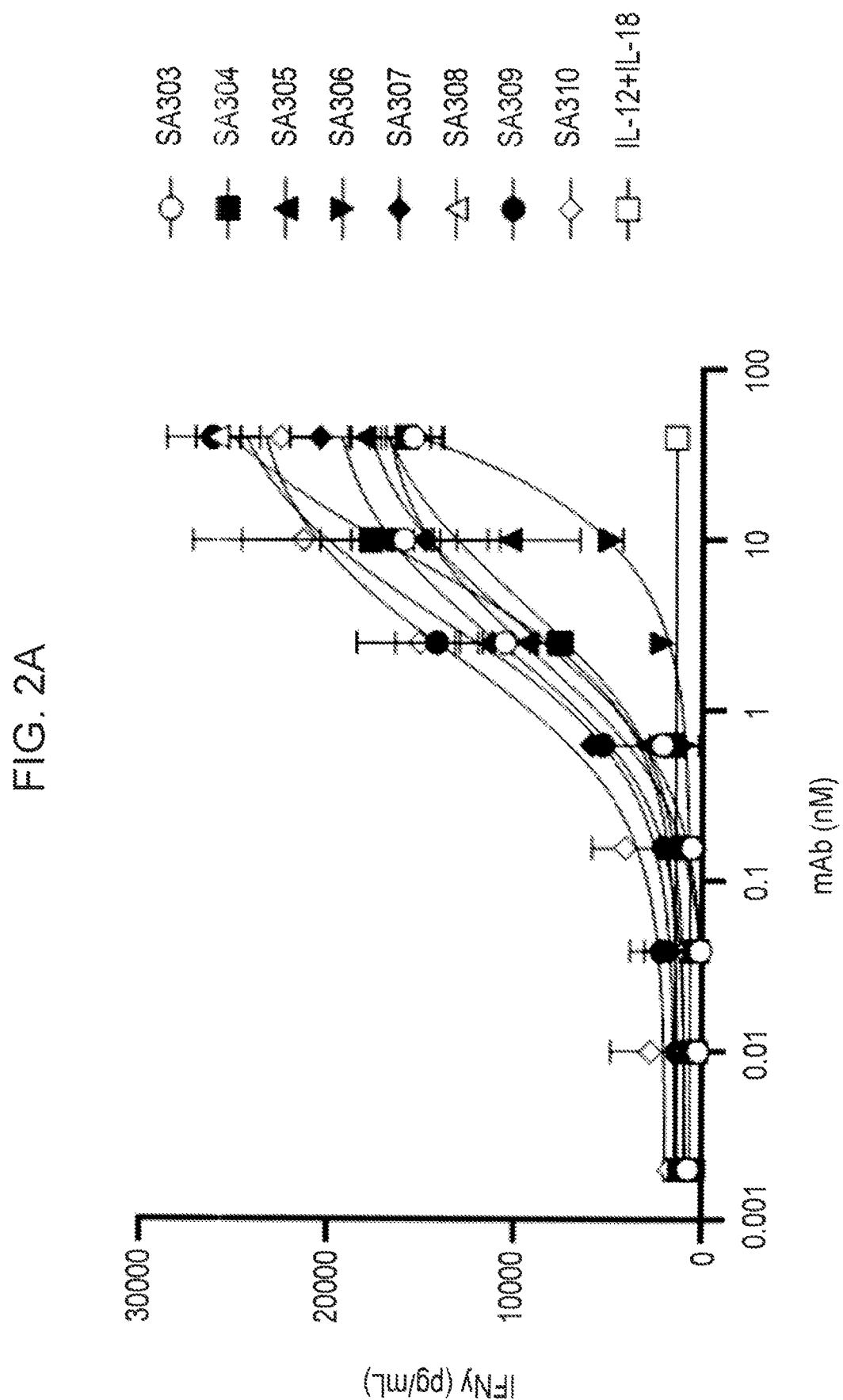

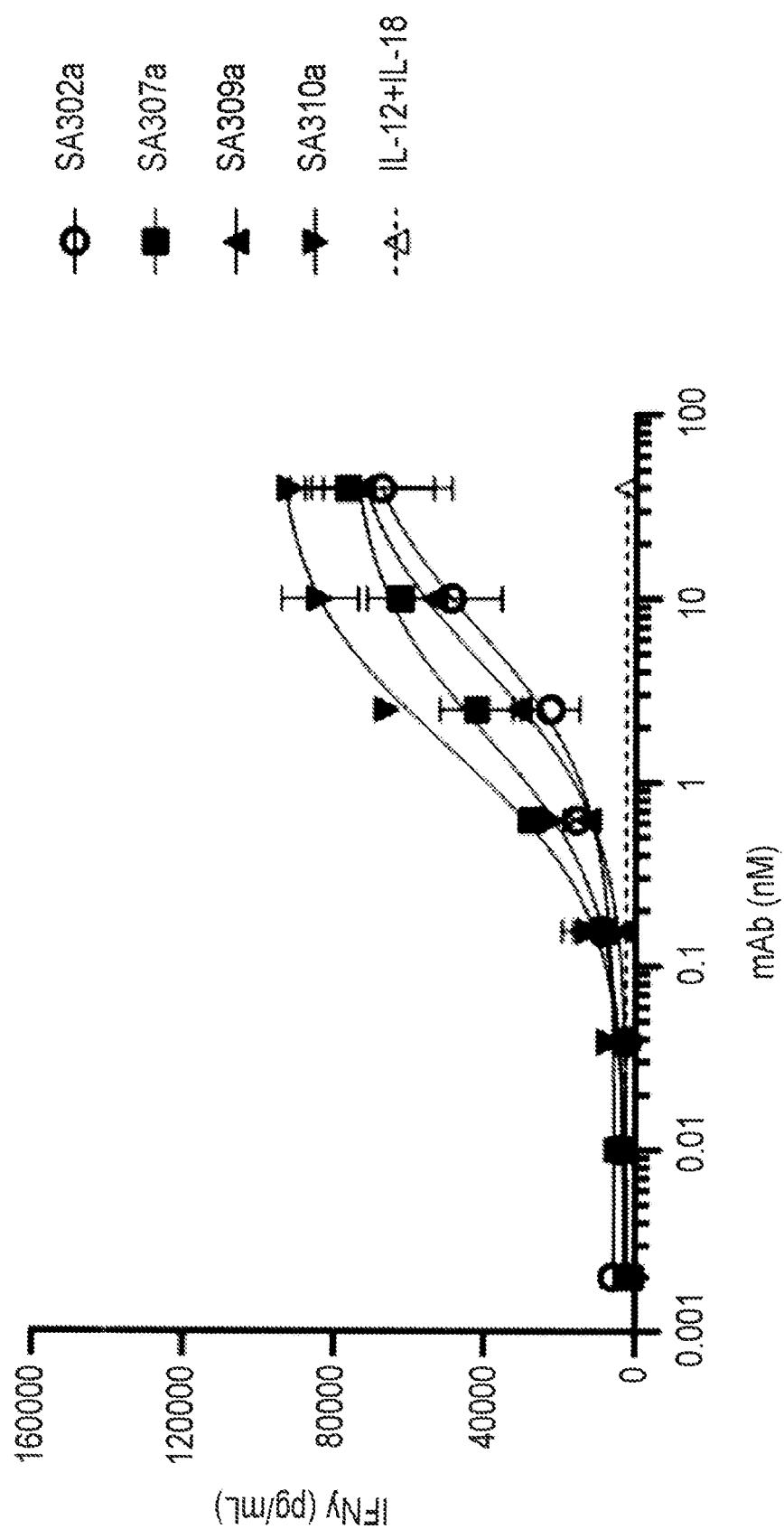

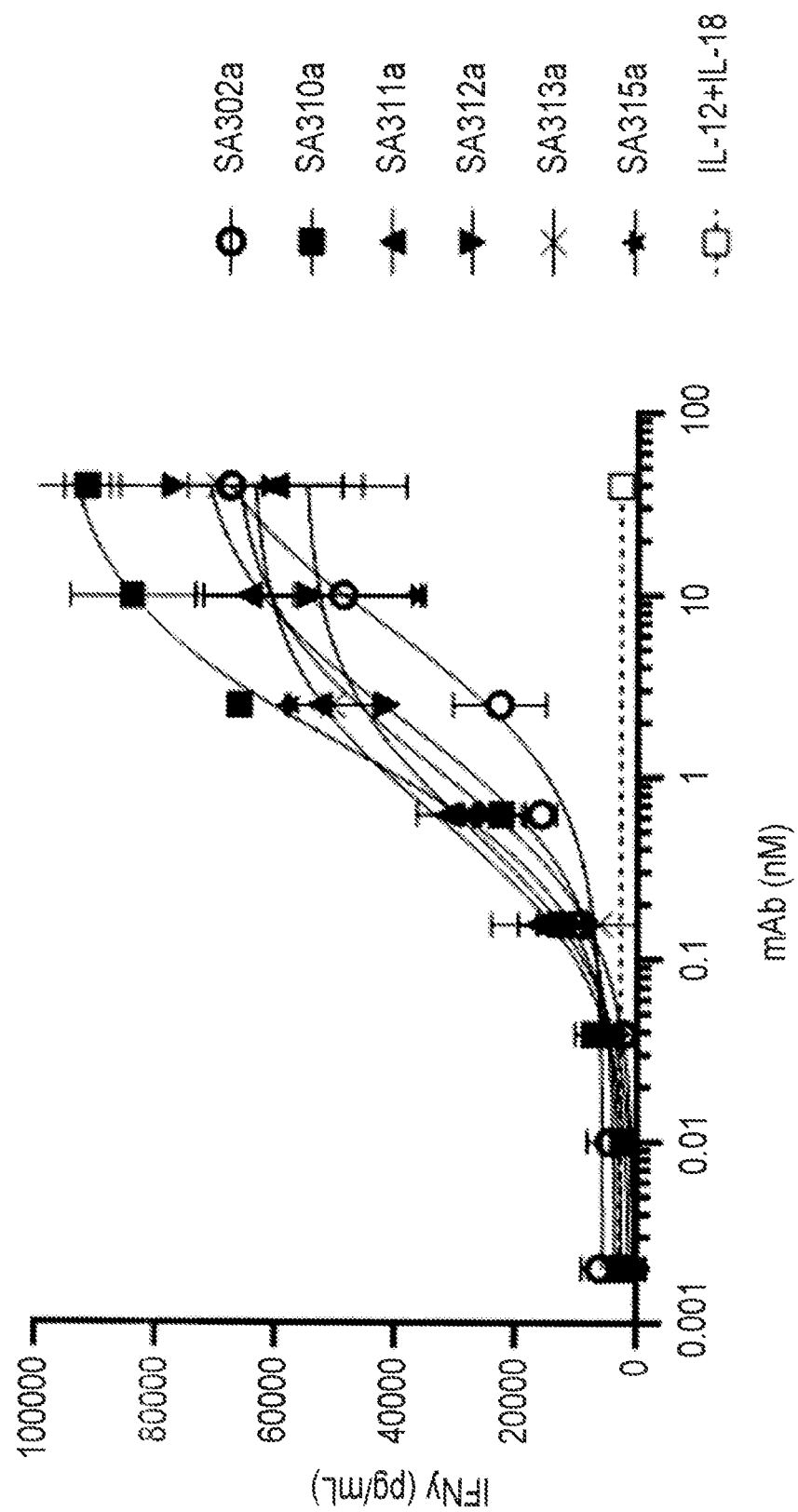

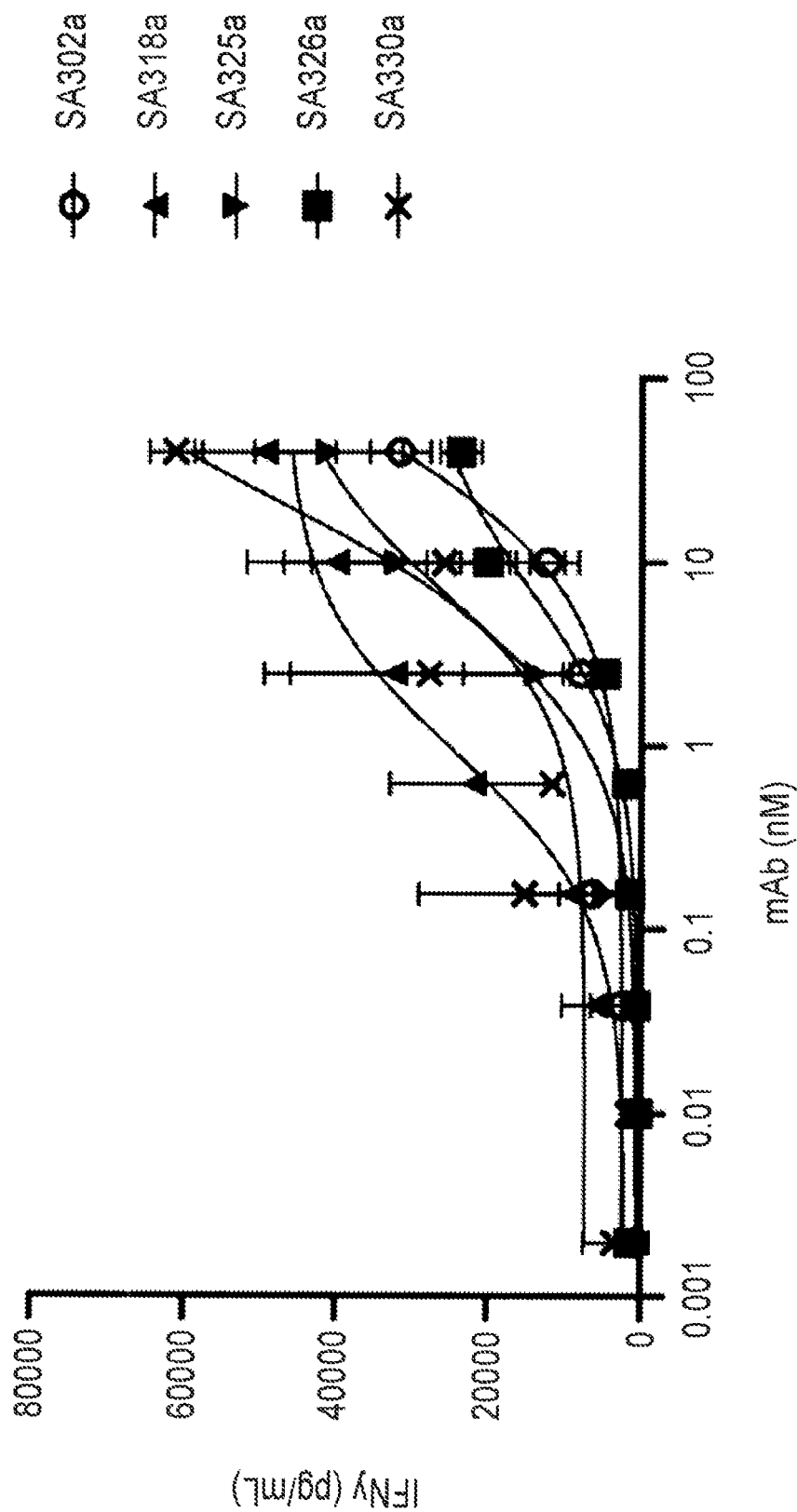

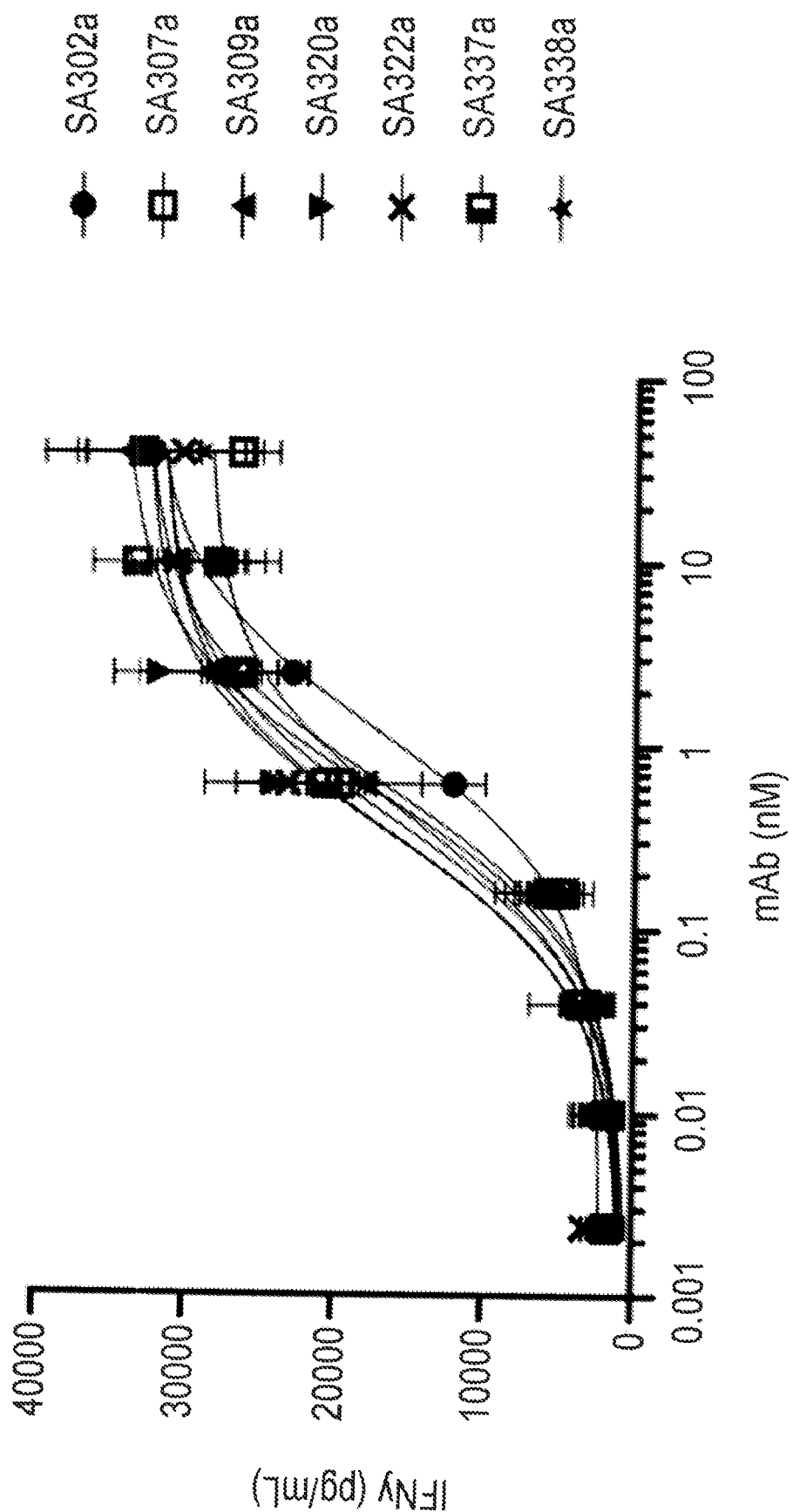

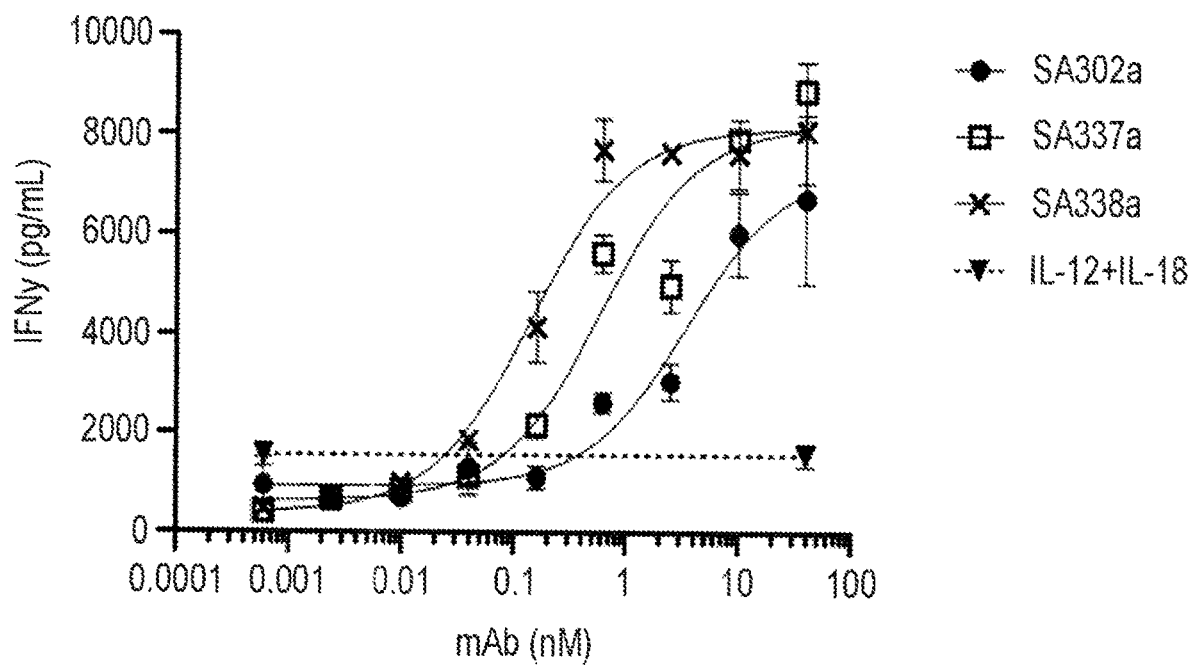

ANTI-IL-18BP ANTIBODIES

CROSS REFERENCE TO RELATED APPLICATIONS

This application is a continuation of International PCT Patent Application Serial No. PCT/US2024/010447, filed Jan. 5, 2024, which claims priority to U.S. Provisional Patent Application No. 63/437,526, filed on Jan. 6, 2023, and to U.S. Provisional Patent Application No. 63/590,348, filed on Oct. 13, 2023, and to U.S. Provisional Patent Application No. 63/596,580, filed on Nov. 6, 2023, the content of which are incorporated by reference herein in their entirety.

STATEMENT REGARDING SEQUENCE LISTING

This Sequence Listing XML associated with this application is provided in XML file format and is hereby incorporated by reference into the specification. The name of the XML file containing the Sequence Listing XML is LASS_008_01US_SeqList_ST26.xml. The XML file is about 327,630 bytes, was created on Aug. 23, 2024, and is being submitted electronically via USPTO Patent Center.

BACKGROUND

Interleukin-18 (IL-18) is an immune-stimulatory cytokine with antitumor activity. It plays pivotal roles in linking inflammatory immune responses and tumor progression. Although, recombinant human IL-18 has been evaluated as a cancer immunotherapeutic agent, this approach has not worked, at least in part because of a feedback loop in humans where administration of IL-18 leads to the induction of increased IL-18BP production, neutralizing the administered IL-18 cytokine (see, for example, Robertson et al., Clinical Cancer Res. 12:4265-4273, 2006).

IL-18BP is a high-affinity IL-18 decoy receptor that is frequently upregulated in tumors. Studies have implicated IL-18BP as a secreted immune checkpoint and a barrier to IL-18 immunotherapy (see, for example, Zhou et al., Nature. 583(7817):609-614, 2020). IL-18BP is believed to inhibit the pro-inflammatory activity of IL-18 by sequestering it away from the cell-surface receptor. The affinity of IL-18 for IL-18BP is higher than that of IL-18 for IL-18 receptor, and IL-18BP is frequently present in amounts in excess of IL-18, ensuring tight regulation. IL-18BP has also been shown to balance Th1 and Th2 immune responses, among others, and plays a critical role in autoimmune diseases (see, for example, Park et al., Biomedicines. 10(7): 1750, 2022). Thus, there is a need for agents and methods that specifically modulate the activity of IL-18BP, provided herein are such agents and methods.

SUMMARY

The present disclosure relates to antibodies that bind to interleukin-18 binding protein (IL-18BP) and related compositions, which may be used in any of a variety of therapeutic and diagnostic methods, including the treatment or diagnosis of cancers and other diseases.

Aspects of the present disclosure include an antibody which binds to interleukin-18 binding protein (IL-18BP), wherein the at least one antibody competes with IL-18 for the binding of IL-18BP. In another aspect, the present disclosure provides an antibody which binds to IL-18BP and interferes with the binding of IL-18 to IL-18BP. In another aspect, the present disclosure provides an antibody which binds to IL-18BP and is an IL-18BP antagonist, which antagonizes the binding activity between IL-18BP and IL-18. In some embodiments, the present disclosure provides an antibody which binds to the preformed IL-18-IL-18BP complex. In some embodiments, the present disclosure provides an antibody which binds to free IL-18BP. In some embodiments, the antibody binds to a conformational epitope of IL-18BP. In some embodiments, the antibody binds two or more of the amino acid residues T51, S53, S75, H79, R83, S88, S90, T110, H114, S115, T116, and S119 of SEQ ID NO: 372. In some embodiments, the antibody binds the amino acid residues T51, S53, S75, H79, R83, S88, S90, T110, H114, S115, T116, and S119 of SEQ ID NO: 372. In some embodiments, the antibody binds to a linear epitope of IL-18BP. In some embodiments, the antibody binds to the binding interface between IL-18 and a mature form of IL-18BP. In some embodiments, the antibody binds the amino acid residues S75, H79, T116, S119 of SEQ ID NO: 372.

In some embodiments, the antibody binds to human IL-18BP and cynomolgus IL-18BP but does not bind to mouse IL-18BP. In some embodiments, the antibody binds to human IL-18BP, cynomolgus IL-18BP, and mouse IL-18BP.

In some embodiments, the present disclosure also include an antibody which binds to interleukin-18 binding protein (IL-18BP), wherein the at least one antibody comprises: a heavy chain variable region ($V_H$) that comprises complementary determining region $V_H$CDR1, $V_H$CDR2, and $V_H$CDR3 sequences selected from Table A1 and variants thereof which specifically bind to IL-18BP; and a light chain variable region ($V_L$) that comprises complementary determining region $V_L$CDR1, $V_L$CDR2, and $V_L$CDR3 sequences selected from Table A1, and variants thereof which specifically bind to IL-18BP.

In some embodiments, the $V_H$ comprises a sequence at least 70, 75, 80, 85, 90, 95, 97, 98, 99, or 100% identical to a sequence selected from Table A2, optionally wherein the $V_H$ has at least 1, 2, 3, 4, 5, 6, 7, 8, 9, or 10 alterations in the framework regions. In some embodiments, the $V_L$ comprises a sequence at least 70, 75, 80, 85, 90, 95, 97, 98, 99, or 100% identical to a sequence selected from Table A2, optionally wherein the $V_L$ has at least 1, 2, 3, 4, 5, 6, 7, 8, 9, or 10 alterations in the framework regions.

Also included are isolated polynucleotides encoding an anti-IL-18BP antibody described herein, an expression vector comprising the isolated polynucleotide, and an isolated host cell comprising the vector. Also provided are one or more isolated polynucleotide encoding an anti-IL-18BP antibody described herein. For instance, provided herein is a first polynucleotide encoding a $V_H$ region of an antibody disclosed herein and a second polynucleotide encoding a $V_L$ region of an antibody disclosed herein.

Certain embodiments include a pharmaceutical composition, comprising an anti-IL-18BP antibody described herein, and a pharmaceutically acceptable carrier. In some embodiments, the composition is a sterile, injectable solution, optionally suitable for intravenous, intramuscular, subcutaneous, or intraperitoneal administration.

Also included are methods of treating a disease or condition in a subject in need thereof, comprising administering to the subject a pharmaceutical composition described herein. In some embodiments, the disease or condition is a cancer or tumor or proliferative disease or disorder, optionally a proliferative disease or disorder selected from a lymphoproliferative disorder, a myeloproliferative disorder, proliferative enteritis, proliferative diabetic retinopathy, and a proliferative kidney disease. In some embodiments, the cancer or tumor expresses or overexpresses IL-18BP and/or IL-18, or the proliferative disease or disorder is associated with increased expression of IL-18BP and/or IL-18. In some embodiments, the cancer is selected from one or more of bone cancer, prostate cancer, melanoma (e.g., metastatic melanoma), pancreatic cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia, hairy cell leukemias, acute lymphoblastic leukemias), lymphoma (e.g., non-Hodgkin's lymphomas, Hodgkin's lymphoma), hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, urothelial cancer, esophageal cancer, brain cancer, head and neck cancers, cervical cancer, testicular cancer, thyroid cancer, and stomach cancer.

Also included are methods of screening an anti-IL-18BP antibody for the ability to block or inhibit binding between IL-18 and IL-18BP, comprising (a) determining binding affinity of the antibody for (i) IL-18BP alone, and (ii) a hypo-IL-18 fusion protein, wherein the hypo-IL-18 fusion protein comprises IL-18 fused to IL-18BP via a flexible linker (and an optional protease cleavage site in between), wherein the IL-18 portion of the fusion protein is bound to the IL-18BP portion of the fusion protein and sterically blocks the IL-18 binding site of the IL-18BP portion of the fusion protein; (b) comparing the binding affinity of (i) to the binding affinity of (ii); and (c) identifying or selecting the antibody as being able to block or inhibit binding between IL-18 and IL-18BP if the binding affinity of (i) is significantly stronger than the binding affinity (ii).

In some aspects the invention includes an isolated hypo-IL-18 fusion protein, comprising, in an N- to C-terminal orientation, a signal peptide, IL-18, a first flexible linker, a protease cleavage site (optionally a TEV protease cleavage site), a flexible linker, and IL-18BP. In some embodiments, the hypo-IL-18 fusion protein comprises, consists, or consists essentially of an amino acid sequence at least 70, 75, 80, 85, 90, 95, 97, 98, 99, or 100% identical to a sequence from Table S1.

Also included are methods of stimulating an immune response in a subject in need thereof, comprising administering to the subject a pharmaceutical composition described herein. In some embodiments, the immune response is an IL-18 mediated immune response. In particular embodiments, the IL-18 mediated immune response comprises induction of IFN-gamma, CXCL10, and/or TNFα in the subject.

BRIEF DESCRIPTION OF THE FIGS

FIG. 1A-1C shows the genealogy of the antibodies of the present disclosure and the design of hypo-IL-18. FIG. 1A shows the genealogy of the antibodies of the present disclosure. FIG. 1B shows a schematic representation of an exemplary hypo-IL-18 expression cassette. Landmarks in the gene from N' to C' terminal include: an osteonectin signal peptide, human IL-18 coding region, a flexible gly-ser linker interrupted by a Tobacco Etch Virus (TEV) protease cleavage site, human IL-18BP coding sequence, and 6×HIS tag. FIG. 1C shows a view of the crystal structure-derived model of human IL-18 in complex with Ectromelia virus IL-18BP (as indicated). The IL-18BP N- and IL-18 C-termini are indicated with a box and arrow.

FIG. 2A-2G shows the effect of anti-IL-18BP antibodies on IL-18 mediated induction of IFNγ in healthy human peripheral blood mononuclear cells (PBMCs) in vitro. The anti-IL-18BP antibodies demonstrate a dose dependent increase in IFNγ.

FIG. 3A-3G depicts the ability of anti-IL-18BP antibodies to liberate IL-18 from a pre-existing complex with IL-18BP. Anti-IL-18BP antibodies were added to human PBMCs after IL-18 was allowed to form a precomplex with IL-18BP, which demonstrated a dose dependent increase in IFNγ.

Figure 5B:
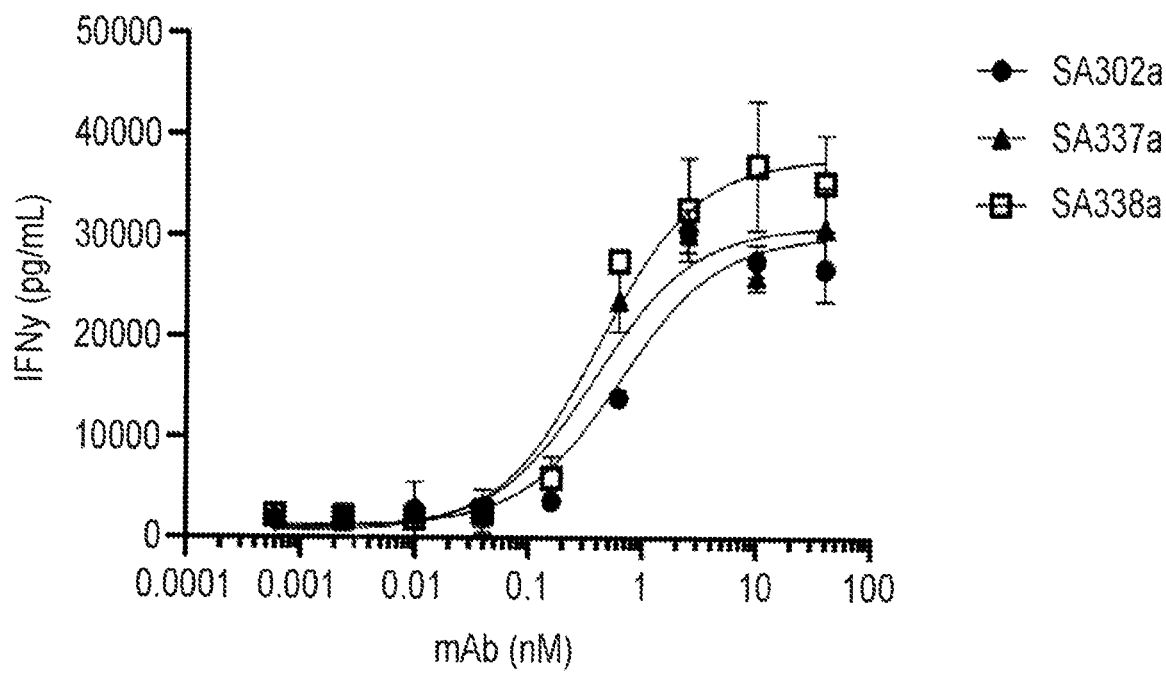

FIG. 5A-5B show the results of cynomolgus monkey PBMC assays. FIG. 5A shows the effect of anti-IL-18BP antibodies on IL-18 mediated induction of IFNγ in cynomolgus monkey PBMCs in vitro. FIG. 5B shows depicts the ability of anti-IL-18BP antibodies to liberate IL-18 from a pre-existing complex with IL-18BP via IFNγ release.

Figure 6:
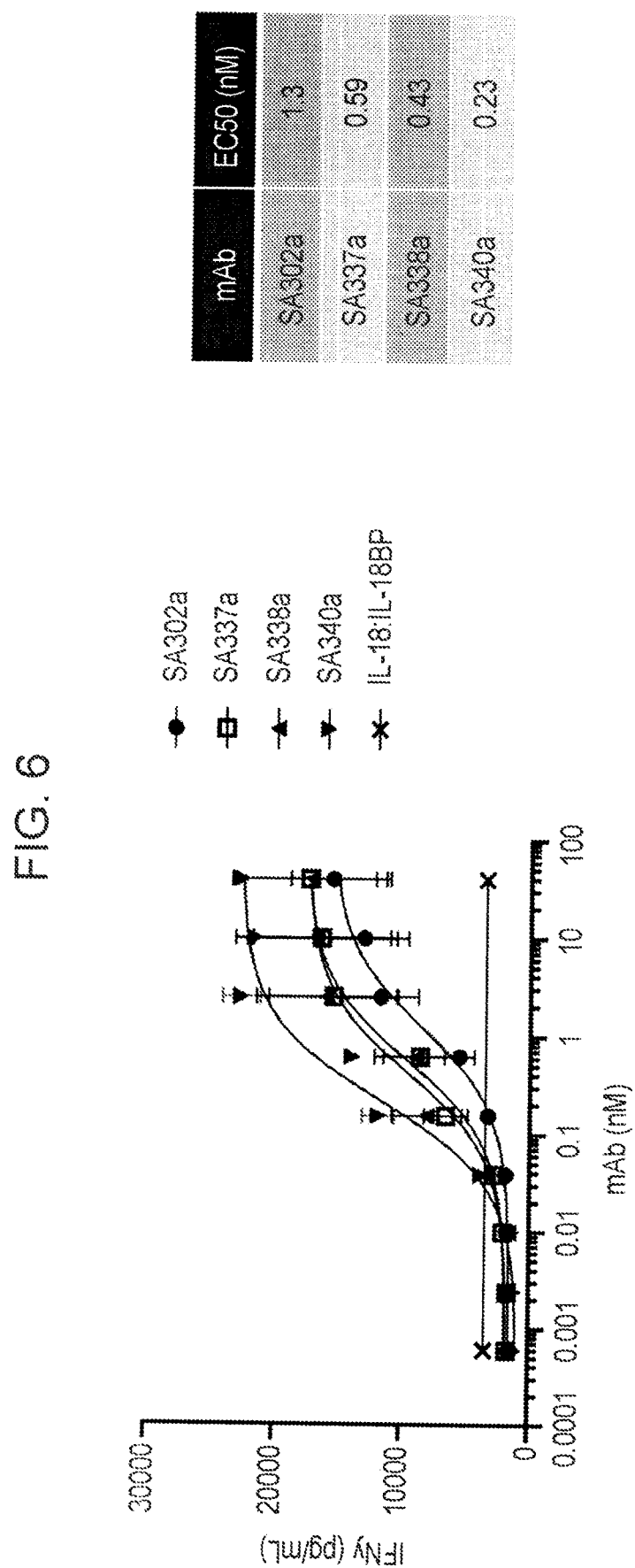

FIG. 6 depicts the ability of the IL-18BP antibodies to disrupt the IL-18:IL-18BP complex and induce secretion of IFNγ from NK cells.

DETAILED DESCRIPTION

The present disclosure relates to antibodies which specifically bind to interleukin-18 binding protein (IL-18BP). Some embodiments include specific humanized antibodies capable of binding to IL-18BP, blocking or reducing the inhibitory binding of IL-18BP to its ligand IL-18, and thereby increasing IL-18 mediated downstream signaling. Thus, in certain embodiments, an anti-IL-18BP antibody is an IL-18BP antagonist or inhibitor.

The IL-18BP antagonist antibodies described herein are useful in the treatment and prevention of various diseases and conditions, such as cancers and others. Some embodiments thus relate to the use of anti-IL-18BP antibodies for the diagnosis, assessment, and treatment of diseases and conditions, including those associated with IL-18 and/or IL-18BP activity or aberrant expression thereof.

The practice of the present disclosure employs, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology or Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Definitions

Unless defined otherwise, all terms of art, notations, and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used in this specification and the appended claims, the singular forms "a," "an" and "the" include plural references unless the content clearly dictates otherwise.

As used herein, the term "about" will be understood by persons of ordinary skill in the art and will vary to some extent on the context in which it is used. In some embodiments, the term "about" when referring to a measurable value such as an amount, a temporal duration, and the like, is meant to encompass art-accepted variations based on standard errors in making such measurements. In some embodiments, the term "about" when referring to such values, is meant to encompass variations of 10% from the specified value.

As used herein, the term "antibody" encompasses not only intact polyclonal or monoclonal antibodies, but also antigen binding fragments thereof (such as dAb, Fab, Fab', F(ab')2, Fv), single chain (scFv), synthetic variants thereof, naturally occurring variants, fusion proteins comprising an antibody portion with an antigen binding fragment of the required specificity, humanized antibodies, chimeric antibodies, and any other modified configuration of the immunoglobulin molecule that comprises an antigen binding site or fragment (epitope recognition site) of the required specificity. Certain features and characteristics of antibodies (and antigen binding fragments thereof) are described in greater detail herein.

The term "antigen binding fragment" as used herein refers to a polypeptide fragment that contains at least one CDR of an immunoglobulin heavy and/or light chain and binds to the antigen of interest. In this regard, an antigen binding fragment of the herein described antibodies may comprise 1, 2, 3, 4, 5, or all 6 CDRs of a $V_H$ and $V_L$ sequence from antibodies that bind to a target molecule. In a particular embodiment, an antigen binding fragment of the present disclosure comprises all 6 CDRs of the $V_H$ and $V_L$ sequences of an antibody disclosed herein.

The binding properties of antibodies and antigen binding fragments thereof can be quantified using methods well known in the art (see Davies et al., Annual Rev. Biochem. 59:439-473, 1990). In certain embodiments, antibodies as described herein include a heavy chain and a light chain complementarity determining region (CDR) set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen binding site.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. The term "monoclonal antibody" encompasses not only intact monoclonal antibodies and full-length monoclonal antibodies, but also fragments thereof (such as Fab, Fab', F(ab')2, Fv), single chain (scFv), variants thereof, fusion proteins comprising an antigen binding portion, humanized monoclonal antibodies, chimeric monoclonal antibodies, and any other modified configuration of the immunoglobulin molecule that comprises an antigen binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

In certain embodiments, the antibodies are made human-like by, e.g. by generating a chimeric antibody. A chimeric antibody is generally prepared using recombinant techniques, having an antigen binding site derived from an immunoglobulin from a non-human species and the remaining immunoglobulin structure of the molecule based upon the structure and/or sequence of a human immunoglobulin. The antigen binding site may comprise either complete variable domains fused onto constant domains or only the CDRs (entire or in part) grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991;

Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In some embodiments, only some of the CDR sequences are grafted from the nonhuman antibody (Bowers et al., *J. Biol. Chem.* 288:7688-7696, 2013). In certain embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies are "chimeric" antibodies. In this regard, a chimeric antibody is comprised of an antigen binding fragment of an antibody operably linked or otherwise fused to a heterologous Fc portion of a different antibody. In certain embodiments, the Fc domain or heterologous Fc domain is of human origin. In certain embodiments, the Fc domain or heterologous Fc domain is of mouse origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of $CH_2$ and $CH_3$ domains from one or more of the different Ig classes. As noted above with regard to humanized antibodies, the antigen binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, $V_H$ or both).

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

"Immune response" means any immunological response originating from immune system, including responses from the cellular and humeral, innate and adaptive immune systems. Exemplary cellular immune cells include for example, lymphocytes, macrophages, T cells, B cells, NK cells, neutrophils, eosinophils, dendritic cells, mast cells, monocytes, and all subsets thereof. Cellular responses include for example, effector function, cytokine release, phagocytosis, efferocytosis, translocation, trafficking, proliferation, differentiation, activation, repression, cell-cell interactions, apoptosis, etc. Humeral responses include for example IgG, IgM, IgA, IgE, responses and their corresponding effector functions.

"Expression control sequences" include regulatory sequences of nucleic acids, or the corresponding amino acids, such as promoters, leaders, enhancers, introns, recognition motifs for RNA, or DNA binding proteins, polyadenylation signals, terminators, internal ribosome entry sites (IRES), secretion signals, subcellular localization signals, and the like, which have the ability to affect the transcription or translation, or subcellular, or cellular location of a coding sequence in a host cell. Exemplary expression control sequences are described in Goeddel; Gene Expression Technology: Methods in Enzymology 185, Academic Press, San Diego, Calif. (1990).

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

Certain embodiments include biologically active "variants" and "fragments" of the polypeptides (e.g., antibodies) described herein, and the polynucleotides that encode the same. "Variants" contain one or more substitutions, additions, deletions, and/or insertions relative to a reference polypeptide or polynucleotide (see, e.g., the Tables and the Sequence Listing). A variant polypeptide or polynucleotide comprises an amino acid or nucleotide sequence with at least about 70%, 75%, 80%, 85%, 90%, 91%, 92%, 93%, 94%, 95%, 96%, 97%, 98%, 99% or more sequence identity or similarity or homology to a reference sequence, as described herein, and substantially retains the activity of that reference sequence. Also included are sequences that consist of or differ from a reference sequences by the addition, deletion, insertion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids or nucleotides and which substantially retain the activity of that reference sequence. In certain embodiments, the additions or deletions include C-terminal and/or N-terminal additions and/or deletions.

The terms "sequence identity" or, for example, comprising a "sequence at least 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The terms "individual," "subject," and "patient" are used interchangeably herein and refer to any subject for whom treatment or therapy is desired. The subject may be a mammalian subject. Mammalian subjects include, e.g., humans, non-human primates, rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate, for example a cynomolgus monkey. In some embodiments, the subject is a companion animal (e.g. cats, dogs).

As used herein, the terms "therapeutically effective amount", "therapeutic dose," "prophylactically effective amount," or "diagnostically effective amount" is the amount of an agent (e.g., anti-IL-18BP antibody, immunotherapy agent) needed to elicit the desired biological response following administration.

As used herein, "treatment" of a subject (e.g., a mammal, such as a human primate, or non-human primate) or a cell is any type of intervention used in an attempt to alter the natural course of the disease or disorder. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

Anti-IL-18BP Antibodies

Certain embodiments include antibodies which bind to IL-18BP. In some embodiments, an antibody modulates (e.g., interferes with, antagonizes, inhibits) binding of IL-18BP to its ligand, interleukin 18 (IL-18). In certain embodiments, an antibody is characterized by or comprises a heavy chain variable region ($V_H$) that comprises complementary determining region $V_H$CDR1, $V_H$CDR2, and $V_H$CDR3 sequences, and a light chain variable region ($V_L$) that comprises complementary determining region $V_L$CDR1, $V_L$CDR2, and $V_L$CDR3 sequences. Exemplary $V_H$, $V_H$CDR1, $V_H$CDR2, $V_H$CDR3, $V_L$, $V_L$CDR1, $V_L$CDR2, and $V_L$CDR3 sequences are provided in Table A1 and Table A2 below.

TABLE A1

Exemplary CDR Sequences

| Description | Sequence | SEQ ID NO: |
|---|---|---|
| SA04a | | |
| $V_H$CDR1 | TEYPMH | 1 |
| $V_H$CDR2 | WIHTYSGEPTYADDFKG | 2 |
| $V_H$CDR3 | GRYYGALDY | 3 |
| $V_L$CDR1 | RASQDISNYLN | 4 |
| $V_L$CDR2 | YTSRLHS | 5 |
| $V_L$CDR3 | QHGNTLPRT | 6 |
| SA50a | | |
| $V_H$CDR1 | TEYPMH | 7 |
| $V_H$CDR2 | WIHTYSGEPTYADDFKG | 8 |
| $V_H$CDR3 | GRYYGALDY | 9 |
| $V_L$CDR1 | RASQDISNYLN | 10 |
| $V_L$CDR2 | YTSRLHS | 11 |
| $V_L$CDR3 | QHGNTLPRT | 12 |
| SA07a | | |
| $V_H$CDR1 | TDYYMN | 13 |
| $V_H$CDR2 | DINPNNGGTSYNQKFKG | 14 |
| $V_H$CDR3 | EGVYSNYGGYFDY | 15 |
| $V_L$CDR1 | SASSSVSYMYW | 16 |
| $V_L$CDR2 | LTSNLAS | 17 |
| $V_L$CDR3 | QQWSSNPPT | 18 |
| SA31a | | |
| $V_H$CDR1 | TSYWMH | 19 |
| $V_H$CDR2 | NIYPGSGNTIYDEKFKS | 20 |
| $V_H$CDR3 | WDNWEGYYFDY | 21 |
| $V_L$CDR1 | RSSKSLLHSNGITYLY | 22 |
| $V_L$CDR2 | QMSNLAS | 23 |
| $V_L$CDR3 | AQNLELPWT | 24 |
| SA32a | | |
| $V_H$CDR1 | TGYYMH | 25 |
| $V_H$CDR2 | YISCYNGATSYNQKFKG | 26 |
| $V_H$CDR3 | TLHYAMDY | 27 |
| $V_L$CDR1 | RSSKSLLHSNGITYLY | 28 |
| $V_L$CDR2 | QMSNLAS | 29 |
| $V_L$CDR3 | AQNLELPWT | 30 |
| SA33a | | |
| $V_H$CDR1 | TDYAMH | 31 |
| $V_H$CDR2 | VISTYYGDASYNQKFKG | 32 |

TABLE A1-continued

Exemplary CDR Sequences

| Description | Sequence | SEQ ID NO: |
|---|---|---|
| $V_H$CDR3 | ERDYYGSRLFDY | 33 |
| $V_L$CDR1 | SANSSISSNYLH | 34 |
| $V_L$CDR2 | GTSNLAS | 35 |
| $V_L$CDR3 | QQGSSIPYT | 36 |
| SA34a | | |
| $V_H$CDR1 | TDYYIN | 37 |
| $V_H$CDR2 | EIYPGSGNTYYNEKFKG | 38 |
| $V_H$CDR3 | GYYGRFAY | 39 |
| $V_L$CDR1 | RSSKSLLHSNGITYLY | 40 |
| $V_L$CDR2 | QMSNLAS | 41 |
| $V_L$CDR3 | DQNLELPFT | 42 |
| SA35a | | |
| $V_H$CDR1 | TDYPMH | 43 |
| $V_H$CDR2 | VISTYYGDASYNQKFKG | 44 |
| $V_H$CDR3 | WRGSFDY | 45 |
| $V_L$CDR1 | RASSSVSSSYLH | 46 |
| $V_L$CDR2 | STSNLAS | 47 |
| $V_L$CDR3 | QQYSGYHT | 48 |
| SA44a | | |
| $V_H$CDR1 | TSDYNCH | 49 |
| $V_H$CDR2 | YIHYSGSTNYNPSLKS | 50 |
| $V_H$CDR3 | NYGSIYVNY | 51 |
| $V_L$CDR1 | SASSSVSYMY | 52 |
| $V_L$CDR2 | RTSNLAS | 53 |
| $V_L$CDR3 | QQYHSYPT | 54 |
| SA301a | | |
| $V_H$CDR1 | TSDYNSH | 55 |
| $V_H$CDR2 | YIHYSGSTNYNPSLKS | 56 |
| $V_H$CDR3 | NYGSIYVNY | 57 |
| $V_L$CDR1 | SASSSVSYMY | 58 |
| $V_L$CDR2 | RTSNLAS | 59 |
| $V_L$CDR3 | QQYHSYPT | 60 |
| SA302a | | |
| $V_H$CDR1 | TSDYNAH | 61 |
| $V_H$CDR2 | YIHYSGSTNYNPSLKS | 62 |
| $V_H$CDR3 | NYGSIYVNY | 63 |
| $V_L$CDR1 | SASSSVSYMY | 64 |
| $V_L$CDR2 | TSNLAS | 65 |
| $V_L$CDR3 | QQYHSYPT | 66 |
| SA303a | | |
| $V_H$CDR1 | TSDYNAH | 67 |
| $V_H$CDR2 | YIHYSGSTNYNPSLKS | 68 |
| $V_H$CDR3 | NFGSIYVNYFDY | 69 |
| $V_L$CDR1 | SASSSVSYMY | 70 |
| $V_L$CDR2 | TSNLAS | 71 |
| $V_L$CDR3 | QQYHSYPT | 72 |
| SA304a | | |
| $V_H$CDR1 | TSDYNAH | 73 |
| $V_H$CDR2 | YIHYSGSTNYNPSLKS | 74 |
| $V_H$CDR3 | NYASIYVNYFDY | 75 |
| $V_L$CDR1 | SASSSVSYMY | 76 |
| $V_L$CDR2 | TSNLAS | 77 |
| $V_L$CDR3 | QQYHSYPT | 78 |
| SA305a | | |
| $V_H$CDR1 | TSDYNAH | 79 |
| $V_H$CDR2 | YIHYSGSTNYNPSLKS | 80 |
| $V_H$CDR3 | NFASIYVNYFDY | 81 |
| $V_L$CDR1 | SASSSVSYMY | 82 |
| $V_L$CDR2 | TSNLAS | 83 |
| $V_L$CDR3 | QQYHSYPT | 84 |
| SA306a | | |
| $V_H$CDR1 | TSDYNNH | 85 |
| $V_H$CDR2 | YIHYSGSTNYNPSLKS | 86 |
| $V_H$CDR3 | NYGSIYVNYFDY | 87 |
| $V_L$CDR1 | SASSSVSYMY | 88 |
| $V_L$CDR2 | TSNLAS | 89 |
| $V_L$CDR3 | QQYHSYPT | 90 |
| SA307a | | |
| $V_H$CDR1 | TQDYNAH | 91 |
| $V_H$CDR2 | YIHYSGSTNYNPSLKS | 92 |
| $V_H$CDR3 | NYGSIYVNYFDY | 93 |
| $V_L$CDR1 | SASSSVSYMY | 94 |
| $V_L$CDR2 | TSNLAS | 95 |
| $V_L$CDR3 | QQYHSYPT | 96 |

TABLE A1-continued

Exemplary CDR Sequences

| Description | Sequence | SEQ ID NO: |
|---|---|---|
| SA308a | | |
| $V_H$CDR1 | TSDYNAH | 97 |
| $V_H$CDR2 | YIHYSGATNYNPSLKS | 98 |
| $V_H$CDR3 | NYGSIYVNYFDY | 99 |
| $V_L$CDR1 | SASSSVSYMY | 100 |
| $V_L$CDR2 | TSNLAS | 101 |
| $V_L$CDR3 | QQYHSYPT | 102 |
| SA309a | | |
| $V_H$CDR1 | TSDYNAH | 103 |
| $V_H$CDR2 | YIHYSGQTNYNPSLKS | 104 |
| $V_H$CDR3 | NYGSIYVNYFDY | 105 |
| $V_L$CDR1 | SASSSVSYMY | 106 |
| $V_L$CDR2 | TSNLAS | 107 |
| $V_L$CDR3 | QQYHSYPT | 108 |
| SA310a | | |
| $V_H$CDR1 | TSDYNAH | 109 |
| $V_H$CDR2 | YIHYSGSTMYNPSLKS | 110 |
| $V_H$CDR3 | NYGSIYVNYFDY | 111 |
| $V_L$CDR1 | SASSSVSYMY | 112 |
| $V_L$CDR2 | TSNLAS | 113 |
| $V_L$CDR3 | QQYHSYPT | 114 |
| SA311a | | |
| $V_H$CDR1 | TSDYNAH | 115 |
| $V_H$CDR2 | YIHYSGQTMYNPSLKS | 116 |
| $V_H$CDR3 | NYGSIYVNYFDY | 117 |
| $V_L$CDR1 | SASSSVSYMY | 118 |
| $V_L$CDR2 | TSNLAS | 119 |
| $V_L$CDR3 | QQYHSYPT | 120 |
| SA312a | | |
| $V_H$CDR1 | TQDYNAH | 121 |
| $V_H$CDR2 | YIHYSGSTMYNPSLKS | 122 |
| $V_H$CDR3 | NYGSIYVNYFDY | 123 |
| $V_L$CDR1 | SASSSVSYMY | 124 |
| $V_L$CDR2 | TSNLAS | 125 |
| $V_L$CDR3 | QQYHSYPT | 126 |
| SA313a | | |
| $V_H$CDR1 | TSDYNAH | 127 |
| $V_H$CDR2 | YIHYSGSTMYNPSLKS | 128 |
| $V_H$CDR3 | NFGSIYVNYFDY | 129 |
| $V_L$CDR1 | SASSSVSYMY | 130 |
| $V_L$CDR2 | TSNLAS | 131 |
| $V_L$CDR3 | QQYHSYPT | 132 |
| SA314a | | |
| $V_H$CDR1 | TSDYNAH | 133 |
| $V_H$CDR2 | YIHYSGQTMYNPSLKS | 134 |
| $V_H$CDR3 | NYGSIYVNYFDY | 135 |
| $V_L$CDR1 | SASSSVSYMY | 136 |
| $V_L$CDR2 | TSNLAS | 137 |
| $V_L$CDR3 | QQYHSYPT | 138 |
| SA315a | | |
| $V_H$CDR1 | TSDYNAH | 139 |
| $V_H$CDR2 | YIHYSGQTMYNPSLKS | 140 |
| $V_H$CDR3 | NFGSIYVNYFDY | 141 |
| $V_L$CDR1 | SASSSVSYMY | 142 |
| $V_L$CDR2 | TSNLAS | 143 |
| $V_L$CDR3 | QQYHSYPT | 144 |
| SA316a | | |
| $V_H$CDR1 | TSDYNAH | 145 |
| $V_H$CDR2 | YIHYSGSTYYNPSLKS | 146 |
| $V_H$CDR3 | NYGSIYVNYFDY | 147 |
| $V_L$CDR1 | SASSSVSYMY | 148 |
| $V_L$CDR2 | TSNLAS | 149 |
| $V_L$CDR3 | QQYHSYPT | 150 |
| SA317a | | |
| $V_H$CDR1 | TSDYNAH | 151 |
| $V_H$CDR2 | YIHYSGSTLYNPSLKS | 152 |
| $V_H$CDR3 | NYGSIYVNYFDY | 153 |
| $V_L$CDR1 | SASSSVSYMY | 154 |
| $V_L$CDR2 | TSNLAS | 155 |
| $V_L$CDR3 | QQYHSYPT | 156 |

TABLE A1-continued

Exemplary CDR Sequences

| Description | Sequence | SEQ ID NO: |
|---|---|---|
| SA318a | | |
| $V_H$CDR1 | TQDYNAH | 157 |
| $V_H$CDR2 | YIHYSGQTMYNPSLKS | 158 |
| $V_H$CDR3 | NFGSIYVNYFDY | 159 |
| $V_L$CDR1 | SASSSVSYMY | 160 |
| $V_L$CDR2 | TSNLAS | 161 |
| $V_L$CDR3 | QQYHSYPT | 162 |
| SA319a | | |
| $V_H$CDR1 | TQDYNAH | 163 |
| $V_H$CDR2 | YIHYSGQTNYNPSLKS | 164 |
| $V_H$CDR3 | NFGSIYVNYFDY | 165 |
| $V_L$CDR1 | SASSSVSYMY | 166 |
| $V_L$CDR2 | TSNLAS | 167 |
| $V_L$CDR3 | QQYHSYPT | 168 |
| SA320a | | |
| $V_H$CDR1 | TQDYNAH | 169 |
| $V_H$CDR2 | YIHYSGQTYYNPSLKS | 170 |
| $V_H$CDR3 | NFGSIYVNYFDY | 171 |
| $V_L$CDR1 | SASSSVSYMY | 172 |
| $V_L$CDR2 | TSNLAS | 173 |
| $V_L$CDR3 | QQYHSYPT | 174 |
| SA321a | | |
| $V_H$CDR1 | TQDYNAH | 175 |
| $V_H$CDR2 | YIHYSGQTLYNPSLKS | 176 |
| $V_H$CDR3 | NFGSIYVNYFDY | 177 |
| $V_L$CDR1 | SASSSVSYMY | 178 |
| $V_L$CDR2 | TSNLAS | 179 |
| $V_L$CDR3 | QQYHSYPT | 180 |
| SA322a | | |
| $V_H$CDR1 | TQDYNAH | 181 |
| $V_H$CDR2 | YIHYSGQTNYNPSLKS | 182 |
| $V_H$CDR3 | YGSIYVNYFDY | 183 |
| $V_L$CDR1 | SASSSVSYMY | 184 |
| $V_L$CDR2 | TSNLAS | 185 |
| $V_L$CDR3 | QQYHSYPT | 186 |

TABLE A1-continued

Exemplary CDR Sequences

| Description | Sequence | SEQ ID NO: |
|---|---|---|
| SA325a | | |
| $V_H$CDR1 | TSDYNAH | 187 |
| $V_H$CDR2 | YIHYSGSTNYNPSLKS | 188 |
| $V_H$CDR3 | NYGSIYVNYFDY | 189 |
| $V_L$CDR1 | SASSSVSYMY | 190 |
| $V_L$CDR2 | TSNLAS | 191 |
| $V_L$CDR3 | QEYHSYPT | 192 |
| SA326a | | |
| $V_H$CDR1 | TSDYNAH | 193 |
| $V_H$CDR2 | YIHYSGSTNYNPSLKS | 194 |
| $V_H$CDR3 | NYGSIYVNYFDY | 195 |
| $V_L$CDR1 | SASSSVSYMY | 196 |
| $V_L$CDR2 | TSNLAS | 197 |
| $V_L$CDR3 | QLYHSYPT | 198 |
| SA327a | | |
| $V_H$CDR1 | TSDYNAH | 199 |
| $V_H$CDR2 | YIHYSGSTNYNPSLKS | 200 |
| $V_H$CDR3 | NYGSIYVNYFDY | 201 |
| $V_L$CDR1 | SASSSVSYMY | 202 |
| $V_L$CDR2 | TSNLAS | 203 |
| $V_L$CDR3 | QQYHGYPT | 204 |
| SA328a | | |
| $V_H$CDR1 | TSDYNAH | 205 |
| $V_H$CDR2 | YIHYSGSTNYNPSLKS | 206 |
| $V_H$CDR3 | NYGSIYVNYFDY | 207 |
| $V_L$CDR1 | SASSSVSYMY | 208 |
| $V_L$CDR2 | TSNLAS | 209 |
| $V_L$CDR3 | QQYHSYVT | 210 |
| SA329a | | |
| $V_H$CDR1 | TSDYNAH | 211 |
| $V_H$CDR2 | YIHYSGSTNYNPSLKS | 212 |
| $V_H$CDR3 | NYGSIYVNYFDY | 213 |
| $V_L$CDR1 | SASSSVSYMY | 214 |
| $V_L$CDR2 | TSNLAS | 215 |
| $V_L$CDR3 | CQQYHSYPK | 216 |

TABLE A1-continued

Exemplary CDR Sequences

SA330a

| Description | Sequence | SEQ ID NO: |
|---|---|---|
| $V_H$CDR1 | TSDYNAH | 217 |
| $V_H$CDR2 | YIHYSGQTYYNPSLKS | 218 |
| $V_H$CDR3 | NFGSIYVNYFDY | 219 |
| $V_L$CDR1 | SASSSVSYMY | 220 |
| $V_L$CDR2 | TSNLAS | 221 |
| $V_L$CDR3 | QQYHSYPT | 222 |

SA331a

| Description | Sequence | SEQ ID NO: |
|---|---|---|
| $V_H$CDR1 | TQDYNAH | 223 |
| $V_H$CDR2 | YIHYSGQTYYNPSLKS | 224 |
| $V_H$CDR3 | NFGSIYVNYFDY | 225 |
| $V_L$CDR1 | SASSSVSYMY | 226 |
| $V_L$CDR2 | TSNLAS | 227 |
| $V_L$CDR3 | QQYHGYPT | 228 |

SA332a

| Description | Sequence | SEQ ID NO: |
|---|---|---|
| $V_H$CDR1 | TQDYNAH | 229 |
| $V_H$CDR2 | YIHYSGQTYYNPSLKS | 230 |
| $V_H$CDR3 | NFGSIYVNYFDY | 231 |
| $V_L$CDR1 | SASSSVSYMY | 232 |
| $V_L$CDR2 | TSNLAS | 233 |
| $V_L$CDR3 | QQYHSYVT | 234 |

SA333a

| Description | Sequence | SEQ ID NO: |
|---|---|---|
| $V_H$CDR1 | TQDYNAH | 235 |
| $V_H$CDR2 | YIHYSGQTYYNPSLKS | 236 |
| $V_H$CDR3 | NFGSIYVNYFDY | 237 |
| $V_L$CDR1 | SASSSVSYMY | 238 |
| $V_L$CDR2 | TSNLAS | 239 |
| $V_L$CDR3 | QQYHSYPK | 240 |

SA337a

| Description | Sequence | SEQ ID NO: |
|---|---|---|
| $V_H$CDR1 | TQDYNAH | 241 |
| $V_H$CDR2 | YIHYSGQTNYNPSLKS | 242 |
| $V_H$CDR3 | NYGSIYVNYFDY | 243 |
| $V_L$CDR1 | SASSSVSYMY | 244 |
| $V_L$CDR2 | TSNLAS | 245 |
| $V_L$CDR3 | QLYHSYPT | 246 |

SA338a

| Description | Sequence | SEQ ID NO: |
|---|---|---|
| $V_H$CDR1 | TQDYNAH | 247 |
| $V_H$CDR2 | YIHYSGQTYYNPSLKS | 248 |
| $V_H$CDR3 | NFGSIYVNYFDY | 249 |
| $V_L$CDR1 | SASSSVSYMY | 250 |
| $V_L$CDR2 | TSNLAS | 251 |
| $V_L$CDR3 | QLYHSYPT | 252 |

SA339a

| Description | Sequence | SEQ ID NO: |
|---|---|---|
| $V_H$CDR1 | TQDYNAH | 253 |
| $V_H$CDR2 | YIHYSGQTYYNPSLKS | 254 |
| $V_H$CDR3 | NFGSIYVNYFDY | 255 |
| $V_L$CDR1 | SASSSVSYMY | 256 |
| $V_L$CDR2 | TSNLAS | 257 |
| $V_L$CDR3 | QQYHGYPT | 258 |

SA340a

| Description | Sequence | SEQ ID NO: |
|---|---|---|
| $V_H$CDR1 | TQDYNAH | 259 |
| $V_H$CDR2 | YIHYSGQTYYNPSLKS | 260 |
| $V_H$CDR3 | NFGSIYVNYFDY | 261 |
| $V_L$CDR1 | SASSSVSYMY | 262 |
| $V_L$CDR2 | TSNLAS | 263 |
| $V_L$CDR3 | QQYHSYVTF | 264 |

Thus, in certain embodiments, an antibody comprises a $V_H$ sequence that comprises complementary determining region $V_H$CDR1, $V_H$CDR2, and $V_H$CDR3 sequences selected from Table A1 and variants thereof which bind to IL-18BP; and a $V_L$ sequence that comprises complementary determining region $V_L$CDR1, $V_L$CDR2, and $V_L$CDR3 sequences selected from Table A1 and variants thereof which bind to IL-18BP. In particular embodiments, an antibody comprises a $V_H$ sequence that comprises a $V_H$CDR1, a $V_H$CDR2, and a $V_H$CDR3 sequence and a $V_L$ sequence that comprises a $V_L$CDR1, a $V_L$CDR2, and a $V_L$CDR3 sequence, wherein all of the CDR sequences are from a single named antibody (e.g. SA04a) in Table A1.

In certain embodiments, the CDR sequences are as follows:
the $V_H$CDR1, $V_H$CDR2, and $V_H$CDR3 sequences comprise SEQ ID NOs: 1-3, respectively, and the $V_L$CDR1, $V_L$CDR2, and $V_L$CDR3 sequences comprise SEQ ID NOs: 4-6, respectively;
the $V_H$CDR1, $V_H$CDR2, and $V_H$CDR3 sequences comprise SEQ ID NOs: 7-9, respectively, and the $V_L$CDR1, $V_L$CDR2, and $V_L$CDR3 sequences comprise SEQ ID NOs: 10-12, respectively;
the $V_H$CDR1, $V_H$CDR2, and $V_H$CDR3 sequences comprise SEQ ID NOs: 13-15, respectively, and the $V_L$CDR1, $V_L$CDR2, and $V_L$CDR3 sequences comprise SEQ ID NOs: 16-18, respectively;

the $V_H$CDR1, $V_H$CDR2, and $V_H$CDR3 sequences comprise SEQ ID NOs: 19-21, respectively, and the $V_L$CDR1, $V_L$CDR2, and $V_L$CDR3 sequences comprise SEQ ID NOs: 22-24, respectively;

the $V_H$CDR1, $V_H$CDR2, and $V_H$CDR3 sequences comprise SEQ ID NOs: 25-27, respectively, and the $V_L$CDR1, $V_L$CDR2, and $V_L$CDR3 sequences comprise SEQ ID NOs: 28-30, respectively;

the $V_H$CDR1, $V_H$CDR2, and $V_H$CDR3 sequences comprise SEQ ID NOs: 31-33, respectively, and the $V_L$CDR1, $V_L$CDR2, and $V_L$CDR3 sequences comprise SEQ ID NOs: 34-36, respectively;

the $V_H$CDR1, $V_H$CDR2, and $V_H$CDR3 sequences comprise SEQ ID NOs: 37-39, respectively, and the $V_L$CDR1, $V_L$CDR2, and $V_L$CDR3 sequences comprise SEQ ID NOs: 40-42, respectively;

the $V_H$CDR1, $V_H$CDR2, and $V_H$CDR3 sequences comprise SEQ ID NOs: 43-45, respectively, and the $V_L$CDR1, $V_L$CDR2, and $V_L$CDR3 sequences comprise SEQ ID NOs: 46-48, respectively;

the $V_H$CDR1, $V_H$CDR2, and $V_H$CDR3 sequences comprise SEQ ID NOs: 49-51, respectively, and the $V_L$CDR1, $V_L$CDR2, and $V_L$CDR3 sequences comprise SEQ ID NOs: 52-54, respectively;

the $V_H$CDR1, $V_H$CDR2, and $V_H$CDR3 sequences comprise SEQ ID NOs: 55-57, respectively, and the $V_L$CDR1, $V_L$CDR2, and $V_L$CDR3 sequences comprise SEQ ID NOs: 58-60, respectively;

the $V_H$CDR1, $V_H$CDR2, and $V_H$CDR3 sequences comprise SEQ ID NOs: 61-63, respectively, and the $V_L$CDR1, $V_L$CDR2, and $V_L$CDR3 sequences comprise SEQ ID NOs: 64-66, respectively;

the $V_H$CDR1, $V_H$CDR2, and $V_H$CDR3 sequences comprise SEQ ID NOs: 67-69, respectively, and the $V_L$CDR1, $V_L$CDR2, and $V_L$CDR3 sequences comprise SEQ ID NOs: 70-72, respectively;

the $V_H$CDR1, $V_H$CDR2, and $V_H$CDR3 sequences comprise SEQ ID NOs: 73-75, respectively, and the $V_L$CDR1, $V_L$CDR2, and $V_L$CDR3 sequences comprise SEQ ID NOs: 76-78, respectively;

the $V_H$CDR1, $V_H$CDR2, and $V_H$CDR3 sequences comprise SEQ ID NOs: 79-81, respectively, and the $V_L$CDR1, $V_L$CDR2, and $V_L$CDR3 sequences comprise SEQ ID NOs: 82-84, respectively;

the $V_H$CDR1, $V_H$CDR2, and $V_H$CDR3 sequences comprise SEQ ID NOs: 85-87, respectively, and the $V_L$CDR1, $V_L$CDR2, and $V_L$CDR3 sequences comprise SEQ ID NOs: 88-90, respectively;

the $V_H$CDR1, $V_H$CDR2, and $V_H$CDR3 sequences comprise SEQ ID NOs: 91-93, respectively, and the $V_L$CDR1, $V_L$CDR2, and $V_L$CDR3 sequences comprise SEQ ID NOs: 94-96, respectively;

the $V_H$CDR1, $V_H$CDR2, and $V_H$CDR3 sequences comprise SEQ ID NOs: 97-99, respectively, and the $V_L$CDR1, $V_L$CDR2, and $V_L$CDR3 sequences comprise SEQ ID NOs: 100-102, respectively;

the $V_H$CDR1, $V_H$CDR2, and $V_H$CDR3 sequences comprise SEQ ID NOs: 103-105, respectively, and the $V_L$CDR1, $V_L$CDR2, and $V_L$CDR3 sequences comprise SEQ ID NOs: 106-108, respectively;

the $V_H$CDR1, $V_H$CDR2, and $V_H$CDR3 sequences comprise SEQ ID NOs: 109-111, respectively, and the $V_L$CDR1, $V_L$CDR2, and $V_L$CDR3 sequences comprise SEQ ID NOs: 112-114, respectively;

the $V_H$CDR1, $V_H$CDR2, and $V_H$CDR3 sequences comprise SEQ ID NOs: 115-117, respectively, and the $V_L$CDR1, $V_L$CDR2, and $V_L$CDR3 sequences comprise SEQ ID NOs: 118-120, respectively;

the $V_H$CDR1, $V_H$CDR2, and $V_H$CDR3 sequences comprise SEQ ID NOs: 121-123, respectively, and the $V_L$CDR1, $V_L$CDR2, and $V_L$CDR3 sequences comprise SEQ ID NOs: 124-126, respectively;

the $V_H$CDR1, $V_H$CDR2, and $V_H$CDR3 sequences comprise SEQ ID NOs: 127-129, respectively, and the $V_L$CDR1, $V_L$CDR2, and $V_L$CDR3 sequences comprise SEQ ID NOs: 130-132, respectively;

the $V_H$CDR1, $V_H$CDR2, and $V_H$CDR3 sequences comprise SEQ ID NOs: 133-135, respectively, and the $V_L$CDR1, $V_L$CDR2, and $V_L$CDR3 sequences comprise SEQ ID NOs: 136-138, respectively;

the $V_H$CDR1, $V_H$CDR2, and $V_H$CDR3 sequences comprise SEQ ID NOs: 139-141, respectively, and the $V_L$CDR1, $V_L$CDR2, and $V_L$CDR3 sequences comprise SEQ ID NOs: 142-144, respectively;

the $V_H$CDR1, $V_H$CDR2, and $V_H$CDR3 sequences comprise SEQ ID NOs: 145-147, respectively, and the $V_L$CDR1, $V_L$CDR2, and $V_L$CDR3 sequences comprise SEQ ID NOs: 148-150, respectively;

the $V_H$CDR1, $V_H$CDR2, and $V_H$CDR3 sequences comprise SEQ ID NOs: 151-153, respectively, and the $V_L$CDR1, $V_L$CDR2, and $V_L$CDR3 sequences comprise SEQ ID NOs: 154-156, respectively;

the $V_H$CDR1, $V_H$CDR2, and $V_H$CDR3 sequences comprise SEQ ID NOs: 157-159, respectively, and the $V_L$CDR1, $V_L$CDR2, and $V_L$CDR3 sequences comprise SEQ ID NOs: 160-162, respectively;

the $V_H$CDR1, $V_H$CDR2, and $V_H$CDR3 sequences comprise SEQ ID NOs: 163-165, respectively, and the $V_L$CDR1, $V_L$CDR2, and $V_L$CDR3 sequences comprise SEQ ID NOs: 166-168, respectively;

the $V_H$CDR1, $V_H$CDR2, and $V_H$CDR3 sequences comprise SEQ ID NOs: 169-171, respectively, and the $V_L$CDR1, $V_L$CDR2, and $V_L$CDR3 sequences comprise SEQ ID NOs: 172-174, respectively;

the $V_H$CDR1, $V_H$CDR2, and $V_H$CDR3 sequences comprise SEQ ID NOs: 175-177, respectively, and the $V_L$CDR1, $V_L$CDR2, and $V_L$CDR3 sequences comprise SEQ ID NOs: 178-180, respectively;

the $V_H$CDR1, $V_H$CDR2, and $V_H$CDR3 sequences comprise SEQ ID NOs: 181-183, respectively, and the $V_L$CDR1, $V_L$CDR2, and $V_L$CDR3 sequences comprise SEQ ID NOs: 184-186, respectively;

the $V_H$CDR1, $V_H$CDR2, and $V_H$CDR3 sequences comprise SEQ ID NOs: 187-189, respectively, and the $V_L$CDR1, $V_L$CDR2, and $V_L$CDR3 sequences comprise SEQ ID NOs: 190-192, respectively;

the $V_H$CDR1, $V_H$CDR2, and $V_H$CDR3 sequences comprise SEQ ID NOs: 193-195, respectively, and the $V_L$CDR1, $V_L$CDR2, and $V_L$CDR3 sequences comprise SEQ ID NOs: 196-198, respectively;

the $V_H$CDR1, $V_H$CDR2, and $V_H$CDR3 sequences comprise SEQ ID NOs: 199-201, respectively, and the $V_L$CDR1, $V_L$CDR2, and $V_L$CDR3 sequences comprise SEQ ID NOs: 202-204, respectively;

the $V_H$CDR1, $V_H$CDR2, and $V_H$CDR3 sequences comprise SEQ ID NOs: 205-207, respectively, and the $V_L$CDR1, $V_L$CDR2, and $V_L$CDR3 sequences comprise SEQ ID NOs: 208-210, respectively;

the $V_H$CDR1, $V_H$CDR2, and $V_H$CDR3 sequences comprise SEQ ID NOs: 211-213, respectively, and the $V_L$CDR1, $V_L$CDR2, and $V_L$CDR3 sequences comprise SEQ ID NOs: 214-216, respectively;

the $V_H$CDR1, $V_H$CDR2, and $V_H$CDR3 sequences comprise SEQ ID NOs: 217-219, respectively, and the $V_L$CDR1, $V_L$CDR2, and $V_L$CDR3 sequences comprise SEQ ID NOs: 220-222, respectively;

the $V_H$CDR1, $V_H$CDR2, and $V_H$CDR3 sequences comprise SEQ ID NOs: 223-225, respectively, and the $V_L$CDR1, $V_L$CDR2, and $V_L$CDR3 sequences comprise SEQ ID NOs: 226-228, respectively;

the $V_H$CDR1, $V_H$CDR2, and $V_H$CDR3 sequences comprise SEQ ID NOs: 229-231, respectively, and the $V_L$CDR1, $V_L$CDR2, and $V_L$CDR3 sequences comprise SEQ ID NOs: 232-234, respectively;

the $V_H$CDR1, $V_H$CDR2, and $V_H$CDR3 sequences comprise SEQ ID NOs: 235-237, respectively, and the $V_L$CDR1, $V_L$CDR2, and $V_L$CDR3 sequences comprise SEQ ID NOs: 238-240, respectively;

the $V_H$CDR1, $V_H$CDR2, and $V_H$CDR3 sequences comprise SEQ ID NOs: 241-243, respectively, and the $V_L$CDR1, $V_L$CDR2, and $V_L$CDR3 sequences comprise SEQ ID NOs: 244-246, respectively;

the $V_H$CDR1, $V_H$CDR2, and $V_H$CDR3 sequences comprise SEQ ID NOs: 247-249, respectively, and the $V_L$CDR1, $V_L$CDR2, and $V_L$CDR3 sequences comprise SEQ ID NOs: 250-252, respectively;

the $V_H$CDR1, $V_H$CDR2, and $V_H$CDR3 sequences comprise SEQ ID NOs: 253-255, respectively, and the $V_L$CDR1, $V_L$CDR2, and $V_L$CDR3 sequences comprise SEQ ID NOs: 256-258, respectively;

the $V_H$CDR1, $V_H$CDR2, and $V_H$CDR3 sequences comprise SEQ ID NOs: 259-261, respectively, and the $V_L$CDR1, $V_L$CDR2, and $V_L$CDR3 sequences comprise SEQ ID NOs: 262-264, respectively;

Also included are variants of the foregoing CDRs. Exemplary variants bind to IL-18BP and have 1, 2, or 3 total alterations in any one or more of the individual CDRs, for example, any one or more the $V_H$CDR1, $V_H$CDR2, $V_H$CDR3, $V_L$CDR1, $V_L$CDR2, and/or $V_L$CDR3 sequences described herein. Exemplary "alterations" include amino acid substitutions, additions, and deletions.

Exemplary $V_H$ and $V_L$ sequences, and $V_H$/$V_L$ sequence pairs are provided in Table A2 below. (the CDRs are underlined)

TABLE A2

Exemplary Polypeptide Sequences

| Description | Sequence | SEQ ID NO: |
|---|---|---|
| | SA04a | |
| Heavy chain variable region ($V_H$) | QIQFVQSGPEVKTPGETVKISCKASVYTFTEYPMHWL KQAPGEDFEWMGWIHTYSGEPTYADDFKGRFAFSLE TSASTAYLQINNLKTEDTATYFCARGRYYGALDYWG QGTALT | 265 |
| Light chain variable region ($V_L$) | DIQMTQTPSSLSASLGDRVTISCRASQDISNYLNWYQQ KPDGTVKLLIYYTSRLHSGVPSRFSGSGSGTDYSLTIS NLEQEDVATYFCQHGNTLPRTFGGGTKLEIK | 266 |
| | SA50a | |
| Heavy chain variable region ($V_H$) | QVQLVQSGSELKKPGASVKVSCKASVYTFTEYPMHW LRQAPGQGFEWMGWIHTYSGEPTYADDFKGRFVESL DTSVSTAYLQISSLKAEDTAVYFCARGRYYGALDYW GQGTALTVSS | 267 |
| Light chain variable region ($V_L$) | DIQMTQSPSSLSASVGDRVTITCRASQDISNYLNWYQ QKPGKAVKLLIYYTSRLHSGVPSRFSGSGSGTDYTFTI SSLQPEDIATYFCQHGNTLPRTFGGGTKLEIK | 268 |
| | SA07a | |
| Heavy chain variable region ($V_H$) | EVQLQQSGPELVKPGASVKISCKASGYTFTDYYMNW VKQSHGKSLEWIGDINPNNGGTSYNQKFKGKATLTV DKSSNTAYMELRSLTSEDSAVYYCAREGVYSNYGGY FDYWGQGTTLTVSS | 269 |
| Light chain variable region ($V_L$) | QIVLTQSPALMSASPGEKVTMTCSASSSVSYMYWYQ QKPRSSPKPWIYLTSNLASGVPARFSGSGSGTSYSLTIS SMEAEDAATYYCQQWSSNPPTFGSGTKLEIK | 270 |
| | SA31a | |
| Heavy chain variable region ($V_H$) | QVQLQQPGSELVRPGASVKLSCKASGYTFTSYWMHW VKQRPGQGLEWIGNIYPGSGNTIYDEKFKSKATLTVD TSSSTAYMQLSSLTSEDSAVYYCTRWDNWEGYYFDY WGQGTTLTVSS | 271 |
| Light chain variable region ($V_L$) | DIVMTQAAFSNPVTLGTSASISCRSSKSLLHSNGITYLY WYLQKPGQSPQLLIYQMSNLASGVPDRESSSGSGTDF TLRISR VEAEDVGVYYCAQNLELPWTFGGGTKLEIK | 272 |

TABLE A2-continued Exemplary Polypeptide Sequences

| Description | Sequence | SEQ ID NO: |
|---|---|---|
| SA32a | | |
| Heavy chain variable region ($V_H$) | EVQLQQSGPELVKTGASVKISCKASGYSFTGYYMHW VKQSHGKSLEWIGYISCYNGATSYNQKFKGKATFTV DTSSSTAYMQFNSLTSEDSAVYYCAITLHYAMDYWG QGTSVAS | 273 |
| Light chain variable region ($V_L$) | DIVMTQAAFSNPVTLGTSASISCRSSKSLLHSNGITYLY WYLQKPGQSPQLLIYQMSNLASGVPDRESSSGSGTDF TLRISRVEAEDVGVYYCAQNLELPWTFGGGTKLEIK | 274 |
| SA33a | | |
| Heavy chain variable region ($V_H$) | QVQLQQSGAELVRPGVSVKISCKGSGYTFTDYAMHW VKQSHAKSLEWIGVISTYYGDASYNQKFKGKATMTV DKSSSTAYMELARLTSEDSAIYYCARERDYYGSRLFD YWGQGTTLTVSS | 275 |
| Light chain variable region ($V_L$) | EIVLTQSPTTMAASPGEKITITCSANSSISSNYLHWYQQ KPGFSPKLLIYGTSNLASGVPARFSGSGSGTSYSLTIGT MEAEDVATYYCQQGSSIPYTFGGGTKLEIK | 276 |
| SA34a | | |
| Heavy chain variable region ($V_H$) | QVQLQQSGAELARPGASVKLSCKASGYTFTDYYINW VKQRTGQGLEWIGEIYPGSGNTYYNEKFKGKATLTA DKSSSTAYMQLSSLTSEDSAVYFCARGYYGRFAYWG QGTLVTVSA | 277 |
| Light chain variable region ($V_L$) | DIVMTQAAFSNPVTLGTSASISCRSSKSLLHSNGITYLY WYLQKPGQSPQLLIYQMSNLASGVPDRESSSGSGTDF TLRISRVEAEDVGVYYCDQNLELPFTFGSGTKLEIK | 278 |
| SA35a | | |
| Heavy chain variable region ($V_H$) | QVQLQQSGAELVRPGVSVKISCKGSGYTFTDYPMHW VKQSHAKSLEWIGVISTYYGDASYNQKFKGKATMTV DKSSSTAYMELARLTSEDSAIYYCARWRGSFDYWGQ GTTLTVSS | 279 |
| Light chain variable region ($V_L$) | ENVLTQSPAIMSASPGEKVTMTCRASSSVSSSYLHWY QQKSGASPKLWIYSTSNLASGVPARFSGSGSGTSYSLT ISSVEAEDAATYYCQQYSGYHTFGGGTKLEIK | 280 |
| SA44a | | |
| Heavy chain variable region ($V_H$) | DVQLQESGPDLVKPSQSLSLTCTVTGYSITSDYNCHWI RQFPGNKLEWMGYIHYSGSTNYNPSLKSRISITRDTSK NQFFLQLNSVTAEDTATYYCARNYGSIYVNYFDYWG QGTTLTVSS | 281 |
| Light chain variable region ($V_L$) | QIVLTQSPAIMSASPGEKVTISCSASSSVSYMYWYQQE PGSSPKPWIYRTSNLASGVPPRFSGSGSGTSYSLTISSM EAEDAATYFCQQYHSYPTFGGGTKLEIK | 282 |
| SA301a | | |
| Heavy chain variable region ($V_H$) | QVQLQESGPGLVKPSQTLSLTCTVSGYSITSDYNSHWI RQPPGKGLEWIGYIHYSGSTNYNPSLKSRVTISRDTSK NQFSLKLSSVTAADTAVYYCARNYGSIYVNYFDYWG QGTLVTVSS | 283 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 284 |
| SA302a | | |
| Heavy chain variable region ($V_H$) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYGSIYVNYFDYWG QGTLVTVSS | 285 |

TABLE A2-continued

Exemplary Polypeptide Sequences

| Description | Sequence | SEQ ID NO: |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 286 |

SA303a

| Heavy chain variable region (V_H) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNFGSIYVNYFDYWG QGTLVTVSS | 287 |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 288 |

SA304a

| Heavy chain variable region (V_H) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYASIYVNYFDYWG QGTLVTVSS | 289 |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 290 |

SA305a

| Heavy chain variable region (V_H) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNFASIYVNYFDYWG QGTLVTVSS | 291 |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 292 |

SA306a

| Heavy chain variable region (V_H) | QVQLQESGPGLVKPSQTLSLTCTVSGYSITSDYNNHWI RQPPGKGLEWIGYIHYSGSTNYNPSLKSRVTISRDTSK NQFSLKLSSVTAADTAVYYCARNYGSIYVNYFDYWG QGTLVTVSS | 293 |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 294 |

SA307a

| Heavy chain variable region (V_H) | QVQLQESGPGLVKPSQTLSLTCTVSGYSITQDYNAHW IRQPPGKGLEWIGYIHYSGSTNYNPSLKSRVTISRDTSK NQFSLKLSSVTAADTAVYYCARNYGSIYVNYFDYWG QGTLVTVSS | 295 |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 296 |

SA308a

| Heavy chain variable region (V_H) | QVQLQESGPGLVKPSQTLSLTCTVSGYSITSDYNAHWI RQPPGKGLEWIGYIHYSGATNYNPSLKSRVTISRDTSK NQFSLKLSSVTAADTAVYYCARNYGSIYVNYFDYWG QGTLVTVSS | 297 |
|---|---|---|
| Light chain variable region (V_L) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 298 |

TABLE A2-continued

Exemplary Polypeptide Sequences

| Description | Sequence | SEQ ID NO: |
|---|---|---|
| SA309a | | |
| Heavy chain variable region ($V_H$) | QVQLQESGPGLVKPSQTLSLTCTVSGYSITSDYNAHWI RQPPGKGLEWIGYIHYSGQTNYNPSLKSRVTISRDTSK NQFSLKLSSVTAADTAVYYCARNYGSIYVNYFDYWG QGTLVTVSS | 299 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 300 |
| SA310a | | |
| Heavy chain variable region ($V_H$) | QVQLQESGPGLVKPSQTLSLTCTVSGYSITSDYNAHWI RQPPGKGLEWIGYIHYSGSTMYNPSLKSRVTISRDTSK NQFSLKLSSVTAADTAVYYCARNYGSIYVNYFDYWG QGTLVTVSS | 301 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 302 |
| SA311a | | |
| Heavy chain variable region ($V_H$) | QVQLQESGPGLVKPSQTLSLTCTVSGYSITSDYNAHWI RQPPGKGLEWIGYIHYSGQTMYNPSLKSRVTISRDTSK NQFSLKLSSVTAADTAVYYCARNYGSIYVNYFDYWG QGTLVTVSS | 303 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 304 |
| SA312a | | |
| Heavy chain variable region ($V_H$) | QVQLQESGPGLVKPSQTLSLTCTVSGYSITQDYNAHW IRQPPGKGLEWIGYIHYSGSTMYNPSLKSRVTISRDTS KNQFSLKLSSVTAADTAVYYCARNYGSIYVNYFDYW GQGTLVTVSS | 305 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 306 |
| SA313a | | |
| Heavy chain variable region ($V_H$) | QVQLQESGPGLVKPSQTLSLTCTVSGYSITSDYNAHWI RQPPGKGLEWIGYIHYSGSTMYNPSLKSRVTISRDTSK NQFSLKLSSVTAADTAVYYCARNFGSIYVNYFDYWG QGTLVTVSS | 307 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 308 |
| SA314a | | |
| Heavy chain variable region ($V_H$) | QVQLQESGPGLVKPSQTLSLTCTVSGYSITSDYNAHWI RQPPGKGLEWIGYIHYSGQTMYNPSLKSRVTISRDTSK NQFSLKLSSVTAADTAVYYCARNYGSIYVNYFDYWG QGTLVTVSS | 309 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 310 |
| SA315a | | |
| Heavy chain variable region ($V_H$) | QVQLQESGPGLVKPSQTLSLTCTVSGYSITSDYNAHWI RQPPGKGLEWIGYIHYSGQTMYNPSLKSRVTISRDTSK NQFSLKLSSVTAADTAVYYCARNFGSIYVNYFDYWG QGTLVTVSS | 311 |

TABLE A2-continued

Exemplary Polypeptide Sequences

| Description | Sequence | SEQ ID NO: |
|---|---|---|
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 312 |

SA316a

| Description | Sequence | SEQ ID NO: |
|---|---|---|
| Heavy chain variable region (V$_H$) | QVQLQESGPGLVKPSQTLSLTCTVSGYSITSDYNAHWI RQPPGKGLEWIGYIHYSGSTYYNPSLKSRVTISRDTSK NQFSLKLSSVTAADTAVYYCARNYGSIYVNYFDYWG QGTLVTVSS | 313 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 314 |

SA317a

| Description | Sequence | SEQ ID NO: |
|---|---|---|
| Heavy chain variable region (V$_H$) | QVQLQESGPGLVKPSQTLSLTCTVSGYSITSDYNAHWI RQPPGKGLEWIGYIHYSGSTLYNPSLKSRVTISRDTSK NQFSLKLSSVTAADTAVYYCARNYGSIYVNYFDYWG QGTLVTVSS | 315 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 316 |

SA318a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTMYNPSLKSRVTISRDTS KNQFSLKLSSVTAADTAVYYCARNFGSIYVNYFDYW GQGTLVTVSS | 317 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 318 |

SA319a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTNYNPSLKSRVTISRDTS KNQFSLKLSSVTAADTAVYYCARNFGSIYVNYFDYW GQGTLVTVSS | 319 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 320 |

SA320a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 321 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 322 |

SA321a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTLYNPSLKSRVTISRDTS KNQFSLKLSSVTAADTAVYYCARNFGSIYVNYFDYW GQGTLVTVSS | 323 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 324 |

TABLE A2-continued

Exemplary Polypeptide Sequences

| Description | Sequence | SEQ ID NO: |
|---|---|---|
| SA322a | | |
| Heavy chain variable region (V$_H$) | QVQLQESGPGLVKPSQTLSLTCTVSGYSITQDYNAHW IRQPPGKGLEWIGYIHYSGQTNYNPSLKSRVTISRDTS KNQFSLKLSSVTAADTAVYYCARNYGSIYVNYFDYW GQGTLVTSS | 325 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 326 |
| SA325a | | |
| Heavy chain variable region (V$_H$) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYGSIYVNYFDYWG QGTLVTSS | 327 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQEYHSYPTFGGGTKVEIK | 328 |
| SA326a | | |
| Heavy chain variable region (V$_H$) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYGSIYVNYFDYWG QGTLVTSS | 329 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQLYHSYPTFGGGTKVEIK | 330 |
| SA327a | | |
| Heavy chain variable region (V$_H$) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYGSIYVNYFDYWG QGTLVTSS | 331 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHGYPTFGGGTKVEIK | 332 |
| SA328a | | |
| Heavy chain variable region (V$_H$) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYGSIYVNYFDYWG QGTLVTSS | 333 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYVTFGGGTKVEIK | 334 |
| SA329a | | |
| Heavy chain variable region (V$_H$) | QVQLQESGPGLVKPSQTLSLTCTVSGYSITSDYNAHWI RQPPGKGLEWIGYIHYSGSTNYNPSLKSRVTISRDTSK NQFSLKLSSVTAADTAVYYCARNYGSIYVNYFDYWG QGTLVTSS | 335 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPKFGGGTKVEIK | 336 |
| SA330a | | |
| Heavy chain variable region (V$_H$) | QVQLQESGPGLVKPSQTLSLTCTVSGYSITSDYNAHWI RQPPGKGLEWIGYIHYSGQTYYNPSLKSRVTISRDTSK NQFSLKLSSVTAADTAVYYCARNFGSIYVNYFDYWG QGTLVTSS | 337 |

TABLE A2-continued

Exemplary Polypeptide Sequences

| Description | Sequence | SEQ ID NO: |
|---|---|---|
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPTFGGGTKVEIK | 338 |

SA331a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 339 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHGYPTFGGGTKVEIK | 340 |

SA332a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 341 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYVTFGGGTKVEIK | 342 |

SA333a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 343 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYPKFGGGTKVEIK | 344 |

SA337a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTNYNPSLKSRVTISRDTS KNQFSLKLSSVTAADTAVYYCARNYGSIYVNYFDYW GQGTLVTVSS | 345 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQLYHSYPTFGGGTKVEIK | 346 |

SA338a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 347 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQLYHSYPTFGGGTKVEIK | 348 |

SA339a

| Description | Sequence | SEQ ID NO: |
|---|---|---|
| Heavy chain variable region (V$_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 349 |
| Light chain variable region (V$_L$) | EIVLTQSPATLSLSPGERATLSCSASSSVSYMYWYQQK PGQAPRPLIYRTSNLASGIPARFSGSGSGTDFTLTISSLE PEDFAVYYCQQYHGYPTFGGGTKVEIK | 350 |

TABLE A2-continued

Exemplary Polypeptide Sequences

| Description | Sequence | SEQ ID NO: |
|---|---|---|
| SA340a | | |
| Heavy chain variable region ($V_H$) | QVQLQESGPGLVKPSQTLSLTCTVSGYSITQDYNAHW IRQPPGKGLEWIGYIHYSGQTYYNPSLKSRVTISRDTS KNQFSLKLSSVTAADTAVYYCARNFGSIYVNYFDYW GQGTLVTVSS | 351 |
| Light chain variable region ($V_L$) | EIVLTQSPATLSLSPGERATLSCSASSSVSYMYWYQQK PGQAPRPLIYRTSNLASGIPARFSGSGSGTDFTLTISSLE PEDFAVYYCQQYHSYVTFGGGTKVEIK | 352 |

Thus, in certain embodiments, an antibody binds to IL-18BP and comprises a $V_H$ sequence and a corresponding $V_L$ sequence selected from Table A2. In certain embodiments, the $V_H$ comprises a sequence least 70, 75, 80, 85, 90, 95, 97, 98, 99, or 100% identical to a sequence selected from Table A2, including, for example, wherein the $V_H$ has at least 1, 2, 3, 4, 5, 6, 7, 8, 9, or 10 alterations in one or more framework regions. In some embodiments, the $V_L$ comprises a sequence at least 70, 75, 80, 85, 90, 95, 97, 98, 99, or 100% identical to a sequence selected from Table A2, including, for example, wherein the $V_L$ has at least 1, 2, 3, 4, 5, 6, 7, 8, 9, or 10 alterations in one or more framework regions. In particular embodiments, the $V_H$ comprises a sequence least 70, 75, 80, 85, 90, 95, 97, 98, 99, or 100% identical to a sequence selected from Table A2 and the $V_L$ comprises a sequence at least 70, 75, 80, 85, 90, 95, 97, 98, 99, or 100% identical to a sequence selected from Table A2 and is from the same single named antibody (e.g. SA04a) as the $V_H$ region. In particular embodiments, the $V_H$ comprises a sequence least 70, 75, 80, 85, 90, 95, 97, 98, 99, or 100% identical to a sequence selected from Table A2 and the $V_L$ comprises a sequence at least 70, 75, 80, 85, 90, 95, 97, 98, 99, or 100% identical to a sequence selected from Table A2 and is from the same single named antibody (e.g. SA04a) as the $V_H$ region, wherein any alterations are not found in the CDRs as underlined in Table A2. Hence, an antibody may comprise $V_H$ and $V_L$ sequences that are at least 70, 75, 80, 85, 90, 95, 97, 98, 99, or 100% identical to the respective sequences from a single named antibody (e.g. SA04a) in Table A2, wherein the antibody comprises the CDRs of said single named antibody (e.g. SA04a) as recited in Table A1.

In some embodiments, the $V_H$ and $V_L$ of an antibody are as follows:
the $V_H$ comprises a sequence at least 70, 75, 80, 85, 90, 95, 97, 98, 99, or 100% identical to SEQ ID NO: 265, and the $V_L$ comprises a sequence at least 70, 75, 80, 85, 90, 95, 97, 98, 99, or 100% identical to SEQ ID NO: 266;
the $V_H$ comprises a sequence at least 70, 75, 80, 85, 90, 95, 97, 98, 99, or 100% identical to SEQ ID NO: 267, and the $V_L$ comprises a sequence at least 70, 75, 80, 85, 90, 95, 97, 98, 99, or 100% identical to SEQ ID NO: 268;
the $V_H$ comprises a sequence at least 70, 75, 80, 85, 90, 95, 97, 98, 99, or 100% identical to SEQ ID NO: 269, and the $V_L$ comprises a sequence at least 70, 75, 80, 85, 90, 95, 97, 98, 99, or 100% identical to SEQ ID NO: 270;
the $V_H$ comprises a sequence at least 70, 75, 80, 85, 90, 95, 97, 98, 99, or 100% identical to SEQ ID NO: 271, and the $V_L$ comprises a sequence at least 70, 75, 80, 85, 90, 95, 97, 98, 99, or 100% identical to SEQ ID NO: 272;
the $V_H$ comprises a sequence at least 70, 75, 80, 85, 90, 95, 97, 98, 99, or 100% identical to SEQ ID NO: 273, and the $V_L$ comprises a sequence at least 70, 75, 80, 85, 90, 95, 97, 98, 99, or 100% identical to SEQ ID NO: 274;
the $V_H$ comprises a sequence at least 70, 75, 80, 85, 90, 95, 97, 98, 99, or 100% identical to SEQ ID NO: 275, and the $V_L$ comprises a sequence at least 70, 75, 80, 85, 90, 95, 97, 98, 99, or 100% identical to SEQ ID NO: 276;
the $V_H$ comprises a sequence at least 70, 75, 80, 85, 90, 95, 97, 98, 99, or 100% identical to SEQ ID NO: 277, and the $V_L$ comprises a sequence at least 70, 75, 80, 85, 90, 95, 97, 98, 99, or 100% identical to SEQ ID NO: 278;
the $V_H$ comprises a sequence at least 70, 75, 80, 85, 90, 95, 97, 98, 99, or 100% identical to SEQ ID NO: 279, and the $V_L$ comprises a sequence at least 70, 75, 80, 85, 90, 95, 97, 98, 99, or 100% identical to SEQ ID NO: 280;
the $V_H$ comprises a sequence at least 70, 75, 80, 85, 90, 95, 97, 98, 99, or 100% identical to SEQ ID NO: 281, and the $V_L$ comprises a sequence at least 70, 75, 80, 85, 90, 95, 97, 98, 99, or 100% identical to SEQ ID NO: 282;
the $V_H$ comprises a sequence at least 70, 75, 80, 85, 90, 95, 97, 98, 99, or 100% identical to SEQ ID NO: 283, and the $V_L$ comprises a sequence at least 70, 75, 80, 85, 90, 95, 97, 98, 99, or 100% identical to SEQ ID NO: 284;
the $V_H$ comprises a sequence at least 70, 75, 80, 85, 90, 95, 97, 98, 99, or 100% identical to SEQ ID NO: 285, and the $V_L$ comprises a sequence at least 70, 75, 80, 85, 90, 95, 97, 98, 99, or 100% identical to SEQ ID NO: 286;
the $V_H$ comprises a sequence at least 70, 75, 80, 85, 90, 95, 97, 98, 99, or 100% identical to SEQ ID NO: 287, and the $V_L$ comprises a sequence at least 70, 75, 80, 85, 90, 95, 97, 98, 99, or 100% identical to SEQ ID NO: 288;
the $V_H$ comprises a sequence at least 70, 75, 80, 85, 90, 95, 97, 98, 99, or 100% identical to SEQ ID NO: 289, and the $V_L$ comprises a sequence at least 70, 75, 80, 85, 90, 95, 97, 98, 99, or 100% identical to SEQ ID NO: 290;
the $V_H$ comprises a sequence at least 70, 75, 80, 85, 90, 95, 97, 98, 99, or 100% identical to SEQ ID NO: 291, and the V$_L$ comprises a sequence at least 70, 75, 80, 85, 90, 95, 97, 98, 99, or 100% identical to SEQ ID NO: 292;

the V$_H$ comprises a sequence at least 70, 75, 80, 85, 90, 95, 97, 98, 99, or 100% identical to SEQ ID NO: 293, and the V$_L$ comprises a sequence at least 70, 75, 80, 85, 90, 95, 97, 98, 99, or 100% identical to SEQ ID NO: 294;

the V$_H$ comprises a sequence at least 70, 75, 80, 85, 90, 95, 97, 98, 99, or 100% identical to SEQ ID NO: 295, and the V$_L$ comprises a sequence at least 70, 75, 80, 85, 90, 95, 97, 98, 99, or 100% identical to SEQ ID NO: 296;

the V$_H$ comprises a sequence at least 70, 75, 80, 85, 90, 95, 97, 98, 99, or 100% identical to SEQ ID NO: 297, and the V$_L$ comprises a sequence at least 70, 75, 80, 85, 90, 95, 97, 98, 99, or 100% identical to SEQ ID NO: 298;

the V$_H$ comprises a sequence at least 70, 75, 80, 85, 90, 95, 97, 98, 99, or 100% identical to SEQ ID NO: 299, and the V$_L$ comprises a sequence at least 70, 75, 80, 85, 90, 95, 97, 98, 99, or 100% identical to SEQ ID NO: 300;

the V$_H$ comprises a sequence at least 70, 75, 80, 85, 90, 95, 97, 98, 99, or 100% identical to SEQ ID NO: 301, and the V$_L$ comprises a sequence at least 70, 75, 80, 85, 90, 95, 97, 98, 99, or 100% identical to SEQ ID NO: 302;

the V$_H$ comprises a sequence at least 70, 75, 80, 85, 90, 95, 97, 98, 99, or 100% identical to SEQ ID NO: 303, and the V$_L$ comprises a sequence at least 70, 75, 80, 85, 90, 95, 97, 98, 99, or 100% identical to SEQ ID NO: 304;

the V$_H$ comprises a sequence at least 70, 75, 80, 85, 90, 95, 97, 98, 99, or 100% identical to SEQ ID NO: 305, and the V$_L$ comprises a sequence at least 70, 75, 80, 85, 90, 95, 97, 98, 99, or 100% identical to SEQ ID NO: 306;

the V$_H$ comprises a sequence at least 70, 75, 80, 85, 90, 95, 97, 98, 99, or 100% identical to SEQ ID NO: 307, and the V$_L$ comprises a sequence at least 70, 75, 80, 85, 90, 95, 97, 98, 99, or 100% identical to SEQ ID NO: 308;

the V$_H$ comprises a sequence at least 70, 75, 80, 85, 90, 95, 97, 98, 99, or 100% identical to SEQ ID NO: 309, and the V$_L$ comprises a sequence at least 70, 75, 80, 85, 90, 95, 97, 98, 99, or 100% identical to SEQ ID NO: 310;

the V$_H$ comprises a sequence at least 70, 75, 80, 85, 90, 95, 97, 98, 99, or 100% identical to SEQ ID NO: 311, and the V$_L$ comprises a sequence at least 70, 75, 80, 85, 90, 95, 97, 98, 99, or 100% identical to SEQ ID NO: 312;

the V$_H$ comprises a sequence at least 70, 75, 80, 85, 90, 95, 97, 98, 99, or 100% identical to SEQ ID NO: 313, and the V$_L$ comprises a sequence at least 70, 75, 80, 85, 90, 95, 97, 98, 99, or 100% identical to SEQ ID NO: 314;

the V$_H$ comprises a sequence at least 70, 75, 80, 85, 90, 95, 97, 98, 99, or 100% identical to SEQ ID NO: 315, and the V$_L$ comprises a sequence at least 70, 75, 80, 85, 90, 95, 97, 98, 99, or 100% identical to SEQ ID NO: 316;

the V$_H$ comprises a sequence at least 70, 75, 80, 85, 90, 95, 97, 98, 99, or 100% identical to SEQ ID NO: 317, and the V$_L$ comprises a sequence at least 70, 75, 80, 85, 90, 95, 97, 98, 99, or 100% identical to SEQ ID NO: 318;

the V$_H$ comprises a sequence at least 70, 75, 80, 85, 90, 95, 97, 98, 99, or 100% identical to SEQ ID NO: 319, and the V$_L$ comprises a sequence at least 70, 75, 80, 85, 90, 95, 97, 98, 99, or 100% identical to SEQ ID NO: 320;

the V$_H$ comprises a sequence at least 70, 75, 80, 85, 90, 95, 97, 98, 99, or 100% identical to SEQ ID NO: 321, and the V$_L$ comprises a sequence at least 70, 75, 80, 85, 90, 95, 97, 98, 99, or 100% identical to SEQ ID NO: 322;

the V$_H$ comprises a sequence at least 70, 75, 80, 85, 90, 95, 97, 98, 99, or 100% identical to SEQ ID NO: 323, and the V$_L$ comprises a sequence at least 70, 75, 80, 85, 90, 95, 97, 98, 99, or 100% identical to SEQ ID NO: 324;

the V$_H$ comprises a sequence at least 70, 75, 80, 85, 90, 95, 97, 98, 99, or 100% identical to SEQ ID NO: 325, and the V$_L$ comprises a sequence at least 70, 75, 80, 85, 90, 95, 97, 98, 99, or 100% identical to SEQ ID NO: 326;

the V$_H$ comprises a sequence at least 70, 75, 80, 85, 90, 95, 97, 98, 99, or 100% identical to SEQ ID NO: 327, and the V$_L$ comprises a sequence at least 70, 75, 80, 85, 90, 95, 97, 98, 99, or 100% identical to SEQ ID NO: 328;

the V$_H$ comprises a sequence at least 70, 75, 80, 85, 90, 95, 97, 98, 99, or 100% identical to SEQ ID NO: 329, and the V$_L$ comprises a sequence at least 70, 75, 80, 85, 90, 95, 97, 98, 99, or 100% identical to SEQ ID NO: 330;

the V$_H$ comprises a sequence at least 70, 75, 80, 85, 90, 95, 97, 98, 99, or 100% identical to SEQ ID NO: 331, and the V$_L$ comprises a sequence at least 70, 75, 80, 85, 90, 95, 97, 98, 99, or 100% identical to SEQ ID NO: 332;

the V$_H$ comprises a sequence at least 70, 75, 80, 85, 90, 95, 97, 98, 99, or 100% identical to SEQ ID NO: 333, and the V$_L$ comprises a sequence at least 70, 75, 80, 85, 90, 95, 97, 98, 99, or 100% identical to SEQ ID NO: 334;

the V$_H$ comprises a sequence at least 70, 75, 80, 85, 90, 95, 97, 98, 99, or 100% identical to SEQ ID NO: 335, and the V$_L$ comprises a sequence at least 70, 75, 80, 85, 90, 95, 97, 98, 99, or 100% identical to SEQ ID NO: 336;

the V$_H$ comprises a sequence at least 70, 75, 80, 85, 90, 95, 97, 98, 99, or 100% identical to SEQ ID NO: 337, and the V$_L$ comprises a sequence at least 70, 75, 80, 85, 90, 95, 97, 98, 99, or 100% identical to SEQ ID NO: 338;

the V$_H$ comprises a sequence at least 70, 75, 80, 85, 90, 95, 97, 98, 99, or 100% identical to SEQ ID NO: 339, and the V$_L$ comprises a sequence at least 70, 75, 80, 85, 90, 95, 97, 98, 99, or 100% identical to SEQ ID NO: 340;

the V$_H$ comprises a sequence at least 70, 75, 80, 85, 90, 95, 97, 98, 99, or 100% identical to SEQ ID NO: 341, and the V$_L$ comprises a sequence at least 70, 75, 80, 85, 90, 95, 97, 98, 99, or 100% identical to SEQ ID NO: 342;

the V$_H$ comprises a sequence at least 70, 75, 80, 85, 90, 95, 97, 98, 99, or 100% identical to SEQ ID NO: 343, and the V_L comprises a sequence at least 70, 75, 80, 85, 90, 95, 97, 98, 99, or 100% identical to SEQ ID NO: 344;

the V_H comprises a sequence at least 70, 75, 80, 85, 90, 95, 97, 98, 99, or 100% identical to SEQ ID NO: 345, and the V_L comprises a sequence at least 70, 75, 80, 85, 90, 95, 97, 98, 99, or 100% identical to SEQ ID NO: 346;

the V_H comprises a sequence at least 70, 75, 80, 85, 90, 95, 97, 98, 99, or 100% identical to SEQ ID NO: 347, and the V_L comprises a sequence at least 70, 75, 80, 85, 90, 95, 97, 98, 99, or 100% identical to SEQ ID NO: 348;

the V_H comprises a sequence at least 70, 75, 80, 85, 90, 95, 97, 98, 99, or 100% identical to SEQ ID NO: 349, and the V_L comprises a sequence at least 70, 75, 80, 85, 90, 95, 97, 98, 99, or 100% identical to SEQ ID NO: 350; or the V_H comprises a sequence at least 70, 75, 80, 85, 90, 95, 97, 98, 99, or 100% identical to SEQ ID NO: 351, and the V_L comprises a sequence at least 70, 75, 80, 85, 90, 95, 97, 98, 99, or 100% identical to SEQ ID NO: 352.

Also included are variants thereof that bind to IL-18BP, for example, variants having 1, 2, 3, 4, 5, 6, 7, 8, 9, or 10 alterations in one or more framework regions of any one or more of the foregoing V_H and/or V_L sequences. Exemplary "alterations" include amino acid substitutions, additions, and deletions.

As noted above, an antibody described herein, binds to IL-18BP. In certain embodiments, an antibody binds to human IL-18BP, cynomolgus IL-18BP, and/or mouse IL-18BP, or a region or fragment or epitope thereof.

Human interleukin-18-binding protein, or IL-18BP, is encoded by the IL18BP gene (see Gene ID: 10068; and UniProt: 095998) and has at least three isoforms. In some embodiments, an antibody of the disclosure binds to isoform A of IL-18BP. In some embodiments, an antibody of the disclosure binds to isoform B of IL-18BP. In some embodiments, an antibody of the disclosure binds to both isoform A and isoform C of IL-18BP. In some embodiments, an antibody of the disclosure binds to all isoforms of IL-18BP. It is an inhibitor of early Th1 cytokine responses and the proinflammatory cytokine IL-18. For instance, IL-18BP binds to IL-18, inhibits the binding of IL-18 to its receptor, and thereby inhibits IL-18-induced IFN-gamma production, among other IL-18 signaling activities. The amino acid sequences of the human, cynomolgus, and mouse IL-18BP isoforms are provided in Table B1 below. Signal peptides are underlined in the table below.

TABLE B1

Exemplary IL-18BP Sequences

| Name | Sequence | SEQ ID NO: |
|---|---|---|
| Full-length Human Isoform A | MRHNWTPDLSPLWVLLLCAHVVTLLVRATPVSQTTT AATASVRSTKDPCPSQPPVFPAAKQCPALEVTWPEVE VPLNGTLSLSCVACSRFPNFSILYWLGNGSFIEHLPGRL WEGSTSRERGSTGTQLCKALVLEQLTPALHSTNFSCV LVDPEQVVQRHVVLAQLWAGLRATLPPTQEALPSSHS SPQQQG | 371 |
| Mature Human Isoform A | TPVSQTTTAATASVRSTKDPCPSQPPVFPAAKQCPALE VTWPEVEVPLNGTLSLSCVACSRFPNFSILYWLGNGSF IEHLPGRLWEGSTSRERGSTGTQLCKALVLEQLTPALH STNFSCVLVDPEQVVQRHVVLAQLWAGLRATLPPTQ EALPSSHSSPQQQG | 372 |
| Full-length Cynomolgus | MRHNWTPDLSFLWVLLCAHIITLLVRATPVSQTTTAA TASSRSTKDPCPSQPPVFPAAKQCPALEVTWPEVEMP LNGTLTLSCTACSRFPNFSMLYWLGNGSFIEHLPGQL WEGSTSREHGSTGTRLYKALVLEQLTPALHSTNFSCV LMDPEQVVQRHVILAQLWAGLRTTLPPTQEALPSSHS TGPQQPTAAGLRLSTGPAAARP | 373 |
| Mature Cynomolgus | TPVSQTTTAATASSRSTKDPCPSQPPVFPAAKQCPALE VTWPEVEMPLNGTLTLSCTACSRFPNFSMLYWLGNG SFIEHLPGQLWEGSTSREHGSTGTRLYKALVLEQLTPA LHSTNFSCVLMDPEQVVQRHVILAQLWAGLRTTLPPT QEALPSSHSTGPQQPTAAGLRLSTGPAAARP | 374 |
| Full-length Mouse | MRHCWTAGPSSWWVLLLYVHVILARATSAPQTTATV LTGSSKDPCSSWSPAVPTKQYPALDVIWPEKEVPLNG TLTLSCTACSRFPYFSILYWLGNGSFIEHLPGRLKEGHT SREHRNTSTWLHRALVLEELSPTLRSTNFSCLFVDPGQ VAQYHIILAQLWDGLKTAPSPSQETLSSHSPVSRSAGP GVA | 375 |
| Mature Mouse | TSAPQTTATVLTGSSKDPCSSWSPAVPTKQYPALDVI WPEKEVPLNGTLTLSCTACSRFPYFSILYWLGNGSFIE HLPGRLKEGHTSREHRNTSTWLHRALVLEELSPTLRS TNFSCLFVDPGQVAQYHIILAQLWDGLKTAPSPSQETL SSHSPVSRSAGPGVA | 376 |

Thus, in certain embodiments, an antibody binds to a mature IL-18BP sequence in Table B1, for example, at a region excluding the signal peptide (underlined).

In certain embodiments, an antibody binds to a conformational epitope of mature IL-18BP sequence of SEQ ID NO: 372 (mature human Isoform A). In exemplary embodiments, an antibody of the disclosure binds to at least two residues selected from the group consisting of T51, S53, S75, H79, R83, S88, S90, T110, H114, S115, T116, and S119 of SEQ ID NO: 372. In exemplary embodiments, an antibody of the disclosure binds to residues T51, S53, S75, H79, R83, S88, S90, T110, H114, S115, T116, and S119 of SEQ ID NO: 372. In exemplary embodiments, such an antibody comprises the $V_H$ of a sequence comprising at least 70, 75, 80, 85, 90, 95, 97, 98, 99, or 100% identity to SEQ ID NO: 347, and the $V_L$ of a sequence comprising at least 70, 75, 80, 85, 90, 95, 97, 98, 99, or 100% identity to SEQ ID NO: 348. In exemplary embodiments, the $V_H$CDR1, $V_H$CDR2, and $V_H$CDR3 sequences comprise SEQ ID NOs: 247-249, respectively, and the $V_L$CDR1, $V_L$CDR2, and $V_L$CDR3 sequences comprise SEQ ID NOs: 250-252, respectively.

In certain embodiments, an antibody binds to an epitope that comprises the IL-18 binding interface of the mature form of IL-18B. Residues on IL-18BP which interact with IL-18 were identified as: R61, Y69, S75, H79, T116, S119 and R131. In exemplary embodiments, an antibody of the disclosure binds to residues S75, H79, T116, S119, which are also recognized by IL-18. In exemplary embodiments, such an antibody comprises the $V_H$ of a sequence comprising at least 70, 75, 80, 85, 90, 95, 97, 98, 99, or 100% identity to SEQ ID NO: 347, and the $V_L$ of a sequence comprising at least 70, 75, 80, 85, 90, 95, 97, 98, 99, or 100% identity to SEQ ID NO: 348. In exemplary embodiments, the $V_H$CDR1, $V_H$CDR2, and $V_H$CDR3 sequences comprise SEQ ID NOs: 247-249, respectively, and the $V_L$CDR1, $V_L$CDR2, and $V_L$CDR3 sequences comprise SEQ ID NOs: 250-252, respectively.

In certain embodiments, an antibody binds to a linear epitope of mature IL-18BP sequence of SEQ ID NO: 372 (mature human Isoform A). In certain embodiments, an antibody has ortholog specificity or ortholog cross-reactivity for IL-18BP. For instance, in certain embodiments, an antibody binds to human IL-18BP and cynomolgus IL-18BP but does not bind (specifically or substantially) to mouse IL-18BP. In some embodiments, an antibody binds to human IL-18BP, cynomolgus IL-18BP, and mouse IL-18BP.

In some embodiments, an antibody binds to human IL-18BP with a binding affinity that is stronger than the binding affinity between IL-18 and IL-18BP ($K_D$~650 pM for human IL-18 and IL-18BP; or specifically measured as 655±136 pM). In some instances, an antibody binds to human IL-18BP with a binding affinity of about 1 pM to about 10 pM to about 600 pM or 65 pM, or about, at least about, or less than about 1, 5, 10, 20, 30, 40, 50, 60, 70, 80, 90, 100, 110, 120, 130, 140, 150, 160, 170, 180, 190, 200, or 300, 400, 500, 600, or 650 pM, or optionally with an affinity that ranges from about 1 pM to about 600 pM, 1 pM to about 500 pM, 1 pM to about 400 pM, 1 pM to about 300 pM, about 1 pM to about 200 pM, about 1 pM to about 100 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 5 pM to about 600 pM, about 5 pM to about 500 pM, about 5 pM to about 400 pM, about 5 pM to about 300 pM, about 5 pM to about 200 pM, about 5 pM to about 100 pM, about 5 pM to about 50 pM, about 5 pM to about 40 pM, about 5 pM to about 30 pM, about 5 pM to about 20 pM, about 5 pM to about 10 pM, about 10 pM to about 600 pM, about 10 pM to about 500 pM, about 10 pM to about 400 pM, about 10 pM to about 300 pM, about 10 pM to about 200 pM, about 10 pM to about 100 pM, about 10 pM to about 50 pM, about 10 pM to about 40 pM, about 10 pM to about 30 pM, about 10 pM to about 20 pM, or about 20 pM to about 600 pM, about 20 pM to about 500 pM, about 20 pM to about 400 pM, about 20 pM to about 300 pM, about 20 pM to about 200 pM, about 20 pM to about 100 pM, about 20 pM to about 50 pM, about 20 pM to about 40 pM, about 20 pM to about 30 pM, or about 30 pM to about 600 pM, about 30 pM to about 500 pM, about 30 pM to about 400 pM, about 30 pM to about 300 pM, about 30 pM to about 200 pM, about 30 pM to about 100 pM, about 30 pM to about 50 pM, or about 30 pM to about 40 pM. The $K_D$ may be determined by the biolayer interferometry (BLI) assay described herein. For instance, binding kinetic measurements may be taken on a Fortébio (now Sartorius) Octet RED96e instrument by loading mAbs onto anti-human constant domain (AHC) biosensors (FortéBio) in 10× kinetics buffer consisting of PBS containing 0.1% BSA, 0.02% polysorbate 20 (TWEEN™) for 90-120 s to achieve a spectral shift value between 0.8 to 1.2 nm. Association may then be carried out in the presence of a 2-fold dilution series of hIL-18BP and allowed to proceed for 90-120 s. Dissociation may be measured for 300 to 1200 s. Dilution series may start at 100 nM for weaker variants or 10 nM for the most potent mAbs.

In some embodiments, an antibody, or antigen binding fragment thereof, is an IL-18BP antagonist. In some instances, an antibody, or antigen binding fragment thereof, antagonizes the binding and/or signaling activity between IL-18BP and its ligand, IL-18. In some embodiments, an antibody, or antigen binding fragment thereof, antagonizes or reduces the binding and/or signaling activity between IL-18BP and IL-18 by about or at least about 10-1000% (e.g., about 20, 25, 30, 35, 40, 45, 50, 55, 60, 65, 70, 75, 80, 90, 100, 200, 300, 400, 500, 600, 700, 800, 900, 1000% or more), for example, in a cell-based assay. In some instances, the antagonistic anti-IL-18BP antibody, or antigen binding fragment thereof, blocks the inhibitory activity of IL-18BP towards IL-18, and thereby increases IL-18-mediated signaling, for example, IL-18-mediated induction of IFN-gamma, CXCL10, and TNFα. These functional activities may be measured by an assay disclosed herein. For instance, the antibody may be incubated with IL-18BP (for instance, human IL-18BP), followed by the addition of IL-18 (e.g. recombinant human IL-18). The resulting solution may then be added to IL-18 Reporter HEK 293 cells that respond to exogenously added IL-18 by expressing an NF-κB/AP-1-inducible secreted embryonic alkaline phosphatase (SEAP) reporter gene. The effect of the antibody can then be assayed by the effect on the reporter cell in comparison to suitable controls, such as isotype control antibodies. Further details are disclosed in the materials and methods section herein. Another potential assay involves the measurement of derepression of IFNγ expression by anti-IL-18BP mAbs in KG-1 cells. In brief, IL-18BP may be pre-blocked with a serial dilution of antibodies, IL-18 may then be added to the mixture, and this mixture may be added to the KG-1 cells and incubated. Secreted IFN-γ can then be measured according to conventional means, such as ELISA, and the test antibody's effect compared to the effect of suitable controls, such as isotype control antibodies. Further details are disclosed in the materials and methods section herein. Yet another potential assay involves the incubation of PBMCs with the test antibody, IL-12, and IL-18 and the measurement of IFNγ and/or CCL2 by conventional means. The test antibody's effect may be compared to the effect of suitable controls, such as isotype control antibodies. Further details are disclosed in the materials and methods section herein. A further assay involves the incubation of NK cells and pre-complexed hIL-18/hIL-18BP, followed by the addition of IL-12, and then serial dilutions of the test antibody. The test antibody's effect compared to the effect of suitable controls, such as isotype control antibodies. Further details are disclosed in the materials and methods section herein.

Certain embodiments include methods of screening an anti-IL-18BP antibody for the ability to block or inhibit binding between IL-18 and IL-18BP, comprising (a) determining binding affinity of the antibody for (i) IL-18BP alone, and (ii) a hypo-IL-18 fusion protein, wherein the hypo-IL-18 fusion protein comprises IL-18 fused to IL-18BP via a flexible linker (and an optional protease cleavage site in between), wherein the IL-18 portion of the fusion protein is bound to the IL-18BP portion of the fusion protein and sterically blocks the IL-18 binding site of the IL-18BP portion of the fusion protein; (b) comparing the binding affinity of (i) to the binding affinity of (ii); and (c) identifying or selecting the antibody as being able to block or inhibit binding between IL-18 and IL-18BP if the binding affinity of (i) is significantly stronger than the binding affinity (ii). Certain embodiments comprise (c) identifying or selecting the antibody as being able to block or inhibit binding between IL-18 and IL-18BP if the binding affinity of (i) is about or at least about 2×, 3×, 4×, 5×, 6×, 7×, 8×, 9×, 10×, 20×, 30×, 40×, 50×, 60×, 70×, 80×, 90×, 100×, 200×, 300×, 400×, 500×, 600×, 700×, 800×, 900×, or 1000× or more stronger than the binding affinity (ii). In certain embodiments, the IL-18 and IL-18BP are mouse IL-18 and IL-18BP. In some embodiments, the IL-18 and IL-18BP are human IL-18 and IL-18BP. In some embodiments, the hypo-IL-18 fusion protein comprises, in an N- to C-terminal orientation, a signal peptide, IL-18, a first flexible linker, a protease cleavage site (optionally a TEV protease cleavage site), a flexible linker, and IL-18BP. In specific embodiments, the hypo-IL-18 fusion protein comprises an amino acid sequence at least 70, 75, 80, 85, 90, 95, 97, 98, 99, or 100% identical to a sequence from Table S1.

Merely for illustrative purposes, the binding interactions (for example, binding affinity) between any combination of IL-18BP, IL-18 (e.g., hypo-IL-18), and/or an anti-IL-18BP antibody described herein, or the binding/signaling between IL-18BP and IL-18, can be detected and quantified using a variety of routine methods, including Biacore® assays (for example, with appropriately tagged soluble reagents, bound to a sensor chip), FACS analyses with cells expressing IL-18BPr on the cell surface (either native, or recombinant), immunoassays, fluorescence staining assays, ELISA assays, and microcalorimetry approaches such as ITC (Isothermal Titration Calorimetry). Similarly, the functional properties of anti-IL-18BP antibodies may be assessed using a variety of methods known to the skilled person affinity/binding assays (for example, surface plasmon resonance, competitive inhibition assays); cytotoxicity assays, cell viability assays, cell proliferation or differentiation assays, cancer cell and/or tumor growth inhibition using in vitro or in vivo models. Other assays may test the ability of antibodies described herein to modulate (e.g., inhibit) IL-18BP and/or IL-18-mediated responses. The antibodies described herein may also be tested for in vitro and in vivo efficacy. Such assays may be performed using well-established protocols known to the skilled person (see e.g., Current Protocols in Molecular Biology (Greene Publ. Assoc. Inc. & John Wiley & Sons, Inc., NY, NY); Current Protocols in Immunology (Edited by: John E. Coligan, Ada M. Kruisbeek, David H. Margulies, Ethan M. Shevach, Warren Strober 2001 John Wiley & Sons, NY, NY); or commercially available kits.

In particular embodiments, the Fc region of an antibody comprises, consists, or consists essentially an IgA (including subclasses IgA1 and IgA2), IgD, IgE, IgG (including subclasses IgG1, IgG2, IgG3, and IgG4), or IgM Fc domain, optionally a human Fc domain, or a hybrid and/or variant thereof. In particular embodiments, the Fc region comprises, consists, or consists essentially of the Fc from human IgG1 or IgG4 (see, e.g., Allberse and Schuurman, Immunology. 105:9-19, 2002), or a fragment or variant thereof.

In certain embodiments, an antibody comprises variant or otherwise modified Fc region(s), including those having altered properties or biological activities relative to wild-type Fc region(s). Examples of modified Fc regions include those having mutated sequences, for instance, by substitution, insertion, deletion, or truncation of one or more amino acids relative to a wild-type sequence, hybrid Fc polypeptides composed of domains from different immunoglobulin classes/subclasses, Fc polypeptides having altered glycosylation/sialylation patterns, and Fc polypeptides that are modified or derivatized, for example, by biotinylation (see, e.g., US Application No. 2010/0209424), phosphorylation, sulfation, etc., or any combination of the foregoing. Such modifications can be employed to alter (e.g., increase, decrease) the binding properties of the Fc region to one or more particular FcRs (e.g., FcγRI, FcγRIIa, FcγRIIb, FcγRIIc, FcγRIIIa, FcγRIIIb, FcRn), its pharmacokinetic properties (e.g., stability or half-life, bioavailability, tissue distribution, volume of distribution, concentration, elimination rate constant, elimination rate, area under the curve (AUC), clearance, $C_{max}$, $T_{max}$, $C_{min}$, fluctuation), its immunogenicity, its complement fixation or activation, and/or the CDC/ADCC/ADCP-related activities of the Fc region, among other properties described herein, relative to a corresponding wild-type Fc sequence of an antibody. Included are modified Fc regions of human and/or mouse origin.

In certain embodiments, an antibody comprises a hybrid Fc region, for example, an Fc region that comprises a combination of Fc domains (e.g., hinge, $CH_2$, $CH_3$, $CH_4$) from immunoglobulins of different species (e.g., human, mouse), different Ig classes, and/or different Ig subclasses. Also included are antibodies that comprise derivatized or otherwise modified Fc regions. In certain aspects, the Fc region is modified by phosphorylation, sulfation, acrylation, glycosylation, methylation, farnesylation, acetylation, amidation, and the like, for instance, relative to a wild-type or naturally-occurring Fc region. In certain embodiments, the Fc region comprises wild-type or native glycosylation patterns, or alternatively, it comprises increased glycosylation relative to a native form, decreased glycosylation relative to a native form, or it is entirely deglycosylated. As one example of a modified Fc glycoform, decreased glycosylation of an Fc region reduces binding to the C1q region of the first complement component C1, a decrease in ADCC-related activity, and/or a decrease in CDC-related activity. Certain embodiments thus employ a deglycosylated or aglycosylated Fc region. See, e.g., WO 2005/047337 for the production of exemplary aglycosylated Fc regions. Another example of an Fc region glycoform is generated by substituting the Q295 position with a cysteine residue (see, e.g., U.S. Application No. 2010/0080794), according to the Kabat et al. numbering system. Certain embodiments include Fc regions where about 80-100% of the glycoprotein in Fc region comprises a mature core carbohydrate structure that lacks fucose (see, e.g., U.S. Application No. 2010/0255013). Some embodiments include Fc regions that are optimized by substitution or deletion to reduce the level of fucosylation, for instance, to increase affinity for FcγRI, FcγRIa, or FcγRIIIa, and/or to improve phagocytosis by FcγRIIa-expressing cells (see U.S. Application Nos. 2010/0249382 and 2007/0148170).

As another example of a modified Fc glycoform, an Fc region of an antibody may comprise oligomannose-type N-glycans, and optionally have one or more of the following: increased ADCC effector activity, increased binding affinity for FcγRIIIA (and certain other FcRs), similar or increased binding specificity for the target of the IL-18BP polypeptide, similar or higher binding affinity for the target of the IL-18BP polypeptide, and/or similar or lower binding affinity for mannose receptor, relative to a corresponding Fc region that contains complex-type N-glycans (see, e.g., U.S. Application No. 2007/0092521 and U.S. Pat. No. 7,700,321). As another example, enhanced affinity of Fc regions for FcγRs has been achieved using engineered glycoforms generated by expression of antibodies in engineered or variant cell lines (see, e.g., Umana et al., Nat Biotechnol. 17:176-180, 1999; Davies et al., Biotechnol Bioeng. 74:288-294, 2001; Shields et al., J Biol Chem. 277:26733-26740, 2002; Shinkawa et al., 2003, J Biol Chem. 278:3466-3473, 2003; and U.S. Application No. 2007/0111281). Certain Fc region glycoforms comprise an increased proportion of N-glycoside bond type complex sugar chains, which do not have the 1-position of fucose bound to the 6-position of N-acetylglucosamine at the reducing end of the sugar chain (see, e.g., U.S. Application No. 2010/0092997). Particular embodiments may include IgG Fc region that is glycosylated with at least one galactose moiety connected to a respective terminal sialic acid moiety by an α-2,6 linkage, optionally where the Fc region has a higher anti-inflammatory activity relative to a corresponding, wild-type Fc region (see U.S. Application No. 2008/0206246). Certain of these and related altered glycosylation approaches have generated substantial enhancements of the capacity of Fc regions to selectively bind FcRs such as FcγRIII, to mediate ADCC, and to alter other properties of Fc regions, as described herein.

Certain variant, fragment, hybrid, or otherwise modified Fc regions of an antibody may have altered binding to one or more FcRs, and/or corresponding changes to effector function, relative to a corresponding, wild-type Fc sequence (e.g., same species, same Ig class, same Ig subclass). For instance, such Fc regions may have increased binding to one or more of Fcγ receptors, Fcα receptors, Fcε receptors, and/or the neonatal Fc receptor, relative to a corresponding, wild-type Fc sequence. In other embodiments, variant, fragment, hybrid, or modified Fc regions may have decreased binding to one or more of Fcγ receptors, Fcα receptors, Fcε receptors, and/or the neonatal Fc receptor, relative to a corresponding, wild-type Fc sequence. Specific FcRs are described elsewhere herein.

In some embodiments, an antibody comprises an Fc domain, comprising one or more mutations to increase binding to one or more of Fcγ receptors, Fcα receptors, Fcε receptors, and/or the neonatal Fc receptor, relative to a corresponding, wild-type Fc sequence. In some embodiments, an antibody comprises an IgG1 or IgG3 Fc domain, comprising one or more mutations to increase binding to one or more of Fcγ receptors, Fcα receptors, Fcε receptors, and/or the neonatal Fc receptor, relative to a corresponding, wild-type Fc sequence. In some embodiments, an antibody comprises an Fc domain, comprising one or more mutations to increase effector function. In some embodiments the at least one antibody comprises an Fc domain selected from a human IgG1 and IgG3, comprising one or more mutations to increase effector function.

In some embodiments, an antibody is a blocking antibody that comprises an Fc domain with high effector activity. In some embodiments, the blocking antibody comprises an Fc domain selected from a human IgG1 and IgG3, comprising one or more mutations to increase effector function. In some embodiments, an antibody is a partial-blocking antibody that comprises an Fc domain with high effector activity. In some embodiments, the partial-blocking antibody comprises an Fc domain selected from a human IgG1 and IgG3, comprising one or more mutations to increase effector function. In some embodiments, an antibody is a non-blocking antibody that comprises an Fc domain with high effector activity. In some embodiments, the non-blocking antibody comprises an Fc domain selected from a human IgG1 or IgG3, comprising one or more mutations to increase effector function.

In some embodiments, an antibody comprises an Fc domain, comprising one or more mutations to decrease binding to one or more of Fcγ receptors, Fcα receptors, Fcε receptors, and/or the neonatal Fc receptor, relative to a corresponding, wild-type Fc sequence. In some embodiments, an antibody comprises an IgG1 or IgG3 Fc domain, comprising one or more mutations to decrease binding to one or more of Fcγ receptors, Fcα receptors, Fcε receptors, and/or the neonatal Fc receptor, relative to a corresponding, wild-type Fc sequence. In some embodiments, an antibody comprises an Fc domain, comprising one or more mutations to decrease effector function. In some embodiments, an antibody comprises an Fc domain selected from a human IgG2 and IgG4, comprising one or more mutations to decrease effector function.

In some embodiments, an antibody is a blocking antibody comprising an Fc domain with low effector activity. In some embodiments, the blocking antibody comprises an Fc domain selected from a human IgG2 and IgG4, comprising one or more mutations to decrease effector function. In some embodiments, an antibody is a partial-blocking antibody comprising an Fc domain with low effector activity. In some embodiments, the partial-blocking antibody comprises an Fc domain selected from a human IgG2 and IgG4, comprising one or more mutations to decrease effector function. In some embodiments, an antibody is a non-blocking antibody comprising an Fc domain with low effector activity. In some embodiments, the non-blocking antibody comprises an Fc domain selected from a human IgG2 and IgG4, comprising one or more mutations to decrease effector function.

Specific examples of Fc variants having altered (e.g., increased, decreased) effector function/FcR binding can be found, for example, in U.S. Pat. Nos. 5,624,821 and 7,425,619; U.S. Application Nos. 2009/0017023, 2009/0010921, and 2010/0203046; and WO 2000/42072 and WO 2004/016750. Certain examples include human Fc regions having a one or more substitutions at position 298, 333, and/or 334, for example, S298A, E333A, and/or K334A (based on the numbering of the EU index of Kabat et al.), which have been shown to increase binding to the activating receptor FcγRIIIa and reduce binding to the inhibitory receptor FcγRIIb. These mutations can be combined to obtain double and triple mutation variants that have further improvements in binding to FcRs. Certain embodiments include a S298A/E333A/K334A triple mutant, which has increased binding to FcγRIIIa, decreased binding to FcγRIIb, and increased ADCC (see, e.g., Shields et al., J Biol Chem. 276:6591-6604, 2001; and Presta et al., Biochem Soc Trans. 30:487-490, 2002). See also engineered Fc glycoforms that have increased binding to FcRs, as disclosed in Umana et al., supra; and U.S. Pat. No. 7,662,925. Some embodiments include Fc regions that comprise one or more substitutions selected from 434S, 252Y/428L, 252Y/434S, and 428L/434S (see U.S. Application Nos. 2009/0163699 and 20060173170), based on the EU index of Kabat et al. Some embodiments include Fc regions that comprise one or more substitutions selected from L234A, L235A, and G237A (see U.S. application Ser. No. 17/779,425), based on the EU index of Kabat et al. Some embodiments include Fc regions that comprise substitutions at L234A and L235A, based on the EU index of Kabat et al. Some embodiments include Fc regions that comprise substitutions at L234A and G237A, based on the EU index of Kabat et al. Some embodiments include Fc regions that comprise substitutions at L235A and G237A, based on the EU index of Kabat et al. Some embodiments include Fc regions that comprise substitutions at L234A, L235A, and G237A, based on the EU index of Kabat et al. Some embodiments include Fc regions that comprise one or more substitutions selected from M252Y, S254T, and T256E, based on the EU index of Kabat et al. Some embodiments include Fc regions that comprise one or more substitutions selected from M428L and N434S, based on the EU index of Kabat et al. In some embodiments, the Fc substitutions disclosed herein are to an Fc domain selected from a human IgG1, IgG2, IgG3 or IgG4. In some embodiments, the Fc substitutions disclosed herein are to a human IgG1 Fc domain. In some embodiments, the Fc substitutions disclosed herein are to a human IgG2 Fc domain. In some embodiments, the Fc substitutions disclosed herein are to a human IgG3 Fc domain. In some embodiments, the Fc substitutions disclosed herein are to a human IgG4 Fc domain. In some embodiments, the antibody of the disclosure comprises one or more of the Fc substitutions disclosed herein and the $V_H$ and $V_L$ sequences that are at least 70, 75, 80, 85, 90, 95, 97, 98, 99, or 100% identical to the respective sequences from a single named antibody (e.g., SA04a) in Table A2, wherein the antibody comprises the CDRs of said single named antibody (e.g., SA04a) as recited in Table A1.

Certain variant hybrid, or modified Fc regions may have altered solubility relative to a corresponding, wild-type Fc sequence. In certain embodiments, such Fc regions may have increased solubility relative to a corresponding, wild-type Fc sequence. In other embodiments, variant hybrid, or modified Fc regions may have decreased solubility relative to a corresponding, wild-type Fc sequence. Solubility can be measured, for example, in vitro (e.g., under physiological conditions) according to routine techniques in the art. Exemplary solubility measurements are described elsewhere herein.

Variant Fc regions can also have one or more mutated hinge regions, as described, for example, in U.S. Application No. 2003/0118592. For instance, one or more cysteines in a hinge region can be deleted or substituted with a different amino acid. The mutated hinge region can comprise no cysteine residues, or it can comprise 1, 2, or 3 fewer cysteine residues than a corresponding, wild-type hinge region. In some embodiments, an Fc region having a mutated hinge region of this type exhibits a reduced ability to dimerize, relative to a wild-type Ig hinge region.

In some embodiments, an antibody or antigen binding fragment thereof may be conjugated to one or more cytotoxic or chemotherapeutic agents. In some embodiments, a herein-disclosed antibody is conjugated or operably linked to a radioisotope to form a radioconjugate and/or macrocyclic chelators useful for conjugating radiometal ions. The antibodies can be used in any of the compositions, methods, and/or kits described herein, and combined with one or more of the additional agents described herein.

Methods of Use and Pharmaceutical Compositions

Certain embodiments relate to methods of treating, ameliorating the symptoms of, and/or reducing the progression of, a disease or condition in a subject in need thereof, comprising administering to the subject an antibody that binds to IL-18BP, as described herein, or a pharmaceutical composition comprising the same. Also included are methods of stimulating an immune response in a subject in need thereof, for example, an IL-18 mediated immune response, comprising administering to the subject a pharmaceutical composition described herein. In some instances, the antibody antagonizes the binding/signaling activity between IL-18BP and its ligand, IL-18, and thereby increases IL-18-mediated signaling or activity (for example, increased induction of IFN-gamma, CXCL10, and/or TNFα). In some embodiments, as noted above, the disease or condition is a cancer or tumor, or an infectious disease. In some embodiments, the disease is any disease where activation of the immune system may be beneficial.

In some embodiments, as noted above, the disease or condition is a cancer or tumor or other proliferative disease or disorder, such as a lymphoproliferative disorder, a myeloproliferative disorder, proliferative enteritis, proliferative diabetic retinopathy, or a proliferative kidney disease. In some instances, the cancer or tumor expresses or overexpresses IL-18BP, IL-18, or both. In some instances, the proliferative disease or disorder is associated with increased expression of IL-18BP, IL-18, or both. In some instances, the cancer is a primary cancer. In some instances, the cancer is a metastatic cancer. Certain embodiments thus include methods of treating, reducing the severity of, or preventing a cancer in a patient in need thereof, comprising administering to the patient a composition described herein, including wherein the antibody is an IL-18BP antagonist, thereby treating, reducing the severity of, or preventing the cancer.

Exemplary cancers include, without limitation, bone cancer, prostate cancer, melanoma (e.g., metastatic melanoma), pancreatic cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia, hairy cell leukemias, acute lymphoblastic leukemias), lymphoma (e.g., non-Hodgkin's lymphomas, Hodgkin's lymphoma), hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, uterine cancer, esophageal cancer, brain cancer, head and neck cancers, cervical cancer, testicular cancer, thyroid cancer, and stomach cancer. In specific embodiments, the cancer is a metastatic cancer, for example, which has metastasized to the bone.

Also provided is an antibody, antigen binding fragment thereof, or pharmaceutical composition of the present disclosure for use as a medicament. An antibody, fragment thereof, or pharmaceutical composition of the present disclosure may be for use in any method of treatment disclosed herein. In particular embodiments, an antibody, fragment thereof, or pharmaceutical composition of the present disclosure may be for use in a method of treating, ameliorating the symptoms of, and/or reducing the progression of any disease or disorder disclosed herein, such as a cancer or tumor or other proliferative disease or disorder, such as a lymphoproliferative disorder, a myeloproliferative disorder, proliferative enteritis, proliferative diabetic retinopathy, or a proliferative kidney disease.

Certain embodiments include combination therapies, for instance, which comprise administering a pharmaceutical composition described herein (comprising an anti-IL-18BP antibody) in combination with one or more additional therapeutic agents, for example, immune-stimulating agents, immune checkpoint modulatory agents, and/or chemotherapeutic agents. In some embodiments, the additional therapeutic agent comprises IL-18, including human IL-18 (or a functional variant or fragment thereof).

In some embodiments, the additional therapeutic agent comprises an immune checkpoint modulatory agent. Particular examples of immune checkpoint modulatory agents include "antagonists" or "inhibitors" of one or more inhibitory immune checkpoint molecules, and "agonists" of one or more stimulatory immune checkpoint molecules. Generally, immune checkpoint molecules are components of the immune system that either turn up a signal (costimulatory molecules) or turn down a signal, the targeting of which has therapeutic potential in cancer because cancer cells can perturb the natural function of immune checkpoint molecules (see, e.g., Sharma and Allison, Science. 348:56-61, 2015; Topalian et al., Cancer Cell. 27:450-461, 2015; Pardoll, Nature Reviews Cancer. 12:252-264, 2012). In some embodiments, the immune checkpoint modulatory agent (e.g., antagonist, agonist) "binds" or "specifically binds" to the one or more immune checkpoint molecules, as described herein.

In particular embodiments, the immune checkpoint modulatory agent is a polypeptide or peptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein Antibodies are also included as polypeptides. Thus, in some embodiments, the immune checkpoint modulatory polypeptide agent is an "antibody as described herein.

In some embodiments, the agent is or comprises a "ligand," for example, a natural ligand, of the immune checkpoint molecule. A "ligand" refers generally to a substance or molecule that forms a complex with a target molecule (e.g., biomolecule) to serve a biological purpose, and includes a "protein ligand," which generally produces a signal by binding to a site on a target molecule or target protein. Thus, certain agents are protein ligands that, in nature, bind to an immune checkpoint molecule and produce a signal. Also included are "modified ligands," for example, protein ligands that are fused to a pharmacokinetic modifier, for example, an Fc region derived from an immunoglobulin.

In some embodiments, the agent is a "small molecule," which refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In some embodiments, the immune checkpoint modulatory agent is an antagonist or inhibitor of one or more inhibitory immune checkpoint molecules. Exemplary inhibitory immune checkpoint molecules include Programmed Death-Ligand 1 (PD-L1), Programmed Death-Ligand 2 (PD-L2), Programmed Death 1 (PD-1), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, and T-cell immunoreceptor with Ig and ITIM domains (TIGIT).

In certain embodiments, the agent is a PD-1 (receptor) antagonist or inhibitor, the targeting of which has been shown to restore immune function in the tumor environment (see, e.g., Phillips et al., Int Immunol. 27:39-46, 2015). PD-1 is a cell surface receptor that belongs to the immunoglobulin superfamily and is expressed on T cells and pro-B cells. PD-1 interacts with two ligands, PD-L1 and PD-L2. PD-1 functions as an inhibitory immune checkpoint molecule, for example, by reducing or preventing the activation of T-cells, which in turn reduces autoimmunity and promotes self-tolerance. The inhibitory effect of PD-1 is accomplished at least in part through a dual mechanism of promoting apoptosis in antigen specific T-cells in lymph nodes while also reducing apoptosis in regulatory T cells (suppressor T cells). Some examples of PD-1 antagonists or inhibitors include an antibody or small molecule that specifically binds to PD-1 and reduces one or more of its immune-suppressive activities, for example, its downstream signaling or its interaction with PD-L1. Specific examples of PD-1 antagonists or inhibitors include the antibodies nivolumab, pembrolizumab, PDR001, MK-3475, AMP-224, AMP-514, and pidilizumab, and antigen binding fragments thereof (see, e.g., U.S. Pat. Nos. 8,008,449; 8,993,731; 9,073,994; 9,084,776; 9,102,727; 9,102,728; 9,181,342; 9,217,034; 9,387,247; 9,492,539; 9,492,540; and U.S. Application Nos. 2012/0039906; 2015/0203579).

In some embodiments, the agent is a PD-L1 antagonist or inhibitor. As noted above, PD-L1 is one of the natural ligands for the PD-1 receptor. General examples of PD-L1 antagonists or inhibitors include an antibody or small molecule that specifically binds to PD-L1 and reduces one or more of its immune-suppressive activities, for example, its binding to the PD-1 receptor. Specific examples of PD-L1 antagonists include the antibodies atezolizumab (MPDL3280A), avelumab (MSB0010718C), and durvalumab (MEDI4736), and antigen binding fragments thereof (see, e.g., U.S. Pat. Nos. 9,102,725; 9,393,301; 9,402,899; 9,439,962).

In some embodiments, the agent is a PD-L2 antagonist or inhibitor. As noted above, PD-L2 is one of the natural ligands for the PD-1 receptor. General examples of PD-L2 antagonists or inhibitors include an antibody or small molecule that specifically binds to PD-L2 and reduces one or more of its immune-suppressive activities, for example, its binding to the PD-1 receptor.

In some embodiments, the agent is a CTLA-4 antagonist or inhibitor. CTLA4 or CTLA-4 (cytotoxic T-lymphocyte-associated protein 4), also known as CD152 (cluster of differentiation 152), is a protein receptor that functions as an inhibitory immune checkpoint molecule, for example, by transmitting inhibitory signals to T-cells when it is bound to CD80 or CD86 on the surface of antigen-presenting cells. General examples CTLA-4 antagonists or inhibitors include an antibody or small molecule that specifically binds to CTLA-4. Particular examples include the antibodies ipilimumab and tremelimumab, and antigen binding fragments thereof. At least some of the activity of ipilimumab is believed to be mediated by antibody-dependent cell-mediated cytotoxicity (ADCC) killing of suppressor Tregs that express CTLA-4.

In some embodiments, the agent is an IDO antagonist or inhibitor, or a TDO antagonist or inhibitor. IDO and TDO are tryptophan catabolic enzymes with immune-inhibitory properties. For example, IDO is known to suppress T-cells and NK cells, generate and activate Tregs and myeloid-derived suppressor cells, and promote tumor angiogenesis. General examples of IDO and TDO antagonists or inhibitors include an antibody or small molecule that specifically binds to IDO or TDO (see, e.g., Platten et al., Front Immunol. 5: 673, 2014) and reduces or inhibits one or more immune-suppressive activities. Specific examples of IDO antagonists or inhibitors include indoximod (NLG-8189), 1-methyl-tryptophan (1MT), β-Carboline (norharmane; 9H-pyrido[3, 4-b]indole), rosmarinic acid, and epacadostat (see, e.g., Sheridan, Nature Biotechnology. 33:321-322, 2015). Specific examples of TDO antagonists or inhibitors include 680C91 and LM10 (see, e.g., Pilotte et al., PNAS USA. 109:2497-2502, 2012).

In some embodiments, the agent is a TIM-3 antagonist or inhibitor. T-cell Immunoglobulin domain and Mucin domain 3 (TIM-3) is expressed on activated human CD4+ T-cells and regulates Th1 and Th17 cytokines. TIM-3 also acts as a negative regulator of Th1/Tc1 function by triggering cell death upon interaction with its ligand, galectin-9. TIM-3 contributes to the suppressive tumor microenvironment and its overexpression is associated with poor prognosis in a variety of cancers (see, e.g., Li et al., Acta Oncol. 54:1706-13, 2015). General examples of TIM-3 antagonists or inhibitors include an antibody or small molecule that specifically binds to TIM-3 and reduces or inhibits one or more of its immune-suppressive activities.

In some embodiments, the agent is a LAG-3 antagonist or inhibitor. Lymphocyte Activation Gene-3 (LAG-3) is expressed on activated T-cells, natural killer cells, B-cells and plasmacytoid dendritic cells. It negatively regulates cellular proliferation, activation, and homeostasis of T-cells, in a similar fashion to CTLA-4 and PD-1 (see, e.g., Workman and Vignali. European Journal of Immun. 33: 970-9, 2003; and Workman et al., Journal of Immun. 172: 5450-5, 2004), and has been reported to play a role in Treg suppressive function (see, e.g., Huang et al., Immunity. 21: 503-13, 2004). LAG3 also maintains CD8+ T-cells in a tolerogenic state and combines with PD-1 to maintain CD8 T-cell exhaustion. General examples of LAG-3 antagonists or inhibitors include an antibody or small molecule that specifically binds to LAG-3 and inhibits one or more of its immune-suppressive activities. Specific examples include the antibody BMS-986016, and antigen binding fragments thereof.

In some embodiments, the agent is a VISTA antagonist or inhibitor. V-domain Ig suppressor of T cell activation (VISTA) is primarily expressed on hematopoietic cells and is an inhibitory immune checkpoint regulator that suppresses T-cell activation, induces Foxp3 expression, and is highly expressed within the tumor microenvironment where it suppresses anti-tumor T cell responses (see, e.g., Lines et al., Cancer Res. 74:1924-32, 2014). General examples of VISTA antagonists or inhibitors include an antibody or small molecule that specifically binds to VISTA and reduces one or more of its immune-suppressive activities.

In some embodiments, the agent is a BTLA antagonist or inhibitor. B- and T-lymphocyte attenuator (BTLA; CD272) expression is induced during activation of T-cells, and it inhibits T-cells via interaction with tumor necrosis family receptors (TNF-R) and B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses, for example, by inhibiting the function of human CD8+ cancer-specific T-cells (see, e.g., Derre et al., J Clin Invest 120:157-67, 2009). General examples of BTLA antagonists or inhibitors include an antibody or small molecule that specifically binds to BTLA-4 and reduce one or more of its immune-suppressive activities.

In some embodiments, the agent is an HVEM antagonist or inhibitor, for example, an antagonist or inhibitor that specifically binds to HVEM and interferes with its interaction with BTLA or CD160. General examples of HVEM antagonists or inhibitors include an antibody or small molecule that specifically binds to HVEM, optionally reduces the HVEM/BTLA and/or HVEM/CD160 interaction, and thereby reduces one or more of the immune-suppressive activities of HVEM.

In some embodiments, the agent is a CD160 antagonist or inhibitor, for example, an antagonist or inhibitor that specifically binds to CD160 and interferes with its interaction with HVEM. General examples of CD160 antagonists or inhibitors include an antibody or small molecule that specifically binds to CD160, optionally reduces the CD160/HVEM interaction, and thereby reduces or inhibits one or more of its immune-suppressive activities.

In some embodiments, the agent is a TIGIT antagonist or inhibitor. T cell Ig and ITIM domain (TIGIT) is a co-inhibitory receptor that is found on the surface of a variety of lymphoid cells, and suppresses antitumor immunity, for example, via Tregs (Kurtulus et al., J Clin Invest. 125:4053-4062, 2015). General examples of TIGIT antagonists or inhibitors include an antibody or small molecule that specifically binds to TIGIT and reduce one or more of its immune-suppressive activities (see, e.g., Johnston et al., Cancer Cell. 26:923-37, 2014).

In certain embodiments, the immune checkpoint modulatory agent is an agonist of one or more stimulatory immune checkpoint molecules. Exemplary stimulatory immune checkpoint molecules include OX40, CD40, Glucocorticoid-Induced TNFR Family Related Gene (GITR), CD137 (4-1BB), CD27, CD28, CD226, and Herpes Virus Entry Mediator (HVEM).

In some embodiments, the agent is an OX40 agonist. OX40 (CD134) promotes the expansion of effector and memory T cells, and suppresses the differentiation and activity of T-regulatory cells (see, e.g., Croft et al., Immunol Rev. 229:173-91, 2009). Its ligand is OX40L (CD252). Since OX40 signaling influences both T-cell activation and survival, it plays a key role in the initiation of an anti-tumor immune response in the lymph node and in the maintenance of the anti-tumor immune response in the tumor microenvironment. General examples of OX40 agonists include an antibody or small molecule or ligand that specifically binds to OX40 and increases one or more of its immunostimulatory activities. Specific examples include OX86, OX-40L, Fc-OX40L, GSK3174998, MEDI0562 (a humanized OX40 agonist), MED16469 (murine OX4 agonist), and MED16383 (an OX40 agonist), and antigen binding fragments thereof.

In some embodiments, the agent is a CD40 agonist. CD40 is expressed on antigen-presenting cells (APC) and some malignancies. Its ligand is CD40L (CD154). On APC, ligation results in upregulation of costimulatory molecules, potentially bypassing the need for T-cell assistance in an antitumor immune response. CD40 agonist therapy plays an important role in APC maturation and their migration from the tumor to the lymph nodes, resulting in elevated antigen presentation and T cell activation. Anti-CD40 agonist antibodies produce substantial responses and durable anticancer immunity in animal models, an effect mediated at least in part by cytotoxic T-cells (see, e.g., Johnson et al. Clin Cancer Res. 21: 1321-1328, 2015; and Vonderheide and Glennie, Clin Cancer Res. 19:1035-43, 2013). General examples of CD40 agonists include an antibody or small molecule or ligand that specifically binds to CD40 and increases one or more of its immunostimulatory activities. Specific examples include sotigalilmab, CP-870,893, dacetuzumab, Chi Lob 7/4, ADC-1013, CD40L, rhCD40L, and antigen binding fragments thereof.

In some embodiments, the agent is a GITR agonist. Glucocorticoid-Induced TNFR family Related gene (GITR) increases T cell expansion, inhibits the suppressive activity of Tregs, and extends the survival of T-effector cells. GITR agonists have been shown to promote an anti-tumor response through loss of Treg lineage stability (see, e.g., Schaer et al., Cancer Immunol Res. 1:320-31, 2013). These diverse mechanisms show that GITR plays an important role in initiating the immune response in the lymph nodes and in maintaining the immune response in the tumor tissue. Its ligand is GITRL. General examples of GITR agonists include an antibody or small molecule or ligand that specifically binds to GITR and increases one or more of its immunostimulatory activities. Specific examples include GITRL, INCAGN01876, DTA-1, MEDI1873, and antigen binding fragments thereof.

In some embodiments, the agent is a CD137 agonist. CD137 (4-1BB) is a member of the tumor necrosis factor (TNF) receptor family, and crosslinking of CD137 enhances T-cell proliferation, IL-2 secretion, survival, and cytolytic activity. CD137-mediated signaling also protects T-cells such as CD8+ T-cells from activation-induced cell death. General examples of CD137 agonists include an antibody or small molecule or ligand that specifically binds to CD137 and increases one or more of its immunostimulatory activities. Specific examples include the CD137 (or 4-1BB) ligand (see, e.g., Shao and Schwarz, J Leukoc Biol. 89:21-9, 2011) and the antibody utomilumab, including antigen binding fragments thereof.

In some embodiments, the agent is a CD27 agonist. Stimulation of CD27 increases antigen-specific expansion of naïve T cells and contributes to T-cell memory and long-term maintenance of T-cell immunity. Its ligand is CD70. The targeting of human CD27 with an agonist antibody stimulates T-cell activation and antitumor immunity (see, e.g., Thomas et al., Oncoimmunology. 2014; 3:e27255. doi:10.4161/onci.27255; and He et al., J Immunol. 191: 4174-83, 2013). General examples of CD27 agonists include an antibody or small molecule or ligand that specifically binds to CD27 and increases one or more of its immunostimulatory activities. Specific examples include CD70 and the antibodies varlilumab and CDX-1127 (1F5), including antigen binding fragments thereof.

In some embodiments, the agent is a CD28 agonist. CD28 is constitutively expressed CD4+ T cells some CD8+ T cells. Its ligands include CD80 and CD86, and its stimulation increases T-cell expansion. General examples of CD28 agonists include an antibody or small molecule or ligand that specifically binds to CD28 and increases one or more of its immunostimulatory activities. Specific examples include CD80, CD86, the antibody TAB08, and antigen binding fragments thereof.

In some embodiments, the agent is CD226 agonist. CD226 is a stimulating receptor that shares ligands with TIGIT, and opposite to TIGIT, engagement of CD226 enhances T-cell activation (see, e.g., Kurtulus et al., J Clin Invest. 125:4053-4062, 2015; Bottino et al., J Exp Med. 1984:557-567, 2003; and Tahara-Hanaoka et al., Int Immunol. 16:533-538, 2004). General examples of CD226 agonists include an antibody or small molecule or ligand (e.g., CD112, CD155) that specifically binds to CD226 and increases one or more of its immunostimulatory activities.

In some embodiments, the agent is an HVEM agonist. Herpesvirus entry mediator (HVEM), also known as tumor necrosis factor receptor superfamily member 14 (TNFRSF14), is a human cell surface receptor of the TNF-receptor superfamily. HVEM is found on a variety of cells including T-cells, APCs, and other immune cells. Unlike other receptors, HVEM is expressed at high levels on resting T-cells and down-regulated upon activation. It has been shown that HVEM signaling plays a crucial role in the early phases of T-cell activation and during the expansion of tumor-specific lymphocyte populations in the lymph nodes. General examples of HVEM agonists include an antibody or small molecule or ligand that specifically binds to HVEM and increases one or more of its immunostimulatory activities.

In some embodiments, the additional therapeutic agent comprises a chemotherapeutic agent, for example, small molecule chemotherapeutic agents. Non-limiting examples of chemotherapeutic agents include alkylating agents, antimetabolites, cytotoxic antibiotics, topoisomerase inhibitors (type 1 or type II), an anti-microtubule agents, among others.

In certain embodiments, the methods and compositions described herein are sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In some embodiments, the methods and compositions described herein reduce the growth rate (e.g., in vivo or in vitro, including cancer cells isolated from a biopsy or other sample and grown in vitro) of the cancer by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some instances, the methods and compositions described herein reduce cancer cell initiation, migration, adhesion, invasiveness, and/or metastasis by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control. In some instances, the methods and compositions described herein reduce angiogenesis in the tumor environment by about or at least about 5, 10, 15, 20, 25, 30, 35, 40, 45, 50, 60, 70, 80, 90, 100, 200, 300, 400, 500, 600, 700, 800, 900, 1000, 2000% or more relative to an untreated control.

In certain embodiments, the disease or condition is a myelodysplastic syndrome (MDS) (see, for example, Wang et al., Blood. 140 (Supplement 1): 12297, 2022), for example, for which antagonizing IL-18BP represents a viable approach. MDS refers to a group of cancers in which immature blood cells in the bone marrow do not mature, and as a result, do not develop into healthy blood cells. Certain embodiments thus include methods of treating, reducing the severity of, or preventing an MDS in a patient in need thereof, comprising administering to the patient a composition described herein, including wherein the antibody is an IL-18BP antagonist, thereby treating, reducing the severity of, or preventing the MDS.

In some embodiments, the disease or condition is an infectious disease. For instance, in certain embodiments, the infectious disease is selected from viral (see, for example, Vecchie et al., J Cell Physiol. 236(3): 1638-1657, 2021), bacterial (see, for example, Kinoshita et al., Ann Surg. 240(2): 313-20, 2004), fungal (for example, yeast), and protozoal infections. Some embodiments thus include methods of treating, reducing the severity of, or preventing an infectious disease in a patient in need thereof, comprising administering to the patient a composition described herein, including wherein the antibody is an IL-18BP antagonist, thereby treating, reducing the severity of, or preventing the infectious disease.

In certain embodiments, the methods and compositions described herein are sufficient to result in stable disease. In certain embodiments, the methods and compositions described herein are sufficient to result in clinically relevant reduction in symptoms of a particular disease indication known to the skilled clinician.

For in vivo use, certain embodiments include pharmaceutical compositions, comprising an antibody, as described herein, and a pharmaceutically acceptable carrier. To prepare a therapeutic or pharmaceutical composition, an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, intraocular, subcutaneous, direct instillation into the bladder, or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate therapeutic or pharmaceutical composition, can be carried out via any of the accepted modes of administration of agents for serving similar utilities. The therapeutic or pharmaceutical compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, ocular, intradermal, intramuscular, subcutaneous, installation into the bladder, transdermal, inhalation, sublingual, buccal, rectal, vaginal or topical. Preferred modes of administration depend upon the nature of the condition to be treated or prevented. Particular embodiments include administration by IV infusion.

Carriers can include, for example, pharmaceutically or physiologically acceptable carriers, excipients, or stabilizers that are non-toxic to the cell or mammal being exposed thereto at the dosages and concentrations employed. Often the physiologically-acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine, histidine, and/or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and in some instances may be determined empirically. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related therapeutic or pharmaceutical compositions thus include, without limitation, oral, parenteral, nasal, intravenous, ocular, intradermal, intramuscular, subcutaneous, installation into the bladder, transdermal, inhalation, sublingual, buccal, rectal, vaginal and topical. The term parenteral as used herein includes subcutaneous injections, intravenous, instillation into the bladder, intramuscular, intrasternal injection or infusion techniques. Therapeutic or pharmaceutical compositions according to certain embodiments of the present disclosure are formulated so as to allow the active ingredients contained therein to be bioavailable upon administration of the composition to a subject or patient. Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see Remington: *The Science and Practice of Pharmacy,* 23th Edition (Philadelphia College of Pharmacy and Science, 2000). The composition to be administered will typically contain a therapeutically effective amount of an agent described herein, for treatment of a disease or condition of interest.

A therapeutic or pharmaceutical composition can be in the form of a solid or liquid. In some embodiments, the carrier(s) are particulate, so that the compositions are, for example, in tablet or powder form. The carrier(s) can be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid. Certain embodiments include sterile, injectable solutions.

As a solid composition for oral administration, the pharmaceutical composition may be formulated into a powder, granule, gel, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The therapeutic or pharmaceutical composition may be in the form of a liquid, for example, an elixir, syrup, solution, gel, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid therapeutic or pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid therapeutic or pharmaceutical composition intended for either parenteral, intraocular, or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral therapeutic or pharmaceutical compositions contain between about 4% and about 75% of the agent of interest. In certain embodiments, therapeutic or pharmaceutical compositions and preparations are prepared so that a parenteral dosage unit contains between 0.01 to 10% by weight of the agent of interest prior to dilution.

The therapeutic or pharmaceutical compositions may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a therapeutic or pharmaceutical composition for topical administration. If intended for transdermal administration, the composition may include a transdermal patch or iontophoresis device.

The therapeutic or pharmaceutical compositions may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The therapeutic or pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The therapeutic or pharmaceutical compositions in solid or liquid form may include a component that binds to agent and thereby assists in the delivery of the compound. Suitable components that may act in this capacity include monoclonal or polyclonal antibodies, one or more proteins or a liposome.

The therapeutic or pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a therapeutic or pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The therapeutic or pharmaceutical compositions may be administered in a therapeutically effective amount, which will vary depending upon a variety of factors including the activity of the specific compound employed; the metabolic stability and length of action of the compound; the age, body weight, general health, sex, and diet of the subject; the mode and time of administration; the rate of excretion; the drug combination; the severity of the particular disorder or condition; and the subject undergoing therapy.

Also included are patient care kits, comprising (a) an antibody that binds to IL-18BP, as described herein; and optionally (b) at least one additional therapeutic agent. In certain kits, (a) and (b) are in separate therapeutic compositions. In some kits, (a) and (b) are in the same therapeutic composition.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

In some embodiments, a patient care kit contains separate containers, dividers, or compartments for the composition(s) and informational material(s). For example, the composition(s) can be contained in a bottle, vial, or syringe, and the informational material(s) can be contained in association with the container. In some embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an antibody and optionally at least one additional therapeutic agent. For example, the kit includes a plurality of syringes, ampules, foil packets, or blister packs, each containing a single unit dose of an antibody and optionally at least one additional therapeutic agent. The containers of the kits can be air tight, waterproof (e.g., impermeable to changes in moisture or evaporation), and/or light-tight.

The patient care kit optionally includes a device suitable for administration of the composition, e.g., a syringe, inhalant, dropper (e.g., eye dropper), swab (e.g., a cotton swab or wooden swab), or any such delivery device. In some embodiments, the device is an implantable device that dispenses metered doses of the agent(s). Also included are methods of providing a kit, e.g., by combining the components described herein.

Expression and Purification Systems

Certain embodiments include methods and related compositions for expressing and purifying an anti-IL-18BP antibody described herein. Such recombinant anti-IL-18BP antibodies can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6. As one general example, anti-IL-18BP antibodies may be prepared by a procedure including one or more of the steps of: (a) preparing a construct that comprises a polynucleotide sequence which encodes an anti-IL-18BP antibody heavy chain and/or light chains, and which is operably linked to a regulatory element; (b) introducing the construct into a host cell; (c) culturing the host cell to express the anti-IL-18BP antibody; and (d) isolating the anti-IL-18BP from the host cell.

Certain embodiments thus include polynucleotides that encode an anti-IL-18BP antibody described herein, including vectors comprising said polynucleotides, and host cells comprising the polynucleotides and/or vectors. In order to express a desired polypeptide, a nucleotide sequence encoding an anti-IL-18BP, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems.

The "control elements" or "regulatory sequences" present in an expression vector are those non-translated regions of the vector-enhancers, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. Coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

Certain embodiments may employ *E. Coli*-based expression systems (see, e.g., Structural Genomics Consortium et al., *Nature Methods.* 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. Coli*, such as ROSETTA™ (DE3) and Rosetta 2 (DE3) strains. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG. Particular embodiments employ hexahistidine tags (such as those sold under the trademark HIS·TAG® fusions), followed by immobilized metal affinity chromatography (IMAC) purification, or related techniques. In certain aspects, however, clinical grade proteins can be isolated from *E. Coli* inclusion bodies, without or without the use of affinity tags (see, e.g., Shimp et al., *Protein Expr Purif* 50:58-67, 2006). As a further example, certain embodiments may employ a cold-shock induced *E. Coli* high-yield production system, because overexpression of proteins in *Escherichia coli* at low temperature improves their solubility and stability (see, e.g., Qing et al., Nature Biotechnology. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544 (1987). Also included are *Pichia pandoris* expression systems (see, e.g., Li et al., Nature Biotechnology. 24, 210-215, 2006; and Hamilton et al., Science, 301:1244, 2003). Certain embodiments include yeast systems that are engineered to selectively glycosylate proteins, including yeast that have humanized N-glycosylation pathways, among others (see, e.g., Hamilton et al., Science. 313:1441-1443, 2006; Wildt et al., Nature Reviews Microbiol. 3:119-28, 2005; and Gerngross et al., Nature-Biotechnology. 22:1409-1414, 2004; U.S. Pat. Nos. 7,629, 163; 7,326,681; and 7,029,872). Merely by way of example, recombinant yeast cultures can be grown in Fernbach Flasks or 15L, 50L, 100L, and 200L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et al., EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. *Frugiperda* cells or *Trichoplusia* cells in which the polypeptide of interest may be expressed (Engelhard et al., Proc. Natl. Acad. Sci. U.S.A. 91:3224-3227 (1994)). Also included are baculovirus expression systems, including those that utilize SF9, SF21, and Tni cells (see, e.g., Murphy and Piwnica-Worms, Curr Protoc Protein Sci. Chapter 5:Unit 5.4, 2001). Insect systems can provide post-translation modifications that are similar to mammalian systems.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., J. Gen Virol. 36:59 (1977)); baby hamster kidney cells (BHK, ATCC CCL 10); mouse sertoli cells (TM4, Mather, Biol. Reprod. 23:243-251 (1980)); monkey kidney cells (CVT ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1L and 5L spinners, 5L, 14L, 40L, 100L and 200L stir tank bioreactors, or 20/50L and 100/200L WAVE bioreactors, among others known in the art.

Also included is the cell-free expression of proteins. These and related embodiments typically utilize purified RNA polymerase, ribosomes, tRNA and ribonucleotides; these reagents may be produced by extraction from cells or from a cell-based expression system.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf Et al., Results Probl. Cell Differ. 20:125-162 (1994)).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Any number of selection systems may be used to recover transformed or transduced cell lines. These include, but are not limited to, the herpes simplex virus thymidine kinase (Wigler et al., Cell 11:223-232 (1977)) and adenine phosphoribosyltransferase (Lowy et al., Cell 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., PNAS USA. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. Sci. U.S.A. 85:8047-51 (1988)). The use of visible markers has gained popularity with such markers as green fluorescent protein (GFP) and other fluorescent proteins (e.g., RFP, YFP), anthocyanins, β-glucuronidase and its substrate GUS, and luciferase and its substrate luciferin, being widely used not only to identify transformants, but also to quantify the amount of transient or stable protein expression attributable to a specific vector system (see, e.g., Rhodes et al., Methods Mol. Biol. 55:121-131 (1995)).

Also included are high-throughput protein production systems, or micro-production systems. Certain aspects may utilize, for example, hexa-histidine fusion tags for protein expression and purification on metal chelate-modified slide surfaces or MagneHis Ni-Particles (see, e.g., Kwon et al., BMC Biotechnol. 9:72, 2009; and Lin et al., Methods Mol Biol. 498:129-41, 2009)). Also included are high-throughput cell-free protein expression systems (see, e.g., Sitaraman et al., Methods Mol Biol. 498:229-44, 2009). These and related embodiments can be used, for example, to generate microarrays of antibodies which can then be used for screening libraries to identify antibodies and antigen binding domains that interact with the IL-18BP polypeptide(s) of interest.

Although the foregoing embodiments have been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

Exemplary Enumerated Embodiments The following non-limiting enumerated embodiments are provided as exemplary.

Embodiment I-1. An antibody specific for interleukin-18 binding protein (IL-18BP), wherein the antibody interferes with the binding of IL-18 to IL-18BP.

Embodiment I-2. The antibody of embodiment I-1, wherein the antibody binds to a conformational epitope of IL-18BP.

Embodiment I-3. The antibody of embodiment I-2, wherein the antibody binds two or more of the amino acid residues T51, S53, S75, H79, R83, S88, S90, T110, H114, S115, T116, and S119 of SEQ ID NO: 372.

Embodiment I-4. The antibody of embodiment I-2, wherein the antibody binds the amino acid residues T51, S53, S75, H79, R83, S88, S90, T110, H114, S115, T116, and S119 of SEQ ID NO: 372.

Embodiment I-5. The antibody of embodiment I-1, wherein the antibody binds to a linear epitope of IL-18BP.

Embodiment I-6. The antibody of any one of embodiments I-1 to I-5, wherein the antibody binds to the binding interface between IL-18 and a mature form of IL-18BP.

Embodiment I-7. The antibody of embodiment I-6, wherein the antibody binds the amino acid residues S75, H79, T116, S119 of SEQ ID NO: 372.

Embodiment I-8. The antibody of any one of embodiments I-1 to I-7, wherein the antibody binds to human IL-18BP and cynomolgus IL-18BP but does not bind to mouse IL-18BP.

Embodiment I-9. The antibody of any one of embodiments I-1- to I-7, wherein the antibody binds to human IL-18BP, cynomolgus IL-18BP, and mouse IL-18BP.

Embodiment I-10. The antibody of any one of embodiments I-1 to I-9, wherein the antibody binds to IL-18BP with a binding affinity that is stronger than the binding affinity between IL-18 and IL-18BP ($K_D$~650 pM), optionally a binding affinity of about 1 µm to about 650 µm, or about or less than about 1, 5, 10, 20, 30, 40, 50, 60, 70, 80, 90, 100, 110, 120, 130, 140, 150, 160, 170, 180, 190, 200, or 300, 400, 500, 600, or 650 pM.

Embodiment I-11. The antibody of any one of embodiments I-1 to I-10, wherein the antibody is an IL-18BP antagonist, which antagonizes the binding activity between IL-18BP and IL-18.

Embodiment I-12. The antibody of embodiment I-11, wherein the antibody blocks the inhibitory activity of IL-18BP towards IL-18, and thereby increases IL-18-mediated signaling, including induction of IFN-gamma, CXCL10, and/or TNFα.

Embodiment I-13. The antibody of any one of embodiments I-1 to I-12, comprising an IgA (including subclasses IgA1 and IgA2), IgD, IgE, IgG (including subclasses IgG1, IgG2, IgG3, and IgG4), or IgM Fc domain, optionally a human Fc domain, or a hybrid and/or variant thereof.

Embodiment I-14. The antibody of embodiment I-13, comprising an IgG Fc domain with high effector function in humans, optionally an IgG1 or IgG3 Fc domain.

Embodiment I-15. The antibody of embodiment I-13, comprising an IgG Fc domain with low effector function in humans, optionally an IgG2 or IgG4 Fc domain.

Embodiment I-16. The antibody of any one of embodiments I-1 to I-15, wherein the antibody is a monoclonal antibody.

Embodiment I-17. The antibody of any one of embodiments I-1 to I-16, wherein the antibody is a humanized antibody.

Embodiment I-18. The antibody of any one of embodiments I-1 to I-17, wherein the antibody is an scFv.

Embodiment I-19. The antibody of any one of embodiments I-1 to I-18, wherein the antibody comprises:
  a) a heavy chain variable region ($V_H$) that comprises complementary determining region $V_H$CDR1, $V_H$CDR2, and $V_H$CDR3 sequences selected from Table A1 and variants thereof which specifically bind to IL-18BP; and
  b) a light chain variable region ($V_L$) that comprises complementary determining region $V_L$CDR1, $V_L$CDR2, and $V_L$CDR3 sequences selected from Table A1 and variants thereof which specifically bind to IL-18BP.

Embodiment I-20. The antibody of embodiment I-19, wherein:
  a) the $V_H$CDR1, $V_H$CDR2, and $V_H$CDR3 sequences comprise SEQ ID NOs: 1-3, respectively, and the $V_L$CDR1, $V_L$CDR2, and $V_L$CDR3 sequences comprise SEQ ID NOs: 4-6, respectively;
  b) the $V_H$CDR1, $V_H$CDR2, and $V_H$CDR3 sequences comprise SEQ ID NOs: 7-9, respectively, and the $V_L$CDR1, $V_L$CDR2, and $V_L$CDR3 sequences comprise SEQ ID NOs: 10-12, respectively;
  c) the $V_H$CDR1, $V_H$CDR2, and $V_H$CDR3 sequences comprise SEQ ID NOs: 13-15, respectively, and the $V_L$CDR1, $V_L$CDR2, and $V_L$CDR3 sequences comprise SEQ ID NOs: 16-18, respectively;
  d) the $V_H$CDR1, $V_H$CDR2, and $V_H$CDR3 sequences comprise SEQ ID NOs: 19-21, respectively, and the $V_L$CDR1, $V_L$CDR2, and $V_L$CDR3 sequences comprise SEQ ID NOs: 22-24, respectively;
  e) the $V_H$CDR1, $V_H$CDR2, and $V_H$CDR3 sequences comprise SEQ ID NOs: 25-27, respectively, and the $V_L$CDR1, $V_L$CDR2, and $V_L$CDR3 sequences comprise SEQ ID NOs: 28-30, respectively;
  f) the $V_H$CDR1, $V_H$CDR2, and $V_H$CDR3 sequences comprise SEQ ID NOs: 31-33, respectively, and the $V_L$CDR1, $V_L$CDR2, and $V_L$CDR3 sequences comprise SEQ ID NOs: 34-36, respectively;
  g) the $V_H$CDR1, $V_H$CDR2, and $V_H$CDR3 sequences comprise SEQ ID NOs: 37-39, respectively, and the $V_L$CDR1, $V_L$CDR2, and $V_L$CDR3 sequences comprise SEQ ID NOs: 40-42, respectively;
  h) the $V_H$CDR1, $V_H$CDR2, and $V_H$CDR3 sequences comprise SEQ ID NOs: 43-45, respectively, and the $V_L$CDR1, $V_L$CDR2, and $V_L$CDR3 sequences comprise SEQ ID NOs: 46-48, respectively;
  i) the $V_H$CDR1, $V_H$CDR2, and $V_H$CDR3 sequences comprise SEQ ID NOs: 49-51, respectively, and the $V_L$CDR1, $V_L$CDR2, and $V_L$CDR3 sequences comprise SEQ ID NOs: 52-54, respectively;
  j) the $V_H$CDR1, $V_H$CDR2, and $V_H$CDR3 sequences comprise SEQ ID NOs: 55-57, respectively, and the $V_L$CDR1, $V_L$CDR2, and $V_L$CDR3 sequences comprise SEQ ID NOs: 58-60, respectively;
  k) the $V_H$CDR1, $V_H$CDR2, and $V_H$CDR3 sequences comprise SEQ ID NOs: 61-63, respectively, and the $V_L$CDR1, $V_L$CDR2, and $V_L$CDR3 sequences comprise SEQ ID NOs: 64-66, respectively;
l) the $V_H$CDR1, $V_H$CDR2, and $V_H$CDR3 sequences comprise SEQ ID NOs: 67-69, respectively, and the $V_L$CDR1, $V_L$CDR2, and $V_L$CDR3 sequences comprise SEQ ID NOs: 70-72, respectively;
m) the $V_H$CDR1, $V_H$CDR2, and $V_H$CDR3 sequences comprise SEQ ID NOs: 73-75, respectively, and the $V_L$CDR1, $V_L$CDR2, and $V_L$CDR3 sequences comprise SEQ ID NOs: 76-78, respectively;
n) the $V_H$CDR1, $V_H$CDR2, and $V_H$CDR3 sequences comprise SEQ ID NOs: 79-81, respectively, and the $V_L$CDR1, $V_L$CDR2, and $V_L$CDR3 sequences comprise SEQ ID NOs: 82-84, respectively;
o) the $V_H$CDR1, $V_H$CDR2, and $V_H$CDR3 sequences comprise SEQ ID NOs: 85-87, respectively, and the $V_L$CDR1, $V_L$CDR2, and $V_L$CDR3 sequences comprise SEQ ID NOs: 88-90, respectively;
p) the $V_H$CDR1, $V_H$CDR2, and $V_H$CDR3 sequences comprise SEQ ID NOs: 91-93, respectively, and the $V_L$CDR1, $V_L$CDR2, and $V_L$CDR3 sequences comprise SEQ ID NOs: 94-96, respectively;
q) the $V_H$CDR1, $V_H$CDR2, and $V_H$CDR3 sequences comprise SEQ ID NOs: 97-99, respectively, and the $V_L$CDR1, $V_L$CDR2, and $V_L$CDR3 sequences comprise SEQ ID NOs: 100-102, respectively;
r) the $V_H$CDR1, $V_H$CDR2, and $V_H$CDR3 sequences comprise SEQ ID NOs: 103-105, respectively, and the $V_L$CDR1, $V_L$CDR2, and $V_L$CDR3 sequences comprise SEQ ID NOs: 106-108, respectively;
s) the $V_H$CDR1, $V_H$CDR2, and $V_H$CDR3 sequences comprise SEQ ID NOs: 109-111, respectively, and the $V_L$CDR1, $V_L$CDR2, and $V_L$CDR3 sequences comprise SEQ ID NOs: 112-114, respectively;
t) the $V_H$CDR1, $V_H$CDR2, and $V_H$CDR3 sequences comprise SEQ ID NOs: 115-117, respectively, and the $V_L$CDR1, $V_L$CDR2, and $V_L$CDR3 sequences comprise SEQ ID NOs: 118-120, respectively;
u) the $V_H$CDR1, $V_H$CDR2, and $V_H$CDR3 sequences comprise SEQ ID NOs: 121-123, respectively, and the $V_L$CDR1, $V_L$CDR2, and $V_L$CDR3 sequences comprise SEQ ID NOs: 124-126, respectively;
v) the $V_H$CDR1, $V_H$CDR2, and $V_H$CDR3 sequences comprise SEQ ID NOs: 127-129, respectively, and the $V_L$CDR1, $V_L$CDR2, and $V_L$CDR3 sequences comprise SEQ ID NOs: 130-132, respectively;
w) the $V_H$CDR1, $V_H$CDR2, and $V_H$CDR3 sequences comprise SEQ ID NOs: 133-135, respectively, and the $V_L$CDR1, $V_L$CDR2, and $V_L$CDR3 sequences comprise SEQ ID NOs: 136-138, respectively;
x) the $V_H$CDR1, $V_H$CDR2, and $V_H$CDR3 sequences comprise SEQ ID NOs: 139-141, respectively, and the $V_L$CDR1, $V_L$CDR2, and $V_L$CDR3 sequences comprise SEQ ID NOs: 142-144, respectively;
y) the $V_H$CDR1, $V_H$CDR2, and $V_H$CDR3 sequences comprise SEQ ID NOs: 145-147, respectively, and the $V_L$CDR1, $V_L$CDR2, and $V_L$CDR3 sequences comprise SEQ ID NOs: 148-150, respectively;
z) the $V_H$CDR1, $V_H$CDR2, and $V_H$CDR3 sequences comprise SEQ ID NOs: 151-153, respectively, and the $V_L$CDR1, $V_L$CDR2, and $V_L$CDR3 sequences comprise SEQ ID NOs: 154-156, respectively;
aa) the $V_H$CDR1, $V_H$CDR2, and $V_H$CDR3 sequences comprise SEQ ID NOs: 157-159, respectively, and the $V_L$CDR1, $V_L$CDR2, and $V_L$CDR3 sequences comprise SEQ ID NOs: 160-162, respectively;
bb) the $V_H$CDR1, $V_H$CDR2, and $V_H$CDR3 sequences comprise SEQ ID NOs: 163-165, respectively, and the $V_L$CDR1, $V_L$CDR2, and $V_L$CDR3 sequences comprise SEQ ID NOs: 166-168, respectively;
cc) the $V_H$CDR1, $V_H$CDR2, and $V_H$CDR3 sequences comprise SEQ ID NOs: 169-171, respectively, and the $V_L$CDR1, $V_L$CDR2, and $V_L$CDR3 sequences comprise SEQ ID NOs: 172-174, respectively;
dd) the $V_H$CDR1, $V_H$CDR2, and $V_H$CDR3 sequences comprise SEQ ID NOs: 175-177, respectively, and the $V_L$CDR1, $V_L$CDR2, and $V_L$CDR3 sequences comprise SEQ ID NOs: 178-180, respectively;
ee) the $V_H$CDR1, $V_H$CDR2, and $V_H$CDR3 sequences comprise SEQ ID NOs: 181-183, respectively, and the $V_L$CDR1, $V_L$CDR2, and $V_L$CDR3 sequences comprise SEQ ID NOs: 184-186, respectively;
ff) the $V_H$CDR1, $V_H$CDR2, and $V_H$CDR3 sequences comprise SEQ ID NOs: 187-189, respectively, and the $V_L$CDR1, $V_L$CDR2, and $V_L$CDR3 sequences comprise SEQ ID NOs: 190-192, respectively;
gg) the $V_H$CDR1, $V_H$CDR2, and $V_H$CDR3 sequences comprise SEQ ID NOs: 193-195, respectively, and the $V_L$CDR1, $V_L$CDR2, and $V_L$CDR3 sequences comprise SEQ ID NOs: 196-198, respectively;
hh) the $V_H$CDR1, $V_H$CDR2, and $V_H$CDR3 sequences comprise SEQ ID NOs: 199-201, respectively, and the $V_L$CDR1, $V_L$CDR2, and $V_L$CDR3 sequences comprise SEQ ID NOs: 202-204, respectively;
ii) the $V_H$CDR1, $V_H$CDR2, and $V_H$CDR3 sequences comprise SEQ ID NOs: 205-207, respectively, and the $V_L$CDR1, $V_L$CDR2, and $V_L$CDR3 sequences comprise SEQ ID NOs: 208-210, respectively;
jj) the $V_H$CDR1, $V_H$CDR2, and $V_H$CDR3 sequences comprise SEQ ID NOs: 211-213, respectively, and the $V_L$CDR1, $V_L$CDR2, and $V_L$CDR3 sequences comprise SEQ ID NOs: 214-216, respectively;
kk) the $V_H$CDR1, $V_H$CDR2, and $V_H$CDR3 sequences comprise SEQ ID NOs: 217-219, respectively, and the $V_L$CDR1, $V_L$CDR2, and $V_L$CDR3 sequences comprise SEQ ID NOs: 220-222, respectively;
ll) the $V_H$CDR1, $V_H$CDR2, and $V_H$CDR3 sequences comprise SEQ ID NOs: 223-225, respectively, and the $V_L$CDR1, $V_L$CDR2, and $V_L$CDR3 sequences comprise SEQ ID NOs: 226-228, respectively;
mm) the $V_H$CDR1, $V_H$CDR2, and $V_H$CDR3 sequences comprise SEQ ID NOs: 229-231, respectively, and the $V_L$CDR1, $V_L$CDR2, and $V_L$CDR3 sequences comprise SEQ ID NOs: 232-234, respectively;
nn) the $V_H$CDR1, $V_H$CDR2, and $V_H$CDR3 sequences comprise SEQ ID NOs: 235-237, respectively, and the $V_L$CDR1, $V_L$CDR2, and $V_L$CDR3 sequences comprise SEQ ID NOs: 238-240, respectively;
oo) the $V_H$CDR1, $V_H$CDR2, and $V_H$CDR3 sequences comprise SEQ ID NOs: 241-243, respectively, and the $V_L$CDR1, $V_L$CDR2, and $V_L$CDR3 sequences comprise SEQ ID NOs: 244-246, respectively;
pp) the $V_H$CDR1, $V_H$CDR2, and $V_H$CDR3 sequences comprise SEQ ID NOs: 247-249, respectively, and the $V_L$CDR1, $V_L$CDR2, and $V_L$CDR3 sequences comprise SEQ ID NOs: 250-252, respectively;
qq) the $V_H$CDR1, $V_H$CDR2, and $V_H$CDR3 sequences comprise SEQ ID NOs: 253-255, respectively, and the $V_L$CDR1, $V_L$CDR2, and $V_L$CDR3 sequences comprise SEQ ID NOs: 256-258, respectively; or
rr) the $V_H$CDR1, $V_H$CDR2, and $V_H$CDR3 sequences comprise SEQ ID NOs: 259-261, respectively, and the V$_L$CDR1, V$_L$CDR2, and V$_L$CDR3 sequences comprise SEQ ID NOs: 262-264, respectively.

Embodiment I-21. The antibody of any one of embodiments I-1 to 1-20, wherein the V$_H$ comprises a sequence at least 70, 75, 80, 85, 90, 95, 97, 98, 99, or 100% identical to a sequence selected from Table A2, optionally wherein the V$_H$ has 1, 2, 3, 4, 5, 6, 7, 8, 9, or 10 alterations in the framework regions.

Embodiment I-22. The antibody of any one of embodiments I-1 to 1-21, wherein the V$_L$ comprises a sequence at least 70, 75, 80, 85, 90, 95, 97, 98, 99, or 100% identical to a sequence selected from Table A2, optionally wherein the V$_L$ has 1, 2, 3, 4, 5, 6, 7, 8, 9, or 10 alterations in the framework regions.

Embodiment I-23. The antibody of any one of embodiments I-1 to 1-22, wherein:
a) the V$_H$ comprises a sequence at least 70, 75, 80, 85, 90, 95, 97, 98, 99, or 100% identical to SEQ ID NO: 265, and the V$_L$ comprises a sequence at least 70, 75, 80, 85, 90, 95, 97, 98, 99, or 100% identical to SEQ ID NO: 266;
b) the V$_H$ comprises a sequence at least 70, 75, 80, 85, 90, 95, 97, 98, 99, or 100% identical to SEQ ID NO: 267, and the V$_L$ comprises a sequence at least 70, 75, 80, 85, 90, 95, 97, 98, 99, or 100% identical to SEQ ID NO: 268;
c) the V$_H$ comprises a sequence at least 70, 75, 80, 85, 90, 95, 97, 98, 99, or 100% identical to SEQ ID NO: 269, and the V$_L$ comprises a sequence at least 70, 75, 80, 85, 90, 95, 97, 98, 99, or 100% identical to SEQ ID NO: 270;
d) the V$_H$ comprises a sequence at least 70, 75, 80, 85, 90, 95, 97, 98, 99, or 100% identical to SEQ ID NO: 271, and the V$_L$ comprises a sequence at least 70, 75, 80, 85, 90, 95, 97, 98, 99, or 100% identical to SEQ ID NO: 272;
e) the V$_H$ comprises a sequence at least 70, 75, 80, 85, 90, 95, 97, 98, 99, or 100% identical to SEQ ID NO: 273, and the V$_L$ comprises a sequence at least 70, 75, 80, 85, 90, 95, 97, 98, 99, or 100% identical to SEQ ID NO: 274;
f) the V$_H$ comprises a sequence at least 70, 75, 80, 85, 90, 95, 97, 98, 99, or 100% identical to SEQ ID NO: 275, and the V$_L$ comprises a sequence at least 70, 75, 80, 85, 90, 95, 97, 98, 99, or 100% identical to SEQ ID NO: 276;
g) the V$_H$ comprises a sequence at least 70, 75, 80, 85, 90, 95, 97, 98, 99, or 100% identical to SEQ ID NO: 277, and the V$_L$ comprises a sequence at least 70, 75, 80, 85, 90, 95, 97, 98, 99, or 100% identical to SEQ ID NO: 278;
h) the V$_H$ comprises a sequence at least 70, 75, 80, 85, 90, 95, 97, 98, 99, or 100% identical to SEQ ID NO: 279, and the V$_L$ comprises a sequence at least 70, 75, 80, 85, 90, 95, 97, 98, 99, or 100% identical to SEQ ID NO: 280;
i) the V$_H$ comprises a sequence at least 70, 75, 80, 85, 90, 95, 97, 98, 99, or 100% identical to SEQ ID NO: 281, and the V$_L$ comprises a sequence at least 70, 75, 80, 85, 90, 95, 97, 98, 99, or 100% identical to SEQ ID NO: 282;
j) the V$_H$ comprises a sequence at least 70, 75, 80, 85, 90, 95, 97, 98, 99, or 100% identical to SEQ ID NO: 283, and the V$_L$ comprises a sequence at least 70, 75, 80, 85, 90, 95, 97, 98, 99, or 100% identical to SEQ ID NO: 284;
k) the V$_H$ comprises a sequence at least 70, 75, 80, 85, 90, 95, 97, 98, 99, or 100% identical to SEQ ID NO: 285, and the V$_L$ comprises a sequence at least 70, 75, 80, 85, 90, 95, 97, 98, 99, or 100% identical to SEQ ID NO: 286;
l) the V$_H$ comprises a sequence at least 70, 75, 80, 85, 90, 95, 97, 98, 99, or 100% identical to SEQ ID NO: 287, and the V$_L$ comprises a sequence at least 70, 75, 80, 85, 90, 95, 97, 98, 99, or 100% identical to SEQ ID NO: 288;
m) the V$_H$ comprises a sequence at least 70, 75, 80, 85, 90, 95, 97, 98, 99, or 100% identical to SEQ ID NO: 289, and the V$_L$ comprises a sequence at least 70, 75, 80, 85, 90, 95, 97, 98, 99, or 100% identical to SEQ ID NO: 290;
n) the V$_H$ comprises a sequence at least 70, 75, 80, 85, 90, 95, 97, 98, 99, or 100% identical to SEQ ID NO: 291, and the V$_L$ comprises a sequence at least 70, 75, 80, 85, 90, 95, 97, 98, 99, or 100% identical to SEQ ID NO: 292;
o) the V$_H$ comprises a sequence at least 70, 75, 80, 85, 90, 95, 97, 98, 99, or 100% identical to SEQ ID NO: 293, and the V$_L$ comprises a sequence at least 70, 75, 80, 85, 90, 95, 97, 98, 99, or 100% identical to SEQ ID NO: 294;
p) the V$_H$ comprises a sequence at least 70, 75, 80, 85, 90, 95, 97, 98, 99, or 100% identical to SEQ ID NO: 295, and the V$_L$ comprises a sequence at least 70, 75, 80, 85, 90, 95, 97, 98, 99, or 100% identical to SEQ ID NO: 296;
q) the V$_H$ comprises a sequence at least 70, 75, 80, 85, 90, 95, 97, 98, 99, or 100% identical to SEQ ID NO: 297, and the V$_L$ comprises a sequence at least 70, 75, 80, 85, 90, 95, 97, 98, 99, or 100% identical to SEQ ID NO: 298;
r) the V$_H$ comprises a sequence at least 70, 75, 80, 85, 90, 95, 97, 98, 99, or 100% identical to SEQ ID NO: 299, and the V$_L$ comprises a sequence at least 70, 75, 80, 85, 90, 95, 97, 98, 99, or 100% identical to SEQ ID NO: 300;
s) the V$_H$ comprises a sequence at least 70, 75, 80, 85, 90, 95, 97, 98, 99, or 100% identical to SEQ ID NO: 301, and the V$_L$ comprises a sequence at least 70, 75, 80, 85, 90, 95, 97, 98, 99, or 100% identical to SEQ ID NO: 302;
t) the V$_H$ comprises a sequence at least 70, 75, 80, 85, 90, 95, 97, 98, 99, or 100% identical to SEQ ID NO: 303, and the V$_L$ comprises a sequence at least 70, 75, 80, 85, 90, 95, 97, 98, 99, or 100% identical to SEQ ID NO: 304;
u) the V$_H$ comprises a sequence at least 70, 75, 80, 85, 90, 95, 97, 98, 99, or 100% identical to SEQ ID NO: 305, and the V$_L$ comprises a sequence at least 70, 75, 80, 85, 90, 95, 97, 98, 99, or 100% identical to SEQ ID NO: 306;
v) the V$_H$ comprises a sequence at least 70, 75, 80, 85, 90, 95, 97, 98, 99, or 100% identical to SEQ ID NO: 307, and the V$_L$ comprises a sequence at least 70, 75, 80, 85, 90, 95, 97, 98, 99, or 100% identical to SEQ ID NO: 308;
w) the V$_H$ comprises a sequence at least 70, 75, 80, 85, 90, 95, 97, 98, 99, or 100% identical to SEQ ID NO: 309, and the V$_L$ comprises a sequence at least 70, 75, 80, 85, 90, 95, 97, 98, 99, or 100% identical to SEQ ID NO: 310;
x) the V$_H$ comprises a sequence at least 70, 75, 80, 85, 90, 95, 97, 98, 99, or 100% identical to SEQ ID NO:

311, and the $V_L$ comprises a sequence at least 70, 75, 80, 85, 90, 95, 97, 98, 99, or 100% identical to SEQ ID NO: 312;

y) the $V_H$ comprises a sequence at least 70, 75, 80, 85, 90, 95, 97, 98, 99, or 100% identical to SEQ ID NO: 313, and the $V_L$ comprises a sequence at least 70, 75, 80, 85, 90, 95, 97, 98, 99, or 100% identical to SEQ ID NO: 314;

z) the $V_H$ comprises a sequence at least 70, 75, 80, 85, 90, 95, 97, 98, 99, or 100% identical to SEQ ID NO: 315, and the $V_L$ comprises a sequence at least 70, 75, 80, 85, 90, 95, 97, 98, 99, or 100% identical to SEQ ID NO: 316;

aa) the $V_H$ comprises a sequence at least 70, 75, 80, 85, 90, 95, 97, 98, 99, or 100% identical to SEQ ID NO: 317, and the $V_L$ comprises a sequence at least 70, 75, 80, 85, 90, 95, 97, 98, 99, or 100% identical to SEQ ID NO: 318;

bb) the $V_H$ comprises a sequence at least 70, 75, 80, 85, 90, 95, 97, 98, 99, or 100% identical to SEQ ID NO: 319, and the $V_L$ comprises a sequence at least 70, 75, 80, 85, 90, 95, 97, 98, 99, or 100% identical to SEQ ID NO: 320;

cc) the $V_H$ comprises a sequence at least 70, 75, 80, 85, 90, 95, 97, 98, 99, or 100% identical to SEQ ID NO: 321, and the $V_L$ comprises a sequence at least 70, 75, 80, 85, 90, 95, 97, 98, 99, or 100% identical to SEQ ID NO: 322;

dd) the $V_H$ comprises a sequence at least 70, 75, 80, 85, 90, 95, 97, 98, 99, or 100% identical to SEQ ID NO: 323, and the $V_L$ comprises a sequence at least 70, 75, 80, 85, 90, 95, 97, 98, 99, or 100% identical to SEQ ID NO: 324;

ee) the $V_H$ comprises a sequence at least 70, 75, 80, 85, 90, 95, 97, 98, 99, or 100% identical to SEQ ID NO: 325, and the $V_L$ comprises a sequence at least 70, 75, 80, 85, 90, 95, 97, 98, 99, or 100% identical to SEQ ID NO: 326;

ff) the $V_H$ comprises a sequence at least 70, 75, 80, 85, 90, 95, 97, 98, 99, or 100% identical to SEQ ID NO: 327, and the $V_L$ comprises a sequence at least 70, 75, 80, 85, 90, 95, 97, 98, 99, or 100% identical to SEQ ID NO: 328;

gg) the $V_H$ comprises a sequence at least 70, 75, 80, 85, 90, 95, 97, 98, 99, or 100% identical to SEQ ID NO: 329, and the $V_L$ comprises a sequence at least 70, 75, 80, 85, 90, 95, 97, 98, 99, or 100% identical to SEQ ID NO: 330;

hh) the $V_H$ comprises a sequence at least 70, 75, 80, 85, 90, 95, 97, 98, 99, or 100% identical to SEQ ID NO: 331, and the $V_L$ comprises a sequence at least 70, 75, 80, 85, 90, 95, 97, 98, 99, or 100% identical to SEQ ID NO: 332;

ii) the $V_H$ comprises a sequence at least 70, 75, 80, 85, 90, 95, 97, 98, 99, or 100% identical to SEQ ID NO: 333, and the $V_L$ comprises a sequence at least 70, 75, 80, 85, 90, 95, 97, 98, 99, or 100% identical to SEQ ID NO: 334;

jj) the $V_H$ comprises a sequence at least 70, 75, 80, 85, 90, 95, 97, 98, 99, or 100% identical to SEQ ID NO: 335, and the $V_L$ comprises a sequence at least 70, 75, 80, 85, 90, 95, 97, 98, 99, or 100% identical to SEQ ID NO: 336;

kk) the $V_H$ comprises a sequence at least 70, 75, 80, 85, 90, 95, 97, 98, 99, or 100% identical to SEQ ID NO: 337, and the $V_L$ comprises a sequence at least 70, 75, 80, 85, 90, 95, 97, 98, 99, or 100% identical to SEQ ID NO: 338;

ll) the $V_H$ comprises a sequence at least 70, 75, 80, 85, 90, 95, 97, 98, 99, or 100% identical to SEQ ID NO: 339, and the $V_L$ comprises a sequence at least 70, 75, 80, 85, 90, 95, 97, 98, 99, or 100% identical to SEQ ID NO: 340;

mm) the $V_H$ comprises a sequence at least 70, 75, 80, 85, 90, 95, 97, 98, 99, or 100% identical to SEQ ID NO: 341, and the $V_L$ comprises a sequence at least 70, 75, 80, 85, 90, 95, 97, 98, 99, or 100% identical to SEQ ID NO: 342;

nn) the $V_H$ comprises a sequence at least 70, 75, 80, 85, 90, 95, 97, 98, 99, or 100% identical to SEQ ID NO: 343, and the $V_L$ comprises a sequence at least 70, 75, 80, 85, 90, 95, 97, 98, 99, or 100% identical to SEQ ID NO: 344;

oo) the $V_H$ comprises a sequence at least 70, 75, 80, 85, 90, 95, 97, 98, 99, or 100% identical to SEQ ID NO: 345, and the $V_L$ comprises a sequence at least 70, 75, 80, 85, 90, 95, 97, 98, 99, or 100% identical to SEQ ID NO: 346;

pp) the $V_H$ comprises a sequence at least 70, 75, 80, 85, 90, 95, 97, 98, 99, or 100% identical to SEQ ID NO: 347, and the $V_L$ comprises a sequence at least 70, 75, 80, 85, 90, 95, 97, 98, 99, or 100% identical to SEQ ID NO: 348;

qq) the $V_H$ comprises a sequence at least 70, 75, 80, 85, 90, 95, 97, 98, 99, or 100% identical to SEQ ID NO: 349, and the $V_L$ comprises a sequence at least 70, 75, 80, 85, 90, 95, 97, 98, 99, or 100% identical to SEQ ID NO: 350; or rr) the $V_H$ comprises a sequence at least 70, 75, 80, 85, 90, 95, 97, 98, 99, or 100% identical to SEQ ID NO: 351, and the $V_L$ comprises a sequence at least 70, 75, 80, 85, 90, 95, 97, 98, 99, or 100% identical to SEQ ID NO: 352.

Embodiment I-24. An isolated polynucleotide encoding the isolated anti IL-18BP antibody according to any one of embodiments I-1 to I-23, an expression vector comprising the isolated polynucleotide, or an isolated host cell comprising the vector.

Embodiment I-25. A pharmaceutical composition, comprising the anti-IL-18BP antibody of any one of embodiments I-1 to I-23, and a pharmaceutically acceptable carrier.

Embodiment I-26. The pharmaceutical composition of embodiment I-25, wherein the composition is a sterile, injectable solution, optionally suitable for intravenous, intramuscular, subcutaneous, or intraperitoneal administration.

Embodiment I-27. A method of treating a disease or condition in a subject in need thereof, comprising administering to the subject a pharmaceutical composition of any one of embodiments I-25 to I-26.

Embodiment I-28. The method of embodiment I-27, wherein the disease or condition is a cancer or tumor or proliferative disease or disorder, optionally a proliferative disease or disorder selected from a lymphoproliferative disorder, a myeloproliferative disorder, proliferative enteritis, proliferative diabetic retinopathy, and a proliferative kidney disease.

Embodiment I-29. The method of embodiment I-28, wherein the cancer or tumor expresses or overexpresses IL-18BP and/or IL-18, or wherein the proliferative disease or disorder is associated with increased expression of IL-18BP and/or IL-18.

Embodiment I-30. The method of embodiment I-28 or I-29, wherein the cancer is selected from one or more of bone cancer, prostate cancer, melanoma (e.g., metastatic melanoma), pancreatic cancer, small cell lung cancer, non-small cell lung cancer (NSCLC), mesothelioma, leukemia (e.g., lymphocytic leukemia, chronic myelogenous leukemia, acute myeloid leukemia, relapsed acute myeloid leukemia, hairy cell leukemias, acute lymphoblastic leukemias), lymphoma (e.g., non-Hodgkin's lymphomas, Hodgkin's lymphoma), hepatoma (hepatocellular carcinoma), sarcoma, B-cell malignancy, breast cancer, ovarian cancer, colorectal cancer, glioma, glioblastoma multiforme, meningioma, pituitary adenoma, vestibular schwannoma, primary CNS lymphoma, primitive neuroectodermal tumor (medulloblastoma), kidney cancer (e.g., renal cell carcinoma), bladder cancer, urothelial cancer, uterine cancer, esophageal cancer, brain cancer, head and neck cancers, cervical cancer, testicular cancer, thyroid cancer, and stomach cancer.

Embodiment I-31. The method of any one of embodiments I-27 to I-30, comprising administering the pharmaceutical composition of embodiment I-25 or I-26 in combination with IL-18.

Embodiment I-32. The method of any one of embodiments I-28 to I-31, comprising administering the pharmaceutical composition of embodiment I-25 or I-26 in combination with an immune checkpoint modulatory agent selected from an antagonist of a inhibitory immune checkpoint molecule and an agonist of a stimulatory immune checkpoint molecule.

Embodiment I-33. The method of embodiment I-32, wherein the immune checkpoint modulatory agent is a polypeptide, optionally an antibody or a ligand, or a small molecule.

Embodiment I-34. The method of embodiment I-32 or 1-33, wherein the inhibitory immune checkpoint molecule is selected from one or more of Programmed Death-Ligand 1 (PD-L1), Programmed Death 1 (PD-1), Programmed Death-Ligand 2 (PD-L2), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, Herpes Virus Entry Mediator (HVEM), and T-cell immunoreceptor with Ig and ITIM domains (TIGIT).

Embodiment I-35. The method of embodiment I-34, wherein:
a) the antagonist is a PD-L1 and/or PD-L2 antagonist optionally selected from one or more of an antibody or small molecule that specifically binds thereto, atezolizumab (MPDL3280A), avelumab (MSB0010718C), and durvalumab (MEDI4736), optionally wherein the cancer is selected from one or more of colorectal cancer, melanoma, breast cancer, non-small-cell lung carcinoma, bladder cancer, and renal cell carcinoma;
b) the antagonist is a PD-1 antagonist optionally selected from one or more of an antibody or small molecule that specifically binds thereto, nivolumab, pembrolizumab, MK-3475, AMP-224, AMP-514PDR001, and pidilizumab, optionally wherein the PD-1 antagonist is nivolumab and the cancer is optionally selected from one or more of Hodgkin's lymphoma, melanoma, non-small cell lung cancer, hepatocellular carcinoma, renal cell carcinoma, and ovarian cancer;
c) the PD-1 antagonist is pembrolizumab and the cancer is optionally selected from one or more of melanoma, non-small cell lung cancer, small cell lung cancer, head and neck cancer, and urothelial cancer;
d) the antagonist is a CTLA-4 antagonist optionally selected from one or more of an antibody or small molecule that specifically binds thereto, ipilimumab, tremelimumab, optionally wherein the cancer is selected from one or more of melanoma, prostate cancer, lung cancer, and bladder cancer;
e) the antagonist is an IDO antagonist optionally selected from one or more of an antibody or small molecule that specifically binds thereto, indoximod (NLG-8189), 1-methyl-tryptophan (1MT), β-Carboline (norharmane; 9H-pyrido[3,4-b]indole), rosmarinic acid, and epacadostat, and wherein the cancer is optionally selected from one or more of metastatic breast cancer and brain cancer optionally glioblastoma multiforme, glioma, gliosarcoma or malignant brain tumor;
f) the antagonist is a TDO antagonist optionally selected from one or more of an antibody or small molecule that specifically binds thereto, 680C91, and LM10;
g) the antagonist is a TIM-3 antagonist optionally selected from one or more of an antibody or small molecule that specifically binds thereto;
h) the antagonist is a LAG-3 antagonist optionally selected from one or more of an antibody or small molecule that specifically binds thereto, and BMS-986016;
i) the antagonist is a VISTA antagonist optionally selected from one or more of an antibody or small molecule that specifically binds thereto;
j) the antagonist is a BTLA, CD160, and/or HVEM antagonist optionally selected from one or more of an antibody or small molecule that specifically binds thereto; or
k) the antagonist is a TIGIT antagonist optionally selected from one or more of an antibody or small molecule that specifically binds thereto.

Embodiment I-36. The method of embodiment I-32 or I-33, wherein the stimulatory immune checkpoint molecule is selected from one or more of OX40, CD40, Glucocorticoid-Induced TNFR Family Related Gene (GITR), CD137 (4-1BB), CD27, CD28, CD226, and Herpes Virus Entry Mediator (HVEM).

Embodiment I-37. The method of embodiment I-36, wherein:
a) the agonist is an OX40 agonist optionally selected from one or more of an antibody or small molecule or ligand that specifically binds thereto, OX86, Fc-OX40L, and GSK3174998;
b) the agonist is a CD40 agonist optionally selected from one or more of an antibody or small molecule or ligand that specifically binds thereto, CP-870,893, dacetuzumab, Chi Lob 7/4, ADC-1013, and rhCD40L, and wherein the cancer is optionally selected from one or more of melanoma, pancreatic cancer, mesothelioma, and hematological cancers optionally lymphoma such as Non-Hodgkin's lymphoma;
c) the agonist is a GITR agonist optionally selected from one or more of an antibody or small molecule or ligand that specifically binds thereto, INCAGN01876, DTA-1, and MEDI1873;
d) the agonist is a CD137 agonist optionally selected from one or more of an antibody or small molecule or ligand that specifically binds thereto, utomilumab, and 4-1BB ligand;
e) the agonist is a CD27 agonist optionally selected from one or more of an antibody or small molecule or ligand that specifically binds thereto, varlilumab, and CDX-1127 (1F5);
f) the agonist is a CD28 agonist optionally selected from one or more of an antibody or small molecule or ligand that specifically binds thereto, and TAB08; and/or
g) the agonist is an HVEM agonist optionally selected from one or more of an antibody or small molecule or ligand that specifically binds thereto.

Embodiment I-38. The method of any one of embodiments I-28 to I-37, comprising administering the pharmaceutical composition of embodiment I-25 or I-26 in combination with at least one chemotherapeutic agent.

Embodiment I-39. The method of embodiment I-38, wherein the at least one chemotherapeutic agent is selected from one or more of an alkylating agent, an anti-metabolite, a cytotoxic antibiotic, a topoisomerase inhibitor (type 1 or type II), and an anti-microtubule agent.

Embodiment I-40. The method of embodiment I-39, wherein:
a) the alkylating agent is selected from one or more of nitrogen mustards (optionally mechlorethamine, cyclophosphamide, mustine, melphalan, chlorambucil, ifosfamide, and busulfan), nitrosoureas (optionally N-Nitroso-N-methylurea (MNU), carmustine (BCNU), lomustine (CCNU), semustine (MeCCNU), fotemustine, and streptozotocin), tetrazines (optionally dacarbazine, mitozolomide, and temozolomide), aziridines (optionally thiotepa, mytomycin, and diaziquone (AZQ)), cisplatins and derivatives thereof (optionally carboplatin and oxaliplatin), and non-classical alkylating agents (optionally procarbazine and hexamethylmelamine);
b) the anti-metabolite is selected from one or more of anti-folates (optionally methotrexate and pemetrexed), fluoropyrimidines (optionally 5-fluorouracil and capecitabine), deoxynucleoside analogues (optionally ancitabine, enocitabine, cytarabine, gemcitabine, decitabine, azacitidine, fludarabine, nelarabine, cladribine, clofarabine, fludarabine, and pentostatin), and thiopurines (optionally thioguanine and mercaptopurine);
c) the cytotoxic antibiotic is selected from one or more of anthracyclines (optionally doxorubicin, daunorubicin, epirubicin, idarubicin, pirarubicin, aclarubicin, and mitoxantrone), bleomycins, mitomycin C, mitoxantrone, and actinomycin;
d) the topoisomerase inhibitor is selected from one or more of camptothecin, irinotecan, topotecan, etoposide, doxorubicin, mitoxantrone, teniposide, novobiocin, merbarone, and aclarubicin; and/or
e) the anti-microtubule agent is selected from one or more of taxanes (optionally paclitaxel and docetaxel) and *vinca* alkaloids (optionally vinblastine, vincristine, vindesine, vinorelbine).

Embodiment I-41. The method of embodiment I-27, wherein the disease or condition is a myelodysplastic syndrome (MDS).

Embodiment I-42. The method of embodiment I-27, wherein the disease or condition is an infectious disease.

Embodiment I-43. The method of embodiment I-42, wherein the infectious disease is selected from viral, bacterial, fungal (optionally yeast), and protozoal infections Embodiment I-44. The method of any one of embodiments I-41 to I-43, comprising administering the pharmaceutical composition of embodiment I-25 or I-26 in combination with IL-18.

Embodiment I-45. A method of screening an anti-IL-18BP antibody for the ability to block or inhibit binding between IL-18 and IL-18BP, comprising
a) determining binding affinity of the antibody for (i) IL-18BP alone, and (ii) a hypo-IL-18 fusion protein, wherein the hypo-IL-18 fusion protein comprises IL-18 fused to IL-18BP via a flexible linker (and an optional protease cleavage site in between), wherein the IL-18 portion of the fusion protein is bound to the IL-18BP portion of the fusion protein and sterically blocks the IL-18 binding site of the IL-18BP portion of the fusion protein;
b) comparing the binding affinity of (i) to the binding affinity of (ii); and
c) identifying or selecting the antibody as being able to block or inhibit binding between IL-18 and IL-18BP if the binding affinity of (i) is significantly stronger than the binding affinity (ii).

Embodiment I-46. The method of embodiment I-45, wherein the IL-18 and IL-18BP are mouse IL-18 and IL-18BP.

Embodiment I-47. The method of embodiment I-45, wherein the IL-18 and IL-18BP are human IL-18 and IL-18BP.

EXAMPLES

Example 1: Generation of Antagonistic Monoclonal Antibodies to Interleukin 18 Binding Protein (IL-18BP Studies were performed to generate potent human and humanized antibodies that bind to and inhibit IL-18/IL-18BP binding, and thereby liberate IL-18 to stimulate immune activity. Potential therapeutic candidates were identified with cross-reactivity to human and cynomolgus monkey IL-18BP. In addition, potent anti-mouse IL-18BP mAbs that are closely related to their anti-human/cyno counterparts were generated to allow investigation of these agents in murine tumor model systems.

Materials and Methods

Immunization and Isolation of Antigen Specific Antibodies from Single B Cells.

Monoclonal antibodies to IL-18BP were generated by immunization of mice with IL-18BP followed by isolation of antigen specific single B cells using the Berkeley Lights Beacon instrument and cloning of genes encoding the antibodies from each cell of interest. The autoimmune mouse strains DiversimAb™ and DivergimAb™ (Abveris Inc.)

were used to generate murine mAbs. Mice were immunized with an alternating schedule of human IL-18BP and cynomolgus monkey IL-18BP with either his or Fc tags, while titers were tested with human, cyno, or mouse IL-18BP using the other tag in each case, to avoid detection of tag specific antibodies.

Following generation of high titers to IL-18BP, antigen specific B cells from the appropriate mice were isolated as single cells using the Berkeley Lights Beacon instrument using procedures recommended by the manufacturer as described (Mullen et al., Antibody Therapeutics. 4(3): 185-196, 2021). Immunoglobulin gene sequences from antigen specific B cells were obtained and used to generate recombinant antibodies using established methodology.
Naming Antibodies.

Some antibodies are named with an "SA" prefix, a sequential 2-digit number, and a single letter suffix that indicates the identity of the HC constant domain: "a" for human IgG1, "d" for murine IgG2a. Thus, SA04a is a human IgG1 antibody.

Variants and mutations were named in the following order: original amino acid, followed by Kabat position number (Kabat 1991), followed by replacement amino acid. For amino acids, the standard single letter code is used. Thus, Y32E indicates that the tyrosine (Y) at Kabat position 32 has been replaced by a glutamic acid (E).
Preparation of Libraries Site-Directed Mutagenesis.

To affinity mature the starting mAbs, libraries of variants were prepared focusing on each of the HC and LC CDRs in turn. To accomplish this, each CDR amino acid was replaced in turn with up to 17 amino acid substitutions. Cysteine and tryptophan were not included in the libraries so as to not introduce unwanted potential sequence liabilities, nor was the parental amino acid already in position included in the screen. To generate the variants at each position, two sets of mutagenic oligonucleotides (Integrated DNA Technologies (IDT), San Diego) containing the degenerate codons NDT, or VHG, (where N=A/C/G/T; D=A/G/T; V=A/C/G; H=A/C/T) were used for each position (Kille, 2013; Acevedo-Rocha, 2015) paired with appropriate 5' and 3' distal oligonucleotides (IDT) designed to permit the amplification and cloning.

PCR was performed with high-fidelity DNA Polymerase (Q5, New England Biolabs) according to the manufacturer's protocols. Parental plasmids (both heavy and light chains) were diluted to 10 ng/µL and 1 µL was used as template for each 50 µL reaction. V-region gene fragments with degenerate codons as described above, were amplified by PCR and purified (Qiagen PCR purification kit used per manufacturer's instructions). Gene fragments were assembled into heavy and light chain clones via either overlap extension PCR (OE-PCR) or Gibson cloning. For OE-PCR, fragments were amplified with corresponding forward and reverse primers containing restriction sites (AgeI-NheI for heavy chain, SbfI-MfeI for light chain) and column purified (Qiagen PCR purification kit). Restriction digests were carried out using high fidelity enzymes (New England Biolabs) and fragments were ligated using T4 DNA ligase (New England Biolabs, Cat #M0202L) into appropriate vectors for heavy and light chain. Empty heavy chain vector contains the majority of the human IgG1 constant region with an engineered NheI site (created by altering wobble positions) 12 amino acids into the constant region. Light chain empty vector contains the majority of the human Kappa constant region with an engineered MfeI site 18 amino acids into the constant region. Gibson Cloning was achieved using the fragments with the same empty vectors (Gibson Assembly® Master Mix Kit, New England Biolabs Cat #ES261IL). Inserts were normalized to 1 ng/µL and a total of 2 ng of insert DNA is used (1 ng per fragment). 10 µL reaction volume was made up of 5 µL of Gibson Master Mix and QS with purified water. The reaction was incubated at 50° C. for 15-60 minutes.

Ligation products from either OE-PCR or Gibson assembly were transformed into competent *E. Coli* (Monserate Biotechnology, San Diego) by adding 2-5 µL of the ligation reaction mix to the cells and incubating on ice for 5 minutes. Cells were heat shocked at 42° C. for 30 seconds and placed on ice. 250 µL of SOC media (BioPioneer, San Diego or Teknova, San Diego) was added and tubes were incubated at 37° C., 200 rpm for 1 hour. 100 µL of culture was plated onto antibiotic selection plates (BioPioneer, San Diego or Teknova, San Diego), and incubated at 37° C. overnight.

Plates were sent for colony sequencing of the antibody genes (Genewiz or Eton) where 24-48 clones per plate are sequenced. Sequences were analyzed with SnapGene Software (GSL Biotech) against the reference sequence which is an in silico cloning of the library. Clones were picked based on sequence alignment and amino acids that are encoded by the mutation primer, and used to generate individual plasmid mini-preps.

Screening of mutants was achieved by small scale expression of the library derived plasmids in Expi293F cells cultured in 48-well plates using methodology described below. Heavy and light chain pairings were done in a 1:2 ratio (0.5 ng HC: 1 ng LC plasmid per well). Replicates of the parental antibody control were included on each plate. Cells were grown in plates for 3 days, after which supernatant from each well was harvested for screening.

Screening of plate transfections was done using biolayer interferometry (BLI). Initially, BLI was used to determine the concentration of antibody present in each sample, prior to screening for binding affinity to IL-18BP. Initial apparent binding kinetic measurements were taken on a Fortebio Octet RED96e instrument. mAbs were loaded onto antihuman constant domain (AHC) biosensors (FortéBio) in 10× kinetics buffer consisting of PBS, 0.1% BSA, 0.02% polysorbate 20 (TWEEN™) for 120 seconds to achieve a spectral shift value of 0.8 to 1.2 nm. The association phase was carried out in the presence of 20 nM of human, cyno, or murine IL-18BP ortholog and was allowed to proceed for 120 s; dissociation was measured for 300 s to determine if any variants displayed improved on- or off-rates as compared to the parental antibody. Candidates presenting with apparent improved binding kinetics based on the single screening concentration were then retested for full binding kinetics vs each ortholog and recombined with other mutations as described below.
Expression and Purification of Recombinant Antibodies.

Expi293F cells from the Expi293 Expression System Kit (Thermo Fisher, cat. No. A14635) were grown in Expi293F expression medium (cat. No. A1435101). Cells were grown to a density of $3-6\times10^6$ cells/mL and then counted using a hemocytometer. Plasmid DNA (1.0 µg per 1.0 mL of culture) was diluted in Opti-MEM Reduced Serum Medium (RSM) (cat. No. 31985062). Values of Opti-MEM RSM were taken from manufacturer's recommendations for transfections. Expifectamine 293 reagent was diluted in Opti-MEM RSM and incubated for 5 min. At room temperature before mixing with diluted plasmid DNA. This mixture was left to incubate for 10-20 minutes at room temperature. While the expifectamine/plasmid DNA complex was incubating, Expi293F cells were diluted to a density of $3\times10^6$ cells/mL and added to Erlenmeyer flasks of desired volume (BioPioneer, DGFPC0125S for 125 mL flask). The expifectamine/plasmid DNA complex was then slowly transferred to a shaker flask with Expi293F cells, and the flasks were placed in a shaking incubator with a 25 mm orbital throw (Infors-HT Multitron) at 37° C., 8% $CO_2$, 125 rpm. 18-22 h post transfection, ExpiFectamine 293 Transfection Enhancer 1 (#100013863) and 2 (#A14350-01) were added to the cells, and the cells were returned to the shaking incubator. Cells were then left to incubate for 4 additional days, then spun down at 4000× g for 20 minutes in a refrigerated centrifuge and 0.22 μm filtered prior to purification.

Antibodies were purified using 5 mL HiTrap MabSelect SuRe (Protein A) columns on an AKTA Explorer FPLC system. Columns were first cleared of any residual bound protein by the addition of 50 mL of 0.1 M glycine, pH 3.0 (elution buffer) followed by 50 mL of 50 mM glycine, 50 mM glycinate pH 8 (binding/washing buffer). Antibodies (25-400 mL) were loaded onto column at 5 mL/min and further washed with 25 mL equilibration/wash buffer until UV reading reached baseline. Mabs were subsequently eluted by using a 25 mL linear gradient of 0-100% elution buffer for 2 min at 5 mL/min. Antibody elution was monitored by absorbance at 280 nm. Peak fractions were collected and pooled in a 15 mL conical tube. Material was then buffer exchanged into storage buffer (PBS, pH 7.4) using PD10 columns (Cytiva cat. No. 17085101), and subsequently filter sterilized (GenClone Syringe Filters, cat. No. 25-244 attached to BD 5 mL [cat. No. 309646] and 20 mL [cat. No. 302830] BD Luer-Lok™ syringes) into a 15 mL conical tube and used for subsequent characterization assays.

Analysis by Size-Exclusion HPLC (SEC-HPLC).

SEC-HPLC was performed on a 5 μm particle size, 7.8 mm I.D. X 30 cm TSKgel G3000SW$_{XL}$ and run isocratically using 50 mM sodium phosphate, 200 mM arginine pH 6.8 at a flow rate of 1 mL/minute on an Agilent 1100 HPLC. Detection was at 280 nm using a diode array detector and peaks were integrated using Agilent ChemStation software. SEC-HPLC standards used to calibrate the column consisted of bovine thyroglobulin, bovine IgG, chicken albumin, bovine ribonuclease A and p-aminobenzoic acid (Sigma Aldrich #69385).

Analysis of Binding Affinity by Biolayer Interferometry (BLI).

Binding kinetic measurements were taken on a Fortebio (now Sartorius) Octet RED96e instrument. mAbs were loaded onto anti-human constant domain (AHC) biosensors (FortéBio) in 10× kinetics buffer consisting of PBS containing 0.1% BSA, 0.02% polysorbate 20 (TWEEN™) for 90-120 s to achieve a spectral shift value between 0.8 to 1.2 nm. Association was carried out in the presence of a 2-fold dilution series of hIL-18BP and was typically allowed to proceed for 90-120 s; dissociation was generally measured for 300 to 1200 s. Dilution series started at 100 nM for weaker variants or 10 nM for the most potent mAbs. Cross-reactivity to cyno IL-18BP and mouse IL-18BP was determined using the same methodology with the appropriate species' IL-18BP.

Activity of Anti-IL-18BP mAbs in IL-18 Reporter HEK 293 Cells.

IL-18 Reporter HEK 293 cells from InvivoGen (hkb-hmil18) respond to exogenously added IL-18 by expressing an NF-κB/AP-1-inducible secreted embryonic alkaline phosphatase (SEAP) reporter gene. To conduct the assay, cells were grown in complete DMEM Media (10% HI FBS, 1% PS) with 1×HEK-Blue Selection (Invivogen, hb-sel). Cells were carefully rinsed twice with 1×PBS and lifted with 1×PBS at 37° C. for 5 min. Cells were counted, spun down at 200× g for 5 min., and resuspended in complete DMEM media without selection at $2.5×10^5$ cells/mL. Cells were then plated at 25,000 cells in 100 μL/well in a 96 well plate (Genesee Scientific, 25-109). Plated cells were then placed in an incubator at 37° C., 5% $CO_2$. Test antibodies solutions were prepared at 90 μg/mL in selection free DMEM and incubated with human IL-18BP at 120 ng/mL for 30 mins at room temperature. A 0.6 ng/mL stock of recombinant human IL-18 (SinoBiological, 10119-HNCE) was then prepared and added to the antibody/IL-18BP complex after incubation. The resulting solution was immediately added to the cells, giving a final concentration of 15 μg/mL test antibody, 20 ng/mL human IL-18BP, and 0.1 ng/mL human IL-18. Cells were left to incubate for 18-22 hours at 37° C., 5% $CO_2$. 10 μL/well of cell supernatant was taken and mixed with 90 μL/well of complete Quanti-Blue Solution (Invivogen,) in a new 96 well plate and placed in an incubator at 37° C. for 1-3 hours, noting a colorimetric change from purple to blue. The plate was then read at 620 nm and the data were analyzed using GraphPad Prism.

Derepression of IFNγ Expression by Anti-IL-18BP mAbs in KG-1 Cells.

Human KG-1 cells (ATCC cat. CCL-246) were plated at 150 k cells/well. IL-18BP (50 ng/mL final, Sino Biologicals, cat. No. 10357-H08H) was pre-blocked with a serial dilution of antibodies for 20 min at RT. IL-18 (10 ng/mL final, R&D Systems, cat. No. 9124-IL/CF) was added to this mixture and incubated for a further 20 min at RT. This mixture was added to cells and incubated overnight at 37° C. Secreted IFNγ was measured in cell culture supernatants using the Human IFN-gamma DuoSet ELISA from R&D Systems (cat. No. DY285B) on Nunc MaxiSorp flat-bottom plate (cat. No. 44-2404-21). Manufacturer's protocol was followed, and supernatants were diluted 1:2 with reagent diluent. Absorbance was measured at 450 nm using a Spectramax iD5 plate reader. Data were analyzed using GraphPad Prism.

PBMC Assays for Human IL-18 Activity.

Human peripheral blood mononuclear cells (PBMC) obtained from the San Diego Blood Bank were seeded into 96 well flat bottom plates (GenClone, cat. No. 25-109) at $2×10^5$ cells/well or round bottom plates (GenClone, cat. No. 25-221) at $1.7×10^5$ cells/well in RPMI+GlutaMAX (Gibco cat. No. 61870036) containing 100 U penicillin, 100 pg streptomycin (Gibco cat. No. 10378016) and 10% FBS (RPMIc). Test antibody was added to wells at 4× final concentration in a volume of 50 μL. 50 μL recombinant human IL-12 (R&D system, cat. No. 219-IL-005) was then added at 4 ng/mL followed by 50 μL recombinant human IL-18 (Sino Biological, cat. No. 10119-HNCE) at 8 ng/mL for final concentrations of 1 ng/mL and 2 ng/mL, respectively. For assays with cyno PBMCs (iQ Biosciences, cat. No. IQB-MnPB102), cells were seeded at $1.7×10^5$ cells/well in round bottom plates. Recombinant cyno IL-12 (R&D Systems, cat. No. 10215-CL) was added at a final concentration of 1 ng/mL and recombinant rhesus macaque IL-18 (R&D Systems cat. No. 2548-RM-025/CF [note that the amino acid IL-18 sequence for rhesus and cynomolgus are identical]) was added at a final concentration of 2 ng/mL. All dilutions were made in RPMIc. Cells were incubated for 48 h at 37° C., 5% $CO_2$. At 48 h, a 50 μL aliquot of supernatant was removed from each well and assayed for the presence of IFNγ using a DuoSet ELISA kit (R&D Systems, cat. No. DY285B for human IFNγ and cat. No. DY961 for primate IFNγ) on a Nunc MaxiSorp Flat-Bottom Plate (Invitrogen, cat. No. 44-2404-21), according to manufacturer's instructions. CCL2 release was measured using DuoSet ELISA kit (R&D Systems, cat. No. DY279 for human CCL2) on a Nunc MaxiSorp Flat-Bottom Plate (Invitrogen, cat. No. 44-2404-21), according to the manufacturer's instructions. Absorbance was measured at 450 nm using a Spectramax iD5 plate reader and data were analyzed using GraphPad Prism software.

In experiments where the reaction was conducted in the presence of precomplexed hIL-18/hIL-18BP, the design was as follows. Recombinant human or cyno IL-18 at 80 ng/mL was incubated with recombinant human (SinoBiological, cat. No. 10357-H08H) or cyno IL-18BP (generated in-house), respectively, at 400 ng/mL for 30 min at RT. Serial dilutions of mAbs were added to 96 well round bottom plates at 4× concentration in 50 µL/well. 50 µL/well of IL-18-IL-18BP complex was added to each well containing mAb and incubated for 1 h at 37° C. After 1 h, 50 µL/well of recombinant human or cyno IL-12 at 4 ng/mL and 50 µL PBMC at 2×10$^6$ cells/mL were added to each well for a final concentration of 20 ng/mL IL-18, 100 ng/mL IL-18BP, 1 ng/mL IL-12 and 1×10$^5$ PBMC in each well. All dilutions were made in RPMIc. Control wells contained IL-12+IL-18 alone or IL-12+IL-18+IL-18BP alone. Cells were incubated at 37° C., 5% CO$_2$ for 48 h, supernatants harvested and assayed for the presence of IFNγ and CCL2.

NK Cell Assays for Human IL-18 Activity.

IL-18 activity was assessed using purified NK cells and pre-complexed hIL-18/hIL-18BP. Recombinant human IL-18 at 10 ng/mL (4× final concentration) was incubated with recombinant human IL-18BP at 50 ng/mL (4× final concentration) for 30 min at RT. NK cells were purified from fresh PBMC using a MojoSort Human NK Cell Isolation Kit (BioLegend, cat. No. 480054) according to the manufacturer's instructions. NK purity was assessed by flow cytometry and was typically >90%. 1.7×10$^5$ NK cells were added per well of a 96 well flat bottom plate in 50 µL RPMIc. Precomplexed hIL-18/hIL-18BP was added in 50 µL/well followed by 50 µL recombinant human IL-12 at 4 ng/mL (for a final concentration of 1 ng/mL) and incubated for 30 min at 37° C. Serial dilutions of test antibodies were added in 50 µL/well at 4× concentration. Plates were incubated for 24 h at 37° C., 5% CO$_2$, supernatants harvested and assayed by ELISA for the presence of IFNγ as described above.

Results

Isolation of Monoclonal Antibody Sequences from Immunized Mice.

Cohorts of DiversimAb™ and DivergimAb™ mice (Abveris) were immunized with human and cynomolgus monkey IL-18BP. Titers to human, cyno, and mouse IL-18BP were measured by ELISA and mice with high titers were selected for isolation of antibody secreting B cells using the Berkeley Lights Beacon Optofluidic System (Mullen, 2021). Screening identified single cells secreting antibodies which cross-reacted to human and cyno IL-18BP and some which also bound mouse IL-18BP. In addition, a novel screen was designed to identify cells secreting antibodies which were unable to recognize a form of IL-18BP in which the active site has been blocked, termed "hypo-IL-18". This enabled the screen to identify putative ligand blocking antibodies.

Figures 1A, 1B:
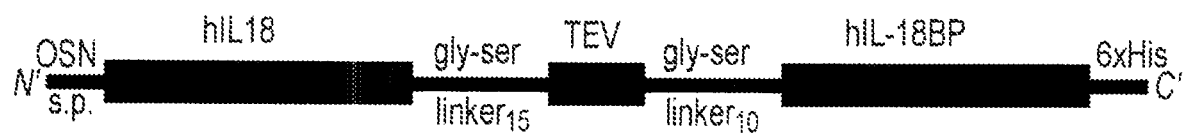
Figure 1C:
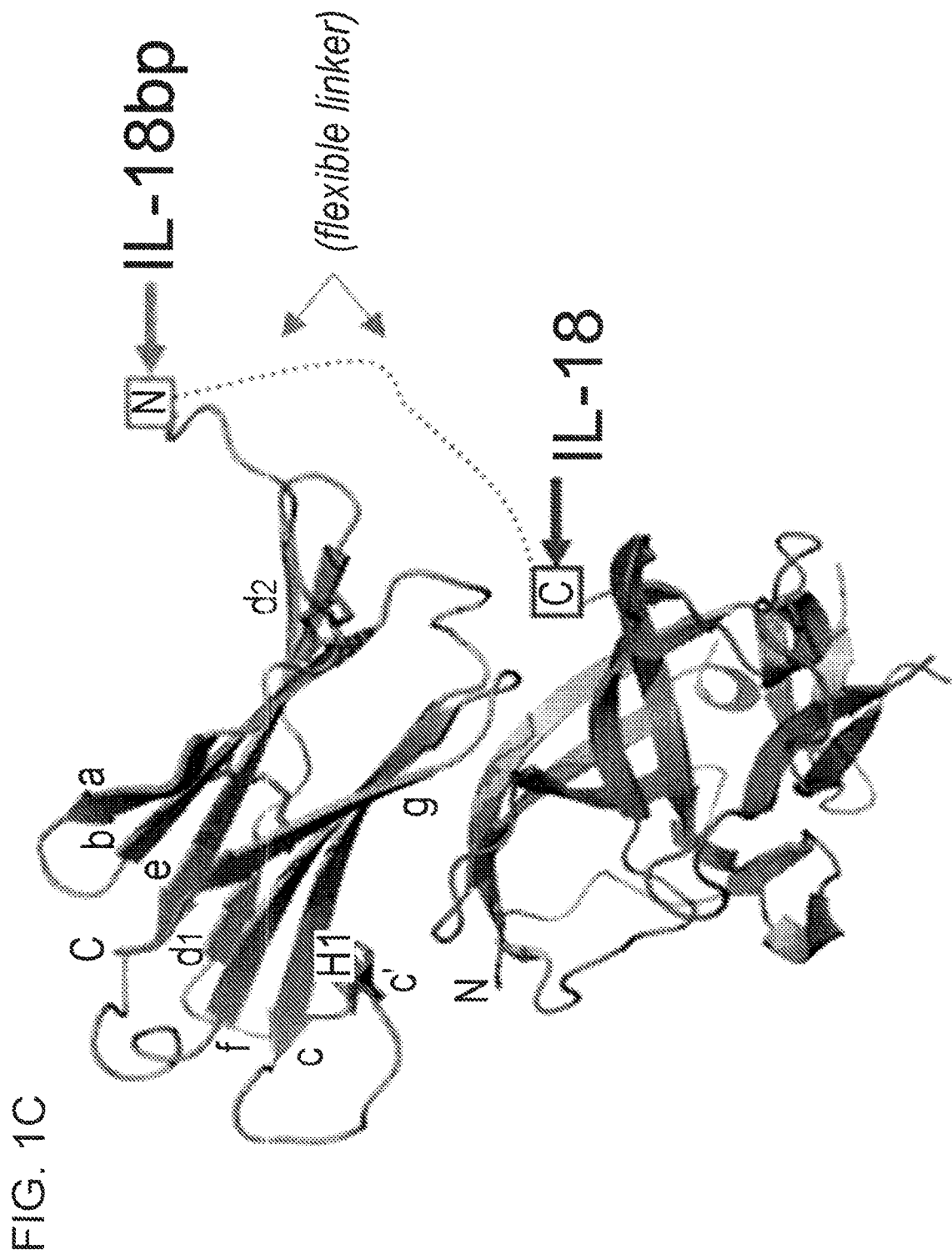
Figure 2D:
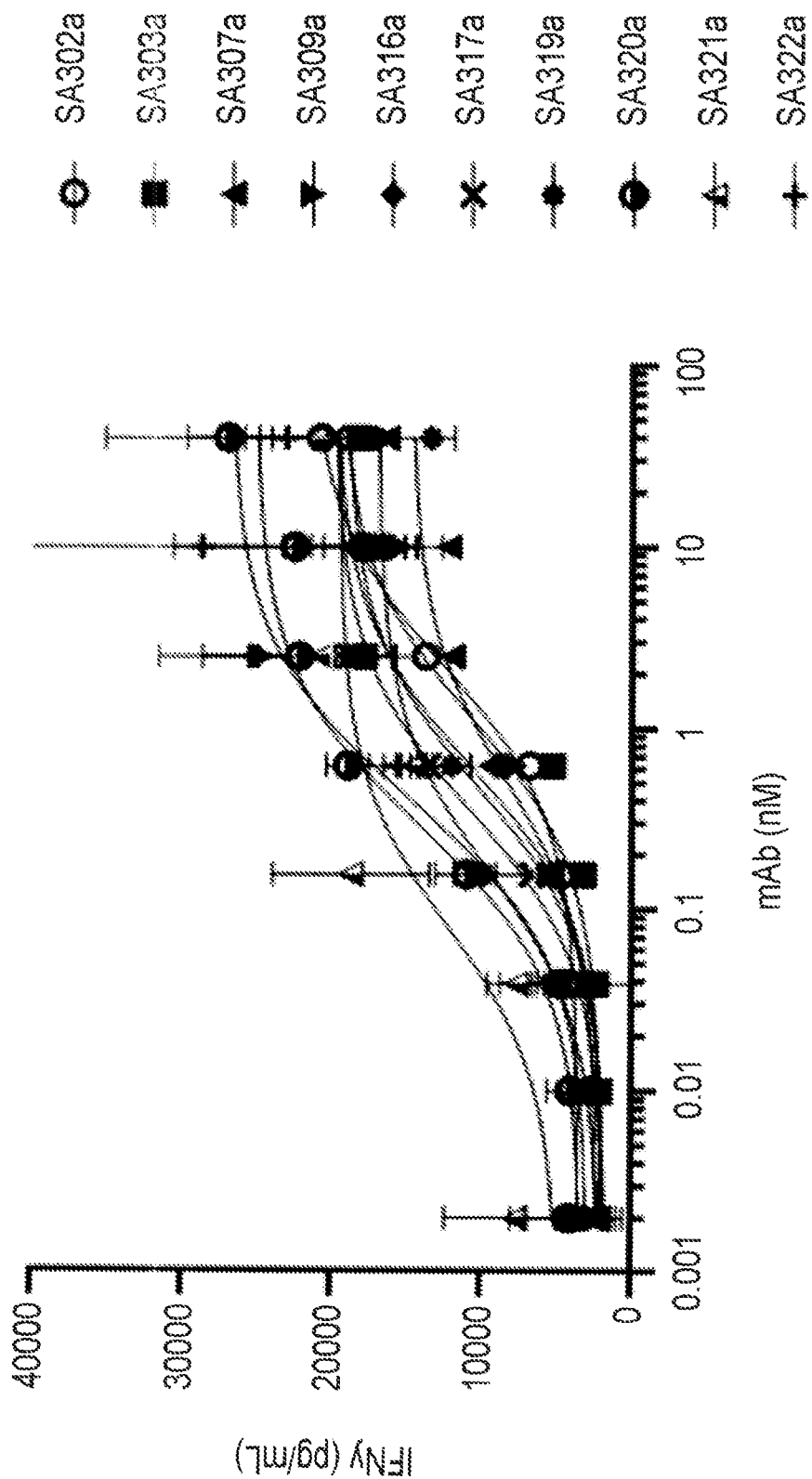
Figure 2E:
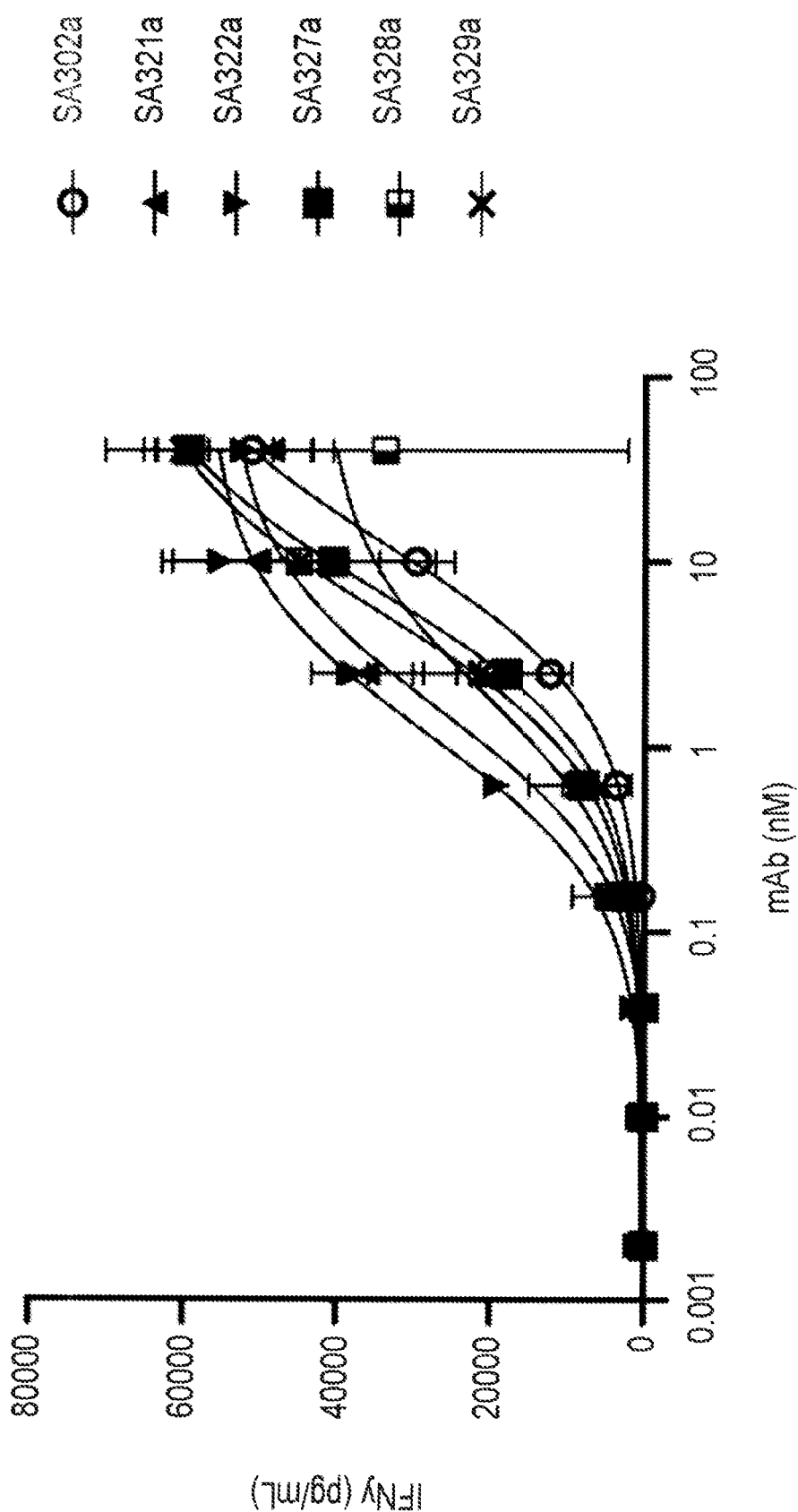
Figure 2G:
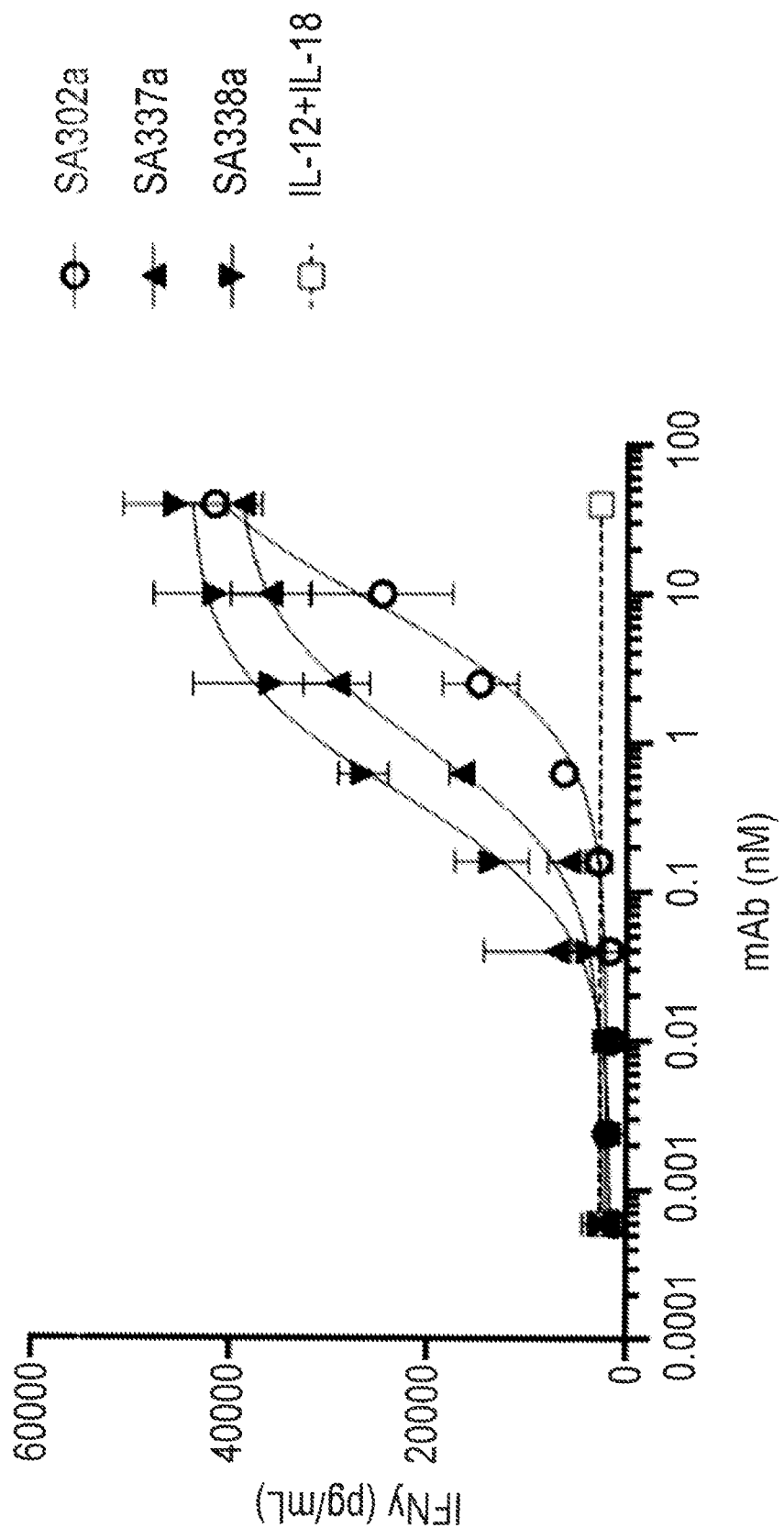
Figure 3A:
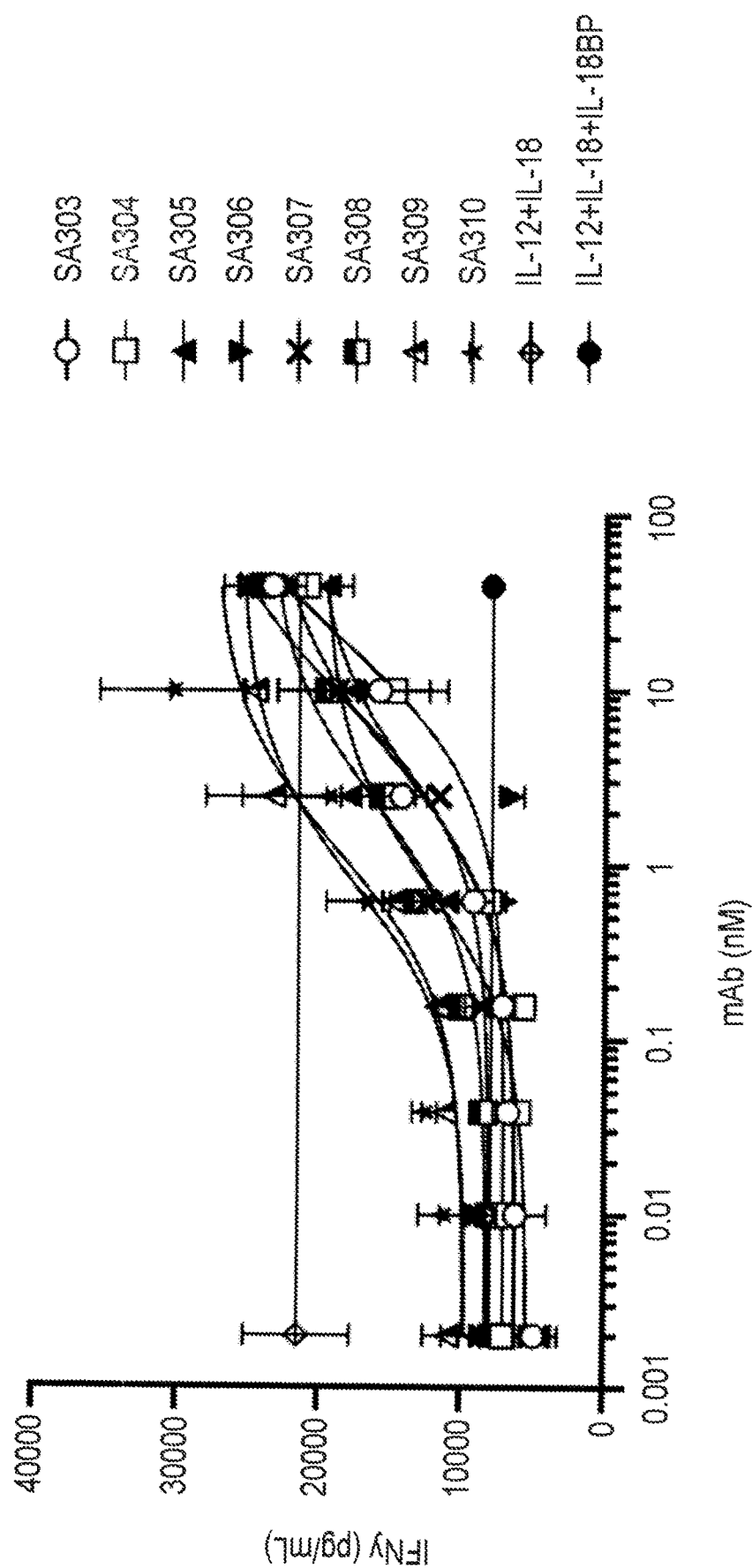
Figure 3B:
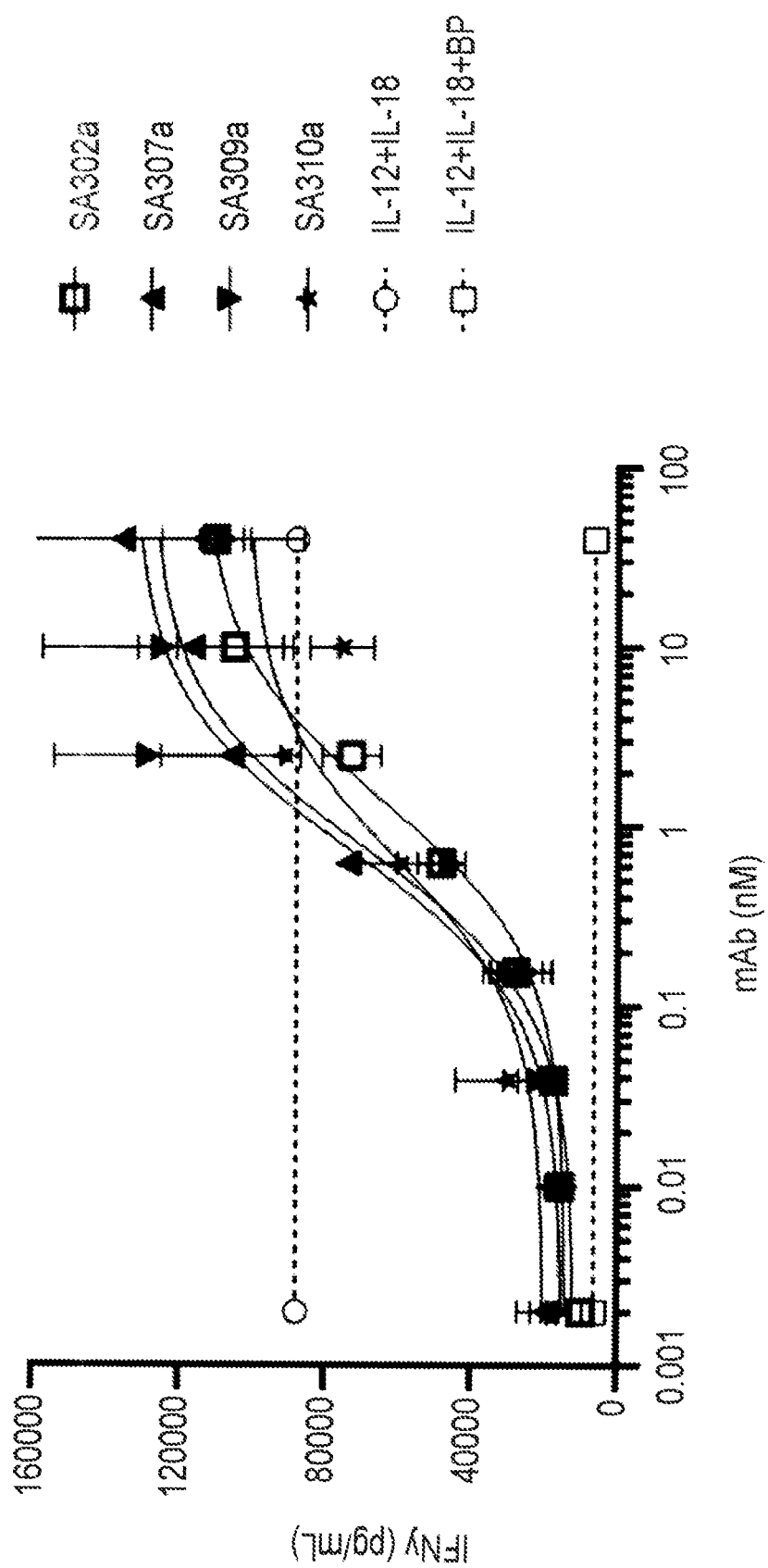
Figure 3C:
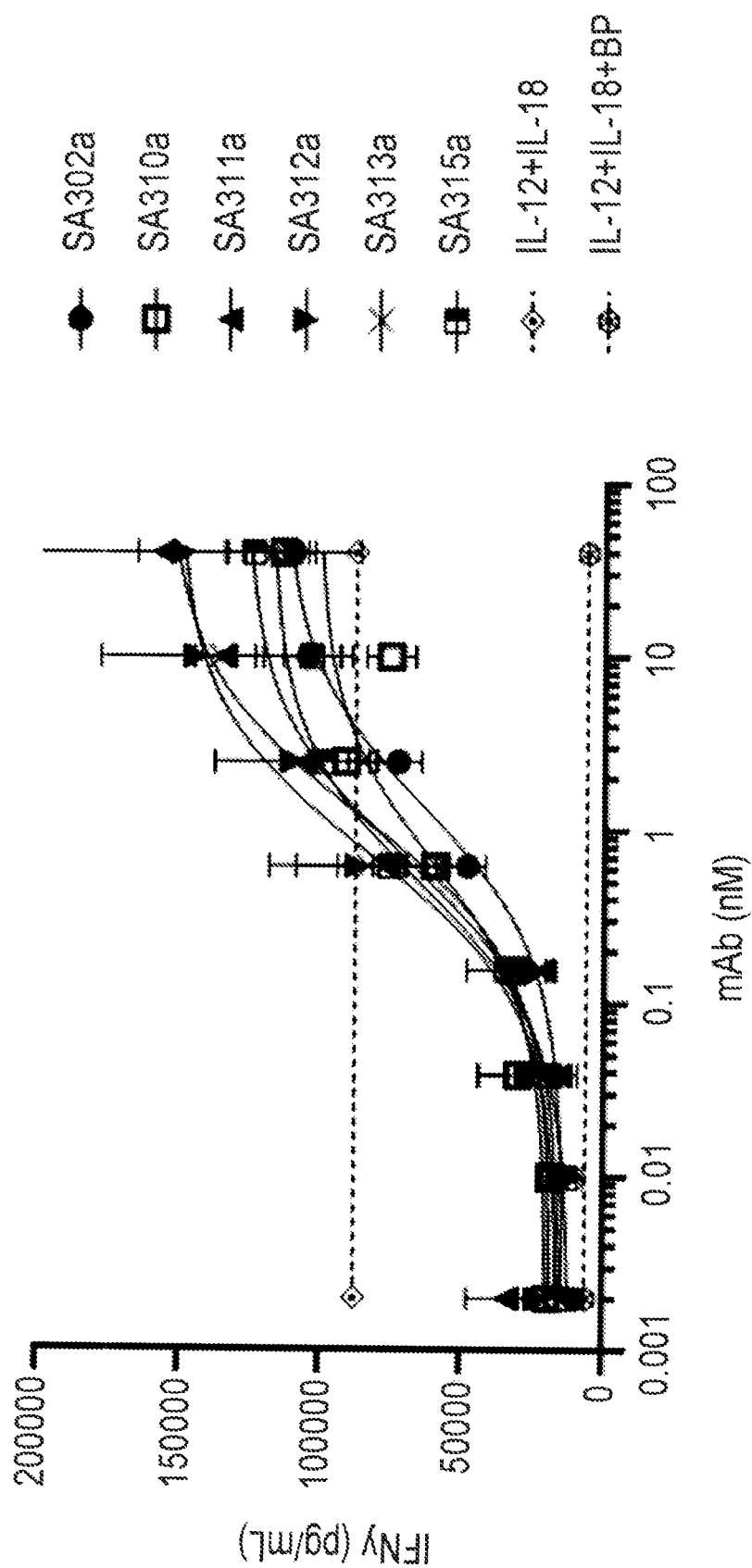
Figure 3D:
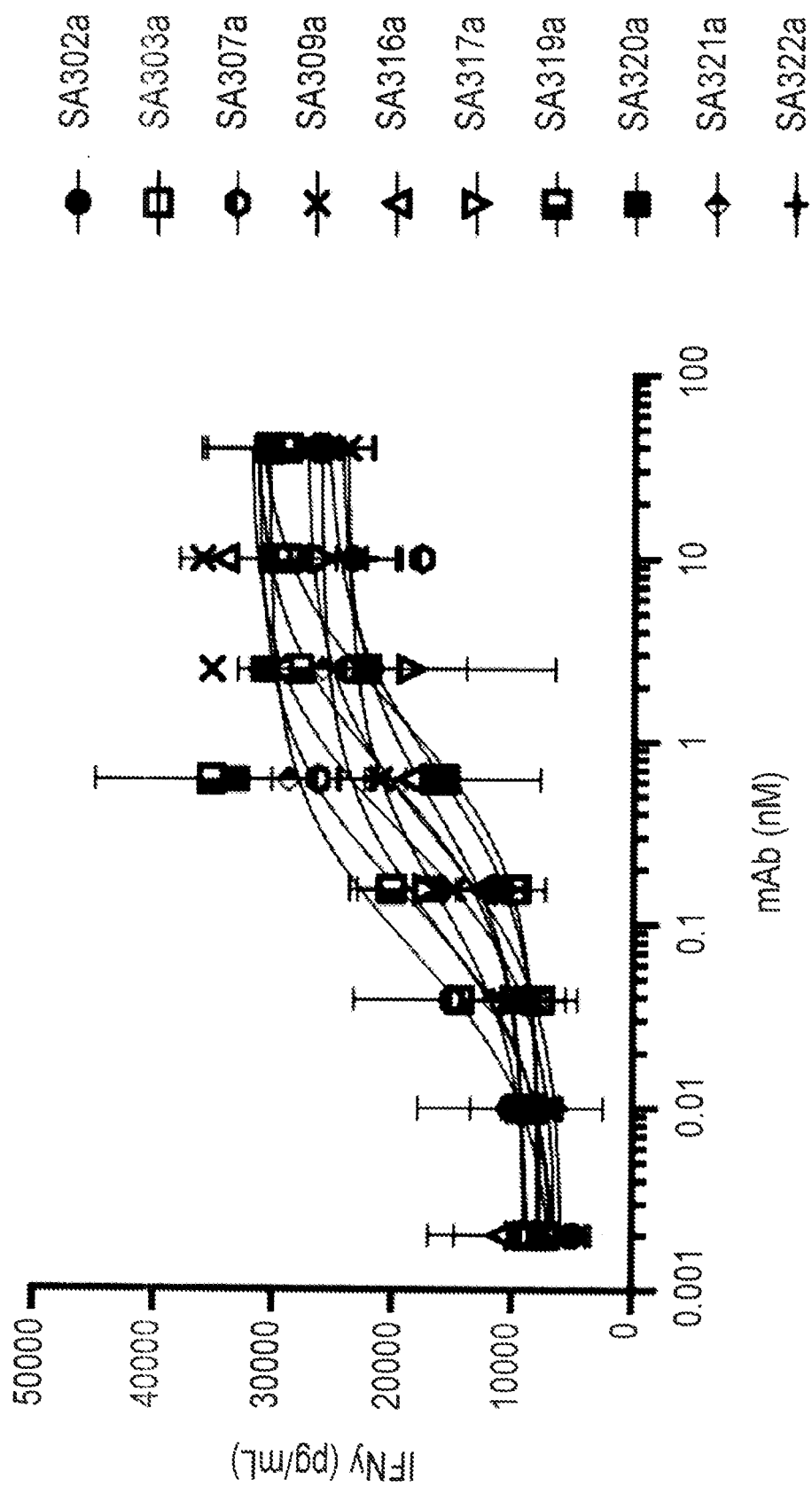
Figure 3E:
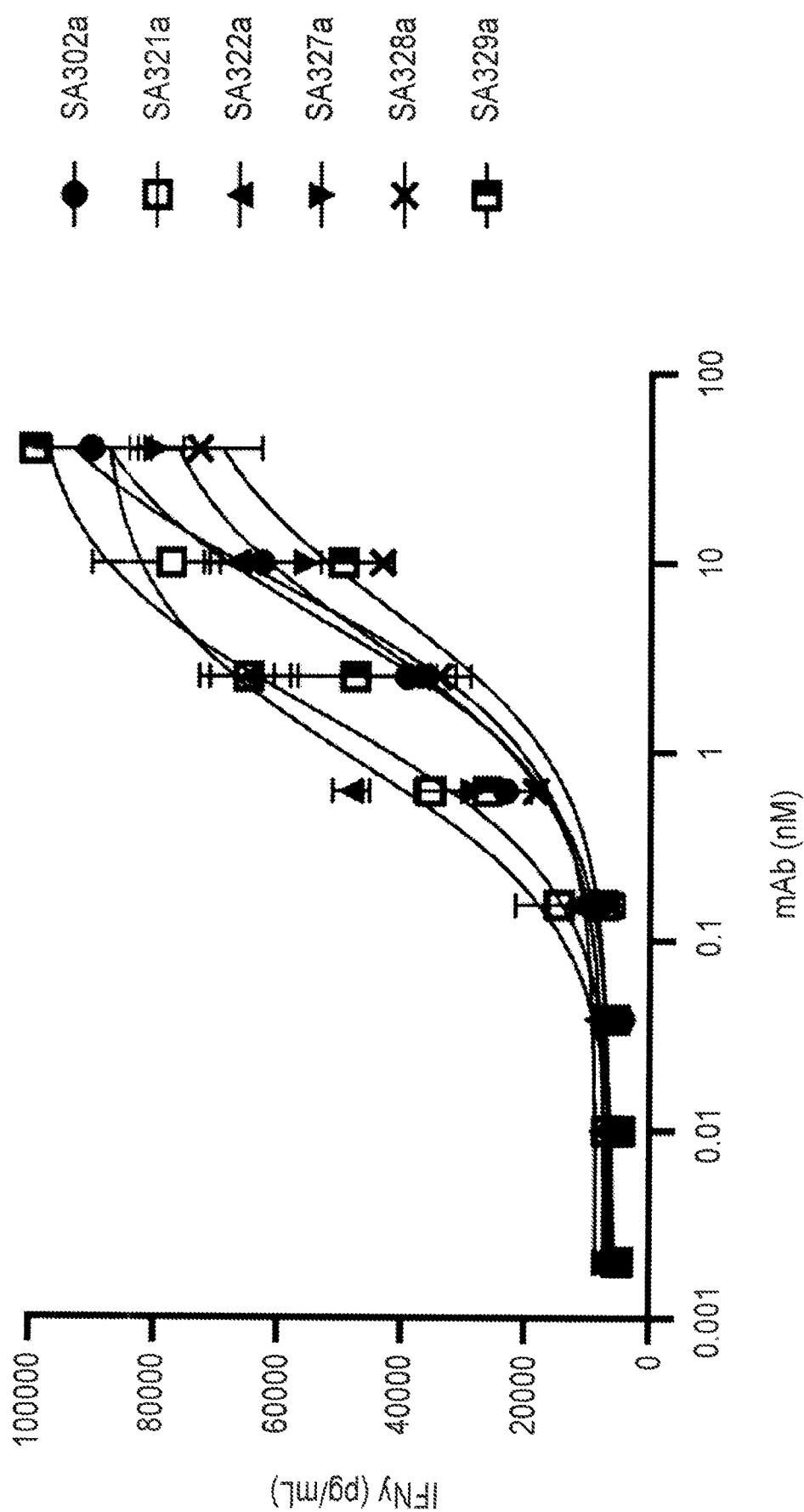
Figure 3F:
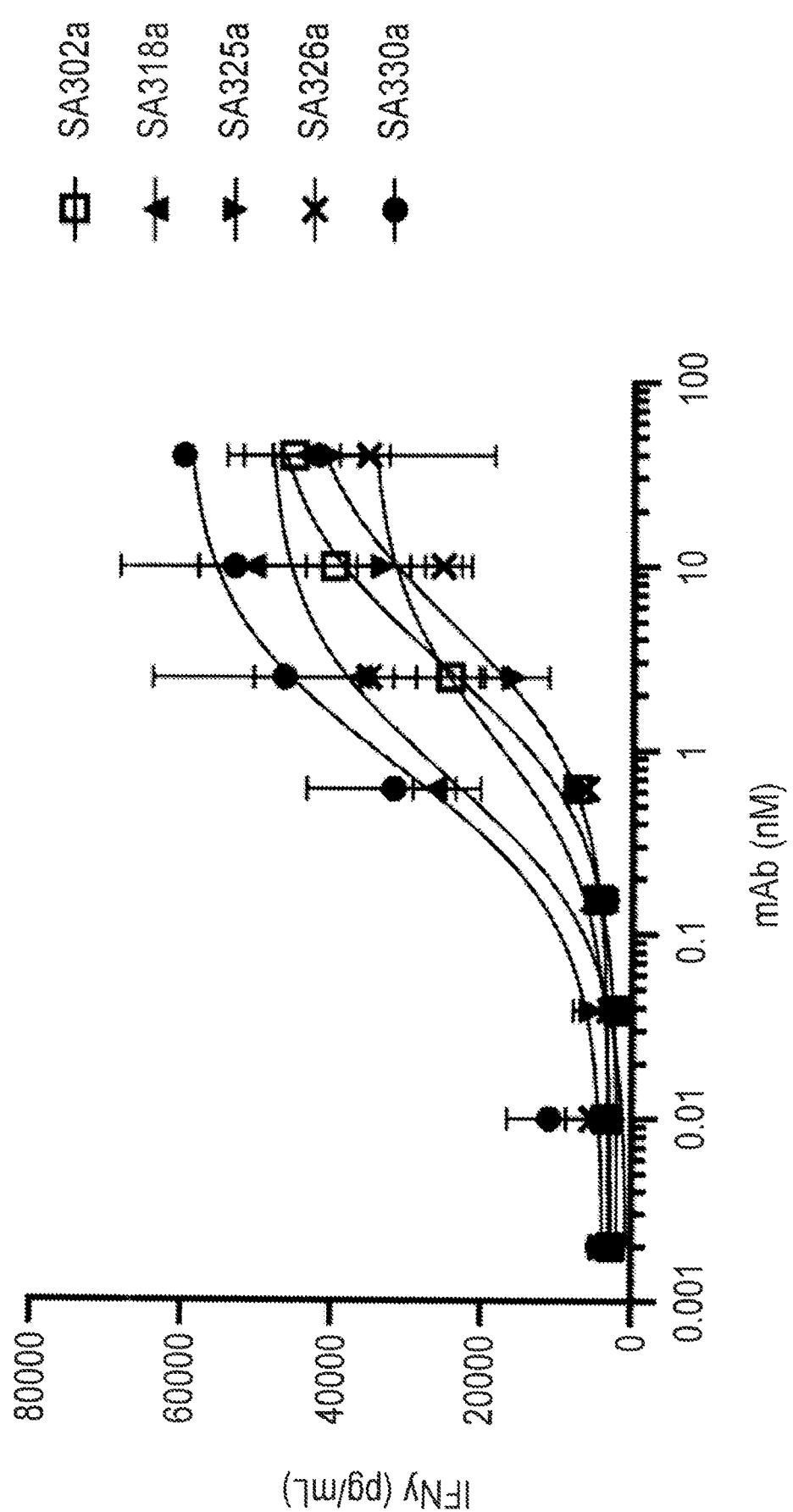

Because IL-18 displays high affinity for the binding protein with a KD of less than 1 nM (Kim et al., PNAS 97(3): 1190-1195, 2000; Kimura et al., Allergol Int. 57(4): 367-76, 2008), it might not be possible for mAbs with affinities in the nM affinity range, such as those typically isolated from antigen specific B cells, to antagonize the IL-18/IL-18BP interaction. Therefore, to assess the potential blocking abilities of newly-identified mAb candidates, the novel chimeric protein "hypo-IL-18" was generated. Hypo-IL-18 is comprised of human or mouse IL-18 tethered to their respective IL-18BPs but separated with a flexible linker peptide (shown schematically in FIGS. 1B-1C). The sequence of hypo-IL-18 is provided in Table S1 below.

TABLE S1

Hypo-IL-18 Sequence

| Species | Sequence | SEQ ID NO: |
|---|---|---|
| Human | MRAWIFFLLCLAGRALAYFGKLES KLSVIRNLNDQVLFIDQGNRPLFE DMTDSDCRDNAPRTIFIISMYKDS QPRGMAVTISVKCEKISTLSCENK IISFKEMNPPDNIKDTKSDIIFFQ RSVPGHDNKMQFESSSYEGYFLAC EKERDLFKLILKKEDELGDRSIMF TVQNEDGGSGGGSGENLYFQSGGG SGGGGTPVSQTTTAATASVRSTKD PCPSQPPVFPAAKQCPALEVTWPE VEVPLNGTLSLSCVACSRFPNFSI LYWLGNGSFIEHLPGRLWEGSTSR ERGSTGTQLCKALVLEQLTPALHS TNFSCVLVDPEQVVQRHVVLAQLW AGLRATLPPTQEALPSSHSSPQQQ GHHHHHH | 377 |
| Mouse | MRAWIFFLLCLAGRALANFGRLHC TTAVIRNINDQVLFVDKRQPVFED MTDIDQSASEPQTRLIIYMYKDSE VRGLAVTLSVKDSKMSTLSCKNKI ISFEEMDPPENIDDIQSDLIFFQK RVPGHNKMEFESSLYEGHFLACQK EDDAFKLILKKKDENGDKSVMFTL TNLHQSGGSGGGSGENLYFQSGGG SGGGGTSAPQTTATVLTGSSKDPC SSWSPAVPTKQYPALDVIWPEKEV PLNGTLTLSCTACSRFPYFSILYW LGNGSFIEHLPGRLKEGHTSREHR NTSTWLHRALVLEELSPTLRSTNF SCLFVDPGQVAQYHIILAQLWDGL KTAPSPSQETLSSHSPVSRSAGPG VAHHHHHH | 378 |

The rational for creating this molecule is that the IL-18BP active site will be blocked since its tethered ligand will be unable to dissociate. Thus, mAbs which recognize the active binding site of the BP will be sterically hindered from recognizing hypo-IL-18, while most non-blocking antibodies will be able to bind to IL-18BP and to hypo-IL-18 equally. A TEV protease cleavage site was also included in the design to provide the ability to separate the hIL-18 from its binding protein.

The design of hypo-IL-18, joining the C-terminus of IL-18 to the N-terminus of IL-18BP was made based on a crystal structure (Protein Data Bank [PDB] structure 3F62), which included human IL-18 in complex with the Ectromelia virus IL-18BP. Because Orthopoxviruses, including Ectromelia, encode functional IL-18BP homologs that exhibit 17-34% amino acid identity to the mammalian orthologous IL-18BP (Calderara, 2001), it was felt that the 3F62 crystal structure would be instructive in the design of the hypo-IL-18 construct. The solved crystal structure indicated that the C-terminus of IL-18 was relatively close to the N-terminus of the binding protein and therefore a fusion protein was possible. Certain embodiments thus include a hypo-IL-18 fusion protein, comprising, in an N- to C-terminal orientation, a signal peptide, IL-18, a first flexible linker, a protease cleavage site (optionally a TEV protease cleavage site), a flexible linker, and IL-18BP; wherein the IL-18 portion of the fusion protein is bound to the IL-18BP portion of the fusion protein and sterically blocks the IL-18 binding site of the IL-18BP portion of the fusion protein. In specific embodiments, the hypo-IL-18 fusion protein comprises, consist, or consists essentially of an amino acid sequence at least 70, 75, 80, 85, 90, 95, 97, 98, 99, or 100% identical to a sequence from Table S1. Also included are nucleic acid molecules encoding the hypo-IL-18 fusion protein.

Confirmation of Activity Ofre-Expressed mAbs, Analysis of Binding Kinetics, Blocking Ability, and Bioactivity.

Antibody sequences were derived from single B cell screening on the Beacon instrument. To confirm activity, antibodies they were re-expressed recombinantly using the isolated murine variable region sequences fused to human IgG1 kappa constant regions. Antibodies were expressed in HEK293 cells and tested from cell culture supernatant or purified for more detailed analyses.

Initial characterization tested binding affinity to human, cyno, and mouse IL-18BP using BLI. In addition, mAbs were tested for binding to hypo-IL-18 to identify mAbs most likely to be blocking antibodies. mAbs were also scored for their expression level and whether sequences were considered problematic. Examples of problematic sequences were poly-tyrosine sequences in CDR3, or low levels of somatic hypermutation indicating that the antibody had not undergone significant in vivo maturation. The results are illustrated in Table E1.

TABLE E1

Characterization of initial anti-IL-18BP mAbs

| mAb | hIL-18BP (KD nM) | cyIL-18BP (KD nM) | mIL-18BP (KD nM) | Hypo-IL-18 binding | Expression level | Sequence features |
|---|---|---|---|---|---|---|
| SA04a | 0.25 | 0.67 | weak | no | +++ | good |
| SA07a | weak | weak | no | yes | +++ | good |
| SA31a | 3 | 5 | nt | no | ++ | poor |
| SA32a | 17 | 19 | nt | no | + | poor |
| SA33a | 3 | 16 | nt | no | +++ | good |
| SA34a | 18 | 12 | nt | no | ± | good |
| SA35a | 11 | 13 | nt | no | ++ | good |
| SA44a | 0.51 | 0.67 | nt | no | ± | good |

ND, not determined; NT, not tested.
For expression, +++, >200 μg/mL; ++, 100-200 μg/mL; +, 50-100 μg/mL; ±, <50 μg/mL.

Antibodies of interest were also tested for activity in a cell-based reporter assay. This assay uses an engineered cell line where IL-18 signaling results in the secretion of alkaline phosphatase, which is readily measured. IL-18 induction of alkaline phosphatase is inhibited by the addition of IL-18BP, and this inhibition is alleviated by the addition of antibodies to IL-18BP provided they are capable of blocking IL-18BP/IL-18 binding. As shown in Table E2, several antibodies were capable of blocking the IL-18/IL-18BP interaction and allowing induction of an IL-18 driven response. The antibodies that resulted in activity in this assay were consistent with those unable to bind hypo-IL-18, verifying the screening approach used to isolate the antibodies of interest.

TABLE E2

Activity of anti-IL-18BP mAbs in HEK293 IL-18 Reporter Assay

| Antibody | EC50 (nM) |
|---|---|
| SA04a | 0.1 |
| SA07a | No activity |
| SA31a | 2.62 |
| SA32a | 6.82 |
| SA33a | 0.36 |
| SA34a | 5.02 |
| SA35a | 21 |

Additionally the antibodies were subsequently tested for bioactivity in KG-I cells. KG-1 is a human bone marrow derived macrophage cell line that responds to IL-18 by producing IFNγ. The addition of IL-18BP blocks the ability of IL-18 to induce IFNγ expression, thereby repressing the response. The further addition of a neutralizing anti-IL-18BP antibody, which binds to IL-18BP disrupting the interaction with IL-18, therefore liberates IL-18 to induce IFNγ. Antibodies demonstrated the ability to liberate IL-18 from IL-18BP inhibition in this assay as shown in table E3.

TABLE E3

Activity of anti-IL-18BP mAbs in KG-1 Assay

| Antibody | EC50 (nM) |
|---|---|
| SA04a | 2.6 |
| SA07a | Not tested |
| SA31a | 185 |
| SA32a | 109 |
| SA33a | 129 |
| SA34a | 51 |
| SA35a | 103 |
| SA301a | 1.3 | mAb Optimization

Two mAbs were prioritized for humanization and optimization: SA04a, and SA44a (see Table E4).

TABLE E4

| mAb | Human KD pM ± SEM (N) | Cyno KD pM ± SEM (N) | Mouse KD pM ± SEM (N) | Human/Cyno Fold Difference |
|---|---|---|---|---|
| SA04a | 260 | 1500 | no binding | 5.8 |
| SA44a | 688 ± 62 (N6) | 525 ± 194 (N3) | no binding | 1.0 |

Humanization of SA04a.

The heavy chain CDRs of SA04a were grafted into 3 different human variable regions—IGHV7-4-1*02 IGHV1-3*04 and IGHV3-23 and the light chain CDRs were grafted into hIGKV1-33*01 with framework backmutations P44V, F71Y, Y87F. The heavy chain grafted was into IGHV7-4-1*02 with framework backmutations G26V, V37L, L45F, Y91F. The binding characteristics of the resulting humanized mAb (SA50a) are shown in Table E5 below.

TABLE E5

Binding kinetics for SA04a and SA50a vs IL-18BP orthologs

| SA04a | | | SA50a | | |
|---|---|---|---|---|---|
| hu (pM) | cy (pM) | mo (pM) | hu (pM) | cy (pM) | mo (pM) |
| 260 | 1500 | IA | 410 ± 65 (N3) | 4270 ± 430 (N3) | IA |

IA, inactive,
± values are SEM,
number of experiments are indicated parenthetically.

Humanization of SA44a.

HC and LC CDRs from the DivergimAb™-derived SA44a antibody were grafted into the human germline variable regions IgHV4-30-4*01 and IGKV3-11*01 respectively. The grafting process significantly decreased binding affinity. Thus, to optimize affinity, two backmutations (G27Y in FW1 and V71R in FW3) were reintroduced into the HC and one backmutation (L46P in FW2) was reintroduced into the LC. As shown in Table E6 below, the resulting humanized mAb (SA301a) restored full activity and superior expression relative to its original murine parent (SA44a).

TABLE E6

Binding kinetics for SA44a and SA301a vs IL-18BP orthologs

| SA44a | | | SA301a | | |
|---|---|---|---|---|---|
| hu (pM) | cy (pM) | mo (pM) | hu (pM) | cy (pM) | mo (pM) |
| 688 ± 62 (N6) | 525 (N2) | IA | 162 ± 46 (N4) | 78 ± 16 (N3) | IA |

IA, inactive,
± values are SEM,
number of experiments are indicated parenthetically.

Maturation of SA301a.

To affinity mature the mAb SA301a, we prepared libraries of mAb variants centered on the HC and LC CDRs. To accomplish this, CDR amino acids were replaced in turn with up to 17 amino acid substitutions—cysteine and tryptophan were not included in the libraries so as to not introduce unwanted potential sequence liabilities, nor was the parental amino acid already in position included in the screen. Upon generation, the variants were first screened at a single concentration of human, and cyno IL-18BP by BLI to determine if any had improved on- or off-rates as compared to the parental antibody SA301a. Screening identified a variety of single point variants that did indeed improve apparent binding kinetics. Individual mutations may be able to be recombined to further improve binding affinity for the target antigen, though not in all cases.

The initial screen identified a subset of amino acid substitutions that specifically improved binding to both human and cyno IL-18BP. Consequently, these changes were recombined in various combinations for further analysis.

Table E7 shows the variants leading to improved binding to human and cyno IL-18BP. Parenthetical (N) values indicate how many data points from independently run experiments are included in the average; ±indicates S.E.M.; NT, not tested; ND, not determined. In cases where a mAb was tested only twice, both values are provided. Cyno/human provides the ratio difference between the two species.

TABLE E7

Variants with improved binding to human and cyno IL-18BP

| mAb | KD human (pM) | KD cyno (pM) | Cyno/human | HC Variations | | | | | LC Variations | | | |
|---|---|---|---|---|---|---|---|---|---|---|---|---|
| | | | | S31 | C34 | S56 | N58 | Y96 | Q90 | S93 | P95 | T96 |
| SA44a | 685 ± 57 (N = 7) | 524 ± 146 (N = 3) | 0.76 | | | | | | | | | |
| SA301a | 217 ± 24 (N = 15) | 102 ± 19 (N = 9) | 0.47 | | C34S | | | | | | | |
| SA302a | 345 ± 23 (N = 23) | 156 ± 35 (N = 7) | 0.45 | | C34A | | | | | | | |
| SA303a | 182 ± 27 (N = 5) | 77 ± 21 (N = 2) | 0.42 | | C34A | | | Y96F | | | | |
| SA307a | 54 ± 14 (N = 3) | 27 ± 8 (N = 2) | 0.50 | S31Q | C34A | | | | | | | |
| SA309a | 61 ± 16 (N = 3) | 24 (N = 1) | 0.39 | | C34A | S56Q | | | | | | |
| SA310a | 175 (N = 2) | 28 (N = 1) | 0.16 | | C34A | | N58M | | | | | |
| SA311a | 243 ± 140 (N = 3) | NT | ND | | C34A | S56Q | N58M | | | | | |
| SA312a | 117 ± 43 (N = 3) | NT | ND | S31Q | C34A | | N58M | | | | | |
| SA313a | 272 ± 170 (N = 3) | NT | ND | | C34A | | N58M | Y96F | | | | |
| SA315a | 39 (N = 1) | NT | ND | | C34A | S56Q | N58M | Y96F | | | | |
| SA316a | 228 ± 114 (N = 3) | NT | ND | | C34A | | N58Y | | | | | |
| SA317a | 329 (N = 2) | NT | ND | | C34A | | N58L | | | | | |

TABLE E7-continued

Variants with improved binding to human and cyno IL-18BP

| mAb | KD human (pM) | KD cyno (pM) | Cyno/ human | HC Variations | | | | | LC Variations | | | |
|---|---|---|---|---|---|---|---|---|---|---|---|---|
| | | | | S31 | C34 | S56 | N58 | Y96 | Q90 | S93 | P95 | T96 |
| SA318a | 15 (N = 2) | NT | ND | S31Q | C34A | S56Q | N58M | Y96F | | | | |
| SA319a | 254 ± 93 (N = 3) | NT | ND | S31Q | C34A | S56Q | | Y96F | | | | |
| SA320a | 52 ± 10 (N = 9) | 20 (N = 1)

TABLE E8-continued

Activity of mAbs in PBMC assays compared to affinity (KD)

| mAb | EC50 in PBMC Assay 1 (endogenous IL-18BP) EC50 (nM) n = 1 unless otherwise indicated | EC50 in PBMC Assay 2 (precomplexed IL-18BP) EC50 (nM) n = 1 unless otherwise indicated | Affinity (KD) KD (pM) |
|---|---|---|---|
| SA308a | 7.9 | 2.20 | |
| SA309a | 2.8 (n = 3) | 0.62 (n = 4) | 61 |
| SA310a | 1.9 (n = 2) | 0.94 (n = 2) | 175 |
| SA311a | 0.6 | 1.24 | 243 |
| SA312a | 2.1 | 0.74 | 117 |
| SA313a | 1.2 | 0.71 | 272 |
| SA315a | 0.5 | 0.49 | 39 |
| SA316a | 0.6 | 0.64 | 228 |
| SA317a | 0.4 | 0.45 | 329 |
| SA318a | 0.9 | 0.70 | 15 |
| SA319a | 0.2 | 0.07 | 254 |
| SA320a | 0.3 | 0.25 (n = 2) | 52 |
| SA321a | 0.9 (n = 2) | 0.85 (n = 2) | 136 |
| SA322a | 0.8 (n = 2) | 0.53 (n = 3) | 54 |
| SA325a | 6.1 | 5.00 | 468 |
| SA326a | 7.5 | 1.20 | 128 |
| SA327a | 7.1 | 4.00 | 249 |
| SA328a | 2 | 5.80 | 133 |
| SA329a | 5.3 | 7.40 | 107 |
| SA330a | 21 | 0.90 | 76 |
| SA337a | 1 | 0.58 | 47 |
| SA338a | 0.5 | 0.33 | 32 |

Figure 4:
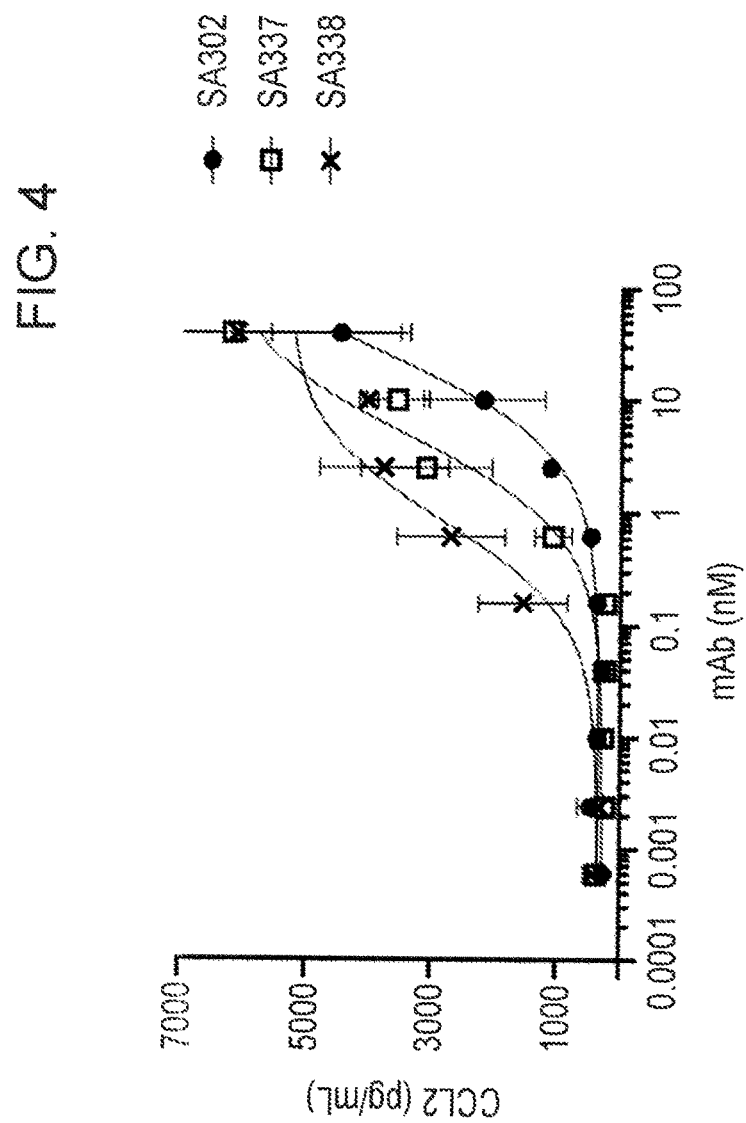
FIG. 4 depicts the ability of anti-human IL-18BP antibodies to elicit IL-18 induced production of the cytokine CCL2 in human PBMCs by ELISA.

Anti-human IL-18BP antibodies were also able to elicit IL-18 induced production of additional cytokines, from PBMC, for example CCL2. Antibodies were tested in the PBMC assay 1 (endogenous Il-18BP assay described above) and CCL2 release was determined by ELISA. The addition of anti-IL-18BP mAbs resulted in increased production of CCL2 by PBMC (FIG. 4).

The activity of the anti-IL-18BP mAbs was also tested using cynomolgus monkey PBMC assays. Assays in both formats described above for human PBMC were performed with PBMC isolated from cynomolgus monkey blood. Antibodies demonstrated activity in both formats as shown in FIG. 5A-5B.

Activity was also tested in an NK cell specific assay. In this assay purified human NK cells were incubated with precomplexed IL-18:IL-18BP with and without test antibodies. Test antibodies were able to disrupt the IL-18:IL-18BP complex and induce secretion of IFNγ from NK cells as shown in FIG. 6.

Library Screening Data

The binding characteristics were tested for variants of parental SA301a and SA302a antibodies.

Heavy Chain Library Screen.

Octet-generated kinetic values measuring at >50 nM are listed as "inactive." Positions providing at 1.5 to 2.0 fold improvement for human and cyno (when tested) were considered for further analyses. Values are presented for each species are apparent KDs since these were calculated from a single binding concentration collected in semi-high throughput format. Samples were compared to the parental background in which they were created (font is normal where parent is SA301a and italic where parent is SA302a with HC-C34A).

TABLE H1

| Loading Sample ID | KD nM hu | KD (nM) cy |
|---|---|---|
| N33bG, C34S | 0.2 | 0.5 |
| N33bL, C34S | 0.8 | 0.6 |
| N33bY, C34S | 1.2 | 0.9 |
| N33bD, C34S | IA | 0.1 |
| N33bS, C34S | 1.4 | 1.0 |
| Parent | 0.2 | 0.1 |
| N33bM, C34S | 1.9 | 1.4 |
| N33bV, C34S | 0.4 | 0.3 |
| N33bP, C34S | 2.5 | 1.3 |
| N33bK, C34S | 0.4 | 0.9 |
| N33bQ, C34S | 1.9 | 1.1 |
| Parent | 0.3 | 0.2 |
| C34R | 1.8 | 0.6 |
| C34P | 20.6 | 9.8 |
| C34E | 0.9 | 0.5 |
| C34K | 1.0 | 0.5 |
| C34Q | 0.6 | 0.4 |
| Parent | 0.4 | 0.2 |
| N33bE, C34S | 0.1 | 0.2 |
| N33bT, C34S | 0.3 | 0.4 |
| N33bH, C34A | 0.8 | 0.6 |
| N33bF, C34A | 1.5 | 1.4 |
| N33bI, C34A | 0.6 | 0.4 |
| Parent | 0.2 | 0.2 |
| N33bT, C34A | 0.1 | 0.3 |
| N33bK, C34A | 0.3 | 0.4 |
| N33bQ, C34A | 1.8 | 1.6 |
| N33bM, C34A | 0.9 | 1.0 |
| C34F | 0.6 | 0.5 |
| Parent | 0.1 | 0.1 |
| C34L | 0.4 | 0.3 |
| C34N | 1.0 | 0.6 |
| C34D | 0.5 | 0.4 |
| C34I | 1.0 | 0.6 |
| C34H | 0.4 | 0.2 |
| Parent | 0.1 | 0.1 |

TABLE H2

| Loading Sample ID | KD nM Hu | KD nM cy |
|---|---|---|
| N95I | IA | NT |
| N95G | 0.17 | NT |
| N95V | IA | NT |
| N95S | IA | NT |
| N95R | 0.02 | NT |
| N95H | IA | NT |
| Parent | 0.17 | NT |
| N95D | IA | NT |
| N95F | IA | NT |
| N95Y | IA | NT |
| N95L | IA | NT |
| N95P | IA | NT |
| N95Q | 5.33 | NT |
| Parent | 0.10 | NT |
| N95M | 0.00 | NT |
| N95T | IA | NT |
| N95A | 46.09 | NT |
| N95E | IA | NT |
| N95K | IA | NT |
| Y96G | 2.50 | NT |
| Parent | 0.17 | NT |
| Y96V | 1.68 | NT |
| Y96L | 1.08 | NT |
| Y96I | 4.02 | NT |
| Y96S | 0.87 | NT |
| Y96R | 0.60 | NT |
| Y96H | 1.24 | NT |
| Parent | 0.13 | NT |
| Y96N | 2.80 | NT |
| Y96F | 0.13 | NT |
| Y96P | 0.46 | NT |

TABLE H2-continued

| Loading Sample ID | KD nM Hu | KD nM cy |
|---|---|---|
| Y96Q | 0.65 | NT |
| Y96T | 0.61 | NT |
| Y96A | 0.47 | NT |
| Parent | 0.20 | NT |
| S98A | 2.29 | NT |
| S98E | 0.00 | NT |
| S98K | 5.41 | NT |
| Parent | 0.35 | NT |
| Y96E | 0.31 | NT |
| Y96K | 15.23 | NT |
| G97V | 4.96 | NT |
| G97L | 3.70 | NT |
| G97I | 7.83 | NT |
| G97R | 25.08 | NT |
| Parent | 0.25 | NT |
| G97H | 1.57 | NT |
| G97D | 0.46 | NT |
| G97N | 5.93 | NT |
| G97F | 6.32 | NT |
| G97P | 1.36 | NT |
| G97Q | 7.04 | NT |
| Parent | 0.19 | NT |
| G97M | 0.19 | NT |
| G97T | 0.01 | NT |
| G97A | 0.44 | NT |
| G97E | 11.58 | NT |
| G97K | 1.46 | NT |
| S98G | 2.57 | NT |
| Parent | 0.22 | NT |
| S98V | IA | NT |
| S98L | 0.00 | NT |
| S98I | 2.10 | NT |
| S98H | 6.42 | NT |
| S98D | 0.99 | NT |
| S98N | 2.98 | NT |
| Parent | 0.15 | NT |
| S98F | 0.00 | NT |
| S98Y | 0.02 | NT |
| S98P | 0.55 | NT |
| S98Q | 12.34 | NT |
| S98M | 0.00 | NT |
| S98T | 26.86 | NT |
| Parent | 0.09 | NT |

TABLE H3

| Loading Sample ID | KD nM hu | KD nM cy |
|---|---|---|
| I99G | 1.04 | 0.67 |
| I99V | 0.05 | 0.33 |
| I99L | 0.49 | 0.89 |
| I99S | 0.56 | 0.53 |
| I99R | 0.46 | 0.69 |
| I99H | 0.61 | 0.83 |
| Parent | 0.13 | 0.16 |
| I99D | 1.01 | 1.07 |
| I99N | 0.55 | 0.66 |
| I99F | 0.64 | 0.97 |
| I99Y | 0.48 | 0.45 |
| I99P | 0.41 | 0.51 |
| I99Q | 0.25 | 0.44 |
| Parent | 0.18 | 0.16 |
| I99M | 0.21 | 0.37 |
| I99A | 0.51 | 0.61 |
| I99E | 1.95 | 3.98 |
| Y100G | 0.51 | 0.48 |
| Y100V | 1.59 | 2.55 |
| Y100L | 1.06 | 1.41 |
| Parent | 0.22 | 0.27 |
| Y100I | 0.94 | 1.02 |
| Y100S | 0.72 | 3.27 |
| Y100R | 1.32 | 2.06 |
| Y100H | 1.30 | 1.10 |

TABLE H3-continued

| Loading Sample ID | KD nM hu | KD nM cy |
|---|---|---|
| Y100D | 0.56 | 3.65 |
| Y100N | 0.90 | 3.59 |
| Parent | 0.13 | 0.19 |
| Y100F | 0.10 | 0.26 |
| Y100P | 0.63 | 2.40 |
| Y100Q | 1.88 | 3.58 |
| Y100M | 2.07 | 2.28 |
| Y100T | 1.08 | 4.48 |
| Y100A | 0.88 | 4.17 |
| Parent | 0.15 | 0.22 |
| Y100E | 0.61 | 1.64 |
| Y100K | 1.49 | 2.18 |
| V100aG | 0.55 | 0.92 |
| V100aL | 2.54 | 0.81 |
| V100aI | 0.09 | 0.25 |
| V100aS | 0.28 | 0.53 |
| Parent | 0.12 | 0.17 |
| V100aR | 0.19 | 0.08 |
| V100aH | 0.41 | 0.06 |
| V100aD | 4.99 | 0.36 |
| V100aN | 0.68 | 0.11 |
| V100aF | IA | 0.44 |
| V100aY | 27.71 | 0.58 |
| Parent | 0.63 | 0.07 |
| V100aP | 0.49 | 0.15 |
| V100aQ | 0.45 | 0.10 |
| V100aM | 0.80 | 0.22 |
| V100aT | 0.27 | 0.06 |
| V100aA | 0.47 | 0.15 |
| V100aE | 0.51 | 0.22 |
| Parent | 0.30 | 0.05 |
| N100bL | IA | IA |
| N100bI | 0.00 | IA |
| N100bS | 0.49 | 0.09 |
| N100bR | 0.25 | IA |
| N100bH | 0.69 | 1.03 |
| N100bD | 2.30 | 0.96 |
| Parent | 0.33 | 0.06 |
| N100bF | IA | IA |
| N100bY | IA | 0.47 |
| N100bV | 2.16 | 1.16 |
| N100bP | IA | 0.11 |
| N100bQ | IA | 0.42 |
| N100bM | IA | 1.83 |
| Parent | 0.43 | 0.07 |
| N100bT | IA | IA |
| N100bA | IA | 0.00 |
| N100bE | 0.31 | 0.91 |
| N100bK | IA | 0.00 |
| Parent | 0.26 | 0.07 |

TABLE H4

| Loading Sample ID | KD nM hu | KD nM cy |
|---|---|---|
| Y50G | 1.03 | 2.85 |
| Y50V | 1.96 | 10.15 |
| Y50L | 2.56 | 1.70 |
| Y50I | 3.37 | 6.42 |
| Y50S | 2.17 | 2.48 |
| Y50R* | 1.19 | 4.98 |
| Parent* | 0.39 | 0.08 |
| Y50H | 1.87 | 3.87 |
| Y50D | 5.28 | 16.47 |
| Y50F | 2.18 | 1.81 |
| Y50P | 1.08 | 4.49 |
| Y50Q | 1.13 | 1.12 |
| Y50M | 2.06 | 1.80 |
| Parent | 0.30 | 0.14 |
| Y50A | 2.97 | 3.80 |
| Y50E | 3.44 | 8.97 |

TABLE H4-continued

| Loading Sample ID | KD nM hu | KD nM cy |
|---|---|---|
| Y50K | 1.08 | 2.43 |
| I51G | 0.92 | 0.87 |
| I51V | 0.30 | 0.55 |
| I51L | 0.69 | 0.64 |
| Parent | 0.34 | 0.19 |
| I51S | 0.57 | 0.82 |
| I51R | 2.00 | 1.57 |
| I51D | 1.99 | 2.17 |
| I51F | 2.38 | 1.55 |
| I51Y | 1.46 | 1.27 |
| I51P | 3.73 | 1.93 |
| Parent | 0.27 | 0.17 |
| I51M | 0.56 | 0.62 |
| I51T | 0.67 | 0.78 |
| I51A | 0.73 | 0.81 |
| I51E | 1.53 | 0.95 |
| I51K | 0.49 | 0.59 |
| H52G | 1.68 | 1.66 |
| Parent | 0.35 | 0.20 |
| H52V | 0.34 | 0.88 |
| H52I | 0.53 | 1.72 |
| H52S | 0.63 | 1.16 |
| H52R | 1.36 | 1.55 |
| H52D | 0.35 | 0.91 |
| H52N | 1.04 | 2.83 |
| Parent | 0.31 | 0.17 |
| H52F | IA | NT |
| H52Y | 0.79 | NT |
| H52L | IA | NT |
| H52P | 0.01 | NT |
| H52Q | IA | NT |
| H52M | IA | NT |
| Parent | 0.28 | NT |
| H52T | 1.92 | NT |
| H52A | 0.24 | NT |
| H52E | IA | NT |
| H52K | 0.01 | NT |
| Y53G | 1.86 | NT |
| Y53V | 2.16 | NT |
| Parent | 0.26 | NT |
| Y53I | 1.87 | NT |
| Y53S | 2.64 | NT |
| Y53R | 7.08 | NT |
| Y53H | 2.41 | NT |
| Y53D | 3.20 | NT |
| Y53F | 0.39 | NT |
| Parent | 0.22 | NT |
| Y53L | 2.42 | NT |
| Y53P | 0.38 | NT |
| Y53Q | 1.81 | NT |
| Y53M | 0.40 | NT |
| Y53T | 1.95 | NT |
| Y53A | 2.60 | NT |
| Parent | 0.23 | NT |
| Y53E | 5.06 | NT |
| Y53K | 3.16 | NT |
| S54Y | 4.66 | NT |
| S54R | 4.06 | NT |
| S54L | 2.64 | NT |
| S54G | 0.33 | NT |
| Parent | 0.23 | NT |
| S54V | 0.55 | NT |
| S54N | 0.36 | NT |
| S54P | 1.11 | NT |
| S54Q | 2.31 | NT |
| S54M | 1.94 | NT |
| S54T | 1.14 | NT |
| Parent | 0.27 | NT |

*This particular well was contaminated & a purified parent was run in it's place

TABLE H5

| Loading Sample ID | KD nM hu | KD nM cy |
|---|---|---|
| G55V | 0.44 | NT |
| G55L | 1.72 | NT |
| G55S | 0.51 | NT |
| G55R | 0.75 | NT |
| G55H | 1.31 | NT |
| G55D | 1.37 | NT |
| Parent | 0.58 | NT |
| G55F | 1.17 | NT |
| G55Y | 2.33 | NT |
| G55Q | 0.79 | NT |
| G55M | 0.84 | NT |
| G55T | 1.00 | NT |
| G55A | 0.75 | NT |
| Parent | 0.48 | NT |
| G55E | 0.40 | NT |
| G55K | 1.04 | NT |
| S56G | 0.46 | NT |
| S56V | 0.25 | NT |
| S56L | 0.36 | NT |
| S56I | 0.48 | NT |
| Parent | 0.53 | NT |
| S56R | 0.17 | NT |
| S56H | 0.55 | NT |
| S56D | 0.62 | NT |
| S56F | 0.70 | NT |
| S56Y | 1.00 | NT |
| S56P | 0.97 | NT |
| Parent | 0.48 | NT |
| S56Q | 0.00 | NT |
| S56M | 0.46 | NT |
| S56T | 0.45 | NT |
| S56A | 0.20 | NT |
| S56E | 0.48 | NT |
| S56K | 0.64 | NT |
| Parent | 0.50 | NT |
| T57G | 0.11 | NT |
| T57V | 0.36 | NT |
| T57L | 0.32 | NT |
| T57I | 0.28 | NT |
| T57S | 0.37 | NT |
| T57R | 0.67 | NT |
| Parent | 0.59 | NT |
| Y59M | 0.18 | NT |
| Y59T | 0.14 | NT |
| Y59A | 0.35 | NT |
| Y59E | 0.18 | NT |
| Y59K | 0.12 | NT |
| Y59V | 0.38 | NT |
| Parent | 0.20 | NT |
| T57H | 0.00 | NT |
| T57D | 1.73 | NT |
| T57N | 0.86 | NT |
| T57F | 1.22 | NT |
| T57Y | 1.74 | NT |
| T57Q | 0.91 | NT |
| Parent | 0.54 | NT |
| T57M | 0.18 | NT |
| T57A | 0.90 | NT |
| T57E | 0.42 | NT |
| T57K | 0.52 | NT |
| N58G | 4.39 | NT |
| N58V | 0.44 | NT |
| Parent | 0.47 | NT |
| N58L | 0.00 | NT |
| N58I | 0.27 | NT |
| N58S | 1.37 | NT |
| N58R | 0.46 | NT |
| N58H | 0.31 | NT |
| N58D | 4.51 | NT |
| Parent | 0.39 | NT |
| N58F | 0.00 | NT |
| N58Y | 0.41 | NT |
| N58P | 0.41 | NT |
| N58Q | 0.62 | NT |
| N58M | 0.23 | NT |
| N58T | 0.47 | NT |
| Parent | 0.64 | NT |

TABLE H5-continued

| Loading Sample ID | KD nM hu | KD nM cy |
|---|---|---|
| N58A | 0.64 | NT |
| N58E | 2.50 | NT |
| N58K | 0.34 | NT |
| Y59G | 1.59 | NT |
| Y59D | 1.25 | NT |
| Y59M | 1.06 | NT |
| Parent | 0.51 | NT |
| Y59I | 0.00 | NT |
| Y59S | 1.57 | NT |
| Y59R | 0.42 | NT |
| Y59D | 0.63 | NT |
| Y59N | 0.79 | NT |
| Y59F | 0.87 | NT |
| Parent | 0.63 | NT |
| Y59L | 0.42 | NT |
| S54A | 0.11 | NT |
| S54F | 0.56 | NT |
| S54D | 0.22 | NT |
| Y59P | 0.08 | NT |
| Y59Q | 0.35 | NT |
| Parent | 0.18 | NT |

TABLE H6

| Loading Sample ID | KD nM hu | KD nM cy |
|---|---|---|
| T30S | 0.66 | NT |
| T30N | 1.50 | NT |
| T30F | 1.29 | NT |
| T30Y | 1.15 | NT |
| T30V | 1.08 | NT |
| T30I | 1.79 | NT |
| Parent | 1.34 | NT |
| T30G | 1.38 | NT |
| T30Q | 1.28 | NT |
| T30E | 2.08 | NT |
| T30A | 1.32 | NT |
| T30L | 1.22 | NT |
| T30M | 1.54 | NT |
| Parent | 1.43 | NT |
| S31V | 1.09 | NT |
| S31N | 0.98 | NT |
| S31F | 0.79 | NT |
| S31L | 0.98 | NT |
| S31H | 0.57 | NT |
| S31Y | 1.11 | NT |
| Parent | 1.42 | NT |
| S31I | 1.01 | NT |
| S31G | 1.64 | NT |
| S31T | 1.02 | NT |
| S31E | 1.53 | NT |
| S31A | 0.92 | NT |
| S31P | 4.37 | NT |
| Parent | 1.25 | NT |
| S31M | 0.61 | NT |
| S31Q | 0.56 | NT |
| D33N | 1.66 | NT |
| D33I | 4.97 | NT |
| D33H | 2.99 | NT |
| D33R | 2.24 | NT |
| Parent | 1.25 | NT |
| D33G | 3.95 | NT |
| D33V | 5.42 | NT |
| D33Y | 3.79 | NT |
| D33T | 5.17 | NT |
| D33E | 1.76 | NT |
| D33Q | 2.92 | NT |
| SA302a | 1.43 | NT |
| D33T | 8.95 | NT |
| Y33aD | 10.48 | NT |
| Y33aL | 2.36 | NT |
| Y33aR | 8.72 | NT |
| Y33aH | 4.11 | NT |

TABLE H6-continued

| Loading Sample ID | KD nM hu | KD nM cy |
|---|---|---|
| Y33aV | 4.49 | NT |
| Parent | 2.29 | NT |
| Y33aS | 4.38 | NT |
| Y33aN | 5.92 | NT |
| Y33aM | 3.05 | NT |
| Y33aE | 8.65 | NT |
| N33bF | 5.24 | NT |
| N33bG | 2.21 | NT |
| Parent | 1.80 | NT |
| N33bY | 6.15 | NT |
| N33bR | 2.23 | NT |
| N33bD | 1.03 | NT |
| N33bH | 2.91 | NT |
| N33bV | 1.36 | NT |
| N33bT | 1.63 | NT |
| Parent | 1.63 | NT |
| N33bQ | 6.01 | NT |
| N33bK | 1.12 | NT |
| N33bA | 5.45 | NT |
| N33bP | 6.05 | NT |
| H35N | 3.02 | NT |
| H35R | 1.18 | NT |
| Parent | 1.37 | NT |
| H35D | 4.23 | NT |
| H35L | 1.74 | NT |
| H35G | 2.05 | NT |
| H35M | 2.18 | NT |
| H35K | 0.44 | NT |
| H35A | 6.41 | NT |
| SA302a | 1.58 | NT |
| H35T | 2.23 | NT |
| H35V | 2.42 | NT |
| H35P | 0.88 | NT |
| H35E | 1.57 | NT |
| Empty | n/a | NT |
| Empty | n/a | NT |
| SA302a | 1.64 | NT |

Light Chain Library Screen.

Octet-generated kinetic values measuring at >50 nM are listed as "inactive." Positions providing at ≥1.5 to 2.0 fold improvement for both human and cyno were considered for further analyses. Values are presented for each species are apparent KDs since these were calculated from a single binding concentration collected in semi-high throughput format. Samples are compared to the parental background in which they were created, that is, font is normal where parent is SA301a and italics where the parent is SA326a (HC-C34A x LC-Q90L).

TABLE L1

| Loading Sample ID | KD nM hu | KD nM cy |
|---|---|---|
| Q89R | IA | NT |
| Q89S | 0.28 | NT |
| Q89G | 0.32 | NT |
| Q89Y | 0.35 | NT |
| Q89V | 0.51 | NT |
| Q89N | 0.28 | NT |
| Parent | 0.21 | NT |
| Q89F | 0.40 | NT |
| Q89D | 0.02 | NT |
| Q89K | 0.97 | NT |
| Q89M | 0.49 | NT |
| Q89A | 0.39 | NT |
| Q89E | 0.46 | NT |
| Parent | 0.20 | NT |
| Q89L | 0.85 | NT |
| Q89P | IA | NT |
| Q90S | 0.41 | NT |
| Q90I | 0.24 | NT |

TABLE L1-continued

| Loading Sample ID | KD nM hu | KD nM cy |
|---|---|---|
| Q90V | 0.29 | NT |
| Q90G | 0.78 | NT |
| Parent | 0.16 | NT |
| Q90F | 0.65 | NT |
| Q90H | 0.25 | NT |
| Q90R | 0.51 | NT |
| Q90Y | 1.04 | NT |
| Q90D | 0.31 | NT |
| Q90P | 0.09 | NT |
| Parent | 0.24 | NT |
| Q90T | 0.40 | NT |
| Q90A | 1.07 | NT |
| Q90K | 0.10 | NT |
| Q90E | 0.18 | NT |
| Q90L | 0.13 | NT |
| Q90M | 0.27 | NT |
| Parent | 0.19 | NT |
| Y91F | 0.26 | NT |
| Y91R | 0.18 | NT |
| Y91G | 0.23 | NT |
| Y91D | IA | NT |
| Y91S | 0.33 | NT |
| Y91V | 1.85 | NT |
| Parent | 0.17 | NT |
| Y91I | 0.42 | NT |
| Y91P | 0.24 | NT |
| Y91T | 0.45 | NT |
| Y91M | 0.22 | NT |
| Y91A | 1.08 | NT |
| Y91K | 1.13 | NT |
| Parent | 0.16 | NT |
| Y91E | 0.31 | NT |
| Y91Q | 0.24 | NT |
| H92Y | 0.10 | NT |
| H92F | 0.70 | NT |
| H92V | 0.20 | NT |
| H92A | 0.95 | NT |
| Parent | 0.17 | NT |
| H92E | 0.36 | NT |
| H92T | 0.15 | NT |
| S93V | 0.19 | NT |
| S93Y | 0.19 | NT |
| S93G | 0.08 | NT |
| S93D | 0.23 | NT |
| Parent | 0.15 | NT |
| S93I | 0.21 | NT |
| S93F | 0.15 | NT |
| S93M | 0.14 | NT |
| S93P | 0.41 | NT |
| S93Q | 0.24 | NT |
| S93A | 0.52 | NT |
| Parent | 0.18 | NT |
| S93L | 0.23 | NT |
| S93K | 0.16 | NT |
| Y94S | 0.63 | NT |
| Y94R | 0.29 | NT |
| Y94F | 0.13 | NT |
| Y94N | 0.22 | NT |
| Parent | 0.17 | NT |
| Y94G | 0.12 | NT |
| Y94L | 0.16 | NT |
| Y94I | 1.27 | NT |
| Y94A | 1.15 | NT |
| Y94E | IA | NT |
| Y94T | IA | NT |
| Parent | 0.13 | NT |
| Y94M | 1.93 | NT |
| Y94Q | IA | NT |
| Y94V | 2.35 | NT |
| P95Y | 0.82 | NT |
| P95G | IA | NT |
| P95F | 2.01 | NT |
| Parent | 0.25 | NT |
| P95V | 0.47 | NT |
| P95L | 2.18 | NT |
| P95N | 0.32 | NT |
| P95A | 0.26 | NT |

TABLE L1-continued

| Loading Sample ID | KD nM hu | KD nM cy |
|---|---|---|
| P95V | 0.01 | NT |
| P95E | 0.44 | NT |
| Parent | 0.31 | NT |
| P95K | 0.22 | NT |
| T96I | 0.12 | NT |
| T96Y | 0.22 | NT |
| T96D | 0.13 | NT |
| T96A | 0.17 | NT |
| T96E | 0.31 | NT |
| Parent | 0.16 | NT |
| T96M | 0.19 | NT |
| T96K | 0.05 | NT |
| T96V | 0.21 | NT |
| T96P | 0.26 | NT |
|  |  | NT |
|  |  | NT |
|  |  | NT |

TABLE L2

| Loading Sample ID | KD nM hu | KD nM cy |
|---|---|---|
| R50N | IA | NT |
| R50G | IA | NT |
| R50S | IA | NT |
| R50I | IA | NT |
| R50D | IA | NT |
| R50F | IA | NT |
| Parent | 0.14 | NT |
| R50E | IA | NT |
| R50V | IA | NT |
| R50M | IA | NT |
| R50L | IA | NT |
| R50P | IA | NT |
| R50Q | IA | NT |
| Parent | 0.27 | NT |
| R50A | IA | NT |
| T51R | IA | NT |
| T51G | 0.89 | NT |
| T51V | 2.27 | NT |
| T51Y | 14.59 | NT |
| T51S | 0.22 | NT |
| Parent | 0.21 | NT |
| T51P | 1.77 | NT |
| T51A | 0.63 | NT |
| T51E | 11.79 | NT |
| S52G | 0.29 | NT |
| S52H | 0.15 | NT |
| S52D | 0.13 | NT |
| Parent | 0.15 | NT |
| S52L | 0.18 | NT |
| S52R | 0.24 | NT |
| S52A | 0.24 | NT |
| S52V | 0.27 | NT |
| S52P | 0.29 | NT |
| S52T | 0.17 | NT |
| Parent | 0.17 | NT |
| S52Q | 0.23 | NT |
| N53L | 0.51 | NT |
| N53G | 0.28 | NT |
| N53D | 0.30 | NT |
| N53Y | 0.34 | NT |
| N53V | 0.33 | NT |
| Parent | 0.18 | NT |
| N53R | 0.23 | NT |
| N53S | 0.20 | NT |
| N53F | 0.36 | NT |
| N53I | 0.22 | NT |
| N53M | 0.16 | NT |
| N53Q | 0.21 | NT |
| Parent | 0.15 | NT |
| N53P | IA | NT |
| N53A | 0.26 | NT |

TABLE L2-continued

| Loading Sample ID | KD nM hu | KD nM cy |
|---|---|---|
| N53T | 0.30 | NT |
| N53E | IA | NT |
| N53Q | 0.25 | NT |
| L54S | 0.09 | NT |
| Parent | 0.18 | NT |
| L54N | IA | NT |
| L54V | 0.98 | NT |
| L54F | 0.16 | NT |
| L54I | 0.16 | NT |
| L54D | IA | NT |
| L54G | 0.11 | NT |
| Parent | 0.18 | NT |
| L54E | 0.07 | NT |
| L54T | 0.15 | NT |
| L54P | 0.18 | NT |
| L54M | 0.16 | NT |
| L54A | 0.11 | NT |
| L54Q | 0.13 | NT |
| Parent | 0.17 | NT |
| L54K | 0.16 | NT |
| A55F | 0.97 | NT |
| A55S | 0.13 | NT |
| A55H | 0.24 | NT |
| A55V | 0.16 | NT |
| A55G | 1.70 | NT |
| Parent | 0.18 | NT |
| A55N | 1.98 | NT |
| A55R | 0.19 | NT |
| A55I | 0.27 | NT |
| A55T | 1.83 | NT |
| A55K | 0.22 | NT |
| A55M | 0.20 | NT |
| Parent | 0.18 | NT |

TABLE L3

| Loading Sample ID | KD nM hu | KD nM cy |
|---|---|---|
| S24L | 0.43 | NT |
| S24Y | 0.45 | NT |
| S24F | 0.50 | NT |
| S24H | 0.14 | NT |
| S24N | 0.39 | NT |
| S24D | 0.41 | NT |
| Parent | 0.48 | NT |
| S24R | 0.39 | NT |
| S24I | 0.44 | NT |
| S24P | 0.41 | NT |
| S24M | 0.16 | NT |
| S24T | 0.36 | NT |
| S24Q | 0.35 | NT |
| Parent | 0.43 | NT |
| S24A | 0.33 | NT |
| S24K | 0.36 | NT |
| A25H | 0.40 | NT |
| A25N | 0.25 | NT |
| A25V | 0.34 | NT |
| A25S | 0.36 | NT |
| Parent | 0.44 | NT |
| A25I | 0.54 | NT |
| A25F | 0.45 | NT |
| A25L | 0.50 | NT |
| A25G | 0.51 | NT |
| A25P | 0.44 | NT |
| A25T | 0.49 | NT |
| Parent | 0.43 | NT |
| A25Q | 0.54 | NT |
| S26N | 0.45 | NT |
| S26H | 0.50 | NT |
| S26G | 0.40 | NT |
| S26Y | 0.44 | NT |
| S26F | 0.41 | NT |
| Parent | 0.37 | NT |

TABLE L3-continued

| Loading Sample ID | KD nM hu | KD nM cy |
|---|---|---|
| S26V | 0.45 | NT |
| S26D | 0.51 | NT |
| S26L | 0.41 | NT |
| S26I | 0.44 | NT |
| S26R | 0.48 | NT |
| S26A | 0.41 | NT |
| Parent | 0.41 | NT |
| S26T | 0.53 | NT |
| S26Q | 0.46 | NT |
| S26P | 0.55 | NT |
| S26K | 0.51 | NT |
| S26M | 0.56 | NT |
| S27I | 0.50 | NT |
| Parent | 0.45 | NT |
| S27D | 0.43 | NT |
| S27Y | 0.37 | NT |
| S27L | 0.44 | NT |
| S27T | 0.53 | NT |
| S27H | 0.49 | NT |
| S27G | 0.49 | NT |
| S27R | 0.45 | NT |
| Parent | 0.47 | NT |
| S27Q | 0.43 | NT |
| S27P | 0.45 | NT |
| S27K | 0.52 | NT |
| S27A | 0.47 | NT |
| S27M | 0.63 | NT |
| S28D | 0.42 | NT |
| Parent | 0.43 | NT |
| S28Y | 0.47 | NT |
| S28N | 0.45 | NT |
| S28H | 0.44 | NT |
| S28F | 0.46 | NT |
| S28G | 0.51 | NT |
| S28M | 0.51 | NT |
| Parent | 0.53 | NT |
| S28E | 0.39 | NT |
| S28T | 0.43 | NT |
| S28P | 0.39 | NT |
| S28Q | 0.45 | NT |
| S28K | 0.51 | NT |
| V29H | 0.47 | NT |
| Parent | 0.50 | NT |
| V29L | 0.33 | NT |
| V29R | 0.38 | NT |
| V29G | 0.41 | NT |
| V29Y | 0.40 | NT |
| V29N | 0.44 | NT |
| V29D | 0.43 | NT |
| Parent | 0.46 | NT |
| V29A | 0.40 | NT |
| V29M | 0.35 | NT |
| V29T | 0.32 | NT |
| V29E | 0.34 | NT |
| V29Q | 0.30 | NT |
| V29P | 0.38 | NT |
| Parent | 0.41 | NT |
| S30L | 0.49 | NT |
| S30D | 0.31 | NT |
| S30N | 0.38 | NT |
| S30H | 0.34 | NT |
| S30F | 0.35 | NT |
| S30V | 0.36 | NT |
| Parent | 0.39 | NT |
| S30R | 0.42 | NT |
| S30M | 0.66 | NT |
| S30K | 0.48 | NT |
| S30Q | IA | NT |
| S30T | 0.45 | NT |
| S30P | IA | NT |
| Parent | 0.43 | NT |
| S30A | 0.32 | NT |
| S30E | 0.32 | NT |
| Y32S | 0.47 | NT |
| Y32H | 0.56 | NT |
| Y32G | 0.39 | NT |
| Y32R | 0.35 | NT |
| Parent | 0.34 | NT |

TABLE L3-continued

| Loading Sample ID | KD nM hu | KD nM cy |
|---|---|---|
| Y32I | 0.69 | NT |
| Y32V | 0.78 | NT |
| Y32F | 0.72 | NT |
| Y32N | 1.06 | NT |
| Y32L | 0.72 | NT |
| Y32T | 0.96 | NT |
| Parent | 8.88 | NT |
| Y32K | 0.30 | NT |
| Y32M | 0.36 | NT |
| Y32A | 0.53 | NT |
| Y32Q | 0.44 | NT |
| M33V | 0.38 | NT |
| M33F | 0.37 | NT |
| Parent | 0.41 | NT |
| M33R | 0.24 | NT |
| M33Y | 0.30 | NT |
| M33G | 0.32 | NT |
| M33H | 0.32 | NT |
| M33N | 0.35 | NT |
| M33S | 0.34 | NT |
| Parent | 0.37 | NT |
| M33D | 0.35 | NT |
| M33T | 0.34 | NT |
| M33Q | 0.41 | NT |
| M33L | 0.36 | NT |
| M33A | 0.38 | NT |
| M33P | 0.38 | NT |
| Parent | 0.39 | NT |
| Y34F | 0.39 | NT |
| Y34V | 0.32 | NT |
| Y34R | 0.33 | NT |
| Y34N | 0.62 | NT |
| Y34L | 0.37 | NT |
| Y34H | 0.18 | NT |
| Parent | 0.35 | NT |
| Y34S | 0.31 | NT |
| Y34G | 0.39 | NT |
| Y34P | 0.34 | NT |
| Y34T | 0.41 | NT |
| Y34E | 0.36 | NT |
| Y34K | 0.34 | NT |
| Parent | 0.34 | NT |
| Y34Q | 0.34 | NT |
| S56D | 0.33 | NT |
| S56N | 0.42 | NT |
| S56F | 0.41 | NT |
| S56V | 0.39 | NT |
| S56Y | 0.37 | NT |
| Parent | 0.36 | NT |
| S56G | 0.33 | NT |
| S56E | 0.32 | NT |
| S56L | 0.36 | NT |
| S56Q | 0.40 | NT |
| S56T | 0.40 | NT |
| S56A | 0.37 | NT |
| Parent | 0.35 | NT |

Epitope Mapping

The epitope of mAb SA338a on IL-18BP was determined by cross-linking/high resolution mass spectrometry methodology developed by CovalX AG (Pimenova et al., 2008, J. Mass Spectrometry 43: 185). In short, human IL-18BP was allowed to bind to SA338a and cross-linked with a heterobifunctional linker. The resulting complexes were digested with 5 different proteases (trypsin, chymotrypsin, ASP-N, elastase and thermolysin) and the resulting peptides, cross-linked or not, were analyzed by high-resolution mass spectrometry.

The results demonstrated that SA338a recognizes a conformational epitope including the residues in IL-18BP indicated below. In addition, the residues on IL-18BP which interact with IL-18 were similarly mapped using the same technique. The results below demonstrate that four residues on IL-18BP which are involved in recognition of IL-18 are also residues recognized by SA338a, supporting the evidence that this a functional blocking antibody (S75, H79, T116, and S119). SA338a interacts with the following residues on IL-18BP: T51, S53, S75, H79, R83, S88, S90, T110, H114, S115, T116, S119. Residues on IL-18BP which interact with IL-18 were identified as: R61, Y69, S75, H79, T116, S119 and R131. The sequence of mature IL-18BP is shown below with the residues interacting with SA338a and IL-18 highlighted as indicated.

```
                                              (SEQ ID NO: 372)
  1 TPVSQTTTAA TASVRSTKDP CPSQPPVFPA

AKQCPALEVT WPEVEVPLNG

51 TLSLSCVACS RFPNFSILYW LGNGSFIEHL

PGRLWEGSTS RERGSTGTQL

101 CKALVLEQLT PALHSTNFSC VLVDPEQVVQ

RHVVLAQLWA GLRATLPPTQ

151 EALPSSHSSP QQQG
```

Residues found to interact with IL-18 are highlighted in bold and underlined. Residues that form the epitope of SA338a are highlighted in bold in italic font. The residues S75, H79, T116, S119 are recognized both by IL-18 and SA338a and are shown in bold, italic and underlined.

SEQUENCE LISTING

Sequence total quantity: 378
```
SEQ ID NO: 1          moltype = AA  length = 6
FEATURE               Location/Qualifiers
source                1..6
                      mol_type = protein
                      organism = synthetic construct
SEQUENCE: 1
TEYPMH                                                                    6

SEQ ID NO: 2          moltype = AA  length = 17
FEATURE               Location/Qualifiers
source                1..17
                      mol_type = protein
                      organism = synthetic construct
```

```
SEQUENCE: 2
WIHTYSGEPT YADDFKG                                                          17

SEQ ID NO: 3            moltype = AA  length = 9
FEATURE                 Location/Qualifiers
source                  1..9
                        mol_type = protein
                        organism = synthetic construct
SEQUENCE: 3
GRYYGALDY                                                                    9

SEQ ID NO: 4            moltype = AA  length = 11
FEATURE                 Location/Qualifiers
source                  1..11
                        mol_type = protein
                        organism = synthetic construct
SEQUENCE: 4
RASQDISNYL N                                                                11

SEQ ID NO: 5            moltype = AA  length = 7
FEATURE                 Location/Qualifiers
source                  1..7
                        mol_type = protein
                        organism = synthetic construct
SEQUENCE: 5
YTSRLHS                                                                      7

SEQ ID NO: 6            moltype = AA  length = 9
FEATURE                 Location/Qualifiers
source                  1..9
                        mol_type = protein
                        organism = synthetic construct
SEQUENCE: 6
QHGNTLPRT                                                                    9

SEQ ID NO: 7            moltype = AA  length = 6
FEATURE                 Location/Qualifiers
source                  1..6
                        mol_type = protein
                        organism = synthetic construct
SEQUENCE: 7
TEYPMH                                                                       6

SEQ ID NO: 8            moltype = AA  length = 17
FEATURE                 Location/Qualifiers
source                  1..17
                        mol_type = protein
                        organism = synthetic construct
SEQUENCE: 8
WIHTYSGEPT YADDFKG                                                          17

SEQ ID NO: 9            moltype = AA  length = 9
FEATURE                 Location/Qualifiers
source                  1..9
                        mol_type = protein
                        organism = synthetic construct
SEQUENCE: 9
GRYYGALDY                                                                    9

SEQ ID NO: 10           moltype = AA  length = 11
FEATURE                 Location/Qualifiers
source                  1..11
                        mol_type = protein
                        organism = synthetic construct
SEQUENCE: 10
RASQDISNYL N                                                                11

SEQ ID NO: 11           moltype = AA  length = 7
FEATURE                 Location/Qualifiers
source                  1..7
                        mol_type = protein
                        organism = synthetic construct
SEQUENCE: 11
YTSRLHS                                                                      7

SEQ ID NO: 12           moltype = AA  length = 9
FEATURE                 Location/Qualifiers
source                  1..9
                        mol_type = protein
```

```
                               -continued

SEQUENCE: 12
QHGNTLPRT                                                                9

SEQ ID NO: 13           moltype = AA  length = 6
FEATURE                 Location/Qualifiers
source                  1..6
                        mol_type = protein
                        organism = synthetic construct
SEQUENCE: 13
TDYYMN                                                                   6

SEQ ID NO: 14           moltype = AA  length = 17
FEATURE                 Location/Qualifiers
source                  1..17
                        mol_type = protein
                        organism = synthetic construct
SEQUENCE: 14
DINPNNGGTS YNQKFKG                                                      17

SEQ ID NO: 15           moltype = AA  length = 13
FEATURE                 Location/Qualifiers
source                  1..13
                        mol_type = protein
                        organism = synthetic construct
SEQUENCE: 15
EGVYSNYGGY FDY                                                          13

SEQ ID NO: 16           moltype = AA  length = 11
FEATURE                 Location/Qualifiers
source                  1..11
                        mol_type = protein
                        organism = synthetic construct
SEQUENCE: 16
SASSSVSYMY W                                                            11

SEQ ID NO: 17           moltype = AA  length = 7
FEATURE                 Location/Qualifiers
source                  1..7
                        mol_type = protein
                        organism = synthetic construct
SEQUENCE: 17
LTSNLAS                                                                  7

SEQ ID NO: 18           moltype = AA  length = 9
FEATURE                 Location/Qualifiers
source                  1..9
                        mol_type = protein
                        organism = synthetic construct
SEQUENCE: 18
QQWSSNPPT                                                                9

SEQ ID NO: 19           moltype = AA  length = 6
FEATURE                 Location/Qualifiers
source                  1..6
                        mol_type = protein
                        organism = synthetic construct
SEQUENCE: 19
TSYWMH                                                                   6

SEQ ID NO: 20           moltype = AA  length = 17
FEATURE                 Location/Qualifiers
source                  1..17
                        mol_type = protein
                        organism = synthetic construct
SEQUENCE: 20
NIYPGSGNTI YDEKFKS                                                      17

SEQ ID NO: 21           moltype = AA  length = 11
FEATURE                 Location/Qualifiers
source                  1..11
                        mol_type = protein
                        organism = synthetic construct
SEQUENCE: 21
WDNWEGYYFD Y                                                            11

SEQ ID NO: 22           moltype = AA  length = 16
FEATURE                 Location/Qualifiers
source                  1..16
```

```
                              mol_type = protein
                              organism = synthetic construct
SEQUENCE: 22
RSSKSLLHSN GITYLY                                                          16

SEQ ID NO: 23                 moltype = AA   length = 7
FEATURE                       Location/Qualifiers
source                        1..7
                              mol_type = protein
                              organism = synthetic construct
SEQUENCE: 23
QMSNLAS                                                                     7

SEQ ID NO: 24                 moltype = AA   length = 9
FEATURE                       Location/Qualifiers
source                        1..9
                              mol_type = protein
                              organism = synthetic construct
SEQUENCE: 24
AQNLELPWT                                                                   9

SEQ ID NO: 25                 moltype = AA   length = 6
FEATURE                       Location/Qualifiers
source                        1..6
                              mol_type = protein
                              organism = synthetic construct
SEQUENCE: 25
TGYYMH                                                                      6

SEQ ID NO: 26                 moltype = AA   length = 17
FEATURE                       Location/Qualifiers
source                        1..17
                              mol_type = protein
                              organism = synthetic construct
SEQUENCE: 26
YISCYNGATS YNQKFKG                                                         17

SEQ ID NO: 27                 moltype = AA   length = 8
FEATURE                       Location/Qualifiers
source                        1..8
                              mol_type = protein
                              organism = synthetic construct
SEQUENCE: 27
TLHYAMDY                                                                    8

SEQ ID NO: 28                 moltype = AA   length = 16
FEATURE                       Location/Qualifiers
source                        1..16
                              mol_type = protein
                              organism = synthetic construct
SEQUENCE: 28
RSSKSLLHSN GITYLY                                                          16

SEQ ID NO: 29                 moltype = AA   length = 7
FEATURE                       Location/Qualifiers
source                        1..7
                              mol_type = protein
                              organism = synthetic construct
SEQUENCE: 29
QMSNLAS                                                                     7

SEQ ID NO: 30                 moltype = AA   length = 9
FEATURE                       Location/Qualifiers
source                        1..9
                              mol_type = protein
                              organism = synthetic construct
SEQUENCE: 30
AQNLELPWT                                                                   9

SEQ ID NO: 31                 moltype = AA   length = 6
FEATURE                       Location/Qualifiers
source                        1..6
                              mol_type = protein
                              organism = synthetic construct
SEQUENCE: 31
TDYAMH                                                                      6

SEQ ID NO: 32                 moltype = AA   length = 17
FEATURE                       Location/Qualifiers
```

```
source                    1..17
                          mol_type = protein
                          organism = synthetic construct
SEQUENCE: 32
VISTYYGDAS YNQKFKG                                                              17

SEQ ID NO: 33             moltype = AA  length = 12
FEATURE                   Location/Qualifiers
source                    1..12
                          mol_type = protein
                          organism = synthetic construct
SEQUENCE: 33
ERDYYGSRLF DY                                                                   12

SEQ ID NO: 34             moltype = AA  length = 12
FEATURE                   Location/Qualifiers
source                    1..12
                          mol_type = protein
                          organism = synthetic construct
SEQUENCE: 34
SANSSISSNY LH                                                                   12

SEQ ID NO: 35             moltype = AA  length = 7
FEATURE                   Location/Qualifiers
source                    1..7
                          mol_type = protein
                          organism = synthetic construct
SEQUENCE: 35
GTSNLAS                                                                          7

SEQ ID NO: 36             moltype = AA  length = 9
FEATURE                   Location/Qualifiers
source                    1..9
                          mol_type = protein
                          organism = synthetic construct
SEQUENCE: 36
QQGSSIPYT                                                                        9

SEQ ID NO: 37             moltype = AA  length = 6
FEATURE                   Location/Qualifiers
source                    1..6
                          mol_type = protein
                          organism = synthetic construct
SEQUENCE: 37
TDYYIN                                                                           6

SEQ ID NO: 38             moltype = AA  length = 17
FEATURE                   Location/Qualifiers
source                    1..17
                          mol_type = protein
                          organism = synthetic construct
SEQUENCE: 38
EIYPGSGNTY YNEKFKG                                                              17

SEQ ID NO: 39             moltype = AA  length = 8
FEATURE                   Location/Qualifiers
source                    1..8
                          mol_type = protein
                          organism = synthetic construct
SEQUENCE: 39
GYYGRFAY                                                                         8

SEQ ID NO: 40             moltype = AA  length = 16
FEATURE                   Location/Qualifiers
source                    1..16
                          mol_type = protein
                          organism = synthetic construct
SEQUENCE: 40
RSSKSLLHSN GITYLY                                                               16

SEQ ID NO: 41             moltype = AA  length = 7
FEATURE                   Location/Qualifiers
source                    1..7
                          mol_type = protein
                          organism = synthetic construct
SEQUENCE: 41
QMSNLAS                                                                          7

SEQ ID NO: 42             moltype = AA  length = 9
```

```
FEATURE                     Location/Qualifiers
source                      1..9
                            mol_type = protein
                            organism = synthetic construct
SEQUENCE: 42
DQNLELPFT                                                                    9

SEQ ID NO: 43               moltype = AA  length = 6
FEATURE                     Location/Qualifiers
source                      1..6
                            mol_type = protein
                            organism = synthetic construct
SEQUENCE: 43
TDYPMH                                                                       6

SEQ ID NO: 44               moltype = AA  length = 17
FEATURE                     Location/Qualifiers
source                      1..17
                            mol_type = protein
                            organism = synthetic construct
SEQUENCE: 44
VISTYYGDAS YNQKFKG                                                          17

SEQ ID NO: 45               moltype = AA  length = 7
FEATURE                     Location/Qualifiers
source                      1..7
                            mol_type = protein
                            organism = synthetic construct
SEQUENCE: 45
WRGSFDY                                                                      7

SEQ ID NO: 46               moltype = AA  length = 12
FEATURE                     Location/Qualifiers
source                      1..12
                            mol_type = protein
                            organism = synthetic construct
SEQUENCE: 46
RASSSVSSSY LH                                                               12

SEQ ID NO: 47               moltype = AA  length = 7
FEATURE                     Location/Qualifiers
source                      1..7
                            mol_type = protein
                            organism = synthetic construct
SEQUENCE: 47
STSNLAS                                                                      7

SEQ ID NO: 48               moltype = AA  length = 8
FEATURE                     Location/Qualifiers
source                      1..8
                            mol_type = protein
                            organism = synthetic construct
SEQUENCE: 48
QQYSGYHT                                                                     8

SEQ ID NO: 49               moltype = AA  length = 7
FEATURE                     Location/Qualifiers
source                      1..7
                            mol_type = protein
                            organism = synthetic construct
SEQUENCE: 49
TSDYNCH                                                                      7

SEQ ID NO: 50               moltype = AA  length = 16
FEATURE                     Location/Qualifiers
source                      1..16
                            mol_type = protein
                            organism = synthetic construct
SEQUENCE: 50
YIHYSGSTNY NPSLKS                                                           16

SEQ ID NO: 51               moltype = AA  length = 9
FEATURE                     Location/Qualifiers
source                      1..9
                            mol_type = protein
                            organism = synthetic construct
SEQUENCE: 51
NYGSIYVNY                                                                    9
```

```
SEQ ID NO: 52           moltype = AA   length = 10
FEATURE                 Location/Qualifiers
source                  1..10
                        mol_type = protein
                        organism = synthetic construct
SEQUENCE: 52
SASSSVSYMY                                                              10

SEQ ID NO: 53           moltype = AA   length = 7
FEATURE                 Location/Qualifiers
source                  1..7
                        mol_type = protein
                        organism = synthetic construct
SEQUENCE: 53
RTSNLAS                                                                 7

SEQ ID NO: 54           moltype = AA   length = 8
FEATURE                 Location/Qualifiers
source                  1..8
                        mol_type = protein
                        organism = synthetic construct
SEQUENCE: 54
QQYHSYPT                                                                8

SEQ ID NO: 55           moltype = AA   length = 7
FEATURE                 Location/Qualifiers
source                  1..7
                        mol_type = protein
                        organism = synthetic construct
SEQUENCE: 55
TSDYNSH                                                                 7

SEQ ID NO: 56           moltype = AA   length = 16
FEATURE                 Location/Qualifiers
source                  1..16
                        mol_type = protein
                        organism = synthetic construct
SEQUENCE: 56
YIHYSGSTNY NPSLKS                                                       16

SEQ ID NO: 57           moltype = AA   length = 9
FEATURE                 Location/Qualifiers
source                  1..9
                        mol_type = protein
                        organism = synthetic construct
SEQUENCE: 57
NYGSIYVNY                                                               9

SEQ ID NO: 58           moltype = AA   length = 10
FEATURE                 Location/Qualifiers
source                  1..10
                        mol_type = protein
                        organism = synthetic construct
SEQUENCE: 58
SASSSVSYMY                                                              10

SEQ ID NO: 59           moltype = AA   length = 7
FEATURE                 Location/Qualifiers
source                  1..7
                        mol_type = protein
                        organism = synthetic construct
SEQUENCE: 59
RTSNLAS                                                                 7

SEQ ID NO: 60           moltype = AA   length = 8
FEATURE                 Location/Qualifiers
source                  1..8
                        mol_type = protein
                        organism = synthetic construct
SEQUENCE: 60
QQYHSYPT                                                                8

SEQ ID NO: 61           moltype = AA   length = 7
FEATURE                 Location/Qualifiers
source                  1..7
                        mol_type = protein
                        organism = synthetic construct
SEQUENCE: 61
TSDYNAH                                                                 7
```

-continued

```
SEQ ID NO: 62            moltype = AA   length = 16
FEATURE                  Location/Qualifiers
source                   1..16
                         mol_type = protein
                         organism = synthetic construct
SEQUENCE: 62
YIHYSGSTNY NPSLKS                                                         16

SEQ ID NO: 63            moltype = AA   length = 9
FEATURE                  Location/Qualifiers
source                   1..9
                         mol_type = protein
                         organism = synthetic construct
SEQUENCE: 63
NYGSIYVNY                                                                  9

SEQ ID NO: 64            moltype = AA   length = 10
FEATURE                  Location/Qualifiers
source                   1..10
                         mol_type = protein
                         organism = synthetic construct
SEQUENCE: 64
SASSSVSYMY                                                                10

SEQ ID NO: 65            moltype = AA   length = 6
FEATURE                  Location/Qualifiers
source                   1..6
                         mol_type = protein
                         organism = synthetic construct
SEQUENCE: 65
TSNLAS                                                                     6

SEQ ID NO: 66            moltype = AA   length = 8
FEATURE                  Location/Qualifiers
source                   1..8
                         mol_type = protein
                         organism = synthetic construct
SEQUENCE: 66
QQYHSYPT                                                                   8

SEQ ID NO: 67            moltype = AA   length = 7
FEATURE                  Location/Qualifiers
source                   1..7
                         mol_type = protein
                         organism = synthetic construct
SEQUENCE: 67
TSDYNAH                                                                    7

SEQ ID NO: 68            moltype = AA   length = 16
FEATURE                  Location/Qualifiers
source                   1..16
                         mol_type = protein
                         organism = synthetic construct
SEQUENCE: 68
YIHYSGSTNY NPSLKS                                                         16

SEQ ID NO: 69            moltype = AA   length = 12
FEATURE                  Location/Qualifiers
source                   1..12
                         mol_type = protein
                         organism = synthetic construct
SEQUENCE: 69
NFGSIYVNYF DY                                                             12

SEQ ID NO: 70            moltype = AA   length = 10
FEATURE                  Location/Qualifiers
source                   1..10
                         mol_type = protein
                         organism = synthetic construct
SEQUENCE: 70
SASSSVSYMY                                                                10

SEQ ID NO: 71            moltype = AA   length = 6
FEATURE                  Location/Qualifiers
source                   1..6
                         mol_type = protein
                         organism = synthetic construct
SEQUENCE: 71
```

TSNLAS                                                                          6

SEQ ID NO: 72           moltype = AA   length = 8
FEATURE                 Location/Qualifiers
source                  1..8
                        mol_type = protein
                        organism = synthetic construct SEQUENCE: 72
QQYHSYPT                                                                        8

SEQ ID NO: 73           moltype = AA   length = 7
FEATURE                 Location/Qualifiers
source                  1..7
                        mol_type = protein
                        organism = synthetic construct SEQUENCE: 73
TSDYNAH                                                                         7

SEQ ID NO: 74           moltype = AA   length = 16
FEATURE                 Location/Qualifiers
source                  1..16
                        mol_type = protein
                        organism = synthetic construct SEQUENCE: 74
YIHYSGSTNY NPSLKS                                                              16

SEQ ID NO: 75           moltype = AA   length = 12
FEATURE                 Location/Qualifiers
source                  1..12
                        mol_type = protein
                        organism = synthetic construct SEQUENCE: 75
NYASIYVNYF DY                                                                  12

SEQ ID NO: 76           moltype = AA   length = 10
FEATURE                 Location/Qualifiers
source                  1..10
                        mol_type = protein
                        organism = synthetic construct SEQUENCE: 76
SASSSVSYMY                                                                     10

SEQ ID NO: 77           moltype = AA   length = 6
FEATURE                 Location/Qualifiers
source                  1..6
                        mol_type = protein
                        organism = synthetic construct SEQUENCE: 77
TSNLAS                                                                          6

SEQ ID NO: 78           moltype = AA   length = 8
FEATURE                 Location/Qualifiers
source                  1..8
                        mol_type = protein
                        organism = synthetic construct SEQUENCE: 78
QQYHSYPT                                                                        8

SEQ ID NO: 79           moltype = AA   length = 7
FEATURE                 Location/Qualifiers
source                  1..7
                        mol_type = protein
                        organism = synthetic construct SEQUENCE: 79
TSDYNAH                                                                         7

SEQ ID NO: 80           moltype = AA   length = 16
FEATURE                 Location/Qualifiers
source                  1..16
                        mol_type = protein
                        organism = synthetic construct SEQUENCE: 80
YIHYSGSTNY NPSLKS                                                              16

SEQ ID NO: 81           moltype = AA   length = 12
FEATURE                 Location/Qualifiers
source                  1..12
                        mol_type = protein
                        organism = synthetic construct

```
SEQUENCE: 81
NFASIYVNYF DY                                                            12

SEQ ID NO: 82         moltype = AA  length = 10
FEATURE               Location/Qualifiers
source                1..10
                      mol_type = protein
                      organism = synthetic construct
SEQUENCE: 82
SASSSVSYMY                                                               10

SEQ ID NO: 83         moltype = AA  length = 6
FEATURE               Location/Qualifiers
source                1..6
                      mol_type = protein
                      organism = synthetic construct
SEQUENCE: 83
TSNLAS                                                                    6

SEQ ID NO: 84         moltype = AA  length = 8
FEATURE               Location/Qualifiers
source                1..8
                      mol_type = protein
                      organism = synthetic construct
SEQUENCE: 84
QQYHSYPT                                                                  8

SEQ ID NO: 85         moltype = AA  length = 7
FEATURE               Location/Qualifiers
source                1..7
                      mol_type = protein
                      organism = synthetic construct
SEQUENCE: 85
TSDYNNH                                                                   7

SEQ ID NO: 86         moltype = AA  length = 16
FEATURE               Location/Qualifiers
source                1..16
                      mol_type = protein
                      organism = synthetic construct
SEQUENCE: 86
YIHYSGSTNY NPSLKS                                                        16

SEQ ID NO: 87         moltype = AA  length = 12
FEATURE               Location/Qualifiers
source                1..12
                      mol_type = protein
                      organism = synthetic construct
SEQUENCE: 87
NYGSIYVNYF DY                                                            12

SEQ ID NO: 88         moltype = AA  length = 10
FEATURE               Location/Qualifiers
source                1..10
                      mol_type = protein
                      organism = synthetic construct
SEQUENCE: 88
SASSSVSYMY                                                               10

SEQ ID NO: 89         moltype = AA  length = 6
FEATURE               Location/Qualifiers
source                1..6
                      mol_type = protein
                      organism = synthetic construct
SEQUENCE: 89
TSNLAS                                                                    6

SEQ ID NO: 90         moltype = AA  length = 8
FEATURE               Location/Qualifiers
source                1..8
                      mol_type = protein
                      organism = synthetic construct
SEQUENCE: 90
QQYHSYPT                                                                  8

SEQ ID NO: 91         moltype = AA  length = 7
FEATURE               Location/Qualifiers
source                1..7
                      mol_type = protein
```

```
                        -continued organism = synthetic construct
SEQUENCE: 91
TQDYNAH                                                              7

SEQ ID NO: 92           moltype = AA  length = 16
FEATURE                 Location/Qualifiers
source                  1..16
                        mol_type = protein
                        organism = synthetic construct
SEQUENCE: 92
YIHYSGSTNY NPSLKS                                                   16

SEQ ID NO: 93           moltype = AA  length = 12
FEATURE                 Location/Qualifiers
source                  1..12
                        mol_type = protein
                        organism = synthetic construct
SEQUENCE: 93
NYGSIYVNYF DY                                                       12

SEQ ID NO: 94           moltype = AA  length = 10
FEATURE                 Location/Qualifiers
source                  1..10
                        mol_type = protein
                        organism = synthetic construct
SEQUENCE: 94
SASSSVSYMY                                                          10

SEQ ID NO: 95           moltype = AA  length = 6
FEATURE                 Location/Qualifiers
source                  1..6
                        mol_type = protein
                        organism = synthetic construct
SEQUENCE: 95
TSNLAS                                                               6

SEQ ID NO: 96           moltype = AA  length = 8
FEATURE                 Location/Qualifiers
source                  1..8
                        mol_type = protein
                        organism = synthetic construct
SEQUENCE: 96
QQYHSYPT                                                             8

SEQ ID NO: 97           moltype = AA  length = 7
FEATURE                 Location/Qualifiers
source                  1..7
                        mol_type = protein
                        organism = synthetic construct
SEQUENCE: 97
TSDYNAH                                                              7

SEQ ID NO: 98           moltype = AA  length = 16
FEATURE                 Location/Qualifiers
source                  1..16
                        mol_type = protein
                        organism = synthetic construct
SEQUENCE: 98
YIHYSGATNY NPSLKS                                                   16

SEQ ID NO: 99           moltype = AA  length = 12
FEATURE                 Location/Qualifiers
source                  1..12
                        mol_type = protein
                        organism = synthetic construct
SEQUENCE: 99
NYGSIYVNYF DY                                                       12

SEQ ID NO: 100          moltype = AA  length = 10
FEATURE                 Location/Qualifiers
source                  1..10
                        mol_type = protein
                        organism = synthetic construct
SEQUENCE: 100
SASSSVSYMY                                                          10

SEQ ID NO: 101          moltype = AA  length = 6
FEATURE                 Location/Qualifiers
source                  1..6
```

```
                        mol_type = protein
                        organism = synthetic construct
SEQUENCE: 101
TSNLAS                                                                    6

SEQ ID NO: 102          moltype = AA   length = 8
FEATURE                 Location/Qualifiers
source                  1..8
                        mol_type = protein
                        organism = synthetic construct
SEQUENCE: 102
QQYHSYPT                                                                  8

SEQ ID NO: 103          moltype = AA   length = 7
FEATURE                 Location/Qualifiers
source                  1..7
                        mol_type = protein
                        organism = synthetic construct
SEQUENCE: 103
TSDYNAH                                                                   7

SEQ ID NO: 104          moltype = AA   length = 16
FEATURE                 Location/Qualifiers
source                  1..16
                        mol_type = protein
                        organism = synthetic construct
SEQUENCE: 104
YIHYSGQTNY NPSLKS                                                        16

SEQ ID NO: 105          moltype = AA   length = 12
FEATURE                 Location/Qualifiers
source                  1..12
                        mol_type = protein
                        organism = synthetic construct
SEQUENCE: 105
NYGSIYVNYF DY                                                            12

SEQ ID NO: 106          moltype = AA   length = 10
FEATURE                 Location/Qualifiers
source                  1..10
                        mol_type = protein
                        organism = synthetic construct
SEQUENCE: 106
SASSSVSYMY                                                               10

SEQ ID NO: 107          moltype = AA   length = 6
FEATURE                 Location/Qualifiers
source                  1..6
                        mol_type = protein
                        organism = synthetic construct
SEQUENCE: 107
TSNLAS                                                                    6

SEQ ID NO: 108          moltype = AA   length = 8
FEATURE                 Location/Qualifiers
source                  1..8
                        mol_type = protein
                        organism = synthetic construct
SEQUENCE: 108
QQYHSYPT                                                                  8

SEQ ID NO: 109          moltype = AA   length = 7
FEATURE                 Location/Qualifiers
source                  1..7
                        mol_type = protein
                        organism = synthetic construct
SEQUENCE: 109
TSDYNAH                                                                   7

SEQ ID NO: 110          moltype = AA   length = 16
FEATURE                 Location/Qualifiers
source                  1..16
                        mol_type = protein
                        organism = synthetic construct
SEQUENCE: 110
YIHYSGSTMY NPSLKS                                                        16

SEQ ID NO: 111          moltype = AA   length = 12
FEATURE                 Location/Qualifiers
```

```
source                  1..12
                        mol_type = protein
                        organism = synthetic construct
SEQUENCE: 111
NYGSIYVNYF DY                                                           12

SEQ ID NO: 112          moltype = AA   length = 10
FEATURE                 Location/Qualifiers
source                  1..10
                        mol_type = protein
                        organism = synthetic construct
SEQUENCE: 112
SASSSVSYMY                                                              10

SEQ ID NO: 113          moltype = AA   length = 6
FEATURE                 Location/Qualifiers
source                  1..6
                        mol_type = protein
                        organism = synthetic construct
SEQUENCE: 113
TSNLAS                                                                  6

SEQ ID NO: 114          moltype = AA   length = 8
FEATURE                 Location/Qualifiers
source                  1..8
                        mol_type = protein
                        organism = synthetic construct
SEQUENCE: 114
QQYHSYPT                                                                8

SEQ ID NO: 115          moltype = AA   length = 7
FEATURE                 Location/Qualifiers
source                  1..7
                        mol_type = protein
                        organism = synthetic construct
SEQUENCE: 115
TSDYNAH                                                                 7

SEQ ID NO: 116          moltype = AA   length = 16
FEATURE                 Location/Qualifiers
source                  1..16
                        mol_type = protein
                        organism = synthetic construct
SEQUENCE: 116
YIHYSGQTMY NPSLKS                                                       16

SEQ ID NO: 117          moltype = AA   length = 12
FEATURE                 Location/Qualifiers
source                  1..12
                        mol_type = protein
                        organism = synthetic construct
SEQUENCE: 117
NYGSIYVNYF DY                                                           12

SEQ ID NO: 118          moltype = AA   length = 10
FEATURE                 Location/Qualifiers
source                  1..10
                        mol_type = protein
                        organism = synthetic construct
SEQUENCE: 118
SASSSVSYMY                                                              10

SEQ ID NO: 119          moltype = AA   length = 6
FEATURE                 Location/Qualifiers
source                  1..6
                        mol_type = protein
                        organism = synthetic construct
SEQUENCE: 119
TSNLAS                                                                  6

SEQ ID NO: 120          moltype = AA   length = 8
FEATURE                 Location/Qualifiers
source                  1..8
                        mol_type = protein
                        organism = synthetic construct
SEQUENCE: 120
QQYHSYPT                                                                8

SEQ ID NO: 121          moltype = AA   length = 7
```

```
FEATURE                      Location/Qualifiers
source                       1..7
                             mol_type = protein
                             organism = synthetic construct
SEQUENCE: 121
TQDYNAH                                                                       7

SEQ ID NO: 122               moltype = AA  length = 16
FEATURE                      Location/Qualifiers
source                       1..16
                             mol_type = protein
                             organism = synthetic construct
SEQUENCE: 122
YIHYSGSTMY NPSLKS                                                            16

SEQ ID NO: 123               moltype = AA  length = 12
FEATURE                      Location/Qualifiers
source                       1..12
                             mol_type = protein
                             organism = synthetic construct
SEQUENCE: 123
NYGSIYVNYF DY                                                                12

SEQ ID NO: 124               moltype = AA  length = 10
FEATURE                      Location/Qualifiers
source                       1..10
                             mol_type = protein
                             organism = synthetic construct
SEQUENCE: 124
SASSSVSYMY                                                                   10

SEQ ID NO: 125               moltype = AA  length = 6
FEATURE                      Location/Qualifiers
source                       1..6
                             mol_type = protein
                             organism = synthetic construct
SEQUENCE: 125
TSNLAS                                                                        6

SEQ ID NO: 126               moltype = AA  length = 8
FEATURE                      Location/Qualifiers
source                       1..8
                             mol_type = protein
                             organism = synthetic construct
SEQUENCE: 126
QQYHSYPT                                                                      8

SEQ ID NO: 127               moltype = AA  length = 7
FEATURE                      Location/Qualifiers
source                       1..7
                             mol_type = protein
                             organism = synthetic construct
SEQUENCE: 127
TSDYNAH                                                                       7

SEQ ID NO: 128               moltype = AA  length = 16
FEATURE                      Location/Qualifiers
source                       1..16
                             mol_type = protein
                             organism = synthetic construct
SEQUENCE: 128
YIHYSGSTMY NPSLKS                                                            16

SEQ ID NO: 129               moltype = AA  length = 12
FEATURE                      Location/Qualifiers
source                       1..12
                             mol_type = protein
                             organism = synthetic construct
SEQUENCE: 129
NFGSIYVNYF DY                                                                12

SEQ ID NO: 130               moltype = AA  length = 10
FEATURE                      Location/Qualifiers
source                       1..10
                             mol_type = protein
                             organism = synthetic construct
SEQUENCE: 130
SASSSVSYMY                                                                   10
```

```
SEQ ID NO: 131          moltype = AA   length = 6
FEATURE                 Location/Qualifiers
source                  1..6
                        mol_type = protein
                        organism = synthetic construct
SEQUENCE: 131
TSNLAS                                                                    6

SEQ ID NO: 132          moltype = AA   length = 8
FEATURE                 Location/Qualifiers
source                  1..8
                        mol_type = protein
                        organism = synthetic construct
SEQUENCE: 132
QQYHSYPT                                                                  8

SEQ ID NO: 133          moltype = AA   length = 7
FEATURE                 Location/Qualifiers
source                  1..7
                        mol_type = protein
                        organism = synthetic construct
SEQUENCE: 133
TSDYNAH                                                                   7

SEQ ID NO: 134          moltype = AA   length = 16
FEATURE                 Location/Qualifiers
source                  1..16
                        mol_type = protein
                        organism = synthetic construct
SEQUENCE: 134
YIHYSGQTMY NPSLKS                                                        16

SEQ ID NO: 135          moltype = AA   length = 12
FEATURE                 Location/Qualifiers
source                  1..12
                        mol_type = protein
                        organism = synthetic construct
SEQUENCE: 135
NYGSIYVNYF DY                                                            12

SEQ ID NO: 136          moltype = AA   length = 10
FEATURE                 Location/Qualifiers
source                  1..10
                        mol_type = protein
                        organism = synthetic construct
SEQUENCE: 136
SASSSVSYMY                                                               10

SEQ ID NO: 137          moltype = AA   length = 6
FEATURE                 Location/Qualifiers
source                  1..6
                        mol_type = protein
                        organism = synthetic construct
SEQUENCE: 137
TSNLAS                                                                    6

SEQ ID NO: 138          moltype = AA   length = 8
FEATURE                 Location/Qualifiers
source                  1..8
                        mol_type = protein
                        organism = synthetic construct
SEQUENCE: 138
QQYHSYPT                                                                  8

SEQ ID NO: 139          moltype = AA   length = 7
FEATURE                 Location/Qualifiers
source                  1..7
                        mol_type = protein
                        organism = synthetic construct
SEQUENCE: 139
TSDYNAH                                                                   7

SEQ ID NO: 140          moltype = AA   length = 16
FEATURE                 Location/Qualifiers
source                  1..16
                        mol_type = protein
                        organism = synthetic construct
SEQUENCE: 140
YIHYSGQTMY NPSLKS                                                        16
```

```
SEQ ID NO: 141           moltype = AA  length = 12
FEATURE                  Location/Qualifiers
source                   1..12
                         mol_type = protein
                         organism = synthetic construct
SEQUENCE: 141
NFGSIYVNYF DY                                                             12

SEQ ID NO: 142           moltype = AA  length = 10
FEATURE                  Location/Qualifiers
source                   1..10
                         mol_type = protein
                         organism = synthetic construct
SEQUENCE: 142
SASSSVSYMY                                                                10

SEQ ID NO: 143           moltype = AA  length = 6
FEATURE                  Location/Qualifiers
source                   1..6
                         mol_type = protein
                         organism = synthetic construct
SEQUENCE: 143
TSNLAS                                                                     6

SEQ ID NO: 144           moltype = AA  length = 8
FEATURE                  Location/Qualifiers
source                   1..8
                         mol_type = protein
                         organism = synthetic construct
SEQUENCE: 144
QQYHSYPT                                                                   8

SEQ ID NO: 145           moltype = AA  length = 7
FEATURE                  Location/Qualifiers
source                   1..7
                         mol_type = protein
                         organism = synthetic construct
SEQUENCE: 145
TSDYNAH                                                                    7

SEQ ID NO: 146           moltype = AA  length = 16
FEATURE                  Location/Qualifiers
source                   1..16
                         mol_type = protein
                         organism = synthetic construct
SEQUENCE: 146
YIHYSGSTYY NPSLKS                                                         16

SEQ ID NO: 147           moltype = AA  length = 12
FEATURE                  Location/Qualifiers
source                   1..12
                         mol_type = protein
                         organism = synthetic construct
SEQUENCE: 147
NYGSIYVNYF DY                                                             12

SEQ ID NO: 148           moltype = AA  length = 10
FEATURE                  Location/Qualifiers
source                   1..10
                         mol_type = protein
                         organism = synthetic construct
SEQUENCE: 148
SASSSVSYMY                                                                10

SEQ ID NO: 149           moltype = AA  length = 6
FEATURE                  Location/Qualifiers
source                   1..6
                         mol_type = protein
                         organism = synthetic construct
SEQUENCE: 149
TSNLAS                                                                     6

SEQ ID NO: 150           moltype = AA  length = 8
FEATURE                  Location/Qualifiers
source                   1..8
                         mol_type = protein
                         organism = synthetic construct
SEQUENCE: 150
```

```
QQYHSYPT                                                                      8

SEQ ID NO: 151          moltype = AA   length = 7
FEATURE                 Location/Qualifiers
source                  1..7
                        mol_type = protein
                        organism = synthetic construct
SEQUENCE: 151
TSDYNAH                                                                       7

SEQ ID NO: 152          moltype = AA   length = 16
FEATURE                 Location/Qualifiers
source                  1..16
                        mol_type = protein
                        organism = synthetic construct
SEQUENCE: 152
YIHYSGSTLY NPSLKS                                                            16

SEQ ID NO: 153          moltype = AA   length = 12
FEATURE                 Location/Qualifiers
source                  1..12
                        mol_type = protein
                        organism = synthetic construct
SEQUENCE: 153
NYGSIYVNYF DY                                                                12

SEQ ID NO: 154          moltype = AA   length = 10
FEATURE                 Location/Qualifiers
source                  1..10
                        mol_type = protein
                        organism = synthetic construct
SEQUENCE: 154
SASSSVSYMY                                                                   10

SEQ ID NO: 155          moltype = AA   length = 6
FEATURE                 Location/Qualifiers
source                  1..6
                        mol_type = protein
                        organism = synthetic construct
SEQUENCE: 155
TSNLAS                                                                        6

SEQ ID NO: 156          moltype = AA   length = 8
FEATURE                 Location/Qualifiers
source                  1..8
                        mol_type = protein
                        organism = synthetic construct
SEQUENCE: 156
QQYHSYPT                                                                      8

SEQ ID NO: 157          moltype = AA   length = 7
FEATURE                 Location/Qualifiers
source                  1..7
                        mol_type = protein
                        organism = synthetic construct
SEQUENCE: 157
TQDYNAH                                                                       7

SEQ ID NO: 158          moltype = AA   length = 16
FEATURE                 Location/Qualifiers
source                  1..16
                        mol_type = protein
                        organism = synthetic construct
SEQUENCE: 158
YIHYSGQTMY NPSLKS                                                            16

SEQ ID NO: 159          moltype = AA   length = 12
FEATURE                 Location/Qualifiers
source                  1..12
                        mol_type = protein
                        organism = synthetic construct
SEQUENCE: 159
NFGSIYVNYF DY                                                                12

SEQ ID NO: 160          moltype = AA   length = 10
FEATURE                 Location/Qualifiers
source                  1..10
                        mol_type = protein
                        organism = synthetic construct
```

-continued

```
SEQUENCE: 160
SASSSVSYMY                                                                      10

SEQ ID NO: 161          moltype = AA  length = 6
FEATURE                 Location/Qualifiers
source                  1..6
                        mol_type = protein
                        organism = synthetic construct
SEQUENCE: 161
TSNLAS                                                                          6

SEQ ID NO: 162          moltype = AA  length = 8
FEATURE                 Location/Qualifiers
source                  1..8
                        mol_type = protein
                        organism = synthetic construct
SEQUENCE: 162
QQYHSYPT                                                                        8

SEQ ID NO: 163          moltype = AA  length = 7
FEATURE                 Location/Qualifiers
source                  1..7
                        mol_type = protein
                        organism = synthetic construct
SEQUENCE: 163
TQDYNAH                                                                         7

SEQ ID NO: 164          moltype = AA  length = 16
FEATURE                 Location/Qualifiers
source                  1..16
                        mol_type = protein
                        organism = synthetic construct
SEQUENCE: 164
YIHYSGQTNY NPSLKS                                                               16

SEQ ID NO: 165          moltype = AA  length = 12
FEATURE                 Location/Qualifiers
source                  1..12
                        mol_type = protein
                        organism = synthetic construct
SEQUENCE: 165
NFGSIYVNYF DY                                                                   12

SEQ ID NO: 166          moltype = AA  length = 10
FEATURE                 Location/Qualifiers
source                  1..10
                        mol_type = protein
                        organism = synthetic construct
SEQUENCE: 166
SASSSVSYMY                                                                      10

SEQ ID NO: 167          moltype = AA  length = 6
FEATURE                 Location/Qualifiers
source                  1..6
                        mol_type = protein
                        organism = synthetic construct
SEQUENCE: 167
TSNLAS                                                                          6

SEQ ID NO: 168          moltype = AA  length = 8
FEATURE                 Location/Qualifiers
source                  1..8
                        mol_type = protein
                        organism = synthetic construct
SEQUENCE: 168
QQYHSYPT                                                                        8

SEQ ID NO: 169          moltype = AA  length = 7
FEATURE                 Location/Qualifiers
source                  1..7
                        mol_type = protein
                        organism = synthetic construct
SEQUENCE: 169
TQDYNAH                                                                         7

SEQ ID NO: 170          moltype = AA  length = 16
FEATURE                 Location/Qualifiers
source                  1..16
                        mol_type = protein
```

```
                                                    -continued

SEQUENCE: 170
YIHYSGQTYY NPSLKS                                                    16

SEQ ID NO: 171          moltype = AA   length = 12
FEATURE                 Location/Qualifiers
source                  1..12
                        mol_type = protein
                        organism = synthetic construct
SEQUENCE: 171
NFGSIYVNYF DY                                                        12

SEQ ID NO: 172          moltype = AA   length = 10
FEATURE                 Location/Qualifiers
source                  1..10
                        mol_type = protein
                        organism = synthetic construct
SEQUENCE: 172
SASSSVSYMY                                                           10

SEQ ID NO: 173          moltype = AA   length = 6
FEATURE                 Location/Qualifiers
source                  1..6
                        mol_type = protein
                        organism = synthetic construct
SEQUENCE: 173
TSNLAS                                                                6

SEQ ID NO: 174          moltype = AA   length = 8
FEATURE                 Location/Qualifiers
source                  1..8
                        mol_type = protein
                        organism = synthetic construct
SEQUENCE: 174
QQYHSYPT                                                              8

SEQ ID NO: 175          moltype = AA   length = 7
FEATURE                 Location/Qualifiers
source                  1..7
                        mol_type = protein
                        organism = synthetic construct
SEQUENCE: 175
TQDYNAH                                                               7

SEQ ID NO: 176          moltype = AA   length = 16
FEATURE                 Location/Qualifiers
source                  1..16
                        mol_type = protein
                        organism = synthetic construct
SEQUENCE: 176
YIHYSGQTLY NPSLKS                                                    16

SEQ ID NO: 177          moltype = AA   length = 12
FEATURE                 Location/Qualifiers
source                  1..12
                        mol_type = protein
                        organism = synthetic construct
SEQUENCE: 177
NFGSIYVNYF DY                                                        12

SEQ ID NO: 178          moltype = AA   length = 10
FEATURE                 Location/Qualifiers
source                  1..10
                        mol_type = protein
                        organism = synthetic construct
SEQUENCE: 178
SASSSVSYMY                                                           10

SEQ ID NO: 179          moltype = AA   length = 6
FEATURE                 Location/Qualifiers
source                  1..6
                        mol_type = protein
                        organism = synthetic construct
SEQUENCE: 179
TSNLAS                                                                6

SEQ ID NO: 180          moltype = AA   length = 8
FEATURE                 Location/Qualifiers
source                  1..8
```

```
SEQUENCE: 180
QQYHSYPT                                                        8

SEQ ID NO: 181          moltype = AA   length = 7
FEATURE                 Location/Qualifiers
source                  1..7
                        mol_type = protein
                        organism = synthetic construct
SEQUENCE: 181
TQDYNAH                                                         7

SEQ ID NO: 182          moltype = AA   length = 16
FEATURE                 Location/Qualifiers
source                  1..16
                        mol_type = protein
                        organism = synthetic construct
SEQUENCE: 182
YIHYSGQTNY NPSLKS                                              16

SEQ ID NO: 183          moltype = AA   length = 11
FEATURE                 Location/Qualifiers
source                  1..11
                        mol_type = protein
                        organism = synthetic construct
SEQUENCE: 183
YGSIYVNYFD Y                                                   11

SEQ ID NO: 184          moltype = AA   length = 10
FEATURE                 Location/Qualifiers
source                  1..10
                        mol_type = protein
                        organism = synthetic construct
SEQUENCE: 184
SASSSVSYMY                                                     10

SEQ ID NO: 185          moltype = AA   length = 6
FEATURE                 Location/Qualifiers
source                  1..6
                        mol_type = protein
                        organism = synthetic construct
SEQUENCE: 185
TSNLAS                                                          6

SEQ ID NO: 186          moltype = AA   length = 8
FEATURE                 Location/Qualifiers
source                  1..8
                        mol_type = protein
                        organism = synthetic construct
SEQUENCE: 186
QQYHSYPT                                                        8

SEQ ID NO: 187          moltype = AA   length = 7
FEATURE                 Location/Qualifiers
source                  1..7
                        mol_type = protein
                        organism = synthetic construct
SEQUENCE: 187
TSDYNAH                                                         7

SEQ ID NO: 188          moltype = AA   length = 16
FEATURE                 Location/Qualifiers
source                  1..16
                        mol_type = protein
                        organism = synthetic construct
SEQUENCE: 188
YIHYSGSTNY NPSLKS                                              16

SEQ ID NO: 189          moltype = AA   length = 12
FEATURE                 Location/Qualifiers
source                  1..12
                        mol_type = protein
                        organism = synthetic construct
SEQUENCE: 189
NYGSIYVNYF DY                                                  12

SEQ ID NO: 190          moltype = AA   length = 10
FEATURE                 Location/Qualifiers
```

| | | |
|---|---|---|
| source | 1..10<br>mol_type = protein<br>organism = synthetic construct | |
| SEQUENCE: 190<br>SASSSVSYMY | | 10 |
| SEQ ID NO: 191<br>FEATURE<br>source | moltype = AA   length = 6<br>Location/Qualifiers<br>1..6<br>mol_type = protein<br>organism = synthetic construct | |
| SEQUENCE: 191<br>TSNLAS | | 6 |
| SEQ ID NO: 192<br>FEATURE<br>source | moltype = AA   length = 8<br>Location/Qualifiers<br>1..8<br>mol_type = protein<br>organism = synthetic construct | |
| SEQUENCE: 192<br>QEYHSYPT | | 8 |
| SEQ ID NO: 193<br>FEATURE<br>source | moltype = AA   length = 7<br>Location/Qualifiers<br>1..7<br>mol_type = protein<br>organism = synthetic construct | |
| SEQUENCE: 193<br>TSDYNAH | | 7 |
| SEQ ID NO: 194<br>FEATURE<br>source | moltype = AA   length = 16<br>Location/Qualifiers<br>1..16<br>mol_type = protein<br>organism = synthetic construct | |
| SEQUENCE: 194<br>YIHYSGSTNY NPSLKS | | 16 |
| SEQ ID NO: 195<br>FEATURE<br>source | moltype = AA   length = 12<br>Location/Qualifiers<br>1..12<br>mol_type = protein<br>organism = synthetic construct | |
| SEQUENCE: 195<br>NYGSIYVNYF DY | | 12 |
| SEQ ID NO: 196<br>FEATURE<br>source | moltype = AA   length = 10<br>Location/Qualifiers<br>1..10<br>mol_type = protein<br>organism = synthetic construct | |
| SEQUENCE: 196<br>SASSSVSYMY | | 10 |
| SEQ ID NO: 197<br>FEATURE<br>source | moltype = AA   length = 6<br>Location/Qualifiers<br>1..6<br>mol_type = protein<br>organism = synthetic construct | |
| SEQUENCE: 197<br>TSNLAS | | 6 |
| SEQ ID NO: 198<br>FEATURE<br>source | moltype = AA   length = 8<br>Location/Qualifiers<br>1..8<br>mol_type = protein<br>organism = synthetic construct | |
| SEQUENCE: 198<br>QLYHSYPT | | 8 |
| SEQ ID NO: 199<br>FEATURE<br>source | moltype = AA   length = 7<br>Location/Qualifiers<br>1..7<br>mol_type = protein<br>organism = synthetic construct | |
| SEQUENCE: 199<br>TSDYNAH | | 7 |
| SEQ ID NO: 200 | moltype = AA   length = 16 | |

```
FEATURE                 Location/Qualifiers
source                  1..16
                        mol_type = protein
                        organism = synthetic construct
SEQUENCE: 200
YIHYSGSTNY NPSLKS                                                    16

SEQ ID NO: 201          moltype = AA  length = 12
FEATURE                 Location/Qualifiers
source                  1..12
                        mol_type = protein
                        organism = synthetic construct
SEQUENCE: 201
NYGSIYVNYF DY                                                        12

SEQ ID NO: 202          moltype = AA  length = 10
FEATURE                 Location/Qualifiers
source                  1..10
                        mol_type = protein
                        organism = synthetic construct
SEQUENCE: 202
SASSSVSYMY                                                           10

SEQ ID NO: 203          moltype = AA  length = 6
FEATURE                 Location/Qualifiers
source                  1..6
                        mol_type = protein
                        organism = synthetic construct
SEQUENCE: 203
TSNLAS                                                               6

SEQ ID NO: 204          moltype = AA  length = 8
FEATURE                 Location/Qualifiers
source                  1..8
                        mol_type = protein
                        organism = synthetic construct
SEQUENCE: 204
QQYHGYPT                                                             8

SEQ ID NO: 205          moltype = AA  length = 7
FEATURE                 Location/Qualifiers
source                  1..7
                        mol_type = protein
                        organism = synthetic construct
SEQUENCE: 205
TSDYNAH                                                              7

SEQ ID NO: 206          moltype = AA  length = 16
FEATURE                 Location/Qualifiers
source                  1..16
                        mol_type = protein
                        organism = synthetic construct
SEQUENCE: 206
YIHYSGSTNY NPSLKS                                                    16

SEQ ID NO: 207          moltype = AA  length = 12
FEATURE                 Location/Qualifiers
source                  1..12
                        mol_type = protein
                        organism = synthetic construct
SEQUENCE: 207
NYGSIYVNYF DY                                                        12

SEQ ID NO: 208          moltype = AA  length = 10
FEATURE                 Location/Qualifiers
source                  1..10
                        mol_type = protein
                        organism = synthetic construct
SEQUENCE: 208
SASSSVSYMY                                                           10

SEQ ID NO: 209          moltype = AA  length = 6
FEATURE                 Location/Qualifiers
source                  1..6
                        mol_type = protein
                        organism = synthetic construct
SEQUENCE: 209
TSNLAS                                                               6
```

-continued

| | | |
|---|---|---|
| SEQ ID NO: 210<br>FEATURE<br>source | moltype = AA   length = 8<br>Location/Qualifiers<br>1..8<br>mol_type = protein<br>organism = synthetic construct | |
| SEQUENCE: 210<br>QQYHSYVT | | 8 |
| SEQ ID NO: 211<br>FEATURE<br>source | moltype = AA   length = 7<br>Location/Qualifiers<br>1..7<br>mol_type = protein<br>organism = synthetic construct | |
| SEQUENCE: 211<br>TSDYNAH | | 7 |
| SEQ ID NO: 212<br>FEATURE<br>source | moltype = AA   length = 16<br>Location/Qualifiers<br>1..16<br>mol_type = protein<br>organism = synthetic construct | |
| SEQUENCE: 212<br>YIHYSGSTNY NPSLKS | | 16 |
| SEQ ID NO: 213<br>FEATURE<br>source | moltype = AA   length = 12<br>Location/Qualifiers<br>1..12<br>mol_type = protein<br>organism = synthetic construct | |
| SEQUENCE: 213<br>NYGSIYVNYF DY | | 12 |
| SEQ ID NO: 214<br>FEATURE<br>source | moltype = AA   length = 10<br>Location/Qualifiers<br>1..10<br>mol_type = protein<br>organism = synthetic construct | |
| SEQUENCE: 214<br>SASSSVSYMY | | 10 |
| SEQ ID NO: 215<br>FEATURE<br>source | moltype = AA   length = 6<br>Location/Qualifiers<br>1..6<br>mol_type = protein<br>organism = synthetic construct | |
| SEQUENCE: 215<br>TSNLAS | | 6 |
| SEQ ID NO: 216<br>FEATURE<br>source | moltype = AA   length = 9<br>Location/Qualifiers<br>1..9<br>mol_type = protein<br>organism = synthetic construct | |
| SEQUENCE: 216<br>CQQYHSYPK | | 9 |
| SEQ ID NO: 217<br>FEATURE<br>source | moltype = AA   length = 7<br>Location/Qualifiers<br>1..7<br>mol_type = protein<br>organism = synthetic construct | |
| SEQUENCE: 217<br>TSDYNAH | | 7 |
| SEQ ID NO: 218<br>FEATURE<br>source | moltype = AA   length = 16<br>Location/Qualifiers<br>1..16<br>mol_type = protein<br>organism = synthetic construct | |
| SEQUENCE: 218<br>YIHYSGQTYY NPSLKS | | 16 |
| SEQ ID NO: 219<br>FEATURE<br>source | moltype = AA   length = 12<br>Location/Qualifiers<br>1..12<br>mol_type = protein<br>organism = synthetic construct | |
| SEQUENCE: 219<br>NFGSIYVNYF DY | | 12 |

```
SEQ ID NO: 220          moltype = AA  length = 10
FEATURE                 Location/Qualifiers
source                  1..10
                        mol_type = protein
                        organism = synthetic construct
SEQUENCE: 220
SASSSVSYMY                                                              10

SEQ ID NO: 221          moltype = AA  length = 6
FEATURE                 Location/Qualifiers
source                  1..6
                        mol_type = protein
                        organism = synthetic construct
SEQUENCE: 221
TSNLAS                                                                  6

SEQ ID NO: 222          moltype = AA  length = 8
FEATURE                 Location/Qualifiers
source                  1..8
                        mol_type = protein
                        organism = synthetic construct
SEQUENCE: 222
QQYHSYPT                                                                8

SEQ ID NO: 223          moltype = AA  length = 7
FEATURE                 Location/Qualifiers
source                  1..7
                        mol_type = protein
                        organism = synthetic construct
SEQUENCE: 223
TQDYNAH                                                                 7

SEQ ID NO: 224          moltype = AA  length = 16
FEATURE                 Location/Qualifiers
source                  1..16
                        mol_type = protein
                        organism = synthetic construct
SEQUENCE: 224
YIHYSGQTYY NPSLKS                                                       16

SEQ ID NO: 225          moltype = AA  length = 12
FEATURE                 Location/Qualifiers
source                  1..12
                        mol_type = protein
                        organism = synthetic construct
SEQUENCE: 225
NFGSIYVNYF DY                                                           12

SEQ ID NO: 226          moltype = AA  length = 10
FEATURE                 Location/Qualifiers
source                  1..10
                        mol_type = protein
                        organism = synthetic construct
SEQUENCE: 226
SASSSVSYMY                                                              10

SEQ ID NO: 227          moltype = AA  length = 6
FEATURE                 Location/Qualifiers
source                  1..6
                        mol_type = protein
                        organism = synthetic construct
SEQUENCE: 227
TSNLAS                                                                  6

SEQ ID NO: 228          moltype = AA  length = 8
FEATURE                 Location/Qualifiers
source                  1..8
                        mol_type = protein
                        organism = synthetic construct
SEQUENCE: 228
QQYHGYPT                                                                8

SEQ ID NO: 229          moltype = AA  length = 7
FEATURE                 Location/Qualifiers
source                  1..7
                        mol_type = protein
                        organism = synthetic construct
SEQUENCE: 229
```

TQDYNAH                                                                                   7

SEQ ID NO: 230          moltype = AA  length = 16
FEATURE                 Location/Qualifiers
source                  1..16
                        mol_type = protein
                        organism = synthetic construct SEQUENCE: 230
YIHYSGQTYY NPSLKS                                                                        16

SEQ ID NO: 231          moltype = AA  length = 12
FEATURE                 Location/Qualifiers
source                  1..12
                        mol_type = protein
                        organism = synthetic construct SEQUENCE: 231
NFGSIYVNYF DY                                                                            12

SEQ ID NO: 232          moltype = AA  length = 10
FEATURE                 Location/Qualifiers
source                  1..10
                        mol_type = protein
                        organism = synthetic construct SEQUENCE: 232
SASSSVSYMY                                                                               10

SEQ ID NO: 233          moltype = AA  length = 6
FEATURE                 Location/Qualifiers
source                  1..6
                        mol_type = protein
                        organism = synthetic construct SEQUENCE: 233
TSNLAS                                                                                    6

SEQ ID NO: 234          moltype = AA  length = 8
FEATURE                 Location/Qualifiers
source                  1..8
                        mol_type = protein
                        organism = synthetic construct SEQUENCE: 234
QQYHSYVT                                                                                  8

SEQ ID NO: 235          moltype = AA  length = 7
FEATURE                 Location/Qualifiers
source                  1..7
                        mol_type = protein
                        organism = synthetic construct SEQUENCE: 235
TQDYNAH                                                                                   7

SEQ ID NO: 236          moltype = AA  length = 16
FEATURE                 Location/Qualifiers
source                  1..16
                        mol_type = protein
                        organism = synthetic construct SEQUENCE: 236
YIHYSGQTYY NPSLKS                                                                        16

SEQ ID NO: 237          moltype = AA  length = 12
FEATURE                 Location/Qualifiers
source                  1..12
                        mol_type = protein
                        organism = synthetic construct SEQUENCE: 237
NFGSIYVNYF DY                                                                            12

SEQ ID NO: 238          moltype = AA  length = 10
FEATURE                 Location/Qualifiers
source                  1..10
                        mol_type = protein
                        organism = synthetic construct SEQUENCE: 238
SASSSVSYMY                                                                               10

SEQ ID NO: 239          moltype = AA  length = 6
FEATURE                 Location/Qualifiers
source                  1..6
                        mol_type = protein
                        organism = synthetic construct

```
SEQUENCE: 239
TSNLAS                                                                          6

SEQ ID NO: 240         moltype = AA  length = 8
FEATURE                Location/Qualifiers
source                 1..8
                       mol_type = protein
                       organism = synthetic construct
SEQUENCE: 240
QQYHSYPK                                                                        8

SEQ ID NO: 241         moltype = AA  length = 7
FEATURE                Location/Qualifiers
source                 1..7
                       mol_type = protein
                       organism = synthetic construct
SEQUENCE: 241
TQDYNAH                                                                         7

SEQ ID NO: 242         moltype = AA  length = 16
FEATURE                Location/Qualifiers
source                 1..16
                       mol_type = protein
                       organism = synthetic construct
SEQUENCE: 242
YIHYSGQTNY NPSLKS                                                              16

SEQ ID NO: 243         moltype = AA  length = 12
FEATURE                Location/Qualifiers
source                 1..12
                       mol_type = protein
                       organism = synthetic construct
SEQUENCE: 243
NYGSIYVNYF DY                                                                  12

SEQ ID NO: 244         moltype = AA  length = 10
FEATURE                Location/Qualifiers
source                 1..10
                       mol_type = protein
                       organism = synthetic construct
SEQUENCE: 244
SASSSVSYMY                                                                     10

SEQ ID NO: 245         moltype = AA  length = 6
FEATURE                Location/Qualifiers
source                 1..6
                       mol_type = protein
                       organism = synthetic construct
SEQUENCE: 245
TSNLAS                                                                          6

SEQ ID NO: 246         moltype = AA  length = 8
FEATURE                Location/Qualifiers
source                 1..8
                       mol_type = protein
                       organism = synthetic construct
SEQUENCE: 246
QLYHSYPT                                                                        8

SEQ ID NO: 247         moltype = AA  length = 7
FEATURE                Location/Qualifiers
source                 1..7
                       mol_type = protein
                       organism = synthetic construct
SEQUENCE: 247
TQDYNAH                                                                         7

SEQ ID NO: 248         moltype = AA  length = 16
FEATURE                Location/Qualifiers
source                 1..16
                       mol_type = protein
                       organism = synthetic construct
SEQUENCE: 248
YIHYSGQTYY NPSLKS                                                              16

SEQ ID NO: 249         moltype = AA  length = 12
FEATURE                Location/Qualifiers
source                 1..12
                       mol_type = protein
```

-continued

```
SEQUENCE: 249
NFGSIYVNYF DY                                                    12

SEQ ID NO: 250        moltype = AA  length = 10
FEATURE               Location/Qualifiers
source                1..10
                      mol_type = protein
                      organism = synthetic construct
SEQUENCE: 250
SASSSVSYMY                                                       10

SEQ ID NO: 251        moltype = AA  length = 6
FEATURE               Location/Qualifiers
source                1..6
                      mol_type = protein
                      organism = synthetic construct
SEQUENCE: 251
TSNLAS                                                            6

SEQ ID NO: 252        moltype = AA  length = 8
FEATURE               Location/Qualifiers
source                1..8
                      mol_type = protein
                      organism = synthetic construct
SEQUENCE: 252
QLYHSYPT                                                          8

SEQ ID NO: 253        moltype = AA  length = 7
FEATURE               Location/Qualifiers
source                1..7
                      mol_type = protein
                      organism = synthetic construct
SEQUENCE: 253
TQDYNAH                                                           7

SEQ ID NO: 254        moltype = AA  length = 16
FEATURE               Location/Qualifiers
source                1..16
                      mol_type = protein
                      organism = synthetic construct
SEQUENCE: 254
YIHYSGQTYY NPSLKS                                                16

SEQ ID NO: 255        moltype = AA  length = 12
FEATURE               Location/Qualifiers
source                1..12
                      mol_type = protein
                      organism = synthetic construct
SEQUENCE: 255
NFGSIYVNYF DY                                                    12

SEQ ID NO: 256        moltype = AA  length = 10
FEATURE               Location/Qualifiers
source                1..10
                      mol_type = protein
                      organism = synthetic construct
SEQUENCE: 256
SASSSVSYMY                                                       10

SEQ ID NO: 257        moltype = AA  length = 6
FEATURE               Location/Qualifiers
source                1..6
                      mol_type = protein
                      organism = synthetic construct
SEQUENCE: 257
TSNLAS                                                            6

SEQ ID NO: 258        moltype = AA  length = 8
FEATURE               Location/Qualifiers
source                1..8
                      mol_type = protein
                      organism = synthetic construct
SEQUENCE: 258
QQYHGYPT                                                          8

SEQ ID NO: 259        moltype = AA  length = 7
FEATURE               Location/Qualifiers
source                1..7
```

```
                        mol_type = protein
                        organism = synthetic construct
SEQUENCE: 259
TQDYNAH                                                              7

SEQ ID NO: 260          moltype = AA   length = 16
FEATURE                 Location/Qualifiers
source                  1..16
                        mol_type = protein
                        organism = synthetic construct
SEQUENCE: 260
YIHYSGQTYY NPSLKS                                                   16

SEQ ID NO: 261          moltype = AA   length = 12
FEATURE                 Location/Qualifiers
source                  1..12
                        mol_type = protein
                        organism = synthetic construct
SEQUENCE: 261
NFGSIYVNYF DY                                                       12

SEQ ID NO: 262          moltype = AA   length = 10
FEATURE                 Location/Qualifiers
source                  1..10
                        mol_type = protein
                        organism = synthetic construct
SEQUENCE: 262
SASSSVSYMY                                                          10

SEQ ID NO: 263          moltype = AA   length = 6
FEATURE                 Location/Qualifiers
source                  1..6
                        mol_type = protein
                        organism = synthetic construct
SEQUENCE: 263
TSNLAS                                                               6

SEQ ID NO: 264          moltype = AA   length = 9
FEATURE                 Location/Qualifiers
source                  1..9
                        mol_type = protein
                        organism = synthetic construct
SEQUENCE: 264
QQYHSYVTF                                                            9

SEQ ID NO: 265          moltype = AA   length = 115
FEATURE                 Location/Qualifiers
source                  1..115
                        mol_type = protein
                        organism = synthetic construct
SEQUENCE: 265
QIQFVQSGPE VKTPGETVKI SCKASVYTFT EYPMHWLKQA PGEDFEWMGW IHTYSGEPTY   60
ADDFKGRFAF SLETSASTAY LQINNLKTED TATYFCARGR YYGALDYWGQ GTALT       115

SEQ ID NO: 266          moltype = AA   length = 107
FEATURE                 Location/Qualifiers
source                  1..107
                        mol_type = protein
                        organism = synthetic construct
SEQUENCE: 266
DIQMTQTPSS LSASLGDRVT ISCRASQDIS NYLNWYQQKP DGTVKLLIYY TSRLHSGVPS   60
RFSGSGSGTD YSLTISNLEQ EDVATYFCQH GNTLPRTFGG GTKLEIK                107

SEQ ID NO: 267          moltype = AA   length = 118
FEATURE                 Location/Qualifiers
source                  1..118
                        mol_type = protein
                        organism = synthetic construct
SEQUENCE: 267
QVQLVQSGSE LKKPGASVKV SCKASVYTFT EYPMHWLRQA PGQGFEWMGW IHTYSGEPTY   60
ADDFKGRFVF SLDTSVSTAY LQISSLKAED TAVYFCARGR YYGALDYWGQ GTALTVSS   118

SEQ ID NO: 268          moltype = AA   length = 107
FEATURE                 Location/Qualifiers
source                  1..107
                        mol_type = protein
                        organism = synthetic construct
SEQUENCE: 268
DIQMTQSPSS LSASVGDRVT ITCRASQDIS NYLNWYQQKP GKAVKLLIYY TSRLHSGVPS   60
```

```
RFSGSGSGTD YTFTISSLQP EDIATYFCQH GNTLPRTFGG GTKLEIK                  107

SEQ ID NO: 269          moltype = AA  length = 122
FEATURE                 Location/Qualifiers
source                  1..122
                        mol_type = protein
                        organism = synthetic construct
SEQUENCE: 269
EVQLQQSGPE LVKPGASVKI SCKASGYTFT DYYMNWVKQS HGKSLEWIGD INPNNGGTSY     60
NQKFKGKATL TVDKSSNTAY MELRSLTSED SAVYYCAREG VYSNYGGYFD YWGQGTTLTV    120
SS                                                                  122

SEQ ID NO: 270          moltype = AA  length = 106
FEATURE                 Location/Qualifiers
source                  1..106
                        mol_type = protein
                        organism = synthetic construct
SEQUENCE: 270
QIVLTQSPAL MSASPGEKVT MTCSASSSVS YMYWYQQKPR SSPKPWIYLT SNLASGVPAR     60
FSGSGSGTSY SLTISSMEAE DAATYYCQQW SSNPPTFGSG TKLEIK                  106

SEQ ID NO: 271          moltype = AA  length = 120
FEATURE                 Location/Qualifiers
source                  1..120
                        mol_type = protein
                        organism = synthetic construct
SEQUENCE: 271
QVQLQQPGSE LVRPGASVKL SCKASGYTFT SYWMHWVKQR PGQGLEWIGN IYPGSGNTIY     60
DEKFKSKATL TVDTSSSTAY MQLSSLTSED SAVYYCTRWD NWEGYYFDYW GQGTTLTVSS    120

SEQ ID NO: 272          moltype = AA  length = 112
FEATURE                 Location/Qualifiers
source                  1..112
                        mol_type = protein
                        organism = synthetic construct
SEQUENCE: 272
DIVMTQAAFS NPVTLGTSAS ISCRSSKSLL HSNGITYLYW YLQKPGQSPQ LLIYQMSNLA     60
SGVPDRFSSS GSGTDFTLRI SRVEAEDVGV YYCAQNLELP WTFGGGTKLE IK           112

SEQ ID NO: 273          moltype = AA  length = 115
FEATURE                 Location/Qualifiers
source                  1..115
                        mol_type = protein
                        organism = synthetic construct
SEQUENCE: 273
EVQLQQSGPE LVKTGASVKI SCKASGYSFT GYYMHWVKQS HGKSLEWIGY ISCYNGATSY     60
NQKFKGKATF TVDTSSSTAY MQFNSLTSED SAVYYCAITL HYAMDYWGQG TSVAS        115

SEQ ID NO: 274          moltype = AA  length = 112
FEATURE                 Location/Qualifiers
source                  1..112
                        mol_type = protein
                        organism = synthetic construct
SEQUENCE: 274
DIVMTQAAFS NPVTLGTSAS ISCRSSKSLL HSNGITYLYW YLQKPGQSPQ LLIYQMSNLA     60
SGVPDRFSSS GSGTDFTLRI SRVEAEDVGV YYCAQNLELP WTFGGGTKLE IK           112

SEQ ID NO: 275          moltype = AA  length = 121
FEATURE                 Location/Qualifiers
source                  1..121
                        mol_type = protein
                        organism = synthetic construct
SEQUENCE: 275
QVQLQQSGAE LVRPGVSVKI SCKGSGYTFT DYAMHWVKQS HAKSLEWIGV ISTYYGDASY     60
NQKFKGKATM TVDKSSSTAY MELARLTSED SAIYYCARER DYYGSRLFDY WGQGTTLTVS    120
S                                                                  121

SEQ ID NO: 276          moltype = AA  length = 108
FEATURE                 Location/Qualifiers
source                  1..108
                        mol_type = protein
                        organism = synthetic construct
SEQUENCE: 276
EIVLTQSPTT MAASPGEKIT ITCSANSSIS SNYLHWYQQK PGFSPKLLIY GTSNLASGVP     60
ARFSGSGSGT SYSLTIGTME AEDVATYYCQ QGSSIPYTFG GGTKLEIK                108

SEQ ID NO: 277          moltype = AA  length = 117
FEATURE                 Location/Qualifiers
source                  1..117
```

```
                              mol_type = protein
                              organism = synthetic construct
SEQUENCE: 277
QVQLQQSGAE LARPGASVKL SCKASGYTFT DYYINWVKQR TGQGLEWIGE IYPGSGNTYY    60
NEKFKGKATL TADKSSSTAY MQLSSLTSED SAVYFCARGY YGRFAYWGQG TLVTVSA      117

SEQ ID NO: 278          moltype = AA   length = 112
FEATURE                 Location/Qualifiers
source                  1..112
                        mol_type = protein
                        organism = synthetic construct
SEQUENCE: 278
DIVMTQAAFS NPVTLGTSAS ISCRSSKSLL HSNGITYLYW YLQKPGQSPQ LLIYQMSNLA    60
SGVPDRFSSS GSGTDFTLRI SRVEAEDVGV YYCDQNLELP FTFGSGTKLE IK           112

SEQ ID NO: 279          moltype = AA   length = 116
FEATURE                 Location/Qualifiers
source                  1..116
                        mol_type = protein
                        organism = synthetic construct
SEQUENCE: 279
QVQLQQSGAE LVRPGVSVKI SCKGSGYTFT DYPMHWVKQS HAKSLEWIGV ISTYYGDASY    60
NQKFKGKATM TVDKSSSTAY MELARLTSED SAIYYCARWR GSFDYWGQGT TLTVSS       116

SEQ ID NO: 280          moltype = AA   length = 107
FEATURE                 Location/Qualifiers
source                  1..107
                        mol_type = protein
                        organism = synthetic construct
SEQUENCE: 280
ENVLTQSPAI MSASPGEKVT MTCRASSSVS SSYLHWYQQK SGASPKLWIY STSNLASGVP    60
ARFSGSGSGT SYSLTISSVE AEDAATYYCQ QYSGYHTFGG GTKLEIK                 107

SEQ ID NO: 281          moltype = AA   length = 121
FEATURE                 Location/Qualifiers
source                  1..121
                        mol_type = protein
                        organism = synthetic construct
SEQUENCE: 281
DVQLQESGPD LVKPSQSLSL TCTVTGYSIT SDYNCHWIRQ FPGNKLEWMG YIHYSGSTNY    60
NPSLKSRISI TRDTSKNQFF LQLNSVTAED TATYYCARNY GSIYVNYFDY WGQGTTLTVS   120
S                                                                    121

SEQ ID NO: 282          moltype = AA   length = 105
FEATURE                 Location/Qualifiers
source                  1..105
                        mol_type = protein
                        organism = synthetic construct
SEQUENCE: 282
QIVLTQSPAI MSASPGEKVT ISCSASSSVS YMYWYQQEPG SSPKPWIYRT SNLASGVPPR    60
FSGSGSGTSY SLTISSMEAE DAATYFCQQY HSYPTFGGGT KLEIK                   105

SEQ ID NO: 283          moltype = AA   length = 121
FEATURE                 Location/Qualifiers
source                  1..121
                        mol_type = protein
                        organism = synthetic construct
SEQUENCE: 283
QVQLQESGPG LVKPSQTLSL TCTVSGYSIT SDYNSHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                    121

SEQ ID NO: 284          moltype = AA   length = 105
FEATURE                 Location/Qualifiers
source                  1..105
                        mol_type = protein
                        organism = synthetic construct
SEQUENCE: 284
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 285          moltype = AA   length = 121
FEATURE                 Location/Qualifiers
source                  1..121
                        mol_type = protein
                        organism = synthetic construct
SEQUENCE: 285
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
```

```
S                                                                      121

SEQ ID NO: 286          moltype = AA  length = 105
FEATURE                 Location/Qualifiers
source                  1..105
                        mol_type = protein
                        organism = synthetic construct
SEQUENCE: 286
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 287          moltype = AA  length = 121
FEATURE                 Location/Qualifiers
source                  1..121
                        mol_type = protein
                        organism = synthetic construct
SEQUENCE: 287
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNF GSIYVNYFDY WGQGTLVTVS   120
S                                                                      121

SEQ ID NO: 288          moltype = AA  length = 105
FEATURE                 Location/Qualifiers
source                  1..105
                        mol_type = protein
                        organism = synthetic construct
SEQUENCE: 288
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 289          moltype = AA  length = 121
FEATURE                 Location/Qualifiers
source                  1..121
                        mol_type = protein
                        organism = synthetic construct
SEQUENCE: 289
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNY ASIYVNYFDY WGQGTLVTVS   120
S                                                                      121

SEQ ID NO: 290          moltype = AA  length = 105
FEATURE                 Location/Qualifiers
source                  1..105
                        mol_type = protein
                        organism = synthetic construct
SEQUENCE: 290
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 291          moltype = AA  length = 121
FEATURE                 Location/Qualifiers
source                  1..121
                        mol_type = protein
                        organism = synthetic construct
SEQUENCE: 291
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNF ASIYVNYFDY WGQGTLVTVS   120
S                                                                      121

SEQ ID NO: 292          moltype = AA  length = 105
FEATURE                 Location/Qualifiers
source                  1..105
                        mol_type = protein
                        organism = synthetic construct
SEQUENCE: 292
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 293          moltype = AA  length = 121
FEATURE                 Location/Qualifiers
source                  1..121
                        mol_type = protein
                        organism = synthetic construct
SEQUENCE: 293
QVQLQESGPG LVKPSQTLSL TCTVSGYSIT SDYNNHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                      121

SEQ ID NO: 294          moltype = AA  length = 105
```

```
FEATURE                 Location/Qualifiers
source                  1..105
                        mol_type = protein
                        organism = synthetic construct
SEQUENCE: 294
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 295          moltype = AA   length = 121
FEATURE                 Location/Qualifiers
source                  1..121
                        mol_type = protein
                        organism = synthetic construct
SEQUENCE: 295
QVQLQESGPG LVKPSQTLSL TCTVSGYSIT QDYNAHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                  121

SEQ ID NO: 296          moltype = AA   length = 105
FEATURE                 Location/Qualifiers
source                  1..105
                        mol_type = protein
                        organism = synthetic construct
SEQUENCE: 296
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 297          moltype = AA   length = 121
FEATURE                 Location/Qualifiers
source                  1..121
                        mol_type = protein
                        organism = synthetic construct
SEQUENCE: 297
QVQLQESGPG LVKPSQTLSL TCTVSGYSIT SDYNAHWIRQ PPGKGLEWIG YIHYSGATNY    60
NPSLKSRVTI SRDTSKNQFS LKLSSVTAAD TAVYYCARNY GSIYVNYFDY WGQGTLVTVS   120
S                                                                  121

SEQ ID NO: 298          moltype = AA   length = 105
FEATURE                 Location/Qualifiers
source                  1..105
                        mol_type = protein
                        organism = synthetic construct
SEQUENCE: 298
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 299          moltype = AA   length = 121
FEATURE                 Location/Qualifiers
source                  1..121
                        mol_type = protein
                        organism = synthetic construct
SEQUENCE: 299
QVQLQESGPG LVKPSQTLSL TCTVSGYSIT SDYNAHWIRQ PPGKGLEWIG YIHYSGQTNY    60
NPSLKSRVTI SRDTSKNQFS LKLSSVTAAD TAVYYCARNY GSIYVNYFDY WGQGTLVTVS   120
S                                                                  121

SEQ ID NO: 300          moltype = AA   length = 105
FEATURE                 Location/Qualifiers
source                  1..105
                        mol_type = protein
                        organism = synthetic construct
SEQUENCE: 300
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                   105

SEQ ID NO: 301          moltype = AA   length = 121
FEATURE                 Location/Qualifiers
source                  1..121
                        mol_type = protein
                        organism = synthetic construct
SEQUENCE: 301
QVQLQESGPG LVKPSQTLSL TCTVSGYSIT SDYNAHWIRQ PPGKGLEWIG YIHYSGSTMY    60
NPSLKSRVTI SRDTSKNQFS LKLSSVTAAD TAVYYCARNY GSIYVNYFDY WGQGTLVTVS   120
S                                                                  121

SEQ ID NO: 302          moltype = AA   length = 105
FEATURE                 Location/Qualifiers
source                  1..105
                        mol_type = protein
```

```
                        organism = synthetic construct
SEQUENCE: 302
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                  105

SEQ ID NO: 303          moltype = AA   length = 121
    FEATURE                 Location/Qualifiers
    source                  1..121
                            mol_type = protein
                            organism = synthetic construct
SEQUENCE: 303
QVQLQESGPG LVKPSQTLSL TCTVSGYSIT SDYNAHWIRQ PPGKGLEWIG YIHYSGQTMY    60
NPSLKSRVTI SRDTSKNQFS LKLSSVTAAD TAVYYCARNY GSIYVNYFDY WGQGTLVTVS   120
S                                                                  121

SEQ ID NO: 304          moltype = AA   length = 105
    FEATURE                 Location/Qualifiers
    source                  1..105
                            mol_type = protein
                            organism = synthetic construct
SEQUENCE: 304
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                  105

SEQ ID NO: 305          moltype = AA   length = 121
    FEATURE                 Location/Qualifiers
    source                  1..121
                            mol_type = protein
                            organism = synthetic construct
SEQUENCE: 305
QVQLQESGPG LVKPSQTLSL TCTVSGYSIT QDYNAHWIRQ PPGKGLEWIG YIHYSGSTMY    60
NPSLKSRVTI SRDTSKNQFS LKLSSVTAAD TAVYYCARNY GSIYVNYFDY WGQGTLVTVS   120
S                                                                  121

SEQ ID NO: 306          moltype = AA   length = 105
    FEATURE                 Location/Qualifiers
    source                  1..105
                            mol_type = protein
                            organism = synthetic construct
SEQUENCE: 306
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                  105

SEQ ID NO: 307          moltype = AA   length = 121
    FEATURE                 Location/Qualifiers
    source                  1..121
                            mol_type = protein
                            organism = synthetic construct
SEQUENCE: 307
QVQLQESGPG LVKPSQTLSL TCTVSGYSIT SDYNAHWIRQ PPGKGLEWIG YIHYSGSTMY    60
NPSLKSRVTI SRDTSKNQFS LKLSSVTAAD TAVYYCARNF GSIYVNYFDY WGQGTLVTVS   120
S                                                                  121

SEQ ID NO: 308          moltype = AA   length = 105
    FEATURE                 Location/Qualifiers
    source                  1..105
                            mol_type = protein
                            organism = synthetic construct
SEQUENCE: 308
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYPTFGGGT KVEIK                  105

SEQ ID NO: 309          moltype = AA   length = 121
    FEATURE                 Location/Qualifiers
    source                  1..121
                            mol_type = protein
                            organism = synthetic construct
SEQUENCE: 309
QVQLQESGPG LVKPSQTLSL TCTVSGYSIT SDYNAHWIRQ PPGKGLEWIG YIHYSGQTMY    60
NPSLKSRVTI SRDTSKNQFS LKLSSVTAAD TAVYYCARNY GSIYVNYFDY WGQGTLVTVS   120
S                                                                  121

SEQ ID NO: 310          moltype = AA   length = 105
    FEATURE                 Location/Qualifiers
    source                  1..105
                            mol_type = protein
                            organism = synthetic construct
SEQUENCE: 310
EIVLTQSPAT LSLSPGERAT LSCSASSSVS YMYWYQQKPG QAPRPLIYRT SNLASGIPAR    60
```

```
FSGSGSGTDF TLTISSLEPE DFAVYYCQQY HSYPTFGGGT KVEIK              105

SEQ ID NO: 311           moltype = AA   length = 121
FEATURE                  Location/Qualifiers
source                   1..121
                         mol_type = protein
                         organism = synthetic construct
SEQUENCE: 311
QVQLQESGPG LVKPSQTLSL TCTVSGYSIT SDYNAHWIRQ PPGKGLEWIG YIHYSGQTMY  60
NPSLKSRVTI SRDTSKNQFS LKLSSVTAAD TAVYYCARNF GSIYVNYFDY WGQGTLVTVS  120
S                                                                121

SEQ ID NO: 312           moltype = AA   length = 105
FEATURE                  Location/Qualifiers
source                   1..105
                         mol_type = protein
                         organism = synthetic construct
SEQUENCE: 312
EIVLTQSPAT LSLSPGERAT LSCSASSSVS YMYWYQQKPG QAPRPLIYRT SNLASGIPAR  60
FSGSGSGTDF TLTISSLEPE DFAVYYCQQY HSYPTFGGGT KVEIK                 105

SEQ ID NO: 313           moltype = AA   length = 121
FEATURE                  Location/Qualifiers
source                   1..121
                         mol_type = protein
                         organism = synthetic construct
SEQUENCE: 313
QVQLQESGPG LVKPSQTLSL TCTVSGYSIT SDYNAHWIRQ PPGKGLEWIG YIHYSGSTYY  60
NPSLKSRVTI SRDTSKNQFS LKLSSVTAAD TAVYYCARNY GSIYVNYFDY WGQGTLVTVS  120
S                                                                121

SEQ ID NO: 314           moltype = AA   length = 105
FEATURE                  Location/Qualifiers
source                   1..105
                         mol_type = protein
                         organism = synthetic construct
SEQUENCE: 314
EIVLTQSPAT LSLSPGERAT LSCSASSSVS YMYWYQQKPG QAPRPLIYRT SNLASGIPAR  60
FSGSGSGTDF TLTISSLEPE DFAVYYCQQY HSYPTFGGGT KVEIK                 105

SEQ ID NO: 315           moltype = AA   length = 121
FEATURE                  Location/Qualifiers
source                   1..121
                         mol_type = protein
                         organism = synthetic construct
SEQUENCE: 315
QVQLQESGPG LVKPSQTLSL TCTVSGYSIT SDYNAHWIRQ PPGKGLEWIG YIHYSGSTLY  60
NPSLKSRVTI SRDTSKNQFS LKLSSVTAAD TAVYYCARNY GSIYVNYFDY WGQGTLVTVS  120
S                                                                121

SEQ ID NO: 316           moltype = AA   length = 105
FEATURE                  Location/Qualifiers
source                   1..105
                         mol_type = protein
                         organism = synthetic construct
SEQUENCE: 316
EIVLTQSPAT LSLSPGERAT LSCSASSSVS YMYWYQQKPG QAPRPLIYRT SNLASGIPAR  60
FSGSGSGTDF TLTISSLEPE DFAVYYCQQY HSYPTFGGGT KVEIK                 105

SEQ ID NO: 317           moltype = AA   length = 121
FEATURE                  Location/Qualifiers
source                   1..121
                         mol_type = protein
                         organism = synthetic construct
SEQUENCE: 317
QVQLQESGPG LVKPSQTLSL TCTVSGYSIT QDYNAHWIRQ PPGKGLEWIG YIHYSGQTMY  60
NPSLKSRVTI SRDTSKNQFS LKLSSVTAAD TAVYYCARNF GSIYVNYFDY WGQGTLVTVS  120
S                                                                121

SEQ ID NO: 318           moltype = AA   length = 105
FEATURE                  Location/Qualifiers
source                   1..105
                         mol_type = protein
                         organism = synthetic construct
SEQUENCE: 318
EIVLTQSPAT LSLSPGERAT LSCSASSSVS YMYWYQQKPG QAPRPLIYRT SNLASGIPAR  60
FSGSGSGTDF TLTISSLEPE DFAVYYCQQY HSYPTFGGGT KVEIK                 105

SEQ ID NO: 319           moltype = AA   length = 121
```

| FEATURE | Location/Qualifiers |
|---|---|
| source | 1..121<br>mol_type = protein<br>organism = synthetic construct |

SEQUENCE: 319
```
QVQLQESGPG LVKPSQTLSL TCTVSGYSIT QDYNAHWIRQ PPGKGLEWIG YIHYSGQTNY   60
NPSLKSRVTI SRDTSKNQFS LKLSSVTAAD TAVYYCARNF GSIYVNYFDY WGQGTLVTVS  120
S                                                                 121
```

| SEQ ID NO: 320 | moltype = AA  length = 105 |
|---|---|
| FEATURE | Location/Qualifiers |
| source | 1..105<br>mol_type = protein<br>organism = synthetic construct |

SEQUENCE: 320
```
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPTFGGGT KVEIK                 105
```

| SEQ ID NO: 321 | moltype = AA  length = 121 |
|---|---|
| FEATURE | Location/Qualifiers |
| source | 1..121<br>mol_type = protein<br>organism = synthetic construct |

SEQUENCE: 321
```
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS  120
S                                                                 121
```

| SEQ ID NO: 322 | moltype = AA  length = 105 |
|---|---|
| FEATURE | Location/Qualifiers |
| source | 1..105<br>mol_type = protein<br>organism = synthetic construct |

SEQUENCE: 322
```
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPTFGGGT KVEIK                 105
```

| SEQ ID NO: 323 | moltype = AA  length = 121 |
|---|---|
| FEATURE | Location/Qualifiers |
| source | 1..121<br>mol_type = protein<br>organism = synthetic construct |

SEQUENCE: 323
```
QVQLQESGPG LVKPSQTLSL TCTVSGYSIT QDYNAHWIRQ PPGKGLEWIG YIHYSGQTLY   60
NPSLKSRVTI SRDTSKNQFS LKLSSVTAAD TAVYYCARNF GSIYVNYFDY WGQGTLVTVS  120
S                                                                 121
```

| SEQ ID NO: 324 | moltype = AA  length = 105 |
|---|---|
| FEATURE | Location/Qualifiers |
| source | 1..105<br>mol_type = protein<br>organism = synthetic construct |

SEQUENCE: 324
```
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPTFGGGT KVEIK                 105
```

| SEQ ID NO: 325 | moltype = AA  length = 121 |
|---|---|
| FEATURE | Location/Qualifiers |
| source | 1..121<br>mol_type = protein<br>organism = synthetic construct |

SEQUENCE: 325
```
QVQLQESGPG LVKPSQTLSL TCTVSGYSIT QDYNAHWIRQ PPGKGLEWIG YIHYSGQTNY   60
NPSLKSRVTI SRDTSKNQFS LKLSSVTAAD TAVYYCARNY GSIYVNYFDY WGQGTLVTVS  120
S                                                                 121
```

| SEQ ID NO: 326 | moltype = AA  length = 105 |
|---|---|
| FEATURE | Location/Qualifiers |
| source | 1..105<br>mol_type = protein<br>organism = synthetic construct |

SEQUENCE: 326
```
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPTFGGGT KVEIK                 105
```

| SEQ ID NO: 327 | moltype = AA  length = 121 |
|---|---|
| FEATURE | Location/Qualifiers |
| source | 1..121<br>mol_type = protein |

-continued

```
                        organism = synthetic construct
SEQUENCE: 327
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                  121

SEQ ID NO: 328          moltype = AA  length = 105
FEATURE                 Location/Qualifiers
source                  1..105
                        mol_type = protein
                        organism = synthetic construct
SEQUENCE: 328
EIVLTQSPAT LSLSPGERAT LSCSASSSVS YMYWYQQKPG QAPRPLIYRT SNLASGIPAR    60
FSGSGSGTDF TLTISSLEPE DFAVYYCQEY HSYPTFGGGT KVEIK                  105

SEQ ID NO: 329          moltype = AA  length = 121
FEATURE                 Location/Qualifiers
source                  1..121
                        mol_type = protein
                        organism = synthetic construct
SEQUENCE: 329
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                  121

SEQ ID NO: 330          moltype = AA  length = 105
FEATURE                 Location/Qualifiers
source                  1..105
                        mol_type = protein
                        organism = synthetic construct
SEQUENCE: 330
EIVLTQSPAT LSLSPGERAT LSCSASSSVS YMYWYQQKPG QAPRPLIYRT SNLASGIPAR    60
FSGSGSGTDF TLTISSLEPE DFAVYYCQLY HSYPTFGGGT KVEIK                  105

SEQ ID NO: 331          moltype = AA  length = 121
FEATURE                 Location/Qualifiers
source                  1..121
                        mol_type = protein
                        organism = synthetic construct
SEQUENCE: 331
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                  121

SEQ ID NO: 332          moltype = AA  length = 105
FEATURE                 Location/Qualifiers
source                  1..105
                        mol_type = protein
                        organism = synthetic construct
SEQUENCE: 332
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HGYPTFGGGT KVEIK                  105

SEQ ID NO: 333          moltype = AA  length = 121
FEATURE                 Location/Qualifiers
source                  1..121
                        mol_type = protein
                        organism = synthetic construct
SEQUENCE: 333
QVQLQESGPG LVKPSQTLSL TCTVSGYSIT SDYNAHWIRQ PPGKGLEWIG YIHYSGSTNY    60
NPSLKSRVTI SRDTSKNQFS LKLSSVTAAD TAVYYCARNY GSIYVNYFDY WGQGTLVTVS   120
S                                                                  121

SEQ ID NO: 334          moltype = AA  length = 105
FEATURE                 Location/Qualifiers
source                  1..105
                        mol_type = protein
                        organism = synthetic construct
SEQUENCE: 334
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYVTFGGGT KVEIK                  105

SEQ ID NO: 335          moltype = AA  length = 121
FEATURE                 Location/Qualifiers
source                  1..121
                        mol_type = protein
                        organism = synthetic construct
SEQUENCE: 335
QVQLQESGPG LVKPSQTLSL TCTVSGYSIT SDYNAHWIRQ PPGKGLEWIG YIHYSGSTNY    60
```

```
NPSLKSRVTI SRDTSKNQFS LKLSSVTAAD TAVYYCARNY GSIYVNYFDY WGQGTLVTVS   120
S                                                                 121

SEQ ID NO: 336          moltype = AA   length = 105
FEATURE                 Location/Qualifiers
source                  1..105
                        mol_type = protein
                        organism = synthetic construct
SEQUENCE: 336
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPKFGGGT KVEIK                  105

SEQ ID NO: 337          moltype = AA   length = 121
FEATURE                 Location/Qualifiers
source                  1..121
                        mol_type = protein
                        organism = synthetic construct
SEQUENCE: 337
QVQLQESGPG LVKPSQTLSL TCTVSGYSIT SDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS   120
S                                                                 121

SEQ ID NO: 338          moltype = AA   length = 105
FEATURE                 Location/Qualifiers
source                  1..105
                        mol_type = protein
                        organism = synthetic construct
SEQUENCE: 338
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPTFGGGT KVEIK                  105

SEQ ID NO: 339          moltype = AA   length = 121
FEATURE                 Location/Qualifiers
source                  1..121
                        mol_type = protein
                        organism = synthetic construct
SEQUENCE: 339
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS   120
S                                                                 121

SEQ ID NO: 340          moltype = AA   length = 105
FEATURE                 Location/Qualifiers
source                  1..105
                        mol_type = protein
                        organism = synthetic construct
SEQUENCE: 340
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HGYPTFGGGT KVEIK                  105

SEQ ID NO: 341          moltype = AA   length = 121
FEATURE                 Location/Qualifiers
source                  1..121
                        mol_type = protein
                        organism = synthetic construct
SEQUENCE: 341
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS   120
S                                                                 121

SEQ ID NO: 342          moltype = AA   length = 105
FEATURE                 Location/Qualifiers
source                  1..105
                        mol_type = protein
                        organism = synthetic construct
SEQUENCE: 342
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYVTFGGGT KVEIK                  105

SEQ ID NO: 343          moltype = AA   length = 121
FEATURE                 Location/Qualifiers
source                  1..121
                        mol_type = protein
                        organism = synthetic construct
SEQUENCE: 343
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS   120
S                                                                 121
```

```
SEQ ID NO: 344          moltype = AA   length = 105
FEATURE                 Location/Qualifiers
source                  1..105
                        mol_type = protein
                        organism = synthetic construct
SEQUENCE: 344
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HSYPKFGGGT KVEIK                  105

SEQ ID NO: 345          moltype = AA   length = 121
FEATURE                 Location/Qualifiers
source                  1..121
                        mol_type = protein
                        organism = synthetic construct
SEQUENCE: 345
QVQLQESGPG LVKPSQTLSL TCTVSGYSIT QDYNAHWIRQ PPGKGLEWIG YIHYSGQTNY   60
NPSLKSRVTI SRDTSKNQFS LKLSSVTAAD TAVYYCARNY GSIYVNYFDY WGQGTLVTVS  120
S                                                                  121

SEQ ID NO: 346          moltype = AA   length = 105
FEATURE                 Location/Qualifiers
source                  1..105
                        mol_type = protein
                        organism = synthetic construct
SEQUENCE: 346
EIVLTQSPAT LSLSPGERAT LSCSASSSVS YMYWYQQKPG QAPRPLIYRT SNLASGIPAR   60
FSGSGSGTDF TLTISSLEPE DFAVYYCQLY HSYPTFGGGT KVEIK                  105

SEQ ID NO: 347          moltype = AA   length = 121
FEATURE                 Location/Qualifiers
source                  1..121
                        mol_type = protein
                        organism = synthetic construct
SEQUENCE: 347
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS  120
S                                                                  121

SEQ ID NO: 348          moltype = AA   length = 105
FEATURE                 Location/Qualifiers
source                  1..105
                        mol_type = protein
                        organism = synthetic construct
SEQUENCE: 348
EIVLTQSPAT LSLSPGERAT LSCSASSSVS YMYWYQQKPG QAPRPLIYRT SNLASGIPAR   60
FSGSGSGTDF TLTISSLEPE DFAVYYCQLY HSYPTFGGGT KVEIK                  105

SEQ ID NO: 349          moltype = AA   length = 121
FEATURE                 Location/Qualifiers
source                  1..121
                        mol_type = protein
                        organism = synthetic construct
SEQUENCE: 349
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS  120
S                                                                  121

SEQ ID NO: 350          moltype = AA   length = 105
FEATURE                 Location/Qualifiers
source                  1..105
                        mol_type = protein
                        organism = synthetic construct
SEQUENCE: 350
EIVLTQSPAT LSLSPGERAT LSCSASSSVS YMYWYQQKPG QAPRPLIYRT SNLASGIPAR   60
FSGSGSGTDF TLTISSLEPE DFAVYYCQQY HGYPTFGGGT KVEIK                  105

SEQ ID NO: 351          moltype = AA   length = 121
FEATURE                 Location/Qualifiers
source                  1..121
                        mol_type = protein
                        organism = synthetic construct
SEQUENCE: 351
QVQLQESGPG LVKPSQTLSL TCTVSGYSIT QDYNAHWIRQ PPGKGLEWIG YIHYSGQTYY   60
NPSLKSRVTI SRDTSKNQFS LKLSSVTAAD TAVYYCARNF GSIYVNYFDY WGQGTLVTVS  120
S                                                                  121

SEQ ID NO: 352          moltype = AA   length = 105
FEATURE                 Location/Qualifiers
source                  1..105
```

```
                        mol_type = protein
                        organism = synthetic construct
SEQUENCE: 352
EIVLTQSPAT LSLSPGERAT LSCSASSSVS YMYWYQQKPG QAPRPLIYRT SNLASGIPAR    60
FSGSGSGTDF TLTISSLEPE DFAVYYCQQY HSYVTFGGGT KVEIK                   105

SEQ ID NO: 353          moltype =   length =
SEQUENCE: 353
000

SEQ ID NO: 354          moltype =   length =
SEQUENCE: 354
000

SEQ ID NO: 355          moltype =   length =
SEQUENCE: 355
000

SEQ ID NO: 356          moltype =   length =
SEQUENCE: 356
000

SEQ ID NO: 357          moltype =   length =
SEQUENCE: 357
000

SEQ ID NO: 358          moltype =   length =
SEQUENCE: 358
000

SEQ ID NO: 359          moltype =   length =
SEQUENCE: 359
000

SEQ ID NO: 360          moltype =   length =
SEQUENCE: 360
000

SEQ ID NO: 361          moltype =   length =
SEQUENCE: 361
000

SEQ ID NO: 362          moltype =   length =
SEQUENCE: 362
000

SEQ ID NO: 363          moltype =   length =
SEQUENCE: 363
000

SEQ ID NO: 364          moltype =   length =
SEQUENCE: 364
000

SEQ ID NO: 365          moltype =   length =
SEQUENCE: 365
000

SEQ ID NO: 366          moltype =   length =
SEQUENCE: 366
000

SEQ ID NO: 367          moltype =   length =
SEQUENCE: 367
000

SEQ ID NO: 368          moltype =   length =
SEQUENCE: 368
000

SEQ ID NO: 369          moltype =   length =
SEQUENCE: 369
000

SEQ ID NO: 370          moltype =   length =
SEQUENCE: 370
000

SEQ ID NO: 371          moltype = AA   length = 192
```

```
FEATURE                 Location/Qualifiers
source                  1..192
                        mol_type = protein
                        organism = Homo sapiens
SEQUENCE: 371
MRHNWTPDLS PLWVLLLCAH VVTLLVRATP VSQTTAATA  SVRSTKDPCP SQPPVFPAAK    60
QCPALEVTWP EVEVPLNGTL SLSCVACSRF PNFSILYWLG NGSFIEHLPG RLWEGSTSRE   120
RGSTGTQLCK ALVLEQLTPA LHSTNFSCVL VDPEQVVQRH VVLAQLWAGL RATLPPTQEA   180
LPSSHSSPQQ QG                                                      192

SEQ ID NO: 372          moltype = AA   length = 164
FEATURE                 Location/Qualifiers
source                  1..164
                        mol_type = protein
                        organism = Homo sapiens
SEQUENCE: 372
TPVSQTTTAA TASVRSTKDP CPSQPPVFPA AKQCPALEVT WPEVEVPLNG TLSLSCVACS    60
RFPNFSILYW LGNGSFIEHL PGRLWEGSTS RERGSTGTQL CKALVLEQLT PALHSTNFSC   120
VLVDPEQVVQ RHVVLAQLWA GLRATLPPTQ EALPSSHSSP QQQG                    164

SEQ ID NO: 373          moltype = AA   length = 207
FEATURE                 Location/Qualifiers
source                  1..207
                        mol_type = protein
                        organism = Macaca fascicularis
SEQUENCE: 373
MRHNWTPDLS FLWVLLCAHI ITLLVRATPV SQTTTAATAS SRSTKDPCPS QPPVFPAAKQ    60
CPALEVTWPE VEMPLNGTLT LSCTACSRFP NFSMLYWLGN GSFIEHLPGQ LWEGSTSREH   120
GSTGTRLYKA LVLEQLTPAL HSTNFSCVLM DPEQVVQRHV ILAQLWAGLR TTLPPTQEAL   180
PSSHSTGPQQ PTAAGLRLST GPAAARP                                      207

SEQ ID NO: 374          moltype = AA   length = 180
FEATURE                 Location/Qualifiers
source                  1..180
                        mol_type = protein
                        organism = Macaca fascicularis
SEQUENCE: 374
TPVSQTTTAA TASSRSTKDP CPSQPPVFPA AKQCPALEVT WPEVEMPLNG TLTLSCTACS    60
RFPNFSMLYW LGNGSFIEHL PGQLWEGSTS REHGSTGTRL YKALVLEQLT PALHSTNFSC   120
VLMDPEQVVQ RHVILAQLWA GLRTTLPPTQ EALPSSHSTG PQQPTAAGLR LSTGPAAARP   180

SEQ ID NO: 375          moltype = AA   length = 191
FEATURE                 Location/Qualifiers
source                  1..191
                        mol_type = protein
                        organism = Mus musculus
SEQUENCE: 375
MRHCWTAGPS SWWVLLLYVH VILARATSAP QTTATVLTGS SKDPCSSWSP AVPTKQYPAL    60
DVIWPEKEVP LNGTLTLSCT ACSRFPYFSI LYWLGNGSFI EHLPGRLKEG HTSREHRNTS   120
TWLHRALVLE ELSPTLRSTN FSCLFVDPGQ VAQYHIILAQ LWDGLKTAPS PSQETLSSHS   180
PVSRSAGPGV A                                                       191

SEQ ID NO: 376          moltype = AA   length = 165
FEATURE                 Location/Qualifiers
source                  1..165
                        mol_type = protein
                        organism = Mus musculus
SEQUENCE: 376
TSAPQTTATV LTGSSKDPCS SWSPAVPTKQ YPALDVIWPE KEVPLNGTLT LSCTACSRFP    60
YFSILYWLGN GSFIEHLPGR LKEGHTSREH RNTSTWLHRA LVLEELSPTL RSTNFSCLFV   120
DPGQVAQYHI ILAQLWDGLK TAPSPSQETL SSHSPVSRSA GPVA                    165

SEQ ID NO: 377          moltype = AA   length = 367
FEATURE                 Location/Qualifiers
source                  1..367
                        mol_type = protein
                        organism = Homo sapiens
SEQUENCE: 377
MRAWIFFLLC LAGRALAYFG KLESKLSVIR NLNDQVLFID QGNRPLFEDM TDSDCRDNAP    60
RTIFIISMYK DSQPRGMAVT ISVKCEKIST LSCENKIISF KEMNPPDNIK DTKSDIIFFQ   120
RSVPGHDNKM QFESSSYEGY FLACEKERDL FKLILKKEDE LGDRSIMFTV QNEDGGSGGG   180
SGENLYFQSG GGSGGGGTPV SQTTTAATAS VRSTKDPCPS QPPVFPAAKQ CPALEVTWPE   240
VEVPLNGTLS LSCVACSRFP NFSILYWLGN GSFIEHLPGR LWEGSTSRER GSTGTQLCKA   300
LVLEQLTPAL HSTNFSCVLV DPEQVVQRHV VLAQLWAGLR ATLPPTQEAL PSSHSSPQQQ   360
GHHHHHH                                                            367

SEQ ID NO: 378          moltype = AA   length = 368
FEATURE                 Location/Qualifiers
source                  1..368
```

```
                    mol_type = protein
                    organism = Mus musculus
SEQUENCE: 378
MRAWIFFLLC LAGRALANFG RLHCTTAVIR NINDQVLFVD KRQPVFEDMT DIDQSASEPQ   60
TRLIIYMYKD SEVRGLAVTL SVKDSKMSTL SCKNKIISFE EMDPPENIDD IQSDLIFFQK  120
RVPGHNKMEF ESSLYEGHFL ACQKEDDAFK LILKKKDENG DKSVMFTLTN LHQSGGSGGG  180
SGENLYFQSG GGSGGGGTSA PQTTATVLTG SSKDPCSSWS PAVPTKQYPA LDVIWPEKEV  240
PLNGTLTLSC TACSRFPYFS ILYWLGNGSF IEHLPGRLKE GHTSREHRNT STWLHRALVL  300
EELSPTLRST NFSCLFVDPG QVAQYHIILA QLWDGLKTAP SPSQETLSSH SPVSRSAGPG  360
VAHHHHHH                                                          368
```

What is claimed is:

1. An antibody specific for interleukin-18 binding protein (IL-18BP), wherein the antibody interferes with the binding of IL-18 to IL-18BP, and wherein the antibody comprises a heavy chain variable region ($V_H$) that comprises complementarity determining region $V_H$CDR1, $V_H$CDR2, and $V_H$CDR3 sequences and a light chain variable region ($V_L$) that comprises complementarity determining region $V_L$CDR1, $V_L$CDR2, and $V_L$CDR3 sequences, wherein:
  a. the $V_H$CDR1 sequence comprises the amino acid sequence of TQDYNAH (SEQ ID NO: 169);
  b. the $V_H$CDR2 sequence comprises the amino acid sequence of YIHYSGQTYYNPSLKS (SEQ ID NO: 170);
  c. the $V_H$CDR3 sequence comprises the amino acid sequence of NFGSIYVNYFDY (SEQ ID NO: 171);
  d. the $V_L$CDR1 sequence comprises the amino acid sequence of SASSSVSYMY (SEQ ID NO: 172);
  e. the $V_L$CDR2 sequence comprises the amino acid sequence of TSNLAS (SEQ ID NO: 173); and
  f. the $V_L$CDR3 sequence comprises an amino acid sequence of QQYHSYPT (SEQ ID NO: 174) or an amino acid sequence comprising 1 to 2 amino acid substitutions thereof.

2. The antibody of claim 1, wherein the $V_L$CDR3 sequence comprises an amino acid sequence selected from the group consisting of SEQ ID NOs: 174, 228, 234, 240, and 252.

3. The antibody of claim 1, wherein:
  a. the $V_H$ comprises a sequence at least 70% identical to SEQ ID NO: 321, and the $V_L$ comprises a sequence at least 70% identical to SEQ ID NO: 322;
  b. the $V_H$ comprises a sequence at least 70% identical to SEQ ID NO: 339, and the $V_L$ comprises a sequence at least 70% identical to SEQ ID NO: 340;
  c. the $V_H$ comprises a sequence at least 70% identical to SEQ ID NO: 341, and the $V_L$ comprises a sequence at least 70% identical to SEQ ID NO: 342;
  d. the $V_H$ comprises a sequence at least 70% identical to SEQ ID NO: 343, and the $V_L$ comprises a sequence at least 70% identical to SEQ ID NO: 344; or
  e. the $V_H$ comprises a sequence at least 70% identical to SEQ ID NO: 347, and the $V_L$ comprises a sequence at least 70% identical to SEQ ID NO: 3481.

4. The antibody of claim 1, wherein the antibody comprises an IgA IgD, IgE, IgG, or IgM Fc domain, or a hybrid and/or variant thereof.

5. The antibody of claim 4, wherein the IgA Fc domain is IgA1 or IgA2.

6. The antibody of claim 4, wherein the IgG Fc domain is IgG1, IgG2, IgG3, or IgG4.

7. The antibody of claim 4, wherein the Fc domain is a human Fc domain.

8. The antibody of claim 1, wherein the antibody comprises variant IgG Fc domain with increased effector function in humans relative to a wild type IgG Fc domain.

9. The antibody of claim 8, wherein the variant IgG Fc domain is an IgG1 or IgG3 Fc domain.

10. The antibody of claim 1, wherein the antibody comprises variant IgG Fc domain with decreased effector function in humans relative to a wild type IgG Fc domain.

11. The antibody of claim 10, wherein the variant IgG Fc domain is an IgG2 or IgG4 Fc domain.

12. The antibody of claim 1, wherein the antibody is a monoclonal antibody, humanized antibody or an scFv.

13. A pharmaceutical composition comprising the antibody of claim 1, and optionally a pharmaceutically acceptable carrier.

14. An antibody specific for interleukin-18 binding protein (IL-18BP), wherein the antibody interferes with the binding of IL-18 to IL-18BP, and wherein the antibody comprises a heavy chain variable region ($V_H$) that comprises complementarity determining region $V_H$CDR1, $V_H$CDR2, and $V_H$CDR3 sequences and a light chain variable region ($V_L$) that comprises complementarity determining region $V_L$CDR1, $V_L$CDR2, and $V_L$CDR3 sequences, wherein:
  a. the $V_H$CDR1, $V_H$CDR2, and $V_H$CDR3 sequences comprise SEQ ID NOs: 1-3, respectively, and the $V_L$CDR1, $V_L$CDR2, and $V_L$CDR3 sequences comprise SEQ ID NOs: 4-6, respectively;
  b. the $V_H$CDR1, $V_H$CDR2, and $V_H$CDR3 sequences comprise SEQ ID NOs: 7-9, respectively, and the $V_L$CDR1, $V_L$CDR2, and $V_L$CDR3 sequences comprise SEQ ID NOs: 10-12, respectively;
  c. the $V_H$CDR1, $V_H$CDR2, and $V_H$CDR3 sequences comprise SEQ ID NOs: 13-15, respectively, and the $V_L$CDR1, $V_L$CDR2, and $V_L$CDR3 sequences comprise SEQ ID NOs: 16-18, respectively;
  d. the $V_H$CDR1, $V_H$CDR2, and $V_H$CDR3 sequences comprise SEQ ID NOs: 19-21, respectively, and the $V_L$CDR1, $V_L$CDR2, and $V_L$CDR3 sequences comprise SEQ ID NOs: 22-24, respectively;
  e. the $V_H$CDR1, $V_H$CDR2, and $V_H$CDR3 sequences comprise SEQ ID NOs: 25-27, respectively, and the $V_L$CDR1, $V_L$CDR2, and $V_L$CDR3 sequences comprise SEQ ID NOs: 28-30, respectively;
  f. the $V_H$CDR1, $V_H$CDR2, and $V_H$CDR3 sequences comprise SEQ ID NOs: 31-33, respectively, and the $V_L$CDR1, $V_L$CDR2, and $V_L$CDR3 sequences comprise SEQ ID NOs: 34-36, respectively;
  g. the $V_H$CDR1, $V_H$CDR2, and $V_H$CDR3 sequences comprise SEQ ID NOs: 37-39, respectively, and the $V_L$CDR1, $V_L$CDR2, and $V_L$CDR3 sequences comprise SEQ ID NOs: 40-42, respectively;
  h. the $V_H$CDR1, $V_H$CDR2, and $V_H$CDR3 sequences comprise SEQ ID NOs: 43-45, respectively, and the V_LCDR1, V_LCDR2, and V_LCDR3 sequences comprise SEQ ID NOs: 46-48, respectively;
i. the V_HCDR1, V_HCDR2, and V_HCDR3 sequences comprise SEQ ID NOs: 49-51, respectively, and the V_LCDR1, V_LCDR2, and V_LCDR3 sequences comprise SEQ ID NOs: 52-54, respectively;
j. the V_HCDR1, V_HCDR2, and V_HCDR3 sequences comprise SEQ ID NOs: 55-57, respectively, and the V_LCDR1, V_LCDR2, and V_LCDR3 sequences comprise SEQ ID NOs: 58-60, respectively;
k. the V_HCDR1, V_HCDR2, and V_HCDR3 sequences comprise SEQ ID NOs: 61-63, respectively, and the V_LCDR1, V_LCDR2, and V_LCDR3 sequences comprise SEQ ID NOs: 64-66, respectively;
l. the V_HCDR1, V_HCDR2, and V_HCDR3 sequences comprise SEQ ID NOs: 67-69, respectively, and the V_LCDR1, V_LCDR2, and V_LCDR3 sequences comprise SEQ ID NOs: 70-72, respectively;
m. the V_HCDR1, V_HCDR2, and V_HCDR3 sequences comprise SEQ ID NOs: 73-75, respectively, and the V_LCDR1, V_LCDR2, and V_LCDR3 sequences comprise SEQ ID NOs: 76-78, respectively;
n. the V_HCDR1, V_HCDR2, and V_HCDR3 sequences comprise SEQ ID NOs: 79-81, respectively, and the V_LCDR1, V_LCDR2, and V_LCDR3 sequences comprise SEQ ID NOs: 82-84, respectively;
o. the V_HCDR1, V_HCDR2, and V_HCDR3 sequences comprise SEQ ID NOs: 85-87, respectively, and the V_LCDR1, V_LCDR2, and V_LCDR3 sequences comprise SEQ ID NOs: 88-90, respectively;
p. the V_HCDR1, V_HCDR2, and V_HCDR3 sequences comprise SEQ ID NOs: 91-93, respectively, and the V_LCDR1, V_LCDR2, and V_LCDR3 sequences comprise SEQ ID NOs: 94-96, respectively;
q. the V_HCDR1, V_HCDR2, and V_HCDR3 sequences comprise SEQ ID NOs: 97-99, respectively, and the V_LCDR1, V_LCDR2, and V_LCDR3 sequences comprise SEQ ID NOs: 100-102, respectively;
r. the V_HCDR1, V_HCDR2, and V_HCDR3 sequences comprise SEQ ID NOs: 103-105, respectively, and the V_LCDR1, V_LCDR2, and V_LCDR3 sequences comprise SEQ ID NOs: 106-108, respectively;
s. the V_HCDR1, V_HCDR2, and V_HCDR3 sequences comprise SEQ ID NOs: 109-111, respectively, and the V_LCDR1, V_LCDR2, and V_LCDR3 sequences comprise SEQ ID NOs: 112-114, respectively;
t. the V_HCDR1, V_HCDR2, and V_HCDR3 sequences comprise SEQ ID NOs: 115-117, respectively, and the V_LCDR1, V_LCDR2, and V_LCDR3 sequences comprise SEQ ID NOs: 118-120, respectively;
u. the V_HCDR1, V_HCDR2, and V_HCDR3 sequences comprise SEQ ID NOs: 121-123, respectively, and the V_LCDR1, V_LCDR2, and V_LCDR3 sequences comprise SEQ ID NOs: 124-126, respectively;
v. the V_HCDR1, V_HCDR2, and V_HCDR3 sequences comprise SEQ ID NOs: 127-129, respectively, and the V_LCDR1, V_LCDR2, and V_LCDR3 sequences comprise SEQ ID NOs: 130-132, respectively;
w. the V_HCDR1, V_HCDR2, and V_HCDR3 sequences comprise SEQ ID NOs: 133-135, respectively, and the V_LCDR1, V_LCDR2, and V_LCDR3 sequences comprise SEQ ID NOs: 136-138, respectively;
x. the V_HCDR1, V_HCDR2, and V_HCDR3 sequences comprise SEQ ID NOs: 139-141, respectively, and the V_LCDR1, V_LCDR2, and V_LCDR3 sequences comprise SEQ ID NOs: 142-144, respectively;
y. the V_HCDR1, V_HCDR2, and V_HCDR3 sequences comprise SEQ ID NOs: 145-147, respectively, and the V_LCDR1, V_LCDR2, and V_LCDR3 sequences comprise SEQ ID NOs: 148-150, respectively;
z. the V_HCDR1, V_HCDR2, and V_HCDR3 sequences comprise SEQ ID NOs: 151-153, respectively, and the V_LCDR1, V_LCDR2, and V_LCDR3 sequences comprise SEQ ID NOs: 154-156, respectively;
aa. the V_HCDR1, V_HCDR2, and V_HCDR3 sequences comprise SEQ ID NOs: 157-159, respectively, and the V_LCDR1, V_LCDR2, and V_LCDR3 sequences comprise SEQ ID NOs: 160-162, respectively;
bb. the V_HCDR1, V_HCDR2, and V_HCDR3 sequences comprise SEQ ID NOs: 163-165, respectively, and the V_LCDR1, V_LCDR2, and V_LCDR3 sequences comprise SEQ ID NOs: 166-168, respectively;
cc. the V_HCDR1, V_HCDR2, and V_HCDR3 sequences comprise SEQ ID NOs: 175-177, respectively, and the V_LCDR1, V_LCDR2, and V_LCDR3 sequences comprise SEQ ID NOs: 178-180, respectively;
dd. the V_HCDR1, V_HCDR2, and V_HCDR3 sequences comprise SEQ ID NOs: 181-183, respectively, and the V_LCDR1, V_LCDR2, and V_LCDR3 sequences comprise SEQ ID NOs: 184-186, respectively;
ee. the V_HCDR1, V_HCDR2, and V_HCDR3 sequences comprise SEQ ID NOs: 187-189, respectively, and the V_LCDR1, V_LCDR2, and V_LCDR3 sequences comprise SEQ ID NOs: 190-192, respectively;
ff. the V_HCDR1, V_HCDR2, and V_HCDR3 sequences comprise SEQ ID NOs: 193-195, respectively, and the V_LCDR1, V_LCDR2, and V_LCDR3 sequences comprise SEQ ID NOs: 196-198, respectively;
gg. the V_HCDR1, V_HCDR2, and V_HCDR3 sequences comprise SEQ ID NOs: 199-201, respectively, and the V_LCDR1, V_LCDR2, and V_LCDR3 sequences comprise SEQ ID NOs: 202-204, respectively;
hh. the V_HCDR1, V_HCDR2, and V_HCDR3 sequences comprise SEQ ID NOs: 205-207, respectively, and the V_LCDR1, V_LCDR2, and V_LCDR3 sequences comprise SEQ ID NOs: 208-210, respectively;
ii. the V_HCDR1, V_HCDR2, and V_HCDR3 sequences comprise SEQ ID NOs: 211-213, respectively, and the V_LCDR1, V_LCDR2, and V_LCDR3 sequences comprise SEQ ID NOs: 238-240, respectively;
jj. the V_HCDR1, V_HCDR2, and V_HCDR3 sequences comprise SEQ ID NOs: 217-219, respectively, and the V_LCDR1, V_LCDR2, and V_LCDR3 sequences comprise SEQ ID NOs: 220-222, respectively;
kk. the V_HCDR1, V_HCDR2, and V_HCDR3 sequences comprise SEQ ID NOs: 241-243, respectively, and the V_LCDR1, V_LCDR2, and V_LCDR3 sequences comprise SEQ ID NOs: 232-234, respectively;
ll. the V_HCDR1, V_HCDR2, and V_HCDR3 sequences comprise SEQ ID NOs: 241-243, respectively, and the V_LCDR1, V_LCDR2, and V_LCDR3 sequences comprise SEQ ID NOs: 238-240, respectively; or
mm. the V_HCDR1, V_HCDR2, and V_HCDR3 sequences comprise SEQ ID NOs: 241-243, respectively, and the V_LCDR1, V_LCDR2, and V_LCDR3 sequences comprise SEQ ID NOs: 244-246, respectively.

15. The antibody of claim 1, wherein:
a. the $V_H$ comprises a sequence at least 70% identical to SEQ ID NO: 265, and the $V_L$ comprises a sequence at least 70% identical to SEQ ID NO: 266;
b. the $V_H$ comprises a sequence at least 70% identical to SEQ ID NO: 267, and the $V_L$ comprises a sequence at least 70% identical to SEQ ID NO: 268;

c. the $V_H$ comprises a sequence at least 70% identical to SEQ ID NO: 269, and the $V_L$ comprises a sequence at least 70% identical to SEQ ID NO: 270;
d. the $V_H$ comprises a sequence at least 70% identical to SEQ ID NO: 271, and the $V_L$ comprises a sequence at least 70% identical to SEQ ID NO: 272;
e. the $V_H$ comprises a sequence at least 70% identical to SEQ ID NO: 273, and the $V_L$ comprises a sequence at least 70% identical to SEQ ID NO: 274;
f. the $V_H$ comprises a sequence at least 70% identical to SEQ ID NO: 275, and the $V_L$ comprises a sequence at least 70% identical to SEQ ID NO: 276;
g. the $V_H$ comprises a sequence at least 70% identical to SEQ ID NO: 277, and the $V_L$ comprises a sequence at least 70% identical to SEQ ID NO: 278;
h. the $V_H$ comprises a sequence at least 70% identical to SEQ ID NO: 279, and the $V_L$ comprises a sequence at least 70% identical to SEQ ID NO: 280;
i. the $V_H$ comprises a sequence at least 70% identical to SEQ ID NO: 281, and the $V_L$ comprises a sequence at least 70% identical to SEQ ID NO: 282;
j. the $V_H$ comprises a sequence at least 70% identical to SEQ ID NO: 283, and the $V_L$ comprises a sequence at least 70% identical to SEQ ID NO: 284;
k. the $V_H$ comprises a sequence at least 70% identical to SEQ ID NO: 285, and the $V_L$ comprises a sequence at least 70% identical to SEQ ID NO: 286;
l. the $V_H$ comprises a sequence at least 70% identical to SEQ ID NO: 287, and the $V_L$ comprises a sequence at least 70% identical to SEQ ID NO: 288;
m. the $V_H$ comprises a sequence at least 70% identical to SEQ ID NO: 289, and the $V_L$ comprises a sequence at least 70% identical to SEQ ID NO: 290;
n. the $V_H$ comprises a sequence at least 70% identical to SEQ ID NO: 291, and the $V_L$ comprises a sequence at least 70% identical to SEQ ID NO: 292;
o. the $V_H$ comprises a sequence at least 70% identical to SEQ ID NO: 293, and the $V_L$ comprises a sequence at least 70% identical to SEQ ID NO: 294;
p. the $V_H$ comprises a sequence at least 70% identical to SEQ ID NO: 295, and the $V_L$ comprises a sequence at least 70% identical to SEQ ID NO: 296;
q. the $V_H$ comprises a sequence at least 70% identical to SEQ ID NO: 297, and the $V_L$ comprises a sequence at least 70% identical to SEQ ID NO: 298;
r. the $V_H$ comprises a sequence at least 70% identical to SEQ ID NO: 299, and the $V_L$ comprises a sequence at least 70% identical to SEQ ID NO: 300;
s. the $V_H$ comprises a sequence at least 70% identical to SEQ ID NO: 301, and the $V_L$ comprises a sequence at least 70% identical to SEQ ID NO: 302;
t. the $V_H$ comprises a sequence at least 70% identical to SEQ ID NO: 303, and the $V_L$ comprises a sequence at least 70% identical to SEQ ID NO: 304;
u. the $V_H$ comprises a sequence at least 70% identical to SEQ ID NO: 305, and the $V_L$ comprises a sequence at least 70% identical to SEQ ID NO: 306;
v. the $V_H$ comprises a sequence at least 70% identical to SEQ ID NO: 307, and the $V_L$ comprises a sequence at least 70% identical to SEQ ID NO: 308;
w. the $V_H$ comprises a sequence at least 70% identical to SEQ ID NO: 309, and the $V_L$ comprises a sequence at least 70% identical to SEQ ID NO: 310;
x. the $V_H$ comprises a sequence at least 70% identical to SEQ ID NO: 311, and the $V_L$ comprises a sequence at least 70% identical to SEQ ID NO: 312;
y. the $V_H$ comprises a sequence at least 70% identical to SEQ ID NO: 313, and the $V_L$ comprises a sequence at least 70% identical to SEQ ID NO: 314;
z. the $V_H$ comprises a sequence at least 70% identical to SEQ ID NO: 315, and the $V_L$ comprises a sequence at least 70% identical to SEQ ID NO: 316;
aa. the $V_H$ comprises a sequence at least 70% identical to SEQ ID NO: 317, and the $V_L$ comprises a sequence at least 70% identical to SEQ ID NO: 318;
bb. the $V_H$ comprises a sequence at least 70% identical to SEQ ID NO: 319, and the $V_L$ comprises a sequence at least 70% identical to SEQ ID NO: 320;
cc. the $V_H$ comprises a sequence at least 70% identical to SEQ ID NO: 323, and the $V_L$ comprises a sequence at least 70% identical to SEQ ID NO: 324;
dd. the $V_H$ comprises a sequence at least 70% identical to SEQ ID NO: 325, and the $V_L$ comprises a sequence at least 70% identical to SEQ ID NO: 326;
ee. the $V_H$ comprises a sequence at least 70% identical to SEQ ID NO: 327, and the $V_L$ comprises a sequence at least 70% identical to SEQ ID NO: 328;
ff. the $V_H$ comprises a sequence at least 70% identical to SEQ ID NO: 329, and the $V_L$ comprises a sequence at least 70% identical to SEQ ID NO: 330;
gg. the $V_H$ comprises a sequence at least 70% identical to SEQ ID NO: 331, and the $V_L$ comprises a sequence at least 70% identical to SEQ ID NO: 332;
hh. the $V_H$ comprises a sequence at least 70% identical to SEQ ID NO: 333, and the $V_L$ comprises a sequence at least 70% identical to SEQ ID NO: 334;
ii. the $V_H$ comprises a sequence at least 70% identical to SEQ ID NO: 335, and the $V_L$ comprises a sequence at least 70% identical to SEQ ID NO: 336;
jj. the $V_H$ comprises a sequence at least 70% identical to SEQ ID NO: 337, and the $V_L$ comprises a sequence at least 70% identical to SEQ ID NO: 338;
kk. the $V_H$ comprises a sequence at least 70% identical to SEQ ID NO: 345, and the $V_L$ comprises a sequence at least 70% identical to SEQ ID NO: 342;
ll. the $V_H$ comprises a sequence at least 70% identical to SEQ ID NO: 345, and the $V_L$ comprises a sequence at least 70% identical to SEQ ID NO: 344; or
mm. the $V_H$ comprises a sequence at least 70% identical to SEQ ID NO: 345, and the $V_L$ comprises a sequence at least 70% identical to SEQ ID NO: 346.

16. The antibody of claim 14, wherein the antibody comprises an IgA IgD, IgE, IgG or IgM Fc domain, mor a hybrid and/or variant thereof.

17. The antibody of claim 16, wherein the IgA Fc domain is IgA1 or IgA2.

18. The antibody of claim 16, wherein the IgG Fc domain is IgG1, IgG2, IgG3, or IgG4.

19. The antibody of claim 16, wherein the Fc domain is a human Fc domain.

20. The antibody of claim 14, wherein the antibody comprises variant IgG Fc domain with increased effector function in humans relative to a wild type IgG Fc domain.

21. The antibody of claim 20, wherein the variant IgG Fc domain is an IgG1 or IgG3 Fc domain.

22. The antibody of claim 14, wherein the antibody comprises variant IgG Fc domain with decreased effector function in humans relative to a wild type IgG Fc domain.

23. The antibody of claim 22, wherein the variant IgG Fc domain is an IgG2 or IgG4 Fc domain.

24. The antibody of claim 14, wherein the antibody is a monoclonal antibody, humanized antibody or an scFv.

25. A pharmaceutical composition comprising the antibody of claim 14, and optionally a pharmaceutically acceptable carrier.

\* \* \* \* \*